US012780928B2

(12) United States Patent
Baret-Cormel et al.

(10) Patent No.: US 12,780,928 B2
(45) **Date of Patent: *Nov. 3, 2026**

(54) COMPOSITIONS AND METHODS FOR TREATING JUVENILE IDIOPATHIC ARTHRITIS

(71) Applicants: SANOFI BIOTECHNOLOGY, Paris (FR); REGENERON PHARMACEUTICALS, INC., Tarrytown, NY (US)

(72) Inventors: Lydie Baret-Cormel, Antony (FR); Tanya Momtahen, North Wales, PA (US); Stefano Fiore, Guttenberg, NJ (US); Janet Van Adelsberg, New York, NY (US)

(73) Assignees: SANOFI BIOTECHNOLOGY, Gentilly (FR); REGENERON PHARMACEUTICALS, INC., Tarrytown, NY (US)

( * ) Notice: Subject to any disclaimer, the term of this patent is extended or adjusted under 35 U.S.C. 154(b) by 993 days.

This patent is subject to a terminal disclaimer.

(21) Appl. No.: 17/934,259

(22) Filed: Sep. 22, 2022

(65) Prior Publication Data

US 2023/0127528 A1 Apr. 27, 2023

Related U.S. Application Data

(63) Continuation of application No. 16/779,187, filed on Jan. 31, 2020, now Pat. No. 11,498,969.

(60) Provisional application No. 62/935,395, filed on Nov. 14, 2019, provisional application No. 62/851,474, filed on May 22, 2019, provisional application No. 62/799,698, filed on Jan. 31, 2019.

(30) Foreign Application Priority Data

Dec. 3, 2019 (EP) .................................... 19306553

(51) Int. Cl.
*A61K 39/395* (2006.01)
*A61P 19/02* (2006.01)
*C07K 16/28* (2006.01)

(52) U.S. Cl.
CPC ...... *C07K 16/2866* (2013.01); *A61K 39/3955* (2013.01); *A61P 19/02* (2018.01)

(58) Field of Classification Search
CPC . A61K 39/3955; A61K 19/02; C07K 16/2866
See application file for complete search history.

(56) References Cited

U.S. PATENT DOCUMENTS

| | | | |
|---|---|---|---|
| 4,997,423 | A | 3/1991 | Okuda et al. |
| 5,016,784 | A | 5/1991 | Batson |
| 5,215,534 | A | 6/1993 | De Harde et al. |
| 5,480,796 | A | 1/1996 | Kishimoto |
| 5,605,690 | A | 2/1997 | Jacobs et al. |
| 5,670,373 | A | 9/1997 | Kishimoto |
| 5,723,120 | A | 3/1998 | Brackenhoff et al. |
| 5,795,965 | A | 8/1998 | Tsuchiya |
| 5,817,790 | A | 10/1998 | Tsuchiya |
| 5,888,510 | A | 3/1999 | Kishimoto |
| 5,888,511 | A | 3/1999 | Skurkovich et al. |
| 5,908,686 | A | 6/1999 | Sudo et al. |
| 6,046,223 | A | 4/2000 | Sponsel et al. |
| 6,086,874 | A | 7/2000 | Yoshida et al. |
| 6,261,560 | B1 | 7/2001 | Tsujinaka et al. |
| 6,286,699 | B1 | 9/2001 | Sudo |
| 6,410,691 | B1 | 6/2002 | Kishimoto |
| 6,629,949 | B1 | 10/2003 | Douglas et al. |
| 6,632,927 | B2 | 10/2003 | Adair |
| 6,645,635 | B2 | 11/2003 | Murakai |
| 6,659,982 | B2 | 12/2003 | Douglas et al. |
| 6,670,373 | B1 | 12/2003 | Bonjouklian et al. |
| 6,692,742 | B1 | 2/2004 | Nakamura et al. |
| 6,723,319 | B1 | 4/2004 | Ito et al. |
| 7,226,554 | B2 | 6/2007 | Sudo et al. |
| 7,320,792 | B2 | 1/2008 | Ito et al. |
| 7,479,543 | B2 | 1/2009 | Tsuchiya et al. |
| 7,521,052 | B2 | 4/2009 | Okuda et al. |
| 7,582,298 | B2 | 9/2009 | Stevens |
| 8,043,617 | B2 | 10/2011 | Stevens et al. |
| 8,080,248 | B2 | 12/2011 | Radin |
| 8,183,014 | B2 | 5/2012 | Stevens et al. |
| 8,192,741 | B2 | 6/2012 | Radin |
| 8,440,890 | B1 | 5/2013 | Carlone, Jr. et al. |
| 8,568,721 | B2 | 10/2013 | Radin |
| 8,709,409 | B2 | 4/2014 | Okuda et al. |

(Continued)

FOREIGN PATENT DOCUMENTS

| | | |
|---|---|---|
| BR | PI0712224-1 A2 | 1/2012 |
| CN | 103476793 A | 12/2013 |

(Continued)

OTHER PUBLICATIONS

Knappik et al., J. Mol. Biol., 2000, vol. 296(1):57-86.*
Rabia et al., Biochem. Eng. J., 2018, vol. 137:365-374.*
U.S. Appl. No. 13/043,617, filed Oct. 25, 2011, Stevens et al.
"Highlights of Prescribing Information" for Kevzara (sarilumab), Reference ID: 4101405—Accessdata.fda.gov, May 2017.

(Continued)

*Primary Examiner* — Xiaozhen Xie
(74) *Attorney, Agent, or Firm* — LATHROP GPM LLP; James H. Velema, Esq.; Judith L. Stone-Hulslander, Esq.

(57) ABSTRACT

The present disclosure provides compositions and methods of treating and improving the symptoms of systemic juvenile idiopathic arthritis and polyarticular-course juvenile idiopathic arthritis using an antibody that specifically binds human interleukin-6 receptor (hIL-6R).

32 Claims, 17 Drawing Sheets

Specification includes a Sequence Listing.

(56) References Cited

U.S. PATENT DOCUMENTS

| | | | |
|---|---|---|---|
| 8,869,904 | B2 | 10/2014 | Jani |
| 8,895,521 | B2 | 11/2014 | Klinman et al. |
| 9,139,646 | B2 | 9/2015 | Solinger et al. |
| 9,173,880 | B2 | 11/2015 | Dix et al. |
| 9,248,242 | B2 | 2/2016 | Verespe et al. |
| 9,308,256 | B2 | 4/2016 | Radin et al. |
| 9,427,531 | B2 | 8/2016 | Hourmand et al. |
| 9,566,395 | B2 | 2/2017 | Dennt et al. |
| 9,884,916 | B2 | 2/2018 | Stevens et al. |
| 9,943,594 | B2 | 4/2018 | Jasson et al. |
| 9,951,130 | B2 | 4/2018 | Schmidt et al. |
| 10,072,086 | B2 | 9/2018 | Dix et al. |
| 10,231,981 | B2 | 3/2019 | Zhang et al. |
| 10,927,435 | B2 | 2/2021 | Huang et al. |
| 10,968,278 | B2 | 4/2021 | Sridhara Sundaram et al. |
| 11,498,969 | B2 | 11/2022 | Baret-Cormel et al. |
| 12,297,279 | B2 | 5/2025 | Boklage et al. |
| 2002/0187150 | A1 | 12/2002 | Mihara et al. |
| 2003/0092606 | A1 | 5/2003 | L'Italien et al. |
| 2003/0113316 | A1 | 6/2003 | Kaisheva et al. |
| 2003/0190316 | A1 | 10/2003 | Katuka et al. |
| 2004/0071706 | A1 | 4/2004 | Ito et al. |
| 2004/0115197 | A1 | 6/2004 | Yoshizaki et al. |
| 2004/0197324 | A1 | 10/2004 | Liu et al. |
| 2004/0202658 | A1 | 10/2004 | Benyunes |
| 2004/0219156 | A1 | 11/2004 | Goldenberg et al. |
| 2005/0142635 | A1 | 6/2005 | Tsuchiya et al. |
| 2005/0238644 | A1 | 10/2005 | Mihara et al. |
| 2006/0078531 | A1 | 4/2006 | Sota |
| 2006/0078532 | A1 | 4/2006 | Omoigui |
| 2006/0078533 | A1 | 4/2006 | Omoigui |
| 2006/0177436 | A1 | 8/2006 | Ghilardi et al. |
| 2006/0251653 | A1 | 11/2006 | Okuda et al. |
| 2006/0275294 | A1 | 12/2006 | Omoigui |
| 2006/0292147 | A1 | 12/2006 | Yoshizaki et al. |
| 2007/0036785 | A1 | 2/2007 | Kishimoto et al. |
| 2007/0036788 | A1 | 2/2007 | Sheriff et al. |
| 2007/0098714 | A1 | 5/2007 | Nishimoto et al. |
| 2007/0143168 | A1 | 6/2007 | Stevens et al. |
| 2007/0148169 | A1 | 6/2007 | Yoshizaki et al. |
| 2007/0280945 | A1 | 12/2007 | Stevens |
| 2008/0124325 | A1 | 5/2008 | Ito et al. |
| 2008/0131374 | A1 | 6/2008 | Medich et al. |
| 2008/0145367 | A1 | 6/2008 | Bove et al. |
| 2008/0269467 | A1 | 10/2008 | Allan et al. |
| 2009/0082288 | A1 | 3/2009 | Klinman et al. |
| 2010/0316627 | A1 | 12/2010 | Stevens et al. |
| 2010/0316636 | A1 | 12/2010 | Radin et al. |
| 2011/0098450 | A1 | 4/2011 | Igawa et al. |
| 2011/0171241 | A1 | 7/2011 | Dix et al. |
| 2011/0245473 | A1 | 10/2011 | Igawa et al. |
| 2012/0003697 | A1 | 1/2012 | Stevens et al. |
| 2012/0171123 | A1 | 7/2012 | Medich et al. |
| 2012/0258098 | A1 | 10/2012 | Radin et al. |
| 2012/0301460 | A1 | 11/2012 | Bao et al. |
| 2013/0014958 | A1 | 1/2013 | Jani |
| 2013/0149310 | A1 | 6/2013 | Jasson et al. |
| 2014/0255390 | A1 | 9/2014 | Radin et al. |
| 2014/0302053 | A1 | 10/2014 | Huang et al. |
| 2015/0050277 | A1 | 2/2015 | Peters et al. |
| 2016/0002341 | A1 | 1/2016 | Dix et al. |
| 2016/0220675 | A1 | 8/2016 | Abrahmson |
| 2016/0229916 | A1 | 8/2016 | Stevens et al. |
| 2016/0280782 | A1 | 9/2016 | Huang et al. |
| 2016/0281106 | A1 | 9/2016 | Kim et al. |
| 2017/0166646 | A1 | 6/2017 | Sridhara Sundaram et al. |
| 2017/0198045 | A1 | 7/2017 | Johnson et al. |
| 2017/0252434 | A1 | 9/2017 | Joseph et al. |
| 2017/0360807 | A1 | 12/2017 | Zhang et al. |
| 2018/0296670 | A1 | 10/2018 | Jasson et al. |
| 2019/0002574 | A1 | 1/2019 | Dix et al. |
| 2019/0100585 | A1 | 4/2019 | Bauer et al. |
| 2020/0047029 | A1 | 2/2020 | Bentley et al. |
| 2020/0339693 | A1 | 10/2020 | Baret-Cormel et al. |
| 2020/0399380 | A1 | 12/2020 | Boklage et al. |
| 2020/0405851 | A1 | 12/2020 | Boyapati et al. |
| 2021/0230719 | A1 | 7/2021 | Huang et al. |
| 2021/0240369 | A1 | 8/2021 | Cain |
| 2021/0301027 | A1 | 9/2021 | Sridhara Sundaram et al. |
| 2022/0242959 | A1 | 8/2022 | Chen et al. |
| 2023/0127528 | A1 | 4/2023 | Baret-Cormel et al. |
| 2023/0174657 | A1 | 6/2023 | Albrecht et al. |
| 2023/0193871 | A1 | 6/2023 | Ford et al. |
| 2025/0333522 | A1 | 10/2025 | Boklage et al. |
| 2026/0027202 | A1 | 1/2026 | Jasson et al. |

FOREIGN PATENT DOCUMENTS

| | | | |
|---|---|---|---|
| CN | 104105505 | A | 10/2014 |
| CN | 104903349 | A | 9/2015 |
| CN | 102869346 | A | 1/2023 |
| EA | 014226 | B1 | 10/2010 |
| EA | 014298 | B1 | 10/2010 |
| EP | 0628639 | A1 | 12/1994 |
| EP | 0409607 | B1 | 10/1996 |
| EP | 0783893 | A1 | 7/1997 |
| EP | 0800829 | A1 | 10/1997 |
| EP | 0811384 | A2 | 12/1997 |
| EP | 0923941 | A2 | 6/1999 |
| EP | 1004315 | A1 | 5/2000 |
| EP | 1074268 | A1 | 2/2001 |
| EP | 1108435 | A1 | 6/2001 |
| EP | 1314437 | A1 | 5/2003 |
| EP | 1327681 | A1 | 7/2003 |
| EP | 1475100 | A1 | 11/2004 |
| EP | 1475101 | A1 | 11/2004 |
| EP | 0413908 | B2 | 8/2005 |
| EP | 1810980 | A1 | 7/2007 |
| EP | 1334731 | B1 | 2/2008 |
| EP | 2451438 | B1 | 2/2014 |
| EP | 2766039 | A1 | 8/2014 |
| EP | 3071230 | A1 | 9/2016 |
| EP | 3193934 | A1 | 7/2017 |
| EP | 3371224 | A1 | 9/2018 |
| EP | 3426295 | A1 | 1/2019 |
| EP | 3770173 | A1 | 1/2021 |
| EP | 3983071 | A1 | 4/2022 |
| FR | 2694767 | A1 | 2/1994 |
| JP | 2009-539349 | A | 11/2009 |
| JP | 2014-530226 | A | 11/2014 |
| JP | 61-22018 | B2 | 4/2017 |
| JP | 2017-137338 | A | 8/2017 |
| JP | 63-36171 | B2 | 5/2018 |
| JP | 2020-045351 | A | 3/2020 |
| RU | 2358762 | C2 | 6/2009 |
| TW | 201141518 | A | 12/2011 |
| WO | WO 1992/016553 | A1 | 10/1992 |
| WO | WO 1992/019759 | A1 | 11/1992 |
| WO | WO 1994/006476 | A1 | 3/1994 |
| WO | WO 1995/009873 | A1 | 4/1995 |
| WO | WO 1996/011020 | A1 | 4/1996 |
| WO | WO 2002/100330 | A2 | 12/2002 |
| WO | WO 2003/009817 | A2 | 2/2003 |
| WO | WO 2004/039826 | A1 | 5/2004 |
| WO | WO 2004/091658 | A1 | 10/2004 |
| WO | WO 2004/096273 | A1 | 11/2004 |
| WO | WO 2005/028514 | A1 | 3/2005 |
| WO | WO 2005/058365 | A1 | 6/2005 |
| WO | WO 2005/016280 | A2 | 2/2006 |
| WO | WO 2006/033702 | A2 | 3/2006 |
| WO | WO 2007/062040 | A1 | 5/2007 |
| WO | WO 2007/070750 | A1 | 6/2007 |
| WO | WO 2007/143168 | A2 | 12/2007 |
| WO | WO 2007/147001 | A2 | 12/2007 |
| WO | WO 2008/020079 | A1 | 2/2008 |
| WO | WO 2008/049897 | A1 | 5/2008 |
| WO | WO 2008/145142 | A1 | 12/2008 |
| WO | WO 2009/095489 | A2 | 8/2009 |
| WO | WO 2009/109584 | A1 | 9/2009 |
| WO | WO 2009/125825 | A1 | 10/2009 |
| WO | WO 2009/140348 | A2 | 11/2009 |
| WO | WO 2010/035769 | A1 | 4/2010 |
| WO | WO 2010/106812 | A1 | 9/2010 |
| WO | WO 2010/149771 | A1 | 12/2010 |

(56) References Cited

FOREIGN PATENT DOCUMENTS

| | | | |
|---|---|---|---|
| WO | WO 2011/085158 | A2 | 7/2011 |
| WO | WO 2012/064627 | A2 | 5/2012 |
| WO | WO 2013/053751 | A1 | 4/2013 |
| WO | WO 2013/056751 | A1 | 4/2013 |
| WO | WO 2015/077582 | A1 | 5/2015 |
| WO | WO 2015/148790 | A1 | 10/2015 |
| WO | WO 2016/044343 | A1 | 3/2016 |
| WO | WO 2017/038986 | A1 | 3/2017 |
| WO | WO 2017/079443 | A1 | 5/2017 |
| WO | WO 2017/106312 | A1 | 6/2017 |
| WO | WO 2017/155990 | A1 | 9/2017 |
| WO | WO 2017/194779 | A1 | 11/2017 |
| WO | WO 2018/007442 | A1 | 1/2018 |
| WO | WO 2020/047029 | A1 | 3/2020 |
| WO | WO 2020/160465 | A1 | 8/2020 |
| WO | WO 2020/219960 | A1 | 10/2020 |
| WO | WO 2020/247461 | A1 | 12/2020 |
| WO | WO 2020/252214 | A1 | 12/2020 |
| WO | WO 2021/240436 | A1 | 12/2021 |

OTHER PUBLICATIONS

Actemra Prescribing Information Genentech. Actemra (tocilizumab): Full Prescribing Information. 2017 Retrieved from: <<https://www.accessdata.fda.gov/drugsatfda_docs/label/2017/125276s114lbl.pdf>>.

Adan, et al., "Tocilizumab Treatment For Refractory Uveitis-Related Cystoid Macular Edema", Graefe's Archive for Clinical and Experimental Ophthalmology, vol. 251, No. 11, pp. 2627-2632, Jul. 27, 2013.

Adlan, et al., Autonomic Function and Rheumatoid Arthritis—A Systematic Review, Seminars in Arthritis and Rheumatism, vol. 44, No. 3, pp. 283-304, 2014.

Advisory Action received for U.S. Appl. No. 13/648,521, mailed on Jul. 19, 2016, 3 Pages.

Alekseeva, "Juvenile Idiopathic Arthritis: Clinical Picture, Diagnosis, Treatment," Current Pediatrics, 2015, 14(1): 78-94, Etiology and Pathogenesis, p. 78; Treatment of Polyarticular (RF−, RF+) JIA, p. 84; and Treatment, p. 92, English Abstract included.

Aletaha et al. (2010) "Rheumatoid Arthritis Classification Criteria, ACR classification," Arthritis & Rheumatism. 62 p):2569-2581.

Amit et al., "Three-Dimensional Structure of an Antigen-Antibody Complex at 2.8 a Resolution" Science (Aug. 1986) 233:747-753.

An et al. (2010) "The addition of tocilizumab to DMARD therapy for rheumatoid arthritis: a meta-analysis of randomized controlled trials," 66(1):49-59.

Andersson M. et al., "SAT0116 Prevalence of unacceptable pain in patients with long-standing RA", Annals of the Rheumatic Diseases, 2017, 76: p. 812-813.

Arevalo, "Tocilizumab Shows Promise For Refractory Uveitis-Related Macular Edema", URL:https://www.aao.org/editors-choice/tocilizumab-shows-promise-refractory-uveitISRWOelate, Nov. 25, 2014.

Atzeni et al., "Il-6 Involvement in pain, fatigue and mood disorders in rheumatoid arthritis and the effects of Il-6 inhibitor sarilumab", Pharmacological Research, 2019, 149: 1-8.

Barry, et al., "Pharmacotherapy for Uveitis: Current Management and Emerging Therapy", Clinical Ophthalmology, vol. 8, pp. 1891-1911, Sep. 1, 2014.

Biswas, et al., Prevalence, Types, Clinical Associations, and Determinants of Peripheral Neuropathy in Rheumatoid Patients, Annals of Indian Academy of Neurology, vol. 14, No. 3, pp. 194-197, 2011.

Boyapati, et al., "Sarilumab Plus Methotrexate Suppresses Circulating Biomarkers of Bone Resorption and Synovial Damage in Patients with Rheumatoid Arthritis and Inadequate Response to Methotrexate: A Biomarker Study of Mobility", Arthritis Research & Therapy, vol. 18, Article No. 225, pp. 1-12, Dec. 1, 2016.

Boyden et al., Non-inflammatory Causes of Pain in Patients with Rheumatoid Arthritis, Curr Rheumatol Rep., 2016, 18: 30.1.

Brenn, et al., Sensitization of Unmyelinated Sensory Fibers of the Joint Nerve to Mechanical Stimuli by Interleukin-6 in the Rat: an Inflammatory Mechanism of Joint Pain, Arthritis & Rheumatology, vol. 56, No. 1, pp. 351-359, Jan. 2007.

Bresnick, "Diabetic Macular Edema—A Review", Ophthalmology, vol. 93, No. 7, pp. 989-997, Jul. 1986.

Burmester et al. (Jul. 31, 2013) "A randomised, double-blind, parallel-group study of the safety and efficacy of subcutaneous tocilizumab versus intravenous tocilizumab in combination with traditional disease-modifying antirheumatic drugs in patients with moderate to severe rheumatoid arthritis (SUMMACTA study) ," Ann. Rheum. Dis. 73:69-74.

Burmester et al., "Efficacy and safety of sarilumab monotherapy versus adalimumab monotherapy for the treatment of patients with active rheumatoid arthritis (Monarch): a randomised, double-blind, parallel-group phase III trial", Ann Rheum Dis., 2017, 76(5): 840-847.

Burmester et al., "Rheumatoid Arthritis—Sarilumab more effective than adalimumab", Nature Reviews, Rheumatology, Research Highlights, Published online Dec. 8, 2016.

Burmester et al., "Safety and efficacy of switching from adalimumab to sarilumab in patients with rheumatoid arthritis in the ongoing Monarch open-label extention", RMD Open, Rheumatic and Musculoskeletal Diseases, 2019, 5: e001017.

Burmester, et al. Unique Changes in Hemoglobin with Sarilumab Versus Adalimumab are Independent of Better Disease Control in Patients with Rheumatoid Arthritis (RA) Arthritis & Rheumatology, 2018 vol. 70, Supplement 10, Abstract 1528.

Bykerk et al., "Impact of Sarilumab on Unacceptable Pain and Inflammation Control in Moderately-to-Severely Active Rheumatoid Arthritis (RA) Patients in 3 Phase 3 Studies", Arthritis & Rheumatology (Hoboken), Oct. 1, 2019, 71(S10): Abstract No. 1393.

Bykerk et al., "Impact of sarilumab on unacceptable pain and inflammation control in moderately-to-severely active rheumatoid arthritis (RA) patients in 3 Phase 3 studies", Rheumatology, Apr. 20, 2020, 59(2): EP25.

Bykerk et al., "Impact of Sarilumab on Unacceptable Pain and Inflammation Control in Moderately-to-Severely Active Rheumatoid Arthritis Patients in 3 Phase 3 Studies", Sep. 11, 2020, retrieved from url: https://pheedloop.s3.amazonaws.com/media/events/EVEVLUEFMPIXU/files/822199_Bykerk-Vivian-RA-Unacceptable%20Pain.pdf.

Calabrese, et al., "IL-6 Biology: Implications for Clinical Targeting in Rheumatic Disease", Nature Reviews Rheumatology, vol. 10, No. 12, pp. 720-727, Dec. 2014.

Cao, et al., "Pharmacological Blockade Of Interleukin 6 Receptor (IL-6R) Inhibits The Development Of Ocular Inflammation In The Murine Model Of Experimental Autoimmune Uveitis (EAU)", Investigative Ophthalmology & Visual Science, vol. 54, Issued 15, p. 5193, Jun. 2013.

Cazzola et al., Physiopathology of Pain in Rheumatology, Reumatismo, vol. 66, No. 1, pp. 4-13, 2014.

Center for Drug Evaluation and Research, Application No. 761037 (Year: 2016).

Challa, et al., Patient-provider Discordance Between Global Assessments of Disease Activity in Rheumatoid Arthritis: a Comprehensive Clinical Evaluation, Arthritis Research & Therapy, vol. 19, No. 212, pp. 1-14, 2017.

Chester (Jul. 24, 2017) E-mail: "<External> CAS Registry No.—RN1189541-98-7".

Cheung, et al., "2-093 Comparative Effectiveness of Biologic Dmards and Jak Inhibitors in Patients With an Inadequate Response to TNF Inhibitors: a Network Meta-analysis", International Journal of Rheumatic Diseases, Retrieved From url: <<https://onlinelibrary.wiley.com/doi/10.1111/1756-185X.13545>>.

Chichasova (2010) "fletieume peama-rompuoro apTpwTa: Taiamyeume Bonpocbi B npaimike krimumumc-ra [Treatment pf rheumatoid arthritis: tactical issues in the practice of the clinician]," fleyaupin Bpati [The Attending Physician]. No. 7/10.—English machine translation only.

Choy et al., "Indirect Treatment Comparison of the Efficacy and Safety of Sarilumab Monotherapy in Rheumatoid Arthritis Patients with Inadequate Response to Conventional Disease-Modifying Antirheumatic Drugs", Mar. 12, 2019, 36(4): 817-827.

(56) References Cited

OTHER PUBLICATIONS

Choy et al., "Therapeutic benefit of blocking interleukin-6 activity with an anti-interleukin-6 receptor monoclonal antibody in rheumatoid arthritis: A randomized, double-blind, placebo-controlled, dose-escalation trial", Arthritis & Rheumatology, Dec. 2002, 46(12): 3143-3150.
Choy, "Understanding the Dynamics: Pathways Involved in the Pathogenesis of Rheumatoid Arthritis", Rheumatology, vol. 51, Supplement 5, pp. v3-v11, Jul. 1, 2012.
Choy, et al., "Cardiovascular Risk in Rheumatoid Arthritis: Recent Advances in the Understanding of the Pivotal Role of Inflammation", Risk Predictors and the Impact of Treatment Rheumatology, vol. 53, pp. 2143-2154, Dec. 1, 2014.
Choy, et al., "Neuroendocrine and Neurophysiological Effects of Interleukin 6 in Rheumatoid Arthritis", Rheumatology, vol. 57, pp. 1885-1895, Nov. 1, 2018.
ClinicalTrials.gov (Oct. 22, 2019) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728.
ClinicalTrials.gov, (Apr. 13, 2015) "Phase II Study to Analyze Sarilumab in Non-Infectious Uveitis", ClinicalTrials.gov Identifier: NCT01900431.
ClinicalTrials.gov, (Dec. 13, 2016) "A Repeated Dose-finding Study of Sarilumab in Children and Adolescents With Systemic Juvenile Idiopathic Arthritis (SKYPS)", ClinicalTrials.gov Identifier: NCT02991469.
ClinicalTrials.gov, (Feb. 26, 2015) "A Study Assessing the Safety and Efficacy of Sarilumab Added to Non-MTX DMARDs or as Monotherapy in Japanese Patients With Active Rheumatoid Arthritis", ClinicalTrials.gov Identifier: NCT02373202.
ClinicalTrials.gov, (Jan. 7, 2015) "Efficacy and Safety of Sarilumab and Adalimumab Monotherapy in Patients With Rheumatoid Arthritis (Saril-RA-Monarch)", ClinicalTrials.gov Identifier: NCT02332590.
ClinicalTrials.gov, (May 18, 2016) "An Open-label, Ascending, Repeated Dose-finding Study of Sarilumab in Children and Adolescents With Polyarticular-course Juvenile Idiopathic Arthritis (pcJIA) (SKYPP)", ClinicalTrials.gov Identifier: NCT02776735.
ClinicalTrials.gov, (Oct. 7, 2010), "Evaluation of Sarilumab (SAR153191/REGN88) on Top of Methotrexate in Rheumatoid Arthritis Patients (RA-Mobility)", ClinicalTrials.gov Identifier: NCT01061736.
ClinicalTrials.gov, (Oct. 18, 2012.) "To Evaluate The Effect Of SAR153191 (REGN88) Added To Other RA Drugs In Patients With RA Who Are Not Responding To Or Intolerant Of Anti-TNF Therapy (Saril-RA-Target)", ClinicalTrials.gov Identifier: NCT01709578.
ClinicalTrials.gov, (Oct. 29, 2012) "Study of the Safety, Tolerability, and Bioactivity of Tocilizumab on Patients with Non-infectious Uveitis, The Stop-Uveitis Study", ClinicalTrials.gov Identifier: NCT01717170.
ClinicalTrials.gov. (Feb. 2, 2010) "Evaluation of SAR153191(REGN88) (Sarilumab) on Top of Methotrexate in Rheumatoid Arthritis Patients (RA-Mobility)," ClinicalTrials.gov. Identifier: NCT01061736.
ClinicalTrials.gov. (Nov. 7, 2013) "Evaluation of SAR153191(REGN88) (Sarilumab) on Top of Methotrexate in Rheumatoid Arthritis Patients (RA-Mobility)," ClinicalTrials.gov Identifier: NCT01061736.
ClinicalTrials.gov. (Oct. 7, 2010) "Effect of SAR153191 (REGN88) With Methotrexate in Patients With Active Rheumatoid Arthritis Who Failed INF-a Blockers," ClinicalTrials.gov Identifier: NCT01217814.
ClinicalTrials.gov. (Sep. 27, 2011) "Effect of SAR153191 (REGN88) With Methotrexate in Patients With Active Rheumatoid Arthritis Who Failed INF-a Blockers," ClinicalTrials.gov Identifier: NCT01217814.
Corevitas, Rheumatoid Arthritis Registry, Available from: https://www.corevitas.com/registry/rheumatoid-arthritis, Accessed on Aug. 26, 2022.
Cronstein, "Low-Dose Methotrexate: A Mainstay in the Treatment of Rheumatoid Arthritis", Pharmacological Reviews, Jun. 2005, 57(2): 163-172.
Curtis et al., "Determining the minimally important difference in the clinical disease activity index for improvement and worsening in early rheumatoid arthritis patients", Arthritis Care Res (Hoboken), 2015, 67(10): 1345-1353.
Curtis, et al. Reanalysis of the Multi-Biomarker Disease Activity Score for Assessing Disease Activity in the Abatacept Versus Adalimumab Comparison in Biologic-Naive Rheumatoid Arthritis Subjects with Background Methotrexate Study: Comment on the Article by Fleischmann, Arthritis & Rheumatology, Apr. 2017, vol. 69, No. 4, pp. 863-872.
Dasgupta et al., "Sarilumab In Patients With Relapsing Polymyalgia Rheumatica: A Phase 3, Multicenter, Randomized, Double Blind, Placebo Controlled Trial (Saphyr)", Annals Of The Rheumatic Diseases, EULAR European Congress Of Rheumatology (EULAR); Copenhagen, Denmark; Jun. 1-4, 2022, British Medical Association, GB, May 31, 2022, 81(Suppl. 1): 210-211.
Daugherty et al., "Formulation and delivery issues for monoclonal antibody therapeutics," Adv. Drug Delivery Reviews, 58:686-706, (2006).
Davis, et al., "Scale For Photographic Grading Of Vitreous Haze In Uveitis", American Journal of Ophthalmology, vol. 150, No. 5, pp. 637-641, Nov. 2010.
De Benedetti et al., "FRI0549—Sarilumab, a Human Monoclonal Antibody to the Interleukin-6 (IL-6) Receptor, In Polyarticular-Course Juvenile Idiopathic Arthritis (pcJIA): A 12-Week Multinational Open-Label Dose-Finding Study", Annals of the Rheumatic Diseases, Jun. 2019, 78(Suppl 2): 969-970.
De Benedetti et al., "Sarilumab, a Human Monoclonal Antibody to the Interleukin-6 Receptor, in Polyarticular-course Juvenile Idiopathic Arthritis: A 12-week, Multinational, Open-label, Dose-Finding Study", Meeting: 2019 ACR/ARP Annual Meeting, American College of Rheumatology, Abstract No. 2710, Nov. 12, 2019.
De Haas, et al., Rheumatoid Arthritis, Typus Robustus, Annals of the Rheumatic Diseases, vol. 32, No. 1, pp. 91-92, 1973.
Deane, et al., Preclinical Rheumatoid Arthritis: Identification, Evaluation, and Future Directions for Investigation, Rheumatic Disease Clinics of North America, vol. 36, No. 2, pp. 213-241, 2010.
Dennis Jr., et al., "Synovial Phenotypes in Rheumatoid Arthritis Correlate with Response to Biologic Therapeutics", Arthritis Research & Therapy, vol. 16, Article No. R90, pp. 1-18, Apr. 2014.
Dhillon, Intravenous Tocilizumab: A Review of Its Use in Adults with Rheumatoid Arthritis, BioDrugs, vol. 28, pp. 75-106, 2014.
Durán, et al., The Effect on Treatment Response of Fibromyalgic Symptoms in Early Rheumatoid Arthritis Patients: Results From the Espoir Cohort, Rheumatology, vol. 54, No. 12, pp. 2166-2170, 2015.
Durrani, et al., "Degree, Duration, And Causes Of Visual Loss In Uveitis", British Journal of Ophthalmology, vol. 88, No. 9, pp. 1159-1162, Sep. 2004.
Eberhard A., et al., "AB0285 Predictors of unacceptalbe pain and unacceptable pain with low inflammation, in early rheumatoid arthritis", Annals of the Rheumatic Diseases, pp. 1600, 2019.
Elixhauser, et al., Comorbidity Measures for Use with Administrative Data, Medical Care, vol. 36, No. 1, pp. 8-27, Jan. 1988.
Emery et al. (2008) "IL-6 receptor inhibition with tocilizumab improves treatment outcomes in patients with rheumatoid arthritis refractory to anti-tumor necrosis factor biologicals: results from a 24-week multicenter randomised placebo-controlled trial," Ann. Rheum. Dis. 67:1516-1523.
European Medicines Agency, Committee for Medicinal Products for Human Use (CHMP), Assessment Report, Apr. 21, 2017, EMA/292840/2017, retrieved from url: https://www.ema.europa.eu/en/documents/assessment-report/kevzara-epar-public-assessment-report_en.pdf.
Extended European Search Report received for European Patent Application No. 20167644.2, mailed on Oct. 21, 2020, 8 Pages.
Feist, et al., "Abstract 0832 Prosara—A Prospective, Multicenter, Noninterventional Study to Evaluate the Safety and Effectiveness of

(56) References Cited

OTHER PUBLICATIONS

Sarilumab for the Treatment of Active Rheumatoid Arthritis in Regular Care in Germany", ACR Convergence, Nov. 5-9, 2020, Meeting Abstracts.
Feist, et al., "THU0165 Prosara—a Prospective, Multicenter, Non-interventional Study to Evaluate the Safety and Effectiveness of Sarilumab for the Treatment of Active Rheumatoid Arthritis in Regular Care in Germany", Annals of the Rheumaic Diseases, Scientific Abstracts, Jun. 2020.
Final Office Action received for U.S. Appl. No. 13/648,521, mailed on Feb. 11, 2016, 13 Pages.
Final Office Action received for U.S. Appl. No. 13/648,521, mailed on Mar. 10, 2014, 9 Pages.
Fleischmann et al. "Comparable Efficacy with Sarilumab Plus Methotrexate in Biologic-Experienced and Biologic-Naive Patients with Moderate-to-Severe Rheumatoid Arthritis from a Phase 3, Randomized, Double-Blind, Placebo-Controlled, International Study." Arthritis & Rheumatology. vol. 66. 111 River St, Hoboken 07030-5774, NJ USA: Wiley-Blackwell, 2014.
Fleischmann et al., "Efficacy and Safety of Sarilumab in Connection with CsDMARDs in Patients with Active Rheumatoid Arthritis Who Were Inadequate Responders or Intolerant of Anti-TNF-alpha Therapy: Results from a Phase 3 Study", ACR Abstract 970; Nov. 8, 2015.
Fleischmann, et al., "Estimating Disease Activity using Multi-Biomarker Disease Activity Scores in Rheumatoid Arthritis Patients Treated with Abatacept or Adalimumab", Arthritis & Rheumatology, vol. 68, No. 9, pp. 2083-2089, Sep. 2016.
Fleischmann, et al., "Sarilumab and Nonbiologic Disease-Modifying Antirheumatic Drugs in Patients with Active Rheumatoid Arthritis and Inadequate Response or Intolerance to Tumor Necrosis Factor Inhibitors", Arthritis & Rheumatology, vol. 69, No. 2, pp. 277-290, Feb. 2017.
Flodin, et al., Intrinsic Brain Connectivity in Chronic Pain: A Resting-State fMRI Study in Patients with Rheumatoid Arthritis, Frontiers in Human Neuroscience, vol. 10, No. 107, pp. 1-8, Mar. 2016.
Fortin, et al., "Glossary of Selected Terms—A Systematic Review of Intravitreal Bevacizumab for the Treatment of Diabetic Macular Edema" NCBI Bookshelf, XP055753991, Retrieved from: <<https://www.ncbi.nlm.nih.gov/books/NBK169468/>>, 2 Pages, May 1, 2012.
Fragiadaki et al., Sleep Disturbances and Interleukin 6 Receptor Inhibition in Rheumatoid Arthritis, J Rheumatol., 2012, 39: 60-62.
Fransen et al., "The Disease Activity Score and the EULAR response criteria", Clinical and Experimental Rheumatology, Aug. 31, 2005, 23(5 Suppl 39): S93-99).
Gabay et al., "Tocilizumab monotherapy versus adalimumab monotherapy for treatment of rheumatoid arthritis (ADACTA): a randomised, double-blind, controlled phase 4 trial", Lancet, 2013, 381(9877): 1541-1550.
Gabay, et al., "Comparison of Lipid and Lipid-Associated Cardiovascular Risk Marker Changes After Treatment With Tocilizumab or Adalimumab in Patients with Rheumatoid Arthritis", Annals of the Rheumatic Diseases, vol. 75, pp. 1806-1812, Oct. 1, 2016.
Gabay, et al., "Effect of Sarilumab on Circulating Biomarkers of Bone and Joint Destruction in Patients with Rheumatoid Arthritis with Inadequate Response to Methotrexate", Arthritis & Rheumatology, vol. 68, Supplement 10, p. 3091, Oct. 2016.
Gabay, et al., "Identification of Sarilumab Pharmacodynamic and Predictive Markers in Patients with Inadequate Response to TNF Inhibition: A Biomarker Substudy of the Phase 3 Target Study", Rheumatic & Musculoskeletal Diseases Open, vol. 4, e000607, pp. 1-11, Mar. 1, 2018.
Gandek et al. (2004) "Psychometric evaluation of the SF-36 health survey in Medicare managed care," Health Care Financ Rev. 25(4):5-25.
Garces, et al., Comparison of Dose Escalation and Costs of Dose Escalation Between Patients With Rheumatoid Arthritis Initiating Biologic Treatment With Etanercept, Adalimumab, or Infliximab, Value in Health, vol. 19, No. 3, pp. A229-A230, 2016.
Gavrilă, et al., "Biomarkers in Rheumatoid Arthritis, What Is New?", Journal of Medicine and Life, vol. 9, Issue 2, pp. 144-148, Apr.-Jun. 2016.
Genbank, "*H.Sapiens* Serum Amyloid A Protein mRNA", Complete cds, Genbank Accession No. M81349.1, Retrieved from: <<https://www.ncbi.nlm.nih.gov/nuccore/M81349.1>>, 1 Page.
Genbank, "*Homo Sapiens* C-Reactive Protein (CRP)", RefSeqGene on Chromosome 1, Genbank Accession No. NG_013007.1, Retrieved from: <<https://www.ncbi.nlm.nih.gov/nuccore/NG_013007.1>>, pp. 1-4.
Genbank, "*Homo Sapiens* C-X-C Motif Chemokine Ligand 13 (CXCL13)", Transcript Variant 1, mRNA, Genbank Accession No. NM_006419.2, Retrieved from: <<https://www.ncbi.nlm.nih.gov/nuccore/NM_006419.2>>, pp. 1-4., Jul. 31, 2008.
Genbank, "*Homo Sapiens* Intercellular Adhesion Molecule 1 (ICAM1)", mRNA, Genbank Accession No. NM_000201.3, Retrieved from: <<https://www.ncbi.nlm.nih.gov/nuccore/NM_000201.3>>, pp. 1-5., Nov. 23, 2018.
Genbank, *Homo Sapiens* Matrix Metallopeptidase 3 (MMP3)', mRNA, Genbank Accession No. NM_002422.5, Retrieved from: <<https://www.ncbi.nlm.nih.gov/nuccore/NM_002422.5>>, pp. 1-4, Nov. 22, 2018.
Genentech (2014) Actemra Subcutaneous Dosing & Administration Pocket Guide. pp. 1-40.
Genovese, et al., "293 A Phase 3 Clinical Program of Three, Randomized, Double-blind, Placebo- and Comparator-controlled Studies to Assess the Efficacy and Safety of Otilimab in RA: Study Design and Methodology", Journal of Clinical Rheumatology, Retrieved From url :<<https://journals.lww.com/jclinrheum/Fulltext/2020/04001/22nd_PANLAR_Congress_Miami, FL,_August_12_15_2020.1.aspx>>.
Genovese, et al., "Efficacy and Safety of Sarilumab in Combination With csDMARDs or as Monotherapy in Subpopulations of Patients With Moderately to Severely Active Rheumatoid Arthritis in Three Phase III Randomized", Controlled Studies, Arthritis Research & Therapy, vol. 22, No. 1, pp. 1-17, 2020.
Genovese, et al., "Long-term Safety and Efficacy of Sarilumab Plus Methotrexate on Disease Activity, Physical Function and Radiographic Progression: 5 Years of Sarilumab Plus Methotrexate Treatment", Rheumatic & Musculoskeletal Disease, vol. 5, No. 2, pp. 1-10, 2019.
Genovese, et al., "Sarilumab Plus Methotrexate in Patients with Active Rheumatoid Arthritis and Inadequate Response to Methotrexate: Results of a Phase III Study", Arthritis & Rheumatology, vol. 67, No. 6, pp. 1424-1437, Jun. 1, 2015.
Genovese, et al., "Switching Between the JAK1-selective Inhibitor Upadacitnib and Adalimumab Following Initial Non-response: Clinical and Functional Outcomes Among Rheumatoid Arthritis Patients", Oral Presentation, Jun. 12, 2019, RA therapy—JAK inhibitors and beyond.
Genovese, et al., Interleukin-6 Receptor Inhibition With Tocilizumab Reduces Disease Activity in Rheumatoid Arthritis With Inadequate Response to Disease-modifying Antirheumatic Drugs: the Tocilizumab in Combination With Traditional Disease-modifying Antirheumatic Drug Ther, Arthritis & Rheumatism: Official Journal of the American College of Rheumatology, vol. 58, No. 10, pp. 2968-2980, Sep. 29, 2008.
Georgy, et al., A Clinical Study to Assess the Pharmacokinetics and Pharmacodynamics of Tocilizumab After a Single Dose Administration by Subcutaneous and Intra Venous Routes to Healthy Subjects, Clinical Pharmacology & Therapeutics, vol. 87, No. S1, p. S60, Feb. 15, 2010.
Gordon, et al., "pANCA Antibodies In Patients With Anterior Uveitis: Identification Of A Marker Antibody Usually Associated With Ulcerative Colitis", Journal of Clinical Immunology, vol. 18, No. 4, pp. 264-271, Jul. 1998.
Hammer, et al., Major Reduction of Ultrasound Detected Synovitis during Subcutaneous Tocilizumab Treatment; Results from a Multicenter 24 Weeks Study of Patients with Rheumatoid Arthritis, Arthritis & Rheumatology, vol. 70, No. S9, pp. 1537-1538, 2018.
HAQ—Health Assessment Questionnaire, Scleroderma Study Conference, English Translation, Retrieved from URL: <<http://derma.

(56) References Cited

OTHER PUBLICATIONS w3.kanazawa-u.ac.jp/SSc/pamphret/HAQ.html >>,6 Pages (4 Pages of English Translation & 2 Pages of Official Copy), Jul. 30, 2019.
Heidari et al., "Rheumatoid Arthritis: Early Diagnosis and Outcomes", Caspian Journ Intern Med., Winter 2011, 2(1): 161-170.
Hennigan et al., "Interleukin-6 inhibitors in the treatment of rheumatoid arthritis", Therapeutic and Clinical Risk Management , 4(4), 767-775. (Year: 2008).
Hirata et al., "Characterization of IL-6 Receptor Expression By Monoclonal and Polyclonal Antibodies" J. Immunol. (1989) 143(9):2900-2906.
Huizinga, et al., "Sarilumab, A Fully Human Monoclonal Antibody Against IL-6Rα in Patients with Rheumatoid Arthritis and an Inadequate Response to Methotrexate: Efficacy and Safety Results from the Randomised Saril-RA-Mobility Part A Trial", Annals of the Rheumatic Diseases, vol. 73, No. 9, pp. 1626-1634, Sep. 1, 2014.
Humira® (Adalimumab) Injection, for Subcutaneous Use, Highlights of Prescribing Information, United States Food and Drug Administration, Retrieved from: <<https://www.accessdata.fda.gov/drugsatfda_docs/label/2018/125057s410lbl.pdf>>, 104 Pages, Dec. 2018.
Hunter, et al., "IL-6 as a Keystone Cytokine in Health and Disease", Nature Immunology, vol. 16, No. 5, pp. 448-457, May 2015.
Imagawa et al., "Safety and efficacy of tocilizumab, an anti-IL-6-receptor monoclonal antibody, in patients with polyarticular-course juvenile idiopathic arthritis", Modern Rheumatology, Jun. 12, 2011, 22(1): 109-115.
International Nonproprietary Names for Pharmaceutical Substances (INN) WHO Drug Information, vol. 25, No. 4, 2011; 53 pages.
International Search Report and Written Opinion for PCT International Patent Application No. PCT/US2020/016203, mailed Jul. 14, 2020.
International Search report and Written Opinion for PCT International Patent Application No. PCT/US2020/035871, mailed on Sep. 28, 2020.
International Search Report and Written Opinion Received for PCT Application No. PCT/US2020/037325, mailed on Oct. 27, 2020.
International Search Report and Written Opinion received for PCT Patent Application No. PCT/IB2021/054546, mailed on Sep. 14, 2021.
International Search Report and Written Opinion received for PCT Patent Application No. PCT/IB2021/054652, mailed on Aug. 30, 2021.
International Search Report and Written Opinion received for PCT Patent Application No. PCT/US2016/060344, mailed on Mar. 13, 2017.
International Search Report and Written Opinion received for PCT Patent Application No. PCT/US2017/021149, mailed on Jul. 18, 2017.
International Search Report and Written Opinion received for PCT Patent Application No. PCT/US2020/029930, mailed on Oct. 8, 2020.
International Search Report with Written Opinion corresponding to International Patent Application No. PCT/EP2012/070052, mailed Dec. 7, 2012.
International Search Report with Written Opinion corresponding to International Patent Application No. PCT/ US2014/066856, mailed Apr. 2, 2015.
International Search Report with Written Opinion corresponding to International Patent Application No. PCT/US2015/050291, mailed Dec. 1, 2015.
International Search Report with Written Opinion corresponding to International Patent Application No. PCT/US2023/065361, mailed Jul. 14, 2023.
Jones, et al., Comparison of Tocilizumab Monotherapy Versus Methotrexate Monotherapy in Patients With Moderate to Severe Rheumatoid Arthritis: the Ambition Study, Annals of the Rheumatic Diseases, vol. 69, No. 01, pp. 88-96, 2010.
Kaneko, Tocilizumab in Rheumatoid Arthritis: Efficacy, Safety and Its Place in Therapy, Therapeutic Advances in Chronic Disease, vol. 4, No. 1, pp. 15-21, 2013.
Karmakar, et al., "Bone Damage in Rheumatoid Arthritis—Mechanistic Insights and Approaches to Prevention", Rheumatic Diseases Clinics of North America, vol. 36, No. 2, 19 Pages, May 1, 2010.
Kawashima, et al., "Soluble IL-6 Receptor In Vitreous Fluid Of Patients With Proliferative Diabetic Retinopathy", Japanese Journal of Ophthalmology, vol. 51, No. 2, pp. 100-104, Apr. 6, 2007.
Khan, et al., Determinants of Discordance in Patients' and Physicians' Rating of Rheumatoid Arthritis Disease Activity, Arthritis Care & Research (Hoboken), vol. 64, No. 2, pp. 206-214, 2012.
Kimel et al., "Adalimumab plus methotrexate improved SF-36 scores and reduced the effect of rheumatoid arthritis (RA) on work activity for patients with early RA", The Journal of Rheumatology, Feb. 2008, 35(2): 206-215.
Kishimoto, et al., "Interleukin-6 (IL-6)", The Cytokine Handbook. Ed.: Thomson. Academic Press. London, United Kingdom, vol. 12, pp. 281-304, Jan. 1, 2003.
Kivitz (Nov. 2014) "Subcutaneous Tocilizumab vs Placebo in Combination with Disease Modifying Antirheumatic Drugs in Patients with Rheumatoid Arthritis," Arthritis Care Res. (Hoboken). 66(11):1653-1661.
Klein, et al. FRI0549—Efficacy and Safety of Tocilizumab in Systemic and Polyarticular Juvenile Idiopathic Arthritis—Data of Toe Biker Registry Squibb, Johnson & Johnson, Novartis, Pfizer, Fieckitt Benkiser, and Roche Jun. 14, 2019 pp. 969-970.
Kojima, et al., Depression, Inflammation, and Pain in Patients With Rheumatoid Arthritis, Arthritis & Rheumatism (Arthritis Care & Research), vol. 61, No. 8, pp. 1018-1024, Aug. 15, 2009.
Kremer, et al., Tocilizumab Inhibits Structural Joint Damage in Rheumatoid Arthritis Patients With Inadequate Responses to Methotrexate, Arthritis & Rheumatism vol. 63, No. 3, pp. 609-621, 2011.
Kringelbach, et al., "Identification of New Biomarkers to Promote Personalised Treatment of Patients with Inflammatory Rheumatic Disease: Protocol for an Open Cohort Study", British Medical Journal Open, vol. 8, e019325, pp. 1-8., Feb. 1, 2018.
Kristensen, et al., Is Swollen to Tender Joint Count Ratio a New and Useful Clinical Marker for Biologic Drug Response in Rheumatoid Arthritis? Results From a Swedish Cohort, Arthritis Care & Research (Hoboken), vol. 66, No. 2, pp. 173-179, 2014.
Lamb et al., "Sarilumab: A Review in Moderate to Severe Rheumatoid Arthritis Drugs", Drugs, 2018, 78: 929-940.
Langer (1990) "New Methods of Drug Delivery," Science. 249:1527-1533.
Lederman et al. "A Single Amino Acid Substitution in a Common African Allele of the CD4 Molecule Ablates Binding of the Monoclonal Antibody, OKT4" Molecular Immunology (1991) 28(11):1171-1181.
Lee et al., "Disease modifying drugs in adult rheumatoid arthritis", Australian Prescriber, Apr. 2003, 26: 36-40.
Lee, et al., Pain Persists in DAS28 Rheumatoid Arthritis Remission but Not in ACR/EULAR Remission: a Longitudinal Observational Study, Arthritis Research & Therapy, vol. 13, No. R83, pp. 1-9, 2011.
Li et al. "Temporal associations between interleukin 22 and the extracellular domains of IL-22R and IL-10R2" International Immunology (2004) 4:693-708.
Lin, "Targeting Interleukin-6 For Noninfectious Uveitis, Clinical Ophthalmology", vol. 9, pp. 1697-1702, Sep. 1, 2015.
Lipsky, "Interleukin-6 and Rheumatic Diseases", Arthritis Research & Therapy, vol. 8, Suppl 2, S4, pp. 1-5, Jan. 1, 2006.
Lourdudoss et al., "Dietary intake of polyunsaturated fatty acids and pain in spite of inflammatory control among methotrexate-treated early rheumatoid arthritis patients", Arthritis Care and Research, Feb. 2018, 70(2): 205-212.
Maini, et al., Double-blind Randomized Controlled Clinical Trial of the Interleukin-6 Receptor Antagonist, Tocilizumab, in European Patients With Rheumatoid Arthritis Who Had an Incomplete Response to Methotrexate, Arthritis & Rheumatism, vol. 54, No. 9, pp. 2817-2829, Aug. 31, 2006.

(56) References Cited

OTHER PUBLICATIONS

Maini, et al., Infliximab (Chimeric Anti-Tumour Necrosis Factor A Monoclonal Antibody) Versus Placebo in Rheumatoid Arthritis Patients Receiving Concomitant Methotrexate: a Randomised Phase III Trial, The Lancet, vol. 354, No. 9194, pp. 1932-1939, 1999.
Matcham, et al., Psychological Correlates of Fatigue in Rheumatoid Arthritis: A Systematic Review, Clinical Psychology Review, vol. 39, pp. 16-29, Jul. 2015.
Matcham, et al., Symptoms of Depression and Anxiety Predict Treatment Response and Long-term Physical Health Outcomes in Rheumatoid Arthritis: Secondary Analysis of a Randomized Controlled Trial, Rheumatology, vol. 55, Issue 2, pp. 268-278, Feb. 2016.
Matcham, et al., The Prevalence of Depression in Rheumatoid Arthritis: A Systematic Review and Meta-analysis, Rheumatology, vol. 52, Issue 12, pp. 2136-2148, Sep. 3, 2013.
Matteson, "Current Treatment Strategies for Rheumatoid Arthritis", Mayo Clinic Proceedings, vol. 75, pp. 69-74, Jan. 2000.
Mcgovern, (Oct. 19, 2016) "Center for Drug Evaluation and Research", Application No. 761037Orig1s000, pp. 01-278.
Mcinnes, et al., "Cytokines in the Pathogenesis of Rheumatoid Arthritis", Nature Reviews, Immunology, vol. 7, pp. 429-442, Jun. 2007.
Mcwilliams, et al., Pain Mechanisms in Rheumatoid Arthritis, Clinical and Experimental Rheumatology, vol. 35, No. 5, pp. S94-S101, 2017.
Medscape, Actemra, Retrieved online: <URL: https://reference.medscape.com/drug/actennra-tocilizunnab-999419>, Retrieved on Feb. 8, 2022.
Meehan et al. (1996) "A microinfusor device for the delivery of therapeutic levels of peptides and macromolecules," Journal of Controlled Release. 46:107-116.
Merida, et al., "New Immunosuppressive Therapies in Uveitis Treatment", International Journal of Molecular Sciences, vol. 16, No. 8, pp. 18778-18795, Aug. 11, 2015.
Mesquida, et al., "Long-Term Effects of Tocilizumab Therapy for Refractory Uveitis-Related Macular Edema", Ophthalmology, vol. 121, No. 12, pp. 2380-2386, Sep. 6, 2014.
Mihara et al., 2005, Tocilizumab inhibits signal transduction mediated by both MIL-6R and sIL-6R, but not by the receptors of other members of IL-6 cyotkine family, International Immunopharmacology 5:1731-1740.
Millar et al., Inflammatory mechanisms in tendinopathy—towards translation, Nature, Feb. 2017, 13: 110-122.
Montaño et al., "Influence of the Isotype of the Light Chain on the Properties of IgG", Journal of Immunology, 2002, 168: 224-231.
Muszbek et al., "Economic Evaluation of Sarilumab in the Treatment of Adult Patients with Moderately-to-Severely Active Rheumatoid Arthritis Who Have an Inadequate Response to Conventional Synthetic Disease-Modifying Antirheumatic Drugs", Advances in Therapy, Apr. 19, 2019, 36(6): 1337-1357.
Nadkarni, et al., Incidence of Dose Escalation and Impact on Biologic Costs Among Patients With Rheumatoid Arthritis Treated With Three Intravenous Agents, Journal of Comparative Effectiveness Research, vol. 6, No. 8, pp. 671-682, 2017.
Nasonov, E.L. et al, "Prospects of pharmacotherapy rheumatoid arthritis: monoclonal antibodies", Nauchnopraktych Rheumatol., 2012, 52(3): 75-82.
NCBI, C-Reactive Protein Isoform 1 Precursor [*Homo Sapiens*], NCBI Reference Sequence: NP_001315986.1, Retrieved from: <<https://www.ncbi.nlm.nih.gov/protein/NP_001315986.1>>, pp. 1-3, Jun. 29, 2016.
NCBI, C-X-C Motif Chemokine 13 Precursor [*Homo Sapiens*], NCBI Reference Sequence: NP_006410.1, Retrieved from: <<https://www.ncbi.nlm.nih.gov/protein/NP_006410.1>>, pp. 1-3.
NCBI, Intercellular Adhesion Molecule 1 Precursor [*Homo Sapiens*], NCBI Reference Sequence: NP_000192.2, Retrieved from: <<https://www.ncbi.nlm.nih.gov/protein/NP_000192.2>>, pp. 1-4, Feb. 8, 2008.
NCBI, Matrix Metallopeptidase 3 (Stromelysin 1, Progelatinase) [*Homo Sapiens*], NCBI Reference Sequence: EAW67032.1, Retrieved from: <<https://www.ncbi.nlm.nih.gov/protein/EAW67032.1>>, pp. 1-2, Mar. 23, 2015.
NCBI, PubChem SID: 135626879, National Library of Medicine, Apr. 5, 2012, Retrieved from: <<https://pubchem.ncbi.nlm.nih.gov/substance/135626879>>.
NCBI, Serum Amyloid A [*Homo Sapiens*], NCBI Reference Sequence: AAB24060.1, Retrieved from: <<https://www.ncbi.nlm.nih.gov/protein/AAB24060.1>>, 1 Page, Jul. 28, 2016.
New Drug Approvals Retrieved from: <<https://www.drugs.com/newdrugs.html>> pp. 1-7, 2019.
Nguyen et al., "The SATURN Study (SARIL-NIU): Sarilumab for the Treatment of Posterior Segment Non-Infectious Uveitis (NIU)", Investigative Ophthalmology & Visual Science, vol. 56, No. 7, 3116, Jun. 2015.
Nicassio, et al. (Jan. 2012) "The Contribution of Pain and Depression to Self-Reported Sleep Disturbance in Patients with Rheumatoid Arthritis", Pain, vol. 153, No. 1, pp. 107-112.
Nieminen, et al., "The Use of the ATF System to Culture Chinese Hamster Ovary Cells in a Concentrated Fed-Batch System", BioPharm International, vol. 24, Issue 6, pp. 1-8, Jun. 1, 2011.
Nihon Naika Gakkai Zasshi, Japan Internal Medical Association Magazine, vol. 101, No. 10, pp. 2893-2898.
Nishimoto et al. (2009) "Study of active controlled tocilizumab monotherapy for rheumatoid arthritis patients with an inadequate response to methotrexate (Satori): significant reduction in disease activity and serum vascular endothelial growth factor by IL-6 receptor inhibition therapy," Modem Rheumatology. 19(1):12-19.
Nishimoto, et al., Humanized Antihuman IL-6 Receptor Antibody, Tocilizumab, Part of the Handbook of Experimental Pharmacology, vol. 181, Therapeutic Antibodies, pp. 151-160, 2008.
Non-Final Office Action received for U.S. Appl. No. 13/648,521, mailed on Jul. 3, 2014.
Non-Final Office Action received for U.S. Appl. No. 13/648,521, mailed on Jun. 26, 2015.
Non-Final Office Action received for U.S. Appl. No. 13/648,521, mailed on Mar. 19, 2015.
Non-Final Office Action received for U.S. Appl. No. 13/648,521, mailed on Oct. 18, 2013.
Non-Final Office Action received for U.S. Appl. No. 14/350,973, mailed on Feb. 5, 2016.
Non-Final Office Action received for U.S. Appl. No. 14/350,973, mailed on Oct. 18, 2019.
Notice of Allowance received for U.S. Appl. No. 14/350,973, mailed on Jun. 14, 2016.
Nussenblatt, et al., "Standardization of Vitreal Inflammatory Activity in Intermediate And Posterior Uveitis", Ophthalmology, vol. 92, No. 4, pp. 467-471, Apr. 1, 1985.
Ogata, et al., Long-term Safety and Efficacy of Weekly Subcutaneous Tocilizumab Monotherapy in Patients With Rheumatoid Arthritis Who Had an Inadequate Response to Subcutaneous Tocilizumab Every Other Week: Results From the Open-label Extension of the Shinobi Study, Modern Rheumatology, vol. 29, Issue 5, pp. 767-774, Sep. 3, 2019.
Ogata, et al., Subcutaneous Tocilizumab: Recent Advances for the Treatment of Rheumatoid Arthritis, Expert Opinion on Drug Delivery, vol. 16, Issue 6, pp. 639-648, Jun. 3, 2019.
Ohta, et al., Optimal Dose Prediction by Pharmacokinetic and Biomarker Response of Subcutaneous Tocilizumab Treatment A Phase I/II Study Evaluating the Safety, Pharmacokinetics and Clinical Response in Patients with Rheumatoid Arthritis, Arthritis & Rheumatism, vol. 62, Supplement 10, pp. 1-2, Oct. 1, 2010.
Ongkosuwito, et al., "Analysis of Immunoregulatory Cytokines in Ocular Fluid Samples From Patients With Uveitis", Investigative Ophthalmology & Visual Science, vol. 39, No. 13, pp. 2659-2665, Dec. 1, 1998.
Overman, et al., The Prospective Association Between Psychological Distress and Disease Activity in Rheumatoid Arthritis: a Multilevel Regression Analysis, Annals of the Rheumatic Diseases, vol. 71, No. 2, pp. 192-197, 2012.

(56) References Cited

OTHER PUBLICATIONS

Panka et al., "Variable Region Framework Differences Result in Decreased or Increased Affinity of Variant Anti-Digoxin Antibodies" Proc. Natl. Acad. Sci. USA (May 1988) 85:3080-3084.
Pappas, et al., Dosing of Intravenous Tocilizumab in a Real-World Setting of Rheumatoid Arthritis: Analyses from the Corrona Registry, Rheumatology and Therapy, vol. 3, pp. 103-115, Feb. 8, 2016.
Patro et al., "Protein formulation and fill-finish operations," Biotechnol Annu Rev, 8:55-84, (2002). Abstract only.
Paul-Pletzer, 2006, Tocilizumab: Blockade of interleukin-6 signaling pathway as a therapeutic strategy for inflammatory disorders, Drugs of Today 42(9):559-576.
Peichl, "Biologikatherapie in der Rheumatologie", DoctorConsult—The Journal. Wissen fur Klinik und Praxis, Nov. 2011, 2(3): e164-e166.
Pelechas et al., "Clinical evaluation of the safety, efficacy and tolerability of sarilumab in the treatment of moderate to severe rheumatoid arthritis", Therapeutics and Clinical Risk Management, Sep. 1, 2019, vol. 15, pp. 1073-1079.
Perez, et al., "Elevated Levels Of Interleukin 6 In The Vitreous Fluid Of Patients With Pars Planitis And Posterior Uveitis: The Massachusetts Eye & Ear Experience And Review Of Previous Studies", Ocular Immunology and Inflammation, vol. 12, No. 3, pp. 193-201, Sep. 2004.
Pham et al., "Patient acceptable symptomatic state (PASS)", Joint Bone Spine, Jul. 2009, 76(4): 321-323.
Pincus, Limitations of a Quantitative Swollen and Tender Joint Count to Assess and Monitor Patients with Rheumatoid Arthritis, Bulletin of the NYU Hospital for Joint Diseases, 2008, 66(3): 216-223.
Pollard, et al., Fibromyalgic Rheumatoid Arthritis and Disease Assessment, Rheumatology, vol. 49, No. 5, pp. 924-928, Jan. 25, 2010.
Powchik (2010), Regeneron Investor Day, p. 1-19.
Powell et al. (1998) "Compendium of Excipients for Parenteral Formulations," PDA Journal of Pharmaceutical Science and Technology. 52:238-311.
Presta, "Engineering of therapeutic antibodies to minimize immunogenicity and optimize function" Advanced Drug Delivery Reviews (2006) 58:640-656.
Pulawski et al., "Certain therapies linked to pulmonary toxicity among patients with rheumatic diseases", Healio, May 20, 2015, obtained from url: https://www.healio.com/news/rheumatology/20150520/certain-therapies-linked-to-pulmonary-toxicity-among-patients-with-rheumatic-diseases.
Radin et al. (Jan. 1, 2010) "Safety and effects on markers of inflammation of subcutaneously administered regn88/ sar153191 (regn88), an interleukin-6 receptor inhibitor, in patients with rheumatoid arthritis: findings from phase 1 studies," [Abstract] Annals of the Rheumatic Diseases. 69(Suppl. 3):99.
Radin et al. (Nov. 2010) "REGN88/SAR153191, a Fully-Human Interleukin-6 Receptor Monoclonal Antibody, Reduces, Acute Phase Reactants in Patients with Rheumatoid Arthritis: Preliminary Observations from Phase 1, Studies," [Abstract] Arthritis. Rheum. 62(Suppl. 10):1121.
Rafique, et al., "Evaluation of The Binding Kinetics and Functional Bioassay Activity Of Sarilumab And Tocilizumab To The Human IL-6 Receptor (IL-6r) alpha", Annals of the Rheumatic Diseases, vol. 72, Issue Suppl 3, pp. A797.1-A797, Jun. 23, 2013.
Raimondo et al., "Profile of sarilumab and its potential in the treatment of rheumatoid arthritis", Drug Design, Development and Therapy, May 24, 2017, 11: 1593-1603.
Reddy et al., "Elimination of Fc Receptor-Dependent Effector Functions of a Modified IgG4 Monoclonal Antibody to Human CD4," Journal of Immunology, 164:1925-1933 (2000).
Redlich et al., "Inflammatory bone loss: pathogenesis and therapeutic intervention", Nat Rev Drug Discov., Mar. 2012, 11(3): 234-250.
Regeneron Pharmaceuticals (Jul. 12, 2011) "Sanofi and Regeneron Report Positive Phase 2b Trial Results with Sarilumab in Rheumatoid Arthritis," Acquire Media. Accessible on the Internet at URL: http://web.archive.org/web/20110818152737/http://investorregeneron.com/releasedetail.cfm?ReleaseID=590869. [Last Accessed May 4, 2016].
Regeneron Pharmaceuticals (Jul. 12, 2011) "Evaluation of Sarilumab (SAR153191/REGN88) on Top of Methotrexate in Rheumatoid Arthritis Patients (RA-Mobility)", Retrieved from the internet from URL: <<https://clinicaltrials.gov/ct2/results?term=SAR+153191=mobility>>.
Regeneron Pharmaceuticals, Inc. (Jun. 12, 2014) "Sanofi and Regeneron announce new, detailed data from positive Sarilumab phase 3 rheumatoid arthritis trial at Eular," Press Release. Acquire Media.
Regeneron Pharmaceuticals, Inc. (Nov. 22, 2013) "Sanofi and Regeneron report positive results with Sarilumab in first phase 3 rheumatoid arthritis registration trial," Press Release. Acquire Media.
Regeneron Pharmaceuticals, Inc., "Sanofi And Regeneron Announce Patient Enrollment In Two Phase 3 Trials With Sarilumab In Rheumatoid Arthritis (RA)", Online Publication, May 15, 2013 at 1:00 AM EDT.
Reichert (Jan. 1, 2011) "Antibody-based therapeutics to watch in 2011," MAbs. 3:76-99.
Restriction Requirement received for U.S. Appl. No. 13/648,521, mailed on Jun. 10, 2013, 7 Pages.
Restriction Requirement received for U.S. Appl. No. 14/350,973, mailed on Aug. 19, 2015, 8 Pages.
Riancho-Zarrabeitia, et al., "Efficacy of Tocilizumab in Patients with Uveitis Refractory to Other Biologic Drugs: A Multicenter Study on 31 Cases", 2014 ACR/ARHP Annual Meeting Abstract No. 1249, Retrieved from: <<https://acrabstracts.org/abstract/efficacy-of-Tocilizumab-in-patients-with-uveitis-refractory-to-other-biologic-drugs-a-multicenter-study-on-31-cases/>>, Retrieved on Sep. 14, 2020.
Roche, Anti-Human IL-6 Receptor Monoclonal Antibody "Actemra" Subcutaneous Injection Demonstrates Efficacy in Rheumatoid Arthritis in Phase III Clinical Study, Jul. 19, 2011, Retrieved online: <URL: https://www.roche.com/dann/jcr:c49f4e4e-d60e-48cc-a14e-c0f1f4107b24/en/inv-update-2011-07-19b-annex.pdf>, Retrieved on Feb. 8, 2022.
Rose-John, et al., "Interleukin-6 Biology is Coordinated by Membrane-Bound and Soluble Receptors: Role in Inflammation and Cancer", Journal of Leukocyte Biology, vol. 80, No. 2, pp. 227-236, May 17, 2006.
Rudikoff et al., "Single Amino Acid Substitution Altering Antigen-Binding Specificity" Proc. Natl. Acad. Sci. USA (Mar. 1982) 79:1979-1983.
Salaffi et al. "The health-related quality of life in rheumatoid arthritis, ankylosing spondylitis, and psoriatic arthritis: a comparison with a selected sample of healthy people", Health and Quality of Life Outcomes, Biomed Central, vol. 7, No. 1, pp. 25, 2009.
Sanofi and Regeneron (May 21, 2015) "Sanofi and Regeneron announce positive topline results from phase 3 studies with sarilumab in patients with rheumatoid arthritis," Press Release. Sanofi. Accessible on the Internet at URL: http://mediaroom.sanofi.com/sanoThand-regeneron-announce-positive-topline-results-from-phase-3-studies-with-sarilumab-in-patients-with-rheumatoid-arthritis-2. [Last Accessed Aug. 30, 2016].
Sanofi and Regeneron (Nov. 8, 2015) "Regeneron and Sanofi Present Results from Pivotal Phase 3 Study of Sarilumab at American College of Rheumatology Annual Meeting," Press Release. Regeneron Pharmaceuticals, Inc. Accessible on the Internet at URL: http://investorregeneron.com/releasedetail.cfm?releaseid=941387. [Last Accessed Aug. 30, 2016].
Sarzi-Puttini, et al., Correlation of the Score for Subjective Pain With Physical Disability, Clinical and Radiographic Scores in Recent Onset Rheumatoid Arthritis, BMC Musculoskeletal Disorders, vol. 3, No. 18, pp. 1-4, Jul. 19, 2002.
Schaible, Nociceptive Neurons Detect Cytokines in Arthritis, Arthritis Research & Therapy, vol. 16, No. 470, pp. 1-9, 2014.
Schett, "Physiological Effects of Modulating the Interleukin-6 Axis", Rheumatology, vol. 57, Supplement 2, pp. ii43-ii50, Feb. 1, 2018.
Schett, et al., "Bone Erosion in Rheumatoid Arthritis: Mechanisms, Diagnosis and Treatment", Nature Reviews Rheumatology, vol. 8, No. 11, 22 Pages, Nov. 2012.

(56) References Cited

OTHER PUBLICATIONS

Scott, "Sarilumab: First Global Approval", Drugs, 2017, 77: 705-712.
Sebba et al., "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", Poster No. 0834, ACR Convergence—Virtual, Nov. 1-10, 2021.
Sebba, "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", SAR-54318 TNFi/IL-6Ri Mono/Combo Audio narration, ACR Convergence—Virtual, Nov. 1-10, 2021.
Sechidis, et al., "Distinguishing Prognostic and Predictive Biomarkers: An Information Theoretic Approach", Bioinformatics, vol. 34, No. 19, pp. 3365-3376, Oct. 1, 2018.
Seth, et al., "Development of a New Bioprocess Scheme Using Frozen Seed Train Intermediates to Initiate CHO Cell Culture Manufacturing Campaigns", Biotechnology and Bioengineering, May 2013, vol. 110, Issue 5, pp. 1376-1385.
Shields et al., "Lack of Fucose on Human IgG1 N-Linked Oligosaccharide Improves Binding to Human Fc gamma RIII and Antibody-dependent Cellular Toxicity," Journal of Biological Chemistry, 277(30):26733-26740 (2002).
Singh, et al., 2015 American College of Rheumatology Guideline for the Treatment of Rheumatoid Arthritis, Arthritis & rheumatology, vol. 68, No. 1, pp. 1-26, 2016.
Smolen et al. (2008) "Effect of interleukin-6 receptor inhibition wtth tocilizumab in patients with rheumatoid arthritic (Option study): a double blind, placebo-controlled, randomised trial," Lancet. 371:987-997.
Smolen et al., "Rheumatoid arthritis", Lancet, 2016, 388(10055): 2023-2038.
Smolen, et al., "The Assessment of Disease Activity in Rheumatoid Arthritis", Clinical and Experimental Rheumatology, vol. 28, Supplement 59, pp. S18-S27, May 1, 2010.
Smolen, et al., EULAR Recommendations for the Management of Rheumatoid Arthritis With Synthetic and Biological Disease-modifying Antirheumatic Drugs: 2016 Update, Annals of the Rheumatic Diseases, vol. 76, No. 6, pp. 960-977, 2017.
Solomon, et al., "Patterns of Cardiovascular Risk in Rheumatoid Arthritis", Annals of the Rheumatic Diseases, vol. 65, pp. 1608-1612, Dec. 1, 2006.
Song, et al., "Comparative Evaluation of the Effects of Treatment With Tocilizumab and TNF-α Inhibitors on Serum Hepcidin, Anemia Response and Disease Activity in Rheumatoid Arthritis Patients", Arthritis Research & Therapy, vol. 15, Article No. R141, pp. 1-10, Oct. 1, 2013.
Spectrum Laboratories, Inc., "Hollow Fiber Filters", Datasheet [online], Spectrumlabs.com, Copyright 1995-2015, Retrieved from: <<URL: http://www.spectrumlabs.com/filtration/mPESKrosFloList.html>>, Retrieved on: Jun. 12, 2015.
Stamp et al., "The use of low dose methotrexate in rheumatoid arthritis—are we entering a new era of therapeutic drug monitoring and pharmacogenomics?", Biomedicine & Pharmacotherapy, 2006, 60: 678-687.
Steel et al., "2015 EULAR-ACR recommendations for polymyalgia rheumatica: the message and next steps", Rheumatology, Jun. 17, 2016, 55(6): 955-956, Advance Acess Publication Dec. 17, 2015.
Strand et al., "Patient-reported outcomes from a randomized phase III trial of sarilumab monotherapy versus adalimumab monotherapy in patients with rheumatoid arthritis", Arthritis Res Ther., 2018, 20(1): 129.
Strand, et al., "Health-related Quality of Life Outcomes of Adalimumab for Patients with Early Rheumatoid Arthritis: Results from a Randomized Multicenter Study", The Journal of Rheumatology, vol. 39, pp. 63-72, Jan. 1, 2012.
Strand, et al., Sarilumab Improves Patient-reported Outcomes in Rheumatoid Arthritis Patients With Inadequate Response/Intolerance to Tumour Necrosis Factor Inhibitors, RMD Open, vol. 3, e000416, 2017.
Strand, et al., Sarilumab Plus Methotrexate Improves Patient-reported Outcomes in Patients With Active Rheumatoid Arthritis and Inadequate Responses to Methotrexate: Results of a Phase III Trial, Arthritis Research & Therapy, vol. 18, No. 198, pp. 1-10, 2016.
Studenic, et al., Discrepancies Between Patients and Physicians in Their Perceptions of Rheumatoid Arthritis Disease Activity, Arthritis & Rheumatology, vol. 64, No. 9, pp. 2814-2823, 2012.
Study of the Safety, Tolerability, and Bioactivity of Tocilizumab On Patients With Non-infectious Uveitis, The Stop-Uveitis Study, ClinicalTrials.gov Archive, Oct. 29, 2012.
Suttorp-Schulten, et al., "Recent Developments In The Treatment Of Posterior Uveitis", Ocular Immunology and Inflammation, vol. 4, No. 4, pp. 207-217, 1996.
Świerkot et al., "Methotrexate in rheumatoid arthritis", Pharmacological Reports, 2006, 58: 473-492.
Taylor, (Jun. 2010) "Pharmacology of TNF Blockade in Rheumatoid Arthritis and Other Chronic Inflammatory Diseases", Current Opinion in Pharmacology, vol. 10, Issue 3, pp. 308-315.
Taylor, et al., "A Transgenic Mouse That Expresses a Diversity of Human Sequence Heavy and Light Chain Immunoglobulins", Nucleic Acids Research, vol. 20, No. 23, pp. 6287-6295, Dec. 11, 1992.
Taylor, et al., Patient Perceptions Concerning Pain Management in the Treatment of Rheumatoid Arthritis, The Journal of International Medical Research, vol. 38, No. 4, pp. 1213-1224, 2010.
The Chemical Abstracts Service (CAS) entry for registration No. 1189541-98-7.
Turnier et al., "Tocilizumab for treating juvenile idiopathic arthritis", Expert Opinion on Biological Therapy, 2016, 16(4): 559-566.
Uchiyama et al., "Tocilizumab, a Humanized Anti-interleukin-6 Receptor Antibody, Ameliorates Joint Swelling in Established Monkey Collagen-Induced Arthritis" Biol. Pharm. Bull. (2008) 31(6):1159-1163.
Ueno et al., "3-145: The efficacy and safety of additional tocilizumab in patients with polymyalgia rheumatica resistant to or intolerant of conventional therapy", AU, Apr. 1, 2019, 22(S3): 204.
United States Adopted Names Council (Date Publicly Available Unclear) "Statement on a nonproprietary name adopted by the USAN council: Sarilumab," CAS Registry No. 1189541-98-7.
United States Census Bureau. Census Regions and Divisions of the United States, Retrieved from: <<https://www2.census.gov/geo/pdfs/maps-data/maps/reference/us_regdiv.pdf>>, Accessed on: Apr. 8, 2019.
Valentincic, et al., "Intraocular And Serum Cytokine Profiles In Patients With Intermediate Uveitis", Molecular Vision, vol. 17, pp. 2003-2010, Jul. 20, 2011.
Van Herwaarden, et al., Dose Reduction of Tocilizumab in Rheumatoid Arthritis Patients With Low Disease Activity, Clinical and Experimental Rheumatology, vol. 32, pp. 390-394, 2014.
Van Vollenhoven, Sex Differences in Rheumatoid Arthritis: More Than Meets the Eye, BMC Medicine, vol. 7, No. 12, pp. 1-4, Mar. 30, 2009.
Vasanthi, et al. (Dec. 2007) "Role of Tumor Necrosis Factor-Alpha in Rheumatoid Arthritis: A Review", APLAR Journal of Rheumatology, vol. 10, No. 4, pp. 270-274.
Walsh, et al., Mechanisms, Impact and Management of Pain in Rheumatoid Arthritis, Nature Reviews Rheumatology, vol. 10, No. 10, pp. 581-592, 2014.
Wang et al., "Minireview: Antibody Structure, Instability, and Formulation," Journal of Pharmaceutical Sciences, 96(1):1-26, (2007).
Wang, "Instability, stabilization, and formulation of liquid protein pharmaceuticals," Int'l J. Pharmaceutics, 185(2):129-188, (1999).
Wei et al., "Serum Levels of IL-6 and TNF-α May Correlate with Activity and Severity of Rheumatoid Arthritis", Med Sci Monit., 2015, 21: 4030-4038.
Wells, et al., "Immunogenicity of Sarilumab Monotherapy in Patients with Rheumatoid Arthritis Who Were Inadequate Responders or Intolerant to Disease-Modifying Antirheumatic Drugs", Rheumatology and Therapy, vol. 6, No. 3, pp. 339-352, May 14, 2019.

(56) References Cited

OTHER PUBLICATIONS

Whalley et al. (1997) "Quality of life in rheumatoid arthritis, " Br. J. Rheumatol. 36:884-888.
Wiens, et al., "A Systematic Review and Meta-Analysis of the Efficacy and Safety of Adalimumab for Treating Rheumatoid Arthritis", Rheumatology International, vol. 30, Issue 8, pp. 1063-1070, Jun. 1, 2010.
Wolfe et al., "Sleep Disturbance in Patients with Rheumatoid Arthritis: Evaluation by Medical Outcomes Study and Visual Analog Sleep Scales", J Rheumatol., 2006, 33:1942-1951.
Woods, et al., "Container System for Enabling Commercial Production of Cryopreserved Cell Therapy Products", Regenerative Medicine, vol. 5, No. 4, pp. 659-667, Jul. 15, 2010.
Wu et al. (1987) "Receptor-mediated in Vitro Gene Transformation by a soluble DNA Carrier System," The Journal of Biological Chemistry. 262:4429-4432.
Yamamura, "FRI0266. The Real-World Efficacy of the 2015 EULAR/ACR Recommendations for the Management of Polymyalgia Rheumatica with Additional Tocilizumab Therapy", Annals of the Rheumatic Diseases, Jun. 13, 2020, 79(Suppl 1), 717.2-718.
Yang, et al., Chronic Pain: Structural and Functional Changes in Brain Structures and Associated Negative Affective States, International Journal of Molecular Sciences, vol. 20, No. 13, p. 3130, Jun. 26, 2019.
Yokota et al., "Efficacy and safety of tocilizumab in patients with systemic-onset juvenile idiopathic arthritis: a randomised, double-blind, placebo-controlled, withdrawal phase III trial", The Lancet, Mar. 22, 2008, 371(9617): pp. 998-1006.
Yoo et al., "Exosomal amyloid A and lymphatic vessel endothelial hyaluronic acid receptor-1 proteins are associated with disease activity in rheumatoid arthritis", Arthritis Research & Therapy, 2017, 19(1): 119.
Yoshiii, I. et al, "Influence of pain score measured by a visual analog scale (PS-VAS) on the Health Assessment Questionnaire Disability Index and 28 joint-Disease Activity Index with C-reactive protei in rheumatoid arthritis patients", Int J, Rheum DID, 2018, 21: 1955-1961.
Yoshimura, et al., "Comprehensive Analysis of Inflammatory Immune Mediators in Vitreoretinal Diseases", PLoS One, vol. 4, No. 12, pp. 1-9, Jan. 1, 2009.
Zhou, et al., Interleukin-6: An Emerging Regulator of Pathological Pain, Journal of Neuroinflammation, vol. 13, No. 141, pp. 1-9, 2016.S.
Avdeeva et al., "Idiopathic Fibrosing Alveolitis", RMJ, Respiratory Diseases, Feb. 17, 1998, 4: 4.
Bharucha et al., "Growth During Tocilizumab Therapy for Polyarticular-course Juvenile Idiopathic Arthritis: 2-year Data from aPhase III Clinical Trial", The Journal of Rheumatology, Jul. 1, 2018, 745(8): 1173-1179.
Boleto et al., "Safety of combination therapy with two bDMARDs in patients with rheumatoid arthritis: A systematic review and meta-analysis", Seminars in Arthritis and Rheumatism, Aug. 2019, 49(1): 35-42.
Chambers et al., "Serum Amyloid A Protein Concentration In Rheumatoid Arthritis And Its Role In Monitoring Disease Activity", Annals Of The Rheumatic Diseases, Jan. 1, 1983, 42(6): 665-667.
Choi, "Issue & Trend: Rheumatoid Arhtritis", Korea Pharmaceutical Information Center, 2000. In Korean.
Ciubotariu et al., "Joint Damage Progression in Patients with RheumatoidArthritis in Clinical Remission. Do Biologics PerformBetter Than Synthetic Antirheumatic Drugs?", Journal of Rheumatology, 2014, 41(8): 1576-1582.
ClinicalTrials.gov (Apr. 14, 2020) "A Randomized, Double-blind, Placebo-controlled Study to Evaluate the Efficacy and Safety of Sarilumab in Patients With Polymyalgia Rheumatica", ClinicalTrials.gov ID NCT03600818.
ClinicalTrials.gov (Jun. 18, 2021) "A Randomized, Double-blind, Placebo-controlled Study to Evaluate the Efficacy and Safety of Sarilumab in Patients With Polymyalgia Rheumatica", ClinicalTrials.gov ID NCT03600818.
ClinicalTrials.gov (May 21, 2020) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728.
Corraliza-Gorjón et al., "New strategies using antibody combinations to increase cancer treatment effectiveness", Frontiers in immunology, 2017, 8: 1804.
Gabay et al., "Sarilumab and adalimumab differential effects on bone remodelling and cardiovascular risk biomarkers, and predictions of treatment outcomes", Arthritis Research & Therapy, Apr. 7, 2020, 22: 70.
Holm et al., "In diabetic retinopathy, foveal thickness of 300 mum seems to correlate with functionally significant loss of vision", Doc Ophthalmol., May 2007, 114(3): 117-124.
Kenny et al., "Therapeutic protein drug-drug interactions: navigating the knowledge gaps—highlights from the 2012 AAPS NBC Roundtable and IQ Consortium/FDA workshop", The AAPS Journal, 2013, 15(4): 933-940.
Lee, "A review of sarilumab for the treatment of rheumatoid arthritis", Immunotherapy, Oct. 18, 2017, 10(1): 57-65.
Mccreary et al., "Development and Validation of a Targeted Next-Generation Sequencing Gene Panel for Children With Neuroinflammation", JAMA Network Open, Oct. 30, 2019, 2(10): e1914274.
Mould et al., "Pharmacokinetics and pharmacodynamics of monoclonal antibodies", BioDrugs, 2010, 24(1): 23-39.
Ohtsubo et al., "Effective combination therapy of TNF antagonists with DMARDs", Nihon Rinsho, Jul. 2007, 65(7): 1287-1291. In Japanese with English abstract.
Papo et al., "Tocilizumab in severe and refractory non-infectious uveitis", Clinical and Experimental Rheumatology, 2014, 32(Suppl. 84): S75-79.
Prodanovic et al., "Matrix Metalloproteinases-3 Baseline Serum Levels in Early Rheumatoid Arthritis Patients without Initial Radiographic Changes: A TwoYear Ultrasonographic Study", Med Princ Pract., 2018, 27(4): 378-386, Epublished May 24, 2018.
Rezaei et al., "In early rheumatoid arthritis, patients with a good initial response to methotrexate have excellent 2-year clinical outcomes, but radiological progression is not fully prevented: data from the methotrexate responders population in the SWEFOT trial", Ann Rheum Dis., 2012, 71: 186-191, Epublished Sep. 19, 2011.
Sack Jr. et al., "Serum amyloid A—a review", Mol Med., Aug. 30, 2018, 24(1): 46.
Sanofi KK, Kezvara for Subcutaneous Injection Report on the Deliberation Results, Pharmaceutical Evaluation Division, Pharmaceutical Safety and Environmental Health Bureau Ministry of Health, Labour, and Welfare, Non-proprietary Name: Sarilumab (genetical Recombination) (JAN*), Date of Application: Oct. 7, 2016.
Santos et al., "Degree of decrease in central retinal thickness predicts visual acuity response to intravitreal ranibizumab in diabetic macular edema", Ophthalmologica, 2014, 231(1): 16-22.
Tallarida et al., "Quantitative Methods for Assessing Drug Synergism", Genes & Cancer, 2011, 2(11): 1003-1008.
Targonska-Stepniak et al., "Serum Amyloid A as a Marker of Persistent Inflammation and an Indicator of Cardiovascular and Renal Involvement in Patients with Rheumatoid Arthritis", Mediators of Inflammation, Jan. 1, 2014.
Tyagi et al., "Chemical Modification and Chemical Crosslinking for Protein/Enzyme Stabilization", Biokhimiya, 1998, 63(3): 395-407.
U.S. Department of Health and Human Services—Food and Drug Administration, "Guidance for Industry—Rheumatoid Arthritis: Developing Drug Products for Treatment", May 2013, Clinical/Medical, Revision 1.
Yukawa et al., "ACR2008 Recommendation: Treatment Strategy for rheumatoid arthritis based on ACR2008 recommendations", Journal of Clinical and Experimental Medicine, 2010, 234(1): 30-36. In Japanese.
Burmester et al., "Efficacy and safety of subcutaneous tocilizumab versus intravenous tocilizumab in combination with traditional DMARDs in patients with RA at week 97 (SUMMACTA)", Annals of the Rheumatic Diseases, Jun. 8, 2015, vol. 75, No. 1, pp. 68-74.

(56) References Cited

OTHER PUBLICATIONS

Choy et al., "Subcutaneous tocilizumab in rheumatoid arthritis: findings from the common-frame work phase 4 study programme TOZURA conducted in 22 countries", Rheumatology, Mar. 1, 2018, 57(3): 499-507.
ClinicalTrials.gov, "Efficacy, Safety and Tolerability of Repeated Dosis of Intravitreous Bevacizumab in Uveitic Macular Oedema", ClinicalTrials.gov ID: NCT01095809, Mar. 23, 2012.
ClinicalTrials.gov, (Jun. 8, 2015) "Phase II Study to Analyze Sarilumab in Non-Infectious Uveitis", ClinicalTrials.gov Identifier: NCT01900431.
ClinicalTrials.gov. (Jan. 17, 2017) "A Study of the Efficacy and Safety of Tocilizumab in Adults With Rheumatoid Arthritis", ClinicalTrials.gov. Identifier: NCT01988012.
ClinicalTrials.gov. (May 11, 2016) "A Study to Compare Subcutaneous Versus. Intravenous Administration of RoActemra/Actemra (Tocilizumab) in Participants With Moderate to Severe Active Rheumatoid Arthritis", ClinicalTrials.gov. Identifier: NCT01194414.
ClinicalTrials.gov. (Sep. 15, 2014) "Torpedo Study: A Study on Rapid Effect of Tocilizumab in Patients With Rheumatoid Arthritis With an Inadequate Response to Disease-Modifying Antirheumatic Drugs (DMARDs) or Anti-TNF", ClinicalTrials.gov. Identifier: NCT00977106.
Emery et al., "Evidence-based review of biologic markers as indicators of disease progression and remission in rheumatoid arthritis", Rheumatol Int., Jul. 2007, 27(9): 793-806, Epublished May 16, 2007.
Genentech (Apr. 11, 2019) Actemra® (tocilizumab) injection, for intravenous or subcutaneous use.
Hashimoto et al., "Increase of Hemoglobin Levels by Anti-IL-6 Receptor Antibody (Tocilizumab) in Rheumatoid Arthritis", PLoS One, May 30, 2014, vol. 9, No. 5, pp. e98202: 1-7.
Heissigerova et al., "Efficacy and Safety of Sarilumab for the Treatment of Posterior Segment Noninfectious Uveitis (SARIL-NIU) :: The Phase 2 Saturn Study", Opthamology, Mar. 2019, 126(3): 428-437.
Huizen et al., "What does it mean if you have a high C-reactive protein level?", Medical News Today, Oct. 11, 2023.
Izumi et al., "Steroid-Sparing Effect of Tocilizumab and Methotrexate in Patients with Polymyalgia Rheumatica: A Retrospective Cohort Study", Journ Clin Med., Jun. 30, 2021, 10: 2948.
Ogata et al., "Phase III Study of the Efficacy and Safety of Subcutaneous Versus Intravenous Tocilizumab Monotherapy in Patients With Rheumatoid Arthritis", Arthritis Care & Research, Aug. 27, 2013, vol. 66, No. 3, pp. 344-354.
Ohta et al., "Mechanism-Based Approach Using a Biomarker Response to Evaluate Tocilizumab Subcutaneous Injection in Patients With Rheumatoid Arthritis With an Inadequate Response to Synthetic DMARDs (MATUSRI Study)", The Journal of Clinical Pharmacology, Jan. 2014, 54(1):109-119, Epublished Oct. 12, 2013.
Patel et al., "The Negative Effect of Carpal Tunnel Syndrome on Sleep Quality", Sleep Disorders, Feb. 17, 2014, Article ID 962746.
Paul et al., "Effectiveness of biologic and non-biologic antirheumatic drugs on anaemia markers in 153,788 patients with rheumatoid arthritis: New evidence from real-world data", Seminars in Arthritis and Rheumatism, Feb. 1, 2018, vol. 47, No. 4, pp. 478-484.
Starkova et al., "ES02. Relatonship between fatigue and IL 6, diseas activity, depression in patients treated with tocilizumab", Rheumatology, Feb. 2012, 51(Suppl 1): i34-i41, Published Jan. 10, 2012.
Starkova et al., "Impact of tocilizumab therapy on fatigue in patients with rheumatoid arthritis", Scientific and Practical Rheumatology, 2012, N 52(3): 33-37, English translation included.
Strand et al., "Sustained benefit in rheumatoid arthritis following one course of rituximab: improvements in physical function over 2 years", Rheumatology, 2006, 45(12): 1505-1513.
Takeuchi, "Rheumatoid Arthritis: Advances in Diagnosis and Treatment", The Journal of the Japanese Society of Internal Medicine, 2012, vol. 101, pp. 2815-2817.
Teper et al., "Update on the Management of Uveitic Macular Edema", J Clin Med., 2021, 10(18): 4133.
Unknown, "Differentiation of Arthritis: Advances in Diagnosis and Treatment 1. Rheumatoid Arthritis", The Journal of the Japanese Society of Internal Medicine, 2010, vol. 99, pp. 2392-2400.
"Highlights of Prescribing Information" for ACTEMRA (tocilizumab), Reference ID: 5639738, Retrieved from url: <https://www.accessdata.fda.gov/drugsatfda_docs/label/2025/125276s149lbl.pdf>, Revised Aug. 2025.
"Highlights of Prescribing Information" for Kevzara (sarilumab), US Approval: 2017, Revised Apr. 2018.
"Highlights of Prescribing Information" for Kevzara (sarilumab), US Approval: 2017, Revised May 2025, Retrieved from url: <https://products.sanofi.us/kevzara/kevzara.pdf>.
Brunner et al., "Efficacy and safety of tocilizumab in patients with polyarticular-course juvenile idiopathic arthritis: results from a phase 3, randomised, double-blind withdrawal trial", Ann. Rheum. Dis., Jun. 2015, 74(6): 1110-1117.
Cell Signaling Technology, "Jak/Stat: IL-6 receptor signaling", Released Nov. 2012, including English translation, Obtained from url: <https://www.cellsignal.jp/pathways/jak-stat-il6-receptor-signaling>.
De Benedetti et al., "Sarilumab in Polyarticular-Course Juvenile Idiopathic Arthritis: Dose-Finding and 1-Year Analysis of a Phase 2b, Open-Label, Multicenter Study", Arthritis Care & Research, Nov. 14, 2025.
Den Broeder et al., "Non-Medical Switching from Tocilizumab to Sarilumab in Rheumatoid Arthritis Patients with Low Disease Activity: An Observational Study", Clin Pharmacol Ther., Oct. 2023, 114(4): 810-814, Epublished Jul. 27, 2023.
Fleischmann et al., "Tocilizumab Inhibits Structural Joint Damage and Improves Physical Function in Patients with Rheumatoid Arthritis and Inadequate Responses to Methotrexate: LITHE Study 2-year Results", Journal of Rheumatology, Feb. 2013, 40(2): 113-126.
General guidelines for clinical evaluations of new drugs (Notification No. 43), issued in 1992 by New Drugs division, Pharmaceutical Affairs Bureau, Ministry of Health of Japan, Japanese language document, [https://www.pmda.go.jp/files/000206739.pdf].
Gill et al., "Multi-modal Imaging in Etanercept-induced Uveitis: A Case Series," The Open Ophthalmology Journal, 2020, 14: 70-74.
Leclercq et al., "Efficacious switching from subcutaneous to intravenous tocilizumab in patients with non-infectious non-anterior uveitis," Journal of Ophthalmic Inflammation and Infection, Jul. 18, 2023, 13(1): 32.
Leipold et al., "Pharmacokinetic and Pharmacodynamic Considerations in the Design of Therapeutic Antibodies", Clin. Transl., Sci., Mar. 2019, 12(2): 130-139.
Onishi et al., "Comparative effectiveness of subcutaneous sarilumab 200 mg biweekly, subcutaneous Tocilizumab 162 mg biweekly, and intravenous Tocilizumab 8 mg/kg every 4 weeks in patients with rheumatoid arthritis: a prospective cohort study," Arthritis Res Ther., Mar. 7, 2025, 27(1): 52.
Pillar et al., "Evaluating the Effectiveness of Escalating to Weekly Adalimumab Dosing for the Treatment of Non-infectious Uveitis: A Multi-Center Study," American Academy of Ophthalmology, Sep. 30, 2025, S0161-6420(25)00606-2.
Saito et al., "Differences in the strength of inhibition of interleukin-6 signalling by subcutaneous sarilumab and tocilizumab in rheumatoid arthritis patients," Clinical and Experimental Rheumatology, Jul. 2023, 41(7): 1451-1455.
Swets et al., "A comparison of the effectiveness of different doses of tocilizumab and sarilumab in the treatment of severe COVID-19: a natural experiment due to drug shortages", International Journal of Infectious Diseases, Apr. 2023, 129: 57-62.
Uhlig et al., "Quantification of reduced health-related quality of life in patients with rheumatoid arthritis compared to the general population", J Rheumatol., Jun. 2007, 34(6): 1241-1247, Epublished May 15, 2007.
Xu et al., "Modeling, Simulation, and Extrapolation to Optimize Pediatric Development Plan: Sarilumab Polyarticular-Course Juvenile Arthritis Application", Journal of Pharmacokinetics and Pharmacodynamics, Mar. 24, 2026, 53:19.

(56) References Cited

OTHER PUBLICATIONS

Yokota et al., "Efficacy, safety and tolerability of tocilizumab in patients with systemic juvenile idiopathic arthritis", Ther. Adv. Musculoskelet. Dis., Dec. 2012;4(6):387-397.

* cited by examiner

Abbreviations: PD = pharmacodynamics, PK = pharmacokinetic, qw = once a week, q2w = once every other week.

SEQUENCE LISTING

```
Sequence total quantity: 11
SEQ ID NO: 1            moltype = AA  length = 116
FEATURE                 Location/Qualifiers
REGION                  1..116
                        note = HCVR
source                  1..116
                        mol_type = protein
                        organism = synthetic construct
SEQUENCE: 1
EVQLVESGGG LVQPGRSLRL SCAASRFTFD DYAMHWVRQA PGKGLEWVSG ISWNSGRIGY  60
ADSVKGRFTI SRDNAENSLF LQMNGLRAED TALYYCAKGR DSFDIWGQGT MVTVSS      116

SEQ ID NO: 2            moltype = AA  length = 107
FEATURE                 Location/Qualifiers
REGION                  1..107
```

```
                        note = LCVR
source                  1..107
                        mol_type = protein
                        organism = synthetic construct
SEQUENCE: 2
DIQMTQSPSS VSASVGDRVT ITCRASQGIS SWLAWYQQKP GKAPKLLIYG ASSLESGVPS  60
RFSGSGSGTD FTLTISSLQP EDFASYYCQQ ANSFPYTFGQ GTKLEIK                107

SEQ ID NO: 3            moltype = AA  length = 8
FEATURE                 Location/Qualifiers
REGION                  1..8
                        note = HCDR1
source                  1..8
                        mol_type = protein
                        organism = synthetic construct
SEQUENCE: 3
RFTFDDYA                                                           8

SEQ ID NO: 4            moltype = AA  length = 8
FEATURE                 Location/Qualifiers
REGION                  1..8
                        note = HCDR2
source                  1..8
                        mol_type = protein
                        organism = synthetic construct
SEQUENCE: 4
ISWNSGRI                                                           8

SEQ ID NO: 5            moltype = AA  length = 9
FEATURE                 Location/Qualifiers
REGION                  1..9
                        note = HCDR3
source                  1..9
                        mol_type = protein
                        organism = synthetic construct
SEQUENCE: 5
AKGRDSFDI                                                          9

SEQ ID NO: 6            moltype = AA  length = 6
FEATURE                 Location/Qualifiers
REGION                  1..6
                        note = LCDR1
source                  1..6
                        mol_type = protein
                        organism = synthetic construct
SEQUENCE: 6
QGISSW                                                             6

SEQ ID NO: 7            moltype =   length =
SEQUENCE: 7
000

SEQ ID NO: 8            moltype = AA  length = 9
FEATURE                 Location/Qualifiers
REGION                  1..9
                        note = LCDR3
source                  1..9
                        mol_type = protein
                        organism = synthetic construct
SEQUENCE: 8
QQANSFPYT                                                          9

SEQ ID NO: 9            moltype = AA  length = 446
FEATURE                 Location/Qualifiers
REGION                  1..446
                        note = heavy chain
source                  1..446
                        mol_type = protein
                        organism = synthetic construct
SEQUENCE: 9
EVQLVESGGG LVQPGRSLRL SCAASRFTFD DYAMHWVRQA PGKGLEWVSG ISWNSGRIGY  60
ADSVKGRFTI SRDNAENSLF LQMNGLRAED TALYYCAKGR DSFDIWGQGT MVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446
```

-continued

```
SEQ ID NO: 10           moltype = AA  length = 214
FEATURE                 Location/Qualifiers
REGION                  1..214
                        note = light chain
source                  1..214
                        mol_type = protein
                        organism = synthetic construct
SEQUENCE: 10
DIQMTQSPSS VSASVGDRVT ITCRASQGIS SWLAWYQQKP GKAPKLLIYG ASSLESGVPS  60
RFSGSGSGTD FTLTISSLQP EDFASYYCQQ ANSFPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 11           moltype = AA  length = 358
FEATURE                 Location/Qualifiers
REGION                  1..358
                        note = extracellular domain of hIL-6R
source                  1..358
                        mol_type = protein
                        organism = synthetic construct
SEQUENCE: 11
MVAVGCALLA ALLAAPGAAL APRRCPAQEV ARGVLTSLPG DSVTLTCPGV EPEDNATVHW  60
VLRKPAAGSH PSRWAGMGRR LLLRSVQLHD SGNYSCYRAG RPAGTVHLLV DVPPEEPQLS  120
CFRKSPLSNV VCEWGPRSTP SLTTKAVLLV RKFQNSPAED FQEPCQYSQE SQKFSCQLAV  180
PEGDSSFYIV SMCVASSVGS KFSKTQTFQG CGILQPDPPA NITVTAVARN PRWLSVTWQD  240
PHSWNSSFYR LRFELRYRAE RSKTFTTWMV KDLQHHCVIH DAWSGLRHVV QLRAQEEFGQ  300
GEWSEWSPEA MGTPWTESRS PPAENEVSTP MQALTTNKDD DNILFRDSAN ATSLPVQD    358
```

COMPOSITIONS AND METHODS FOR TREATING JUVENILE IDIOPATHIC ARTHRITIS

RELATED APPLICATIONS

This application is a continuation of U.S. patent application Ser. No. 16/779,187, filed Jan. 31, 2020, now U.S. Pat. No. 11,498,969, which claims the benefit of U.S. Provisional Application No. 62/799,698, filed Jan. 31, 2019; U.S. Provisional Application No. 62/851,474, filed May 22, 2019; U.S. Provisional Application No. 62/935,395, filed Nov. 14, 2019; and European Application No. 19306553.9, filed on Dec. 3, 2019; each of which is incorporated herein by reference in its entirety.

SEQUENCE LISTING

The instant application contains a Sequence Listing which has been submitted electronically in XML format and is hereby incorporated by reference in its entirety. Said Sequence Listing, created on Sep. 22, 2022, is named "734229 SA9-244CON_ST26.txt" and is 14,749 bytes in size.

FIELD

The present disclosure relates to the field of therapeutic treatment of juvenile idiopathic arthritis, such as systemic juvenile idiopathic arthritis and polyarticular-course juvenile idiopathic arthritis (which comprises polyarticular and extended oligoarticular juvenile idiopathic arthritis). Certain aspects of the invention relate to the use of interleukin-6 receptor (IL-6R) antagonists, such as anti-IL-6R antibodies, to treat systemic juvenile idiopathic arthritis and polyarticular-course juvenile idiopathic arthritis.

BACKGROUND

Juvenile idiopathic arthritis (JIA) is the most common rheumatic disease of childhood. JIA is defined by the International League of Associations for Rheumatology (ILAR) as arthritis of unknown etiology with onset before 16 years of age and persists for at least 6 weeks with other known conditions excluded (Petty, R. E. et al., 2001. J Rheumatol. 2004; 31(2):390-2; Giannini, E. H. et al., 1997 Arthritis Rheum. 40(7):1202-9; and Macaubas, C. et al., 2009 Nat Rev Rheumatol. 5(11):616-26). The condition comprises seven subtypes as defined by the ILAR including polyarticular-course JIA and systemic JIA. See Petty, R. E. et al., 2001. J Rheumatol. 2004; 31(2):390-2, incorporated by reference herein in its entirety.

There is no known cure for JIA. While conventional treatments may be utilized for the treatment of affected individuals, more effective treatments for treating persistent types of JIA are needed.

SUMMARY

This disclosure provides, inter alia, methods for treating JIA in a subject in need thereof comprising administering an effective amount of an antibody that specifically binds IL-6R.

In an embodiment, the JIA is systemic JIA (sJIA).

In an embodiment, the antibody that specifically binds to the IL-6R comprises a heavy chain variable region of sequence SEQ ID NO: 1 and the light chain variable region sequence of SEQ ID NO: 2.

In various embodiments, the antibody comprises a heavy chain variable region (VH) and a light chain variable region (VL), wherein the VH comprises the three complementarity determining regions (CDRs) found within the sequence of SEQ ID NO:1 and wherein the VL comprises the three CDRs found within the sequence of SEQ ID NO:2. In various embodiments, the anti-IL-6R antibody or antigen-binding fragment thereof comprises three heavy chain complementarity determining regions (HCDRs; i.e., HCDR1, HCDR2 and HCDR3) and three light chain complementarity determining regions (LCDRs; i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In an embodiment, the antibody is sarilumab.

In various embodiments, no other disease modifying antirheumatic drug (DMARD) is administered with the antibody. In some embodiments, at least one other DMARD is administered to the subject. In an embodiment, at least one other DMARD is administered to the subject concurrently with or at the same time as the antibody.

In some embodiments, the subject is suffering from at least one symptom of sJIA such as arthritis in at least 1 joint for at least 6 weeks duration with or preceded by fever lasting at least 2 weeks; evanescent erythematous rash predominantly on the trunk and the extremities; generalized lymphadenopathy; hepatomegaly and/or splenomegaly; polyserositis; weight loss; fatigue; malaise; fever; elevated peripheral white blood cell (WBC) count (25 000 to 50 000/$mL^3$); increased platelet count (e.g., $>1\times10^6$), markedly elevated erythrocyte sedimentation rate (ESR) of >100 mm/h; anemia; and/or a high ferritin level relative to a healthy subject. In an embodiment, treating the subject comprises reducing, slowing or halting the progression of, or otherwise ameliorating any one of (or any combination of) these symptoms.

As used herein, a "symptom" associated with JIA includes any clinical or laboratory (e.g., diagnostic) manifestation associated with JIA and is not limited to what the subject can feel or observe.

In various embodiments, the subject is suffering from at least one symptom of sJIA, such as limping; stiffness when awakening; reluctance of the subject to use an arm or leg; reduced activity level; quotidian, high spiking (e.g., reaching about 40° C. or at least 40° C.) fever; joint swelling; and/or difficulty with fine motor activities. In an embodiment of the method, the at least one symptom of sJIA in the subject is improved after administering the antibody.

In various embodiments of the method, the antibody improves at least one score or metric such as JIA ACR (e.g., JIA ACR30, JIA ACR50, JIA ACR70, JIA ACR90, and JIA ACR100), a JIA ACR component (e.g., count of joints with active arthritis, count of joints with limited range of motion, physician global assessment of disease activity, acute phase reactant such as erythrocyte sedimentation rate or C-reactive protein (CRP), childhood health assessment questionnaire, patient (or parent) global assessment of overall well-being,), and/or reduced fever (e.g., in subjects with a fever when the antibody is first administered), reduction from baseline of amount of corticosteroid use (e.g., glucocorticoids), and/or Juvenile Arthritis Disease Activity Score (such as Juvenile Arthritis Disease Activity Score-27). In various embodiments of the method, the improvement is characterized by at least one score or metric, such as JIA ACR30, JIA ACR50, JIA ACR70, JIA ACR90, and/or JIA ACR100. In various embodiments of the method, the improvement is characterized by at least one score or metric, such as physician global assessment of disease activity score, patient or parent assessment of overall well-being, childhood health assessment questionnaire, number of joints with active arthritis, number of joints with limited motion, high sensitivity C-reactive protein, and/or reduced fever (e.g., in subjects with a fever when the antibody is first administered). In various embodiments, the improvement is characterized by at least one biomarker. In various embodiments of the method, the antibody causes clinically inactive disease, as defined by Wallace criteria. Wallace criteria are defined as physician global VAS<1/10, no active arthritis, no active uveitis, and CRP<10 mg/L. In various embodiments of the method, the antibody causes clinically inactive disease, as defined by Juvenile Arthritis Disease Activity Score-27-CRP≤1. In various embodiments of the method, the antibody causes clinically inactive disease or low disease activity, as defined by Juvenile Arthritis Disease Activity Score-27-CRP 53.8.

In an embodiment of the method, the subject has an inadequate response to current treatment and is considered as a candidate for a biologic disease modifying antirheumatic drug.

In an embodiment of the method, the subject is between the ages of about 1 and about 17. In other embodiments, the subject is between the ages of about 4 and about 6 or between the ages of about 12 and about 18.

In an embodiment of the method, the subject has either 5 or more active joints, or 2 active joints and systemic symptoms (e.g., a fever). In an embodiment of the method, the subject has either 5 or more active joints or 2 or more active joints and sJIA fever of greater than about 37.5° C. for at least 3 out of any 7 consecutive days despite glucocorticoids at a dose stable for at least 3 days.

An "active joint" is a joint with (i) swelling within the joint not due to deformity, and/or (ii) limitation of motion with either pain or tenderness.

In an embodiment of the method, the JIA is polyarticular-course JIA (pcJIA). In certain embodiments, the pcJIA is extended oligoarticular JIA. In various embodiments, the pcJIA is Rheumatoid factor (RF)-positive polyarticular JIA. In some embodiments, the pcJIA is RF-negative polyarticular JIA. In an embodiment of the method, the subject is between the ages of about 12 and about 14 or between the ages of about 7 and about 9.

In an embodiment, the antibody that specifically binds to the IL-6R comprises a heavy chain variable region of sequence SEQ ID NO: 1 and the light chain variable region sequence of SEQ ID NO: 2.

In various embodiments, the antibody comprises a VH and a VL, wherein the VH comprises the three CDRs found within the sequence of SEQ ID NO:1 and wherein the VL comprises the three CDRs found within the sequence of SEQ ID NO:2. In various embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In an embodiment, the antibody is sarilumab.

In various embodiments, no other DMARD is administered with the antibody. In some embodiments, at least one other DMARD is administered to the subject. In an embodiment, at least one other DMARD is administered to the subject concurrently with or at the same time as the antibody.

In some embodiments, the subject is suffering from at least one symptom of RF-positive polyarticular JIA. In some embodiments, the subject is suffering from at least one symptom of RF-positive polyarticular JIA such as deforming symmetrical polyarthritis that can evolve to joint subluxation (e.g., in a wrist and/or thumb); a joint contracture (e.g., proximal and distal interphalangeals, bone overgrowth of proximal interphalangeals, and finger deformities such as swan-neck or boutonniere deformities); chronic synovial inflammation; articular cartilage loss and erosion of juxta-articular bone; normocytic chronic anemia; elevated ESR and C-reactive protein; white blood cell count; asymptomatic arthritis of the cervical spine; and/or micrognathia. In various embodiments, a subject has joint subluxation (e.g., in a wrist and/or thumb) and/or a joint contracture (e.g., proximal and distal interphalangeals, bone overgrowth of proximal interphalangeals, and finger deformities such as swan-neck or boutonniere deformities). In an embodiment, treating the subject comprises reducing, slowing or halting the progression of, or otherwise ameliorating any one of (or any combination of) these symptoms. In an embodiment of the method, the subject is between the ages of about 12 and about 14.

In various embodiments, the subject is suffering from at least one symptom of RF-negative polyarticular JIA. In various embodiments, the subject is suffering from at least one symptom of RF-negative polyarticular JIA such as symmetrical polyarthritis with reduced motion, muscle weakness, and/or decreased physical function. In an embodiment, treating the subject comprises reducing, slowing or halting the progression of, or otherwise ameliorating any one of (or any combination of) these symptoms. In an embodiment of the method, the subject is between the ages of about 7 and about 9.

In an embodiment, the subject is suffering from at least one symptom of extended oligoarticular JIA. In various embodiments, the subject is suffering from at least one symptom of extended oligoarticular JIA such as an aseptic inflammatory synovitis that affects more than 4 joints (e.g., in larger joints, such as knees, ankles, wrists) after the first 6 months of disease; ambulating with a limp; chronic anterior uveitis; chronic arthritis in a knee or ankle leading to overgrowth of that limb with subsequent leg length discrepancy; muscle atrophy (e.g., in extensor muscles such as vastus lateralis, quadriceps when knee affected); and/or flexion contractures in the knees or wrists. In an embodiment, treating the subject comprises reducing, slowing or halting the progression of, or otherwise ameliorating any one of (or any combination of) these symptoms.

In various embodiments, the subject is suffering from at least one symptom of pcJIA, such as limping; stiffness when awakening; reluctance of the subject to use an arm or leg; reduced activity level; joint swelling; and/or difficulty with fine motor activities.

In an embodiment of the method, the at least one symptom of pcJIA in the subject is improved after administering the antibody. In various embodiments of the method, the improvement is characterized by at least one score or metric, such as JIA ACR30, JIA ACR50, JIA ACR70, JIA ACR90, and JIA ACR100 defined as improvement in ≥3/6 of the following core set variables with no more than 1/6 worsened: (i) a physician global assessment of disease activity (e.g., by Visual Analogue Scale (VAS)), (ii) patient or parent assessment of overall well-being, (iii) childhood health assessment questionnaire (e.g., by a Childhood Health Assessment Questionnaire Disability Index (CHAQ-DI)), (iv) number of joints with active arthritis, (v) number of joints with limited motion, and (vi) an index of inflammation (e.g., high sensitivity C-reactive protein). In an embodiment, a JIA ACR30 response is when the ≥3/6 core set variables improve ≥30% from baseline with no more than 1/6 worsened by ≥30%.

In various embodiments of the method, the improvement in disease activity is characterized by at least one Juvenile Arthritis Disease Activity Score (such as the Juvenile Arthritis Disease Activity Score-27 that includes 4 measures: Physician global assessment of disease activity, Parent/patient global assessment of well-being, Count of joints with active disease, and Index of inflammation (hs-CRP or ESR level)).

In various embodiments of the method, the improvement is characterized by at least one score or metric, such as physician global assessment of disease activity, patient or parent assessment of overall well-being, childhood health assessment questionnaire, number of joints with active arthritis, number of joints with limited motion, high sensitivity C-reactive protein, and/or Juvenile Arthritis Disease Activity Score (such as Juvenile Arthritis Disease Activity Score-27).

In various embodiments of the method, the antibody causes clinically inactive disease, as defined by Wallace criteria. Wallace criteria are defined as physician global VAS<1/10, no active arthritis, no active uveitis, and CRP<10 mg/L. In various embodiments of the method, the antibody causes clinically inactive disease, as defined by Juvenile Arthritis Disease Activity Score-27-CRP≤1. In various embodiments of the method, the antibody causes clinically inactive disease or low disease activity, as defined by Juvenile Arthritis Disease Activity Score-27-CRP≤3.8.

In an embodiment of the method, the subject is between the ages of about 2 and about 17.

In various embodiments, the subject has had JIA for at least 6 months. In an embodiment, the subject has had arthritis that affected up to 4-joints during at least the first 6 months of the disease and then evolved to 5 or more joints affected after the at least first 6 months. In some embodiments, the subject has had arthritis that affected up to 4 joints during the first 6 months of the disease and then evolved to 5 or more joints affected after the first 6 months.

In an embodiment of the method, the subject has at least 5 joints with active arthritis. In an embodiment of the method, the subject has arthritis affecting 5 or more joints during the first 6 months of the disease. In an embodiment of the method, the arthritis is rheumatoid factor-negative. Alternatively, in an embodiment, the arthritis is rheumatoid factor-positive.

In an embodiment of the method, the antibody is administered subcutaneously. In various embodiments of the method, the antibody is administered every week, or every two weeks.

In an embodiment of the method, the antibody is administered at a dose from about 2 mg/kg to about 4 mg/kg. In an embodiment, the dose is administered once every week or once every 2 weeks. In various embodiments of the method, the antibody is used at a dose of about 2 mg/kg every week, about 2.5 mg/kg every week, about 2 mg/kg every two weeks, about 2.5 mg/kg every two weeks, about 3 mg/kg every two weeks, and about 4 mg/kg every two weeks.

In various embodiments of the method, the antibody is used at a dose listed in Tables 1-5.

In some embodiments of the method, the subject has a body weight less than 30 kg.

In some embodiments of the method, the subject has a body weight of at least about 30 kg. In some embodiments of the method, the subject has a body weight less than 60 kg.

In some embodiments of the method, the subject is 1 to 17 years old.

In some embodiments of the method, the subject is a human and the antibody is a human antibody.

This disclosure further provides a method for treating pcJIA in a subject in need thereof comprising administering an effective amount of an antibody that specifically binds IL-6R, wherein the antibody that specifically binds to the IL-6R comprises a heavy chain variable region of sequence SEQ ID NO: 1 and a light chain variable region sequence of SEQ ID NO: 2, wherein the antibody is administered at a dose of from about 2 mg/kg to about 4 mg/kg per week or per two weeks, wherein the body weight of the subject is greater than or equal to 10 kg and less than or equal to 60 kg.

In some embodiments of the method, the body weight of the subject is greater than or equal to 30 kg and less than or equal to 60 kg and wherein the antibody is administered at a dose from about 2 mg/kg to about 3 mg/kg every other week or a dose of about 2 mg/kg every week.

In some embodiments of the method, the body weight of the subject is greater than or equal to 30 kg and less than or equal to 60 kg and wherein the antibody is administered at a dose from about 2 mg/kg to about 3 mg/kg once every other week or a dose of about 2 mg/kg once every week.

In some embodiments of the method, the body weight of the subject is greater than or equal to 30 kg and less than or equal to 60 kg and wherein the antibody is administered at a dose of about 2 mg/kg or about 3 mg/kg every other week.

In some embodiments of the method, the body weight of the subject is greater than or equal to 30 kg and less than or equal to 60 kg and wherein the antibody is administered at a dose of about 2 mg/kg or about 3 mg/kg once every other week.

In some embodiments of the method, the body weight of the subject is greater than or equal to 30 kg and less than or equal to 60 kg and wherein the antibody is administered at a dose of 2 mg/kg or 3 mg/kg every other week or 2 mg/kg every week.

In some embodiments of the method, the body weight of the subject is greater than or equal to 30 kg and less than or equal to 60 kg and wherein the antibody is administered at a dose of 2 mg/kg or 3 mg/kg once every other week or 2 mg/kg once every week.

In some embodiments of the method, the body weight of the subject is greater than or equal to 10 kg and less than 30 kg and wherein the antibody is administered at a dose from about 2.5 mg/kg to about 4 mg/kg every other week or a dose of about 2.5 mg/kg every week.

In some embodiments of the method, the body weight of the subject is greater than or equal to 10 kg and less than 30 kg and wherein the antibody is administered at a dose from about 2.5 mg/kg to about 4 mg/kg once every other week or a dose of about 2.5 mg/kg once every week.

In some embodiments of the method, the body weight of the subject is greater than or equal to 10 kg and less than 30 kg and wherein the antibody is administered at a dose of about 2.5 mg/kg or about 4 mg/kg every other week.

In some embodiments of the method, the body weight of the subject is greater than or equal to 10 kg and less than 30 kg and wherein the antibody is administered at a dose of about 2.5 mg/kg or about 4 mg/kg once every other week.

In some embodiments of the method, the body weight of the subject is greater than or equal to 10 kg and less than 30 kg and wherein the antibody is administered at a dose of 2.5 mg/kg or 4 mg/kg every other week or 2.5 mg/kg every week.

In some embodiments of the method, the body weight of the subject is greater than or equal to 10 kg and less than 30 kg and wherein the antibody is administered at a dose of 2.5 mg/kg or 4 mg/kg once every other week or 2.5 mg/kg once every week.

This disclosure further provides a method for treating pcJIA in a subject in need thereof-comprising administering an effective amount of an antibody that specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 30 kg and less than 33 kg and the antibody is administered at a dose of 61.25 mg once every other week or once every week; wherein the body weight of the subject is greater than or equal to 33 kg and less than 37.5 kg and the antibody is administered at a dose of 70 mg once every other week or once every week; wherein the body weight of the subject is greater than or equal to 37.5 kg and less than 42 kg and the antibody is administered at a dose of 78.75 mg once every other week or once every week; wherein the body weight of the subject is greater than or equal to 42 kg and less than 46.5 kg and the antibody is administered at a dose of 87.5 mg once every other week or once every week; wherein the body weight of the subject is greater than or equal to 46.5 kg and less than 50.5 kg and the antibody is administered at a dose of 96.25 mg once every other week or once every week; wherein the body weight of the subject is greater than or equal to 50.5 kg and less than 55 kg and the antibody is administered at a dose of 105 mg once every other week or once every week; wherein the body weight of the subject is greater than or equal to 55 kg and less than 59.5 kg and the antibody is administered at a dose of 113.75 mg once every other week or once every week; wherein the body weight of the subject is greater than or equal to 59.5 kg and less than 64 kg and the antibody is administered at a dose of 122.5 mg once every other week or once every week; wherein the body weight of the subject is greater than or equal to 64 kg and less than 68 kg and the antibody is administered at a dose of 131.25 mg once every other week or once every week; wherein the body weight of the subject is greater than or equal to 68 kg and less than 72.5 kg and the antibody is administered at a dose of 140 mg once every other week or once every week; or wherein the body weight of the subject is greater than or equal to 72.5 kg and the antibody is administered at a dose of 148.75 mg once every other week or once every week.

This disclosure further provides a method for treating pcJIA in a subject in need thereof comprising administering an effective amount of an antibody that specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 30 kg and less than 31 kg and the antibody is administered at a dose of 87.5 mg once every other week or once every week; wherein the body weight of the subject is greater than or equal to 31 kg and less than 34 kg and the antibody is administered at a dose of 96.25 mg once every other week or once every week; wherein the body weight of the subject is greater than or equal to 34 kg and less than 37 kg and the antibody is administered at a dose of 105 mg once every other week or once every week; wherein the body weight of the subject is greater than or equal to 37 kg and less than 39.5 kg and the antibody is administered at a dose of 113.75 mg once every other week or once every week; wherein the body weight of the subject is greater than or equal to 39.5 kg and less than 42.5 kg and the antibody is administered at a dose of 122.5 mg once every other week or once every week; wherein the body weight of the subject is greater than or equal to 42.5 kg and less than 45 kg and the antibody is administered at a dose of 131.25 mg once every other week or once every week; wherein the body weight of the subject is greater than or equal to 45 kg and less than 48.5 kg and the antibody is administered at a dose of 140 mg once every other week or once every week; wherein the body weight of the subject is greater than or equal to 48.5 kg and less than 51.5 kg and the antibody is administered at a dose of 148.75 mg once every other week or once every week; wherein the body weight of the subject is greater than or equal to 51.5 kg and less than 54.5 kg and the antibody is administered at a dose of 157.5 mg once every other week or once every week; wherein the body weight of the subject is greater than or equal to 54.5 kg and less than 57 kg and the antibody is administered at a dose of 166.25 mg once every other week or once every week; wherein the body weight of the subject is greater than or equal to 57 kg and less than 63 kg and the antibody is administered at a dose of 175 mg once every other week or once every week; wherein the body weight of the subject is greater than or equal to 63 kg and the antibody is administered at a dose of 192.5 mg once every other week or once every week.

This disclosure further provides a method for treating pcJIA in a subject in need thereof comprising administering an effective amount of an antibody that specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 10 kg and less than 12.5 kg and the antibody is administered at a dose of 26.25 mg once every other week or once every week; wherein the body weight of the subject is greater than or equal to 12.5 kg and less than 16 kg and the antibody is administered at a dose of 35 mg once every other week or once every week; wherein the body weight of the subject is greater than or equal to 16 kg and less than 19.5 kg and the antibody is administered at a dose of 43.75 mg once every other week or once every week; wherein the body weight of the subject is greater than or equal to 19.5 kg and less than 23 kg and the antibody is administered at a dose of 52.5 mg once every other week or once every week; wherein the body weight of the subject is greater than or equal to 23 kg and less than 26.5 kg and the antibody is administered at a dose of 61.25 mg once every other week or once every week; wherein the body weight of the subject is greater than or equal to 26.5 kg and less than 30 kg and the antibody is administered at a dose of 70 mg once every other week or once every week; wherein the body weight of the subject is greater than or equal to 30 kg and less than 37.5 kg and the antibody is administered at a dose of 70 mg once every other week or once every week; wherein the body weight of the subject is greater than or equal to 37.5 kg and less than 42 kg and the antibody is administered at a dose of 78.75 mg once every other week or once every week; wherein the body weight of the subject is greater than or equal to 42 kg and less than 46.5 kg and the antibody is administered at a dose of 87.5 mg once every other week or once every week; wherein the body weight of the subject is greater than or equal to 46.5 kg and less than 50.5 kg and the antibody is administered at a dose of 96.25 mg once every other week or once every week; wherein the body weight of the subject is greater than or equal to 50.5 kg and less than 55 kg and the antibody is administered at a dose of 105 mg once every other week or once every week; wherein the body weight of the subject is greater than or equal to 55 kg and less than 59.5 kg and the antibody is administered at a dose of 113.75 mg once every other week or once every week; wherein the body weight of the subject is greater than or equal to 59.5 kg and less than 64 kg and the antibody is administered at a dose of 122.5 mg once every other week or once every week; wherein the body weight of the subject is greater than or equal to 64 kg and less than 68 kg and the antibody is administered at a dose of 131.25 mg once every other week or once every week; wherein the body weight of the subject is greater than or equal to 68 kg and less than 72.5 kg and the antibody is administered at a dose of 140 mg once every other week or once every week; or wherein the body weight of the subject is greater than or equal to 72.5 kg and the antibody is administered at a dose of 148.75 mg once every other week or once every week.

This disclosure further provides a method for treating pcJIA in a subject in need thereof comprising administering an effective amount of an antibody that specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 10 kg and less than 12.5 kg and the antibody is administered at a dose of 43.75 mg once every other week or once every week; wherein the body weight of the subject is greater than or equal to 12.5 kg and less than 14.5 kg and the antibody is administered at a dose of 52.5 mg once every other week or once every week; wherein the body weight of the subject is greater than or equal to 14.5 kg and less than 16.5 kg and the antibody is administered at a dose of 61.25 mg once every other week or once every week; wherein the body weight of the subject is greater than or equal to 16.5 kg and less than 19 kg and the antibody is administered at a dose of 70 mg once every other week or once every week; wherein the body weight of the subject is greater than or equal to 19 kg and less than 21 kg and the antibody is administered at a dose of 78.75 mg once every other week or once every week; wherein the body weight of the subject is greater than or equal to 21 kg and less than 23.5 kg and the antibody is administered at a dose of 87.5 mg once every other week or once every week; wherein the body weight of the subject is greater than or equal to 23.5 kg and less than 25.5 kg and the antibody is administered at a dose of 96.25 mg once every other week or once every week; wherein the body weight of the subject is greater than or equal to 25.5 kg and less than 27.5 kg and the antibody is administered at a dose of 105 mg once every other week or once every week; wherein the body weight of the subject is greater than or equal to 27.5 kg and less than 30 kg and the antibody is administered at a dose of 113.75 mg once every other week or once every week; wherein the body weight of the subject is greater than or equal to 30 kg and less than 39.5 kg and the antibody is administered at a dose of 113.75 mg once every other week or once every week; wherein the body weight of the subject is greater than or equal to 39.5 kg and less than 42.5 kg and the antibody is administered at a dose of 122.5 mg once every other week or once every week; wherein the body weight of the subject is greater than or equal to 42.5 kg and less than 45 kg and the antibody is administered at a dose of 131.25 mg once every other week or once every week; wherein the body weight of the subject is greater than or equal to 45 kg and less than 48.5 kg and the antibody is administered at a dose of 140 mg once every other week or once every week; wherein the body weight of the subject is greater than or equal to 48.5 kg and less than 51.5 kg and the antibody is administered at a dose of 148.75 mg once every other week or once every week; wherein the body weight of the subject is greater than or equal to 51.5 kg and less than 54.5 kg and the antibody is administered at a dose of 157.5 mg once every other week or once every week; wherein the body weight of the subject is greater than or equal to 54.5 kg and less than 57 kg and the antibody is administered at a dose of 166.25 mg once every other week or once every week; wherein the body weight of the subject is greater than or equal to 57 kg and less than 60.5 kg and the antibody is administered at a dose of 175 mg once every other week or once every week; wherein the body weight of the subject is greater than or equal to 60.5 kg and less than 63 kg and the antibody is administered at a dose of 175 mg once every other week or once every week; wherein the body weight of the subject is greater than or equal to 63 kg and the antibody is administered at a dose of 192.5 mg once every other week or once every week.

This disclosure further provides a method for treating sJIA in a subject in need thereof comprising administering an effective amount of an antibody that specifically binds IL-6R, wherein the antibody that specifically binds to the IL-6R comprises a heavy chain variable region of sequence SEQ ID NO: 1 and a light chain variable region sequence of SEQ ID NO: 2, wherein the antibody is administered at a dose of from about 2 mg/kg to about 2.5 mg/kg per week or from about 3 mg/kg to about 4 mg/kg per two weeks, wherein the body weight of the subject is greater than or equal to 30 kg and less than or equal to 210 kg.

In some embodiments of the method, the body weight of the subject is greater than or equal to 30 kg and less than or equal to 60 kg and wherein the antibody is administered at a dose of about 2 mg/kg every week or a dose of about 3 mg/kg every other week.

In some embodiments of the method, the body weight of the subject is greater than or equal to 30 kg and less than or equal to 60 kg and wherein the antibody is administered at a dose of about 2 mg/kg once every week or a dose of about 3 mg/kg once every other week.

In some embodiments of the method, the body weight of the subject is greater than or equal to 30 kg and less than or equal to 60 kg and wherein the antibody is administered at a dose of 2 mg/kg every week or a dose of 3 mg/kg every other week.

In some embodiments of the method, the body weight of the subject is greater than or equal to 30 kg and less than or equal to 60 kg and wherein the antibody is administered at a dose of 2 mg/kg once every week or a dose of 3 mg/kg once every other week.

In some embodiments of the method, the body weight of the subject is greater than or equal to 30 kg and less than or equal to 210 kg and wherein the antibody is administered at a dose of about 2.5 mg/kg every week or a dose of about 4 mg/kg every other week.

In some embodiments of the method, the body weight of the subject is greater than or equal to 30 kg and less than or equal to 210 kg and wherein the antibody is administered at a dose of about 2.5 mg/kg once every week or a dose of about 4 mg/kg once every other week.

In some embodiments of the method, the body weight of the subject is greater than or equal to 30 kg and less than or equal to 210 kg and wherein the antibody is administered at a dose of 2.5 mg/kg every week or a dose of 4 mg/kg every other week.

In some embodiments of the method, the body weight of the subject is greater than or equal to 30 kg and less than or equal to 210 kg and wherein the antibody is administered at a dose of 2.5 mg/kg once every week or a dose of 4 mg/kg once every other week.

This disclosure shows an antibody for use in treating JIA in a subject in need thereof, wherein the antibody specifically binds IL-6R.

In an embodiment, the JIA is sJIA.

In an embodiment, the antibody that specifically binds to the IL-6R comprises a heavy chain variable region of sequence SEQ ID NO: 1 and the light chain variable region sequence of SEQ ID NO: 2.

In various embodiments, the antibody comprises a VH and a VL, wherein the VH comprises the three CDRs found within the sequence of SEQ ID NO:1 and wherein the VL comprises the three CDRs found within the sequence of SEQ ID NO:2. In various embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In an embodiment, the antibody is sarilumab.

In various embodiments, no other DMARD is administered with the antibody. In some embodiments, at least one other DMARD is administered to the subject. In an embodiment, at least one other DMARD is administered to the subject concurrently with or at the same time as the antibody.

In some embodiments, the subject is suffering from at least one symptom of sJIA such as arthritis in at least 1 joint for at least 6 weeks duration with or preceded by fever lasting at least 2 weeks; evanescent erythematous rash predominantly on the trunk and the extremities; generalized lymphadenopathy; hepatomegaly and/or splenomegaly; polyserositis; weight loss; fatigue; malaise; fever; elevated peripheral WBC count (25 000 to 50 000/mL$^3$); increased platelet count (e.g., $>1\times10^6$), markedly elevated ESR of >100 mm/h; anemia; and/or a high ferritin level relative to a healthy subject. In an embodiment, treating the subject comprises reducing, slowing or halting the progression of, or otherwise ameliorating any one of (or any combination of) these symptoms.

In various embodiments, the subject is suffering from at least one symptom of sJIA, such as limping; stiffness when awakening; reluctance of the subject to use an arm or leg; reduced activity level; quotidian, high spiking (e.g., reaching about 40° C. or at least 40° C.) fever; joint swelling; and/or difficulty with fine motor activities. In an embodiment of the antibody, the at least one symptom of sJIA in the subject is improved after administering the antibody.

In various embodiments, the antibody improves at least one score or metric such as JIA ACR (e.g., JIA ACR30, JIA ACR50, JIA ACR70, JIA ACR90, and JIA ACR100), a JIA ACR component (e.g., count of joints with active arthritis, count of joints with limited range of motion, physician global assessment of disease activity, acute phase reactant such as erythrocyte sedimentation rate or C-reactive protein, childhood health assessment questionnaire, patient (or parent) global assessment of overall well-being,), and/or reduced fever (e.g., in subjects with a fever when the antibody is first administered), reduction from baseline of amount of corticosteroid use (e.g., glucocorticoids), and/or Juvenile Arthritis Disease Activity Score (such as Juvenile Arthritis Disease Activity Score-27). In various embodiments of the antibody, the improvement is characterized by at least one score or metric, such as JIA ACR30, JIA ACR50, JIA ACR70, JIA ACR90, and/or JIA ACR100. In various embodiments of the antibody, the improvement is characterized by at least one score or metric, such as physician global assessment of disease activity score, patient or parent assessment of overall well-being, childhood health assessment questionnaire, number of joints with active arthritis, number of joints with limited motion, high sensitivity C-reactive protein, and/or reduced fever (e.g., in subjects with a fever when the antibody is first administered). In various embodiments, the improvement is characterized by at least one biomarker.

In various embodiments of the method, the antibody causes clinically inactive disease, as defined by Wallace criteria. Wallace criteria are defined as physician global VAS<1/10, no active arthritis, no active uveitis, and CRP<10 mg/L. In various embodiments of the method, the antibody causes clinically inactive disease, as defined by Juvenile Arthritis Disease Activity Score-27-CRP≤1. In various embodiments of the method, the antibody causes clinically inactive disease or low disease activity, as defined by Juvenile Arthritis Disease Activity Score-27-CRP≤3.8.

In an embodiment of the use, the subject has an inadequate response to current treatment and is considered as a candidate for a biologic disease modifying antirheumatic drug.

In an embodiment of the use, the subject is between the ages of about 1 and about 17. In other embodiments, the subject is between the ages of about 4 and about 6 or between the ages of about 12 and about 18.

In an embodiment of the use, the subject has either 5 or more active joints, or 2 active joints and systemic symptoms (e.g., a fever). In an embodiment of the antibody, the subject has either 5 or more active joints or 2 or more active joints and sJIA fever of greater than about 37.5° C. for at least 3 out of any 7 consecutive days despite glucocorticoids at a dose stable for at least 3 days.

In an embodiment of the use, the JIA is pcJIA. In certain embodiments, the pcJIA is extended oligoarticular JIA. In various embodiments, the pcJIA is RF-positive polyarticular JIA. In some embodiments, the pcJIA is RF-negative polyarticular JIA.

In an embodiment, the antibody that specifically binds to the IL-6R comprises a heavy chain variable region of sequence SEQ ID NO: 1 and the light chain variable region sequence of SEQ ID NO: 2.

In various embodiments, the antibody comprises a VH and a VL, wherein the VH comprises the three CDRs found within the sequence of SEQ ID NO:1 and wherein the VL comprises the three CDRs found within the sequence of SEQ ID NO:2. In various embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO:

3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In an embodiment, the antibody is sarilumab.

In various embodiments, no other DMARD is administered with the antibody. In some embodiments, at least one other DMARD is administered to the subject. In an embodiment, at least one other DMARD is administered to the subject concurrently with or at the same time as the antibody.

In some embodiments, the subject is suffering from at least one symptom of RF-positive polyarticular JIA. In some embodiments, the subject is suffering from at least one symptom of RF-positive polyarticular JIA such as deforming symmetrical polyarthritis that can evolve to joint subluxation (e.g., in a wrist and/or thumb); a joint contracture (e.g., proximal and distal interphalangeals, bone overgrowth of proximal interphalangeals, and finger deformities such as swan-neck or boutonniere deformities); chronic synovial inflammation; articular cartilage loss and erosion of juxta-articular bone; normocytic chronic anemia; elevated ESR and C-reactive protein; white blood cell count; asymptomatic arthritis of the cervical spine; and/or micrognathia. In various embodiments, a subject has joint subluxation (e.g., in a wrist and/or thumb) and/or a joint contracture (e.g., proximal and distal interphalangeals, bone overgrowth of proximal interphalangeals, and finger deformities such as swan-neck or boutonniere deformities). In an embodiment, treating the subject comprises reducing, slowing or halting the progression of, or otherwise ameliorating any one of (or any combination of) these symptoms.

In various embodiments, the subject is suffering from at least one symptom of RF-negative polyarticular JIA. In various embodiments, the subject is suffering from at least one symptom of RF-negative polyarticular JIA such as symmetrical polyarthritis with reduced motion, muscle weakness, and/or decreased physical function. In an embodiment, treating the subject comprises reducing, slowing or halting the progression of, or otherwise ameliorating any one of (or any combination of) these symptoms.

In an embodiment, the subject is suffering from at least one symptom of extended oligoarticular JIA, In an embodiment, the subject is suffering from at least one symptom of extended oligoarticular JIA such as an aseptic inflammatory synovitis that affects more than 4 joints (e.g., in larger joints, such as knees, ankles, wrists) after the first 6 months of disease; ambulating with a limp; chronic anterior uveitis; chronic arthritis in a knee or ankle leading to overgrowth of that limb with subsequent leg length discrepancy; muscle atrophy (e.g., in extensor muscles such as vastus lateralis, quadriceps when knee affected); and/or flexion contractures in the knees or wrists. In an embodiment, treating the subject comprises reducing, slowing or halting the progression of, or otherwise ameliorating any one of (or any combination of) these symptoms.

In various embodiments, the subject is suffering from at least one symptom of pcJIA, such as limping; stiffness when awakening; reluctance of the subject to use an arm or leg; reduced activity level; joint swelling; and/or difficulty with fine motor activities.

In an embodiment of the antibody, the at least one symptom of pcJIA in the subject is improved after administering the antibody. In various embodiments of the antibody, the improvement is characterized by at least one score or metric, such as JIA ACR30, JIA ACR50, JIA ACR70, JIA ACR90, and JIA ACR100 defined as improvement in ≥3/6 of the following core set variables with no more than 1/6 worsened: (i) a physician global assessment of disease activity (e.g., by Visual Analogue Scale (VAS)), (ii) patient or parent assessment of overall well-being, (iii) childhood health assessment questionnaire (e.g., by a CHAQ-DI), (iv) number of joints with active arthritis, (v) number of joints with limited motion, and (vi) an index of inflammation (e.g., high sensitivity C-reactive protein). In an embodiment, a JIA ACR30 response is when the ≥3/6 core set variables improve ≥30% from baseline with no more than 1/6 worsened by ≥30%.

In various embodiments of the antibody, the improvement in disease activity is characterized by at least one Juvenile Arthritis Disease Activity Score (such as the Juvenile Arthritis Disease Activity Score-27 that includes 4 measures: Physician global assessment of disease activity, Parent/patient global assessment of well-being, Count of joints with active disease, and Index of inflammation (hs-CRP or ESR level)).

In various embodiments of the antibody, the improvement is characterized by at least one score or metric, such as physician global assessment of disease activity, patient or parent assessment of overall well-being, childhood health assessment questionnaire, number of joints with active arthritis, number of joints with limited motion, high sensitivity C-reactive protein, and/or Juvenile Arthritis Disease Activity Score (such as Juvenile Arthritis Disease Activity Score-27).

In an embodiment of the antibody, the subject is between the ages of about 2 and about 17.

In various embodiments, the subject has had JIA for at least 6 months. In an embodiment, the subject has had arthritis that affected up to 4 joints during at least the first 6 months of the disease and then evolved to 5 or more joints affected after the at least first 6 months. In some embodiments, the subject has had arthritis that affected up to 4 joints during the first 6 months of the disease and then evolved to 5 or more joints affected after the first 6 months.

In an embodiment of the antibody, the subject has at least 5 joints with active arthritis. In an embodiment of the antibody, the subject has arthritis affecting 5 or more joints during the first 6 months of the disease. In an embodiment of the antibody, the arthritis is rheumatoid factor-negative. Alternatively, in an embodiment, the arthritis is rheumatoid factor-positive.

In an embodiment, the antibody is administered subcutaneously. In various embodiments, the antibody is administered every week, or every two weeks.

In an embodiment, the antibody is administered at a dose from about 2 mg/kg to about 4 mg/kg. In an embodiment, the dose is administered once every week or once every 2 weeks. In various embodiments, the antibody is used at a dose of about 2 mg/kg every week, about 2.5 mg/kg every week, about 2 mg/kg every two weeks, about 2.5 mg/kg every two weeks, about 3 mg/kg every two weeks, and about 4 mg/kg every two weeks. In various embodiments, the antibody is used at a dose listed in Tables 1-5.

In some embodiments, the subject has a body weight of at least about 10 kg. In some embodiments, the subject has a body weight less than 30 kg.

In some embodiments, the subject has a body weight of at least about 30 kg.

In some embodiments, the subject has a body weight less than 60 kg.

In various embodiments, the subject is 1-to 17 years old.

In certain embodiments, the subject is a human and the antibody is a human antibody.

This disclosure further provides an antibody for use in treating pcJIA in a subject in need thereof, wherein the antibody specifically binds IL-6R, wherein the antibody that specifically binds to the IL-6R comprises a heavy chain variable region of sequence SEQ ID NO: 1 and a light chain variable region sequence of SEQ ID NO: 2, wherein the antibody is administered at a dose of from about 2 mg/kg to about 4 mg/kg per week or per two weeks, wherein the body weight of the subject is greater than or equal to 10 kg and less than or equal to 60 kg.

In some embodiments, the body weight of the subject is greater than or equal to 30 kg and less than or equal to 60 kg and wherein the antibody is administered at a dose from about 2 mg/kg to about 3 mg/kg every other week or a dose of about 2 mg/kg every week.

In certain embodiments, the body weight of the subject is greater than or equal to 30 kg and less than or equal to 60 kg and wherein the antibody is administered at a dose from about 2 mg/kg to about 3 mg/kg once every other week or a dose of about 2 mg/kg once every week.

In various embodiments, the body weight of the subject is greater than or equal to 30 kg and less than or equal to 60 kg and wherein the antibody is administered at a dose of about 2 mg/kg or about 3 mg/kg every other week.

In some embodiments, the body weight of the subject is greater than or equal to 30 kg and less than or equal to 60 kg and wherein the antibody is administered at a dose of about 2 mg/kg or about 3 mg/kg once every other week.

In various embodiments, the body weight of the subject is greater than or equal to 30 kg and less than or equal to 60 kg and wherein the antibody is administered at a dose of 2 mg/kg or 3 mg/kg every other week or 2 mg/kg every week.

In certain embodiments, the body weight of the subject is greater than or equal to 30 kg and less than or equal to 60 kg and wherein the antibody is administered at a dose of 2 mg/kg or 3 mg/kg once every other week or 2 mg/kg once every week.

In some embodiments, the body weight of the subject is greater than or equal to 10 kg and less than 30 kg and wherein the antibody is administered at a dose from about 2.5 mg/kg to about 4 mg/kg every other week or a dose of about 2.5 mg/kg every week.

In various embodiments, the body weight of the subject is greater than or equal to 10 kg and less than 30 kg and wherein the antibody is administered at a dose from about 2.5 mg/kg to about 4 mg/kg once every other week or a dose of about 2.5 mg/kg once every week.

In certain embodiments, the body weight of the subject is greater than or equal to 10 kg and less than 30 kg and wherein the antibody is administered at a dose of about 2.5 mg/kg or about 4 mg/kg every other week.

In some embodiments, the body weight of the subject is greater than or equal to 10 kg and less than 30 kg and wherein the antibody is administered at a dose of about 2.5 mg/kg or about 4 mg/kg once every other week.

In various embodiments, the body weight of the subject is greater than or equal to 10 kg and less than 30 kg and wherein the antibody is administered at a dose of 2.5 mg/kg or 4 mg/kg every other week or 2.5 mg/kg every week.

In certain embodiments, the body weight of the subject is greater than or equal to 10 kg and less than 30 kg and wherein the antibody is administered at a dose of 2.5 mg/kg or 4 mg/kg once every other week or 2.5 mg/kg once every week.

This disclosure further provides an antibody for use in treating pcJIA in a subject in need thereof, wherein the antibody specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 30 kg and less than 33 kg and the antibody is administered at a dose of 61.25 mg once every other week or once every week; wherein the body weight of the subject is greater than or equal to 33 kg and less than 37.5 kg and the antibody is administered at a dose of 70 mg once every other week or once every week; wherein the body weight of the subject is greater than or equal to 37.5 kg and less than 42 kg and the antibody is administered at a dose of 78.75 mg once every other week or once every week; wherein the body weight of the subject is greater than or equal to 42 kg and less than 46.5 kg and the antibody is administered at a dose of 87.5 mg once every other week or once every week; wherein the body weight of the subject is greater than or equal to 46.5 kg and less than 50.5 kg and the antibody is administered at a dose of 96.25 mg once every other week or once every week; wherein the body weight of the subject is greater than or equal to 50.5 kg and less than 55 kg and the antibody is administered at a dose of 105 mg once every other week or once every week; wherein the body weight of the subject is greater than or equal to 55 kg and less than 59.5 kg and the antibody is administered at a dose of 113.75 mg once every other week or once every week; wherein the body weight of the subject is greater than or equal to 59.5 kg and less than 64 kg and the antibody is administered at a dose of 122.5 mg once every other week or once every week; wherein the body weight of the subject is greater than or equal to 64 kg and less than 68 kg and the antibody is administered at a dose of 131.25 mg once every other week or once every week; wherein the body weight of the subject is greater than or equal to 68 kg and less than 72.5 kg and the antibody is administered at a dose of 140 mg once every other week or once every week; or wherein the body weight of the subject is greater than or equal to 72.5 kg and the antibody is administered at a dose of 148.75 mg once every other week or once every week.

This disclosure further-provides an antibody for use in treating pcJIA in a subject in need thereof, wherein the antibody specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 30 kg and less than 31 kg and the antibody is administered at a dose of 87.5 mg once every other week or once every week; wherein the body weight of the subject is greater than or equal to 31 kg and less than 34 kg and the antibody is administered at a dose of 96.25 mg once every other week or once every week; wherein the body weight of the subject is greater than or equal to 34 kg and less than 37 kg and the antibody is administered at a dose of 105 mg once every other week or once every week; wherein the body weight of the subject is greater than or equal to 37 kg and less than 39.5 kg and the antibody is administered at a dose of 113.75 mg once every other week or once every week; wherein the body weight of the subject is greater than or equal to 39.5 kg and less than 42.5 kg and the antibody is administered at a dose of 122.5 mg once every other week or once every week; wherein the body weight of the subject is greater than or equal to 425 kg and less than 45 kg and the antibody is administered at a dose of 131.25 mg once every other week or once every week; wherein the body weight of the subject is greater than or equal to 45 kg and less than 48.5 kg and the antibody is administered at a dose of 140 mg once every other week or once every week; wherein the body weight of the subject is greater than or equal to 48.5 kg and less than 51.5 kg and the antibody is administered at a dose of 148.75 mg once every other week or once every week; wherein the body weight of the subject is greater than or equal to 51.5 kg and less than 54.5 kg and the antibody is administered at a dose of 157.5 mg once every other week or once every week; wherein the body weight of the subject is greater than or equal to 54.5 kg and less than 57 kg and the antibody is administered at a dose of 166.25 mg once every other week or once every week; wherein the body weight of the subject is greater than or equal to 57 kg and less than 63 kg and the antibody is administered at a dose of 175 mg once every other week or once every week; wherein the body weight of the subject is greater than or equal to 63 kg and the antibody is administered at a dose of 192.5 mg once every other week or once every week.

This disclosure further provides an antibody for use in treating pcJIA in a subject in need thereof, wherein the antibody specifically binds IL-6R, wherein the antibody that specifically binds to the IL-6R comprises a heavy chain variable region of sequence SEQ ID NO: 1 and a light chain-variable region sequence of SEQ ID NO: 2, wherein the body weight of the subject is greater than or equal to 10 kg and less than 12.5 kg and the antibody is administered at a dose of 26.25 mg once every other week or once every week; wherein the body weight of the subject is greater than or equal to 12.5 kg and less than 16 kg and the antibody is administered at a dose of 35 mg once every other week or once every week; wherein the body weight of the subject is greater than or equal to 16 kg and less than 19.5 kg and the antibody is administered at a dose of 43.75 mg once every other week or once every week; wherein the body weight of the subject is greater than or equal to 19.5 kg and less than 23 kg and the antibody is administered at a dose of 52.5 mg once every other week or once every week; wherein the body weight of the subject is greater than or equal to 23 kg and less than 26.5 kg and the antibody is administered at a dose of 61.25 mg once every other week or once every week; wherein the body weight of the subject is greater than or equal to 26.5 kg and less than 30 kg and the antibody is administered at a dose of 70 mg once every other week or once every week; wherein the body weight of the subject is greater than or equal to 30 kg and less than 37.5 kg and the antibody is administered at a dose of 70 mg once every other week or once every week; wherein the body weight of the subject is greater than or equal to 37.5 kg and less than 42 kg and the antibody is administered at a dose of 78.75 mg once every other week or once every week; wherein the body weight of the subject is greater than or equal to 42 kg and less than 46.5 kg and the antibody is administered at a dose of 87.5 mg once every other week or once every week; wherein the body weight of the subject is greater than or equal to 46.5 kg and less than 50.5 kg and the antibody is administered at a dose of 96.25 mg once every other week or once every week; wherein the body weight of the subject is greater than or equal to 50.5 kg and less than 55 kg and the antibody is administered at a dose of 105 mg once every other week or once every week; wherein the body weight of the subject is greater than or equal to 55 kg and less than 59.5 kg and the antibody is administered at a dose of 113.75 mg once every other week or once every week; wherein the body weight of the subject is greater than or equal to 59.5 kg and less than 64 kg and the antibody is administered at a dose of 122.5 mg once every other week or once every week; wherein the body weight of the subject is greater than or equal to 64 kg and less than 68 kg and the antibody is administered at a dose of 131.25 mg once every other week or once every week; wherein the body weight of the subject is greater than or equal to 68 kg and less than 72.5 kg and the antibody is administered at a dose of 140 mg once every other week or once every week; or wherein the body weight of the subject is greater than or equal to 72.5 kg and the antibody is administered at a dose of 148.75 mg once every other week or once every week.

This disclosure further provides an antibody for use in treating pcJIA in a subject in need thereof, wherein the antibody specifically binds IL-6R, wherein the antibody that specifically binds to the IL-6R comprises a heavy chain variable region of sequence SEQ ID NO: 1 and a light chain variable region sequence of SEQ ID NO: 2, wherein the body weight of the subject is greater than or equal to 10 kg and less than 12.5 kg and the antibody is administered at a dose of 43.75 mg once every other week or once every week; wherein the body weight of the subject is greater than or equal to 12.5 kg and less than 14.5 kg and the antibody is administered at a dose of 52.5 mg once every other week or once every week; wherein the body weight of the subject is greater than or equal to 14.5 kg and less than 16.5 kg and the antibody is administered at a dose of 61.25 mg once every other week or once every week; wherein the body weight of the subject is greater than or equal to 16.5 kg and less than 19 kg and the antibody is administered at a dose of 70 mg once every other week or once every week; wherein the body weight of the subject is greater than or equal to 19 kg and less than 21 kg and the antibody is administered at a dose of 78.75 mg once every other week or once every week; wherein the body weight of the subject is greater than or equal to 21 kg and less than 23.5 kg and the antibody is administered at a dose of 87.5 mg once every other week or once every week; wherein the body weight of the subject is greater than or equal to 23.5 kg and less than 25.5 kg and the antibody is administered at a dose of 96.25 mg once every other week or once every week; wherein the body weight of the subject is greater than or equal to 25.5 kg and less than 27.5 kg and the antibody is administered at a dose of 105 mg once every other week or once every week; wherein the body weight of the subject is greater than or equal to 27.5 kg and less than 30 kg and the antibody is administered at a dose of 113.75 mg once every other week or once every week; wherein the body weight of the subject is greater than or equal to 30 kg and less than 39.5 kg and the antibody is administered at a dose of 113.75 mg once every other week or once every week; wherein the body weight of the subject is greater than or equal to 39.5 kg and less than 42.5 kg and the antibody is administered at a dose of 122.5 mg once every other week or once every week; wherein the body weight of the subject is greater than or equal to 42.5 kg and less than 45 kg and the antibody is administered at a dose of 131.25 mg once every other week or once every week; wherein the body weight of the subject is greater than or equal to 45 kg and less than 48.5 kg and the antibody is administered at a dose of 140 mg once every other week or once every week; wherein the body weight of the subject is greater than or equal to 48.5 kg and less than 51.5 kg and the antibody is administered at a dose of 148.75 mg once every other week or once every week; wherein the body weight of the subject is greater than or equal to 51.5 kg and less than 54.5 kg and the antibody is administered at a dose of 157.5 mg once every other week or once every week; wherein the body weight of the subject is greater than or equal to 54.5 kg and less than 57 kg and the antibody is administered at a dose of 166.25 mg once every other week or once every week; wherein the body weight of the subject is greater than or equal to 57 kg and less than 60.5 kg and the antibody is administered at a dose of 175 mg once every other week or once every week; wherein the body weight of the subject is greater than or equal to 60.5 kg and less than 63 kg and the antibody is administered at a dose of 175 mg once every other week or once every week; wherein the body weight of the subject is greater than or equal to 63 kg and the antibody is administered at a dose of 192.5 mg once every other week or once every week.

This disclosure further provides an antibody for use in treating sJIA in a subject in need thereof, wherein the antibody specifically binds IL-6R, wherein the antibody that specifically binds to the IL-6R comprises a heavy chain variable region of sequence SEQ ID NO: 1 and a light chain variable region sequence of SEQ ID NO: 2, wherein the antibody is administered at a dose of from about 2 mg/kg to about 2.5 mg/kg per week or from about 3 mg/kg to about 4 mg/kg per two weeks, wherein the body weight of the subject is greater than or equal to 30 kg and less than or equal to 210 kg.

In some embodiments, the body weight of the subject is greater than or equal to 30 kg and less than or equal to 60 kg and wherein the antibody is administered at a dose of about 2 mg/kg every week or a dose of about 3 mg/kg every other week.

In various embodiments, the body weight of the subject is greater than or equal to 30 kg and less than or equal to 60 kg and wherein the antibody is administered at a dose of about 2 mg/kg once every week or a dose of about 3 mg/kg once every other week.

In certain embodiments, the body weight of the subject is greater than or equal to 30 kg and less than or equal to 60 kg and wherein the antibody is administered at a dose of 2 mg/kg every week or a dose of 3 mg/kg every other week.

In some embodiments, the body weight of the, subject is greater than or equal to 30 kg and less than or equal to 60 kg and wherein the antibody is administered at a dose of 2 mg/kg once every week or a dose of 3 mg/kg once every other week.

In various embodiments, the body weight of the subject is greater than or equal to 30 kg and less than or equal to 210 kg and wherein the antibody is administered at a dose of about 2.5 mg/kg every week or a dose of about 4 mg/kg every other week.

In certain embodiments, the body weight of the subject is greater than or equal to 30 kg and less than or equal to 210 kg and wherein the antibody is administered at a dose of about 2.5 mg/kg once every-week or a dose of about 4 mg/kg once every other week.

In some embodiments, the body weight of the subject is greater than or equal to 30 kg and less than or equal to 210 kg and wherein the antibody is administered at a dose of 2.5 mg/kg every week or a dose of 4 mg/kg every other week.

In various embodiments, the body weight of the subject is greater than or equal to 30 kg and less than or equal to 210 kg and wherein the antibody is administered at a dose of 2.5 mg/kg once every week or a dose of 4 mg/kg once every other week.

In certain embodiments, the antibody is in a pharmaceutical composition. In some embodiments, is an aqueous solution with a volume of less than about 1 mL. In various embodiments, is an aqueous solution with a volume of from about 0.5 to 1 mL. In certain embodiments, is an aqueous solution with a volume of from about 0.75 to 1 mL. In some embodiments, is an aqueous solution with a volume of from about 0.5 to 0.75 mL. In various embodiments, is an aqueous solution with a volume of from about 0.15 to 0.25 mL. In certain embodiments, is an aqueous solution with a volume of from about 0.25 to 0.5 mL.

Notes: All patients must have completed an end of treatment (EOT) Visit (V27, Week 156) at the completion of treatment (last IMP injection at Week 154 for Dose Cohort 1 and 2 and at Week 155 for Dose Cohort 3) or at the time of early permanent treatment discontinuation (regardless of treatment phase).

For a patient who discontinued study treatment prematurely during the 12-week core treatment phase, an additional PK Visit 2 weeks after the EOT Visit was required for blood sampling (V88) and IL-6 and total sIL-6Rα was measured at EOT Visit.

All patients must have completed a post-treatment follow-up Visit (V28) 6 weeks after the EOT Visit, ie, Week 162 for patients who had completed treatment and EOT+6 weeks for patients who had discontinued treatment prematurely. However, patients who had discontinued treatment prematurely during the core treatment phase should have continued to return for the study visits as protocol scheduled without treatment administration through Week 12 (as per FDA guidelines for missing data).

Figure 1:
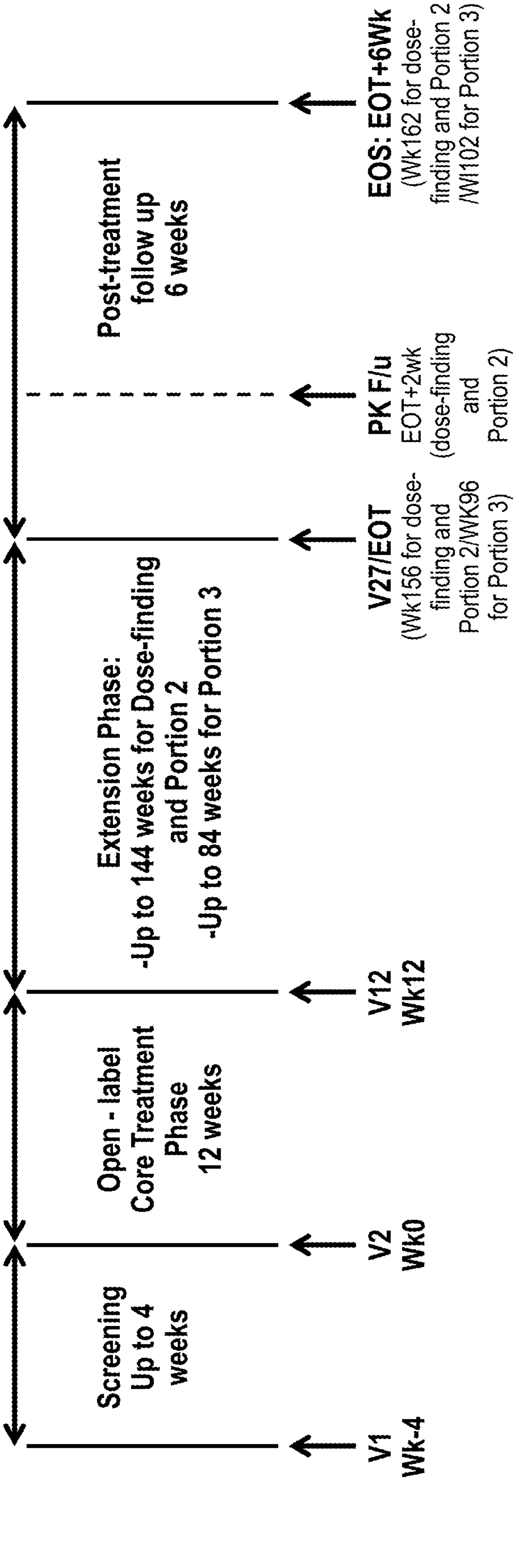
FIG. 1 is a drawing of a study flow chart for the two dose cohorts for the multinational, multicenter, open-label, 2-phase, and 2-portion study in children and adolescents aged 2 to 17 years with pcJIA who had inadequate response to or who were intolerant to current therapy or who were considered as a candidate for a biologic DMARD. The 2 phases of the study were an initial 12-week core treatment phase followed by a 144-week extension phase. Abbreviations: EOS=end of study, EOT=end of treatment, FDA=Food and Drug Administration, f/u=follow-up, IMP=investigational medicinal product, PK=pharmacokinetic, sIL-6Rα=soluble interleukin 6 receptor α subunit, V=visit, Wk=week.
Figure 2:
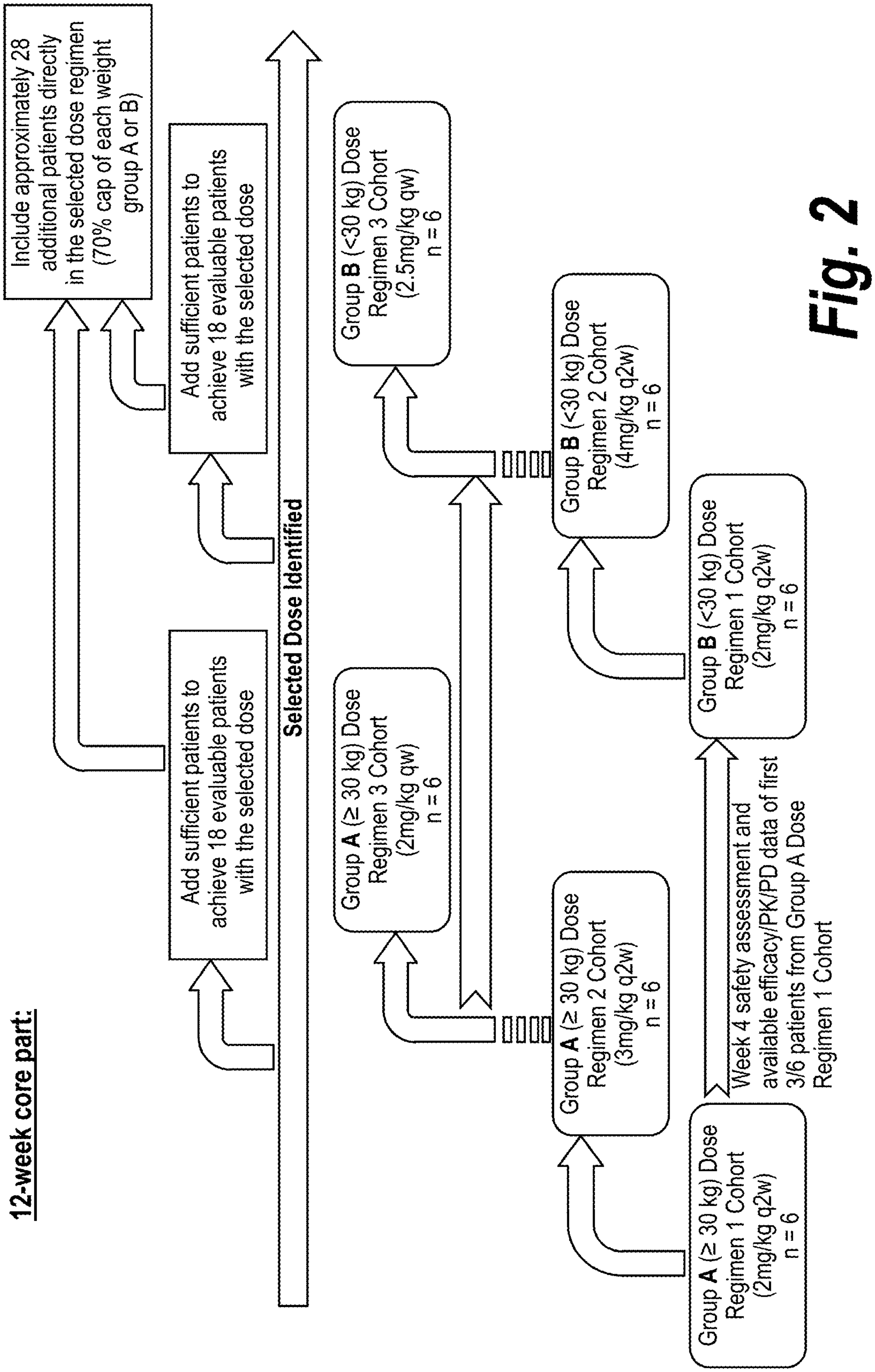

FIG. 2 is a graph study design of the 12-week core treatment phase described in FIG. 1.

Figure 3:
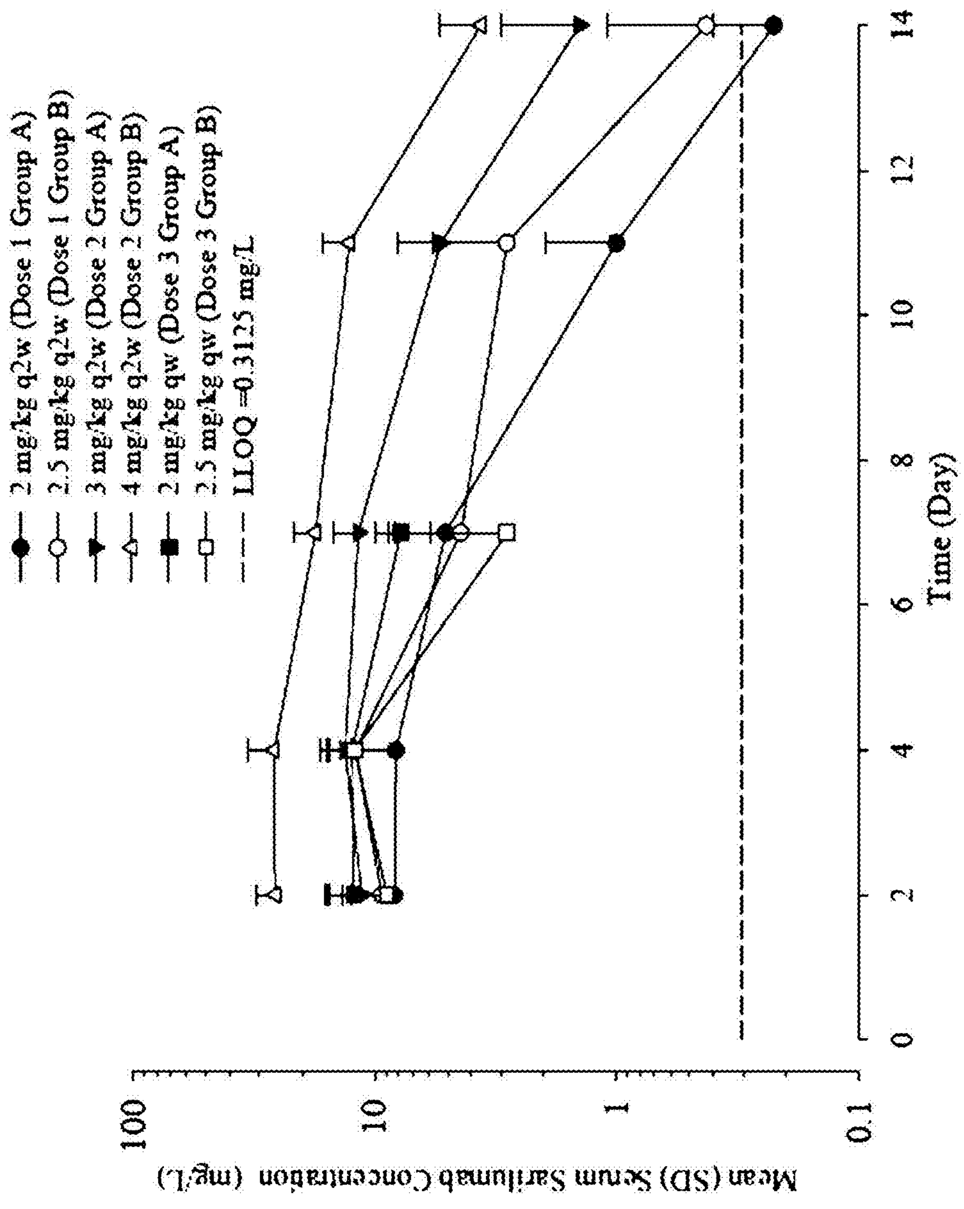

FIG. 3 is a graph showing the mean (with standard deviation; SD) functional sarilumab concentrations in serum over a period of time after the first subcutaneous administration of sarilumab in pcJIA patients. Abbreviations in the graph include: q2w=once every other week, qw=once every week, SC=subcutaneous, SD=standard deviation. Post-treatment concentrations below LLOQ were replaced by LLOQ/2.

Figure 4:
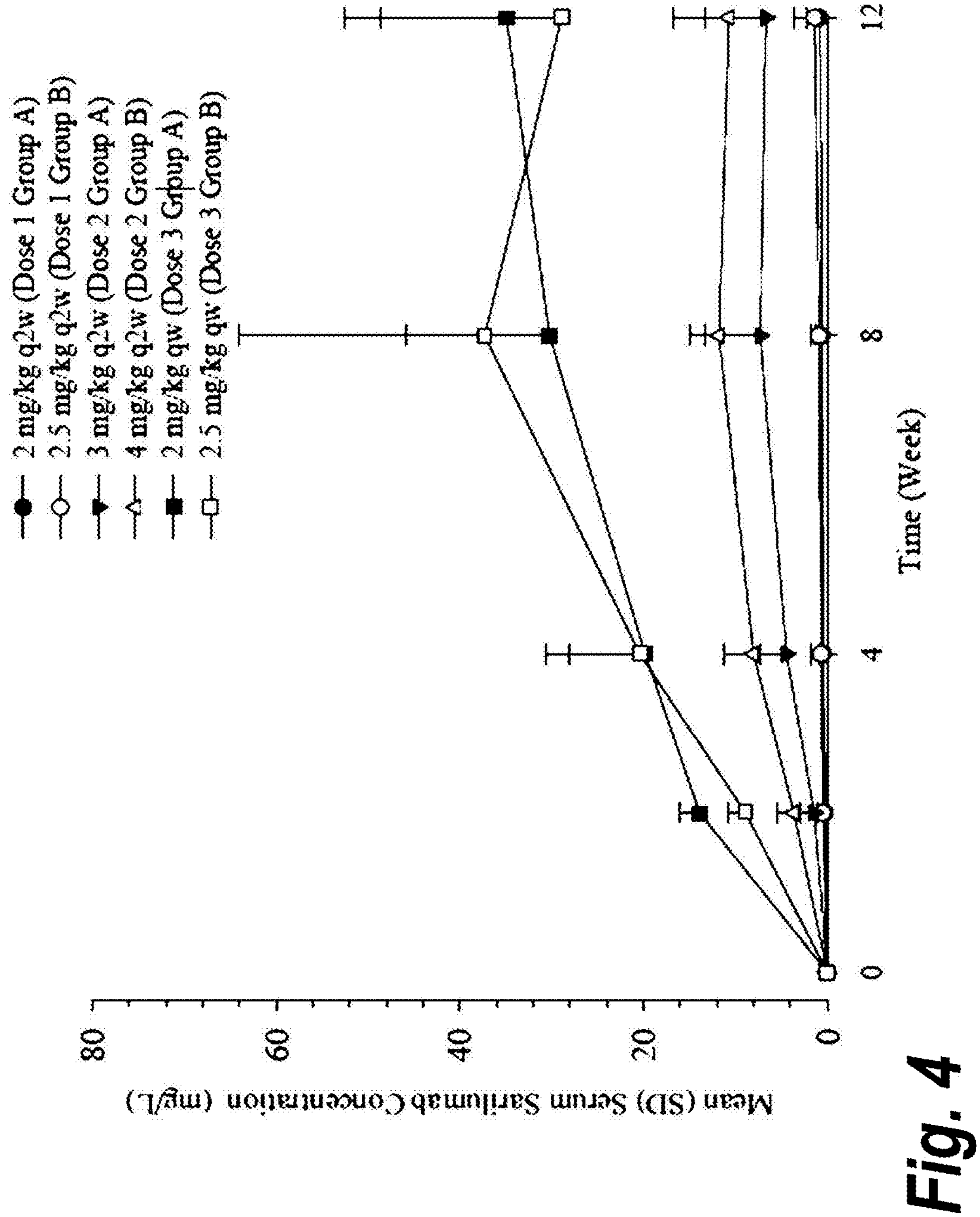

FIG. 4 is a graph showing the mean (with standard deviation; SD) observed sarilumab trough concentrations in serum over a period of time after the first subcutaneous administration of sarilumab in pcJIA patients.

Figure 5:
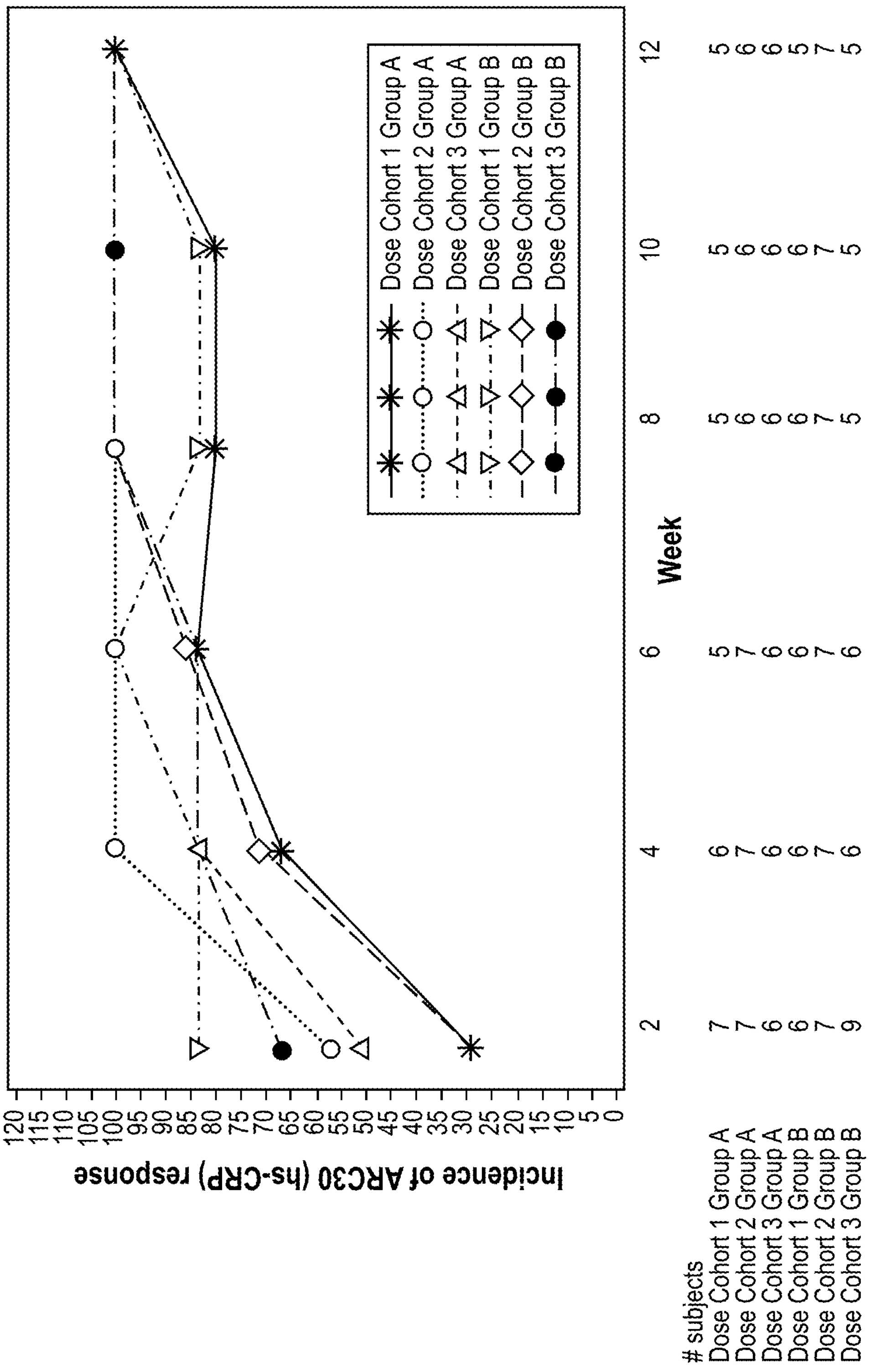

FIG. 5 is a graph showing the incidence of JIA ACR30 (hs-CRP) response (as observed while on-treatment) during the 12-week core treatment phase.

Figure 6:
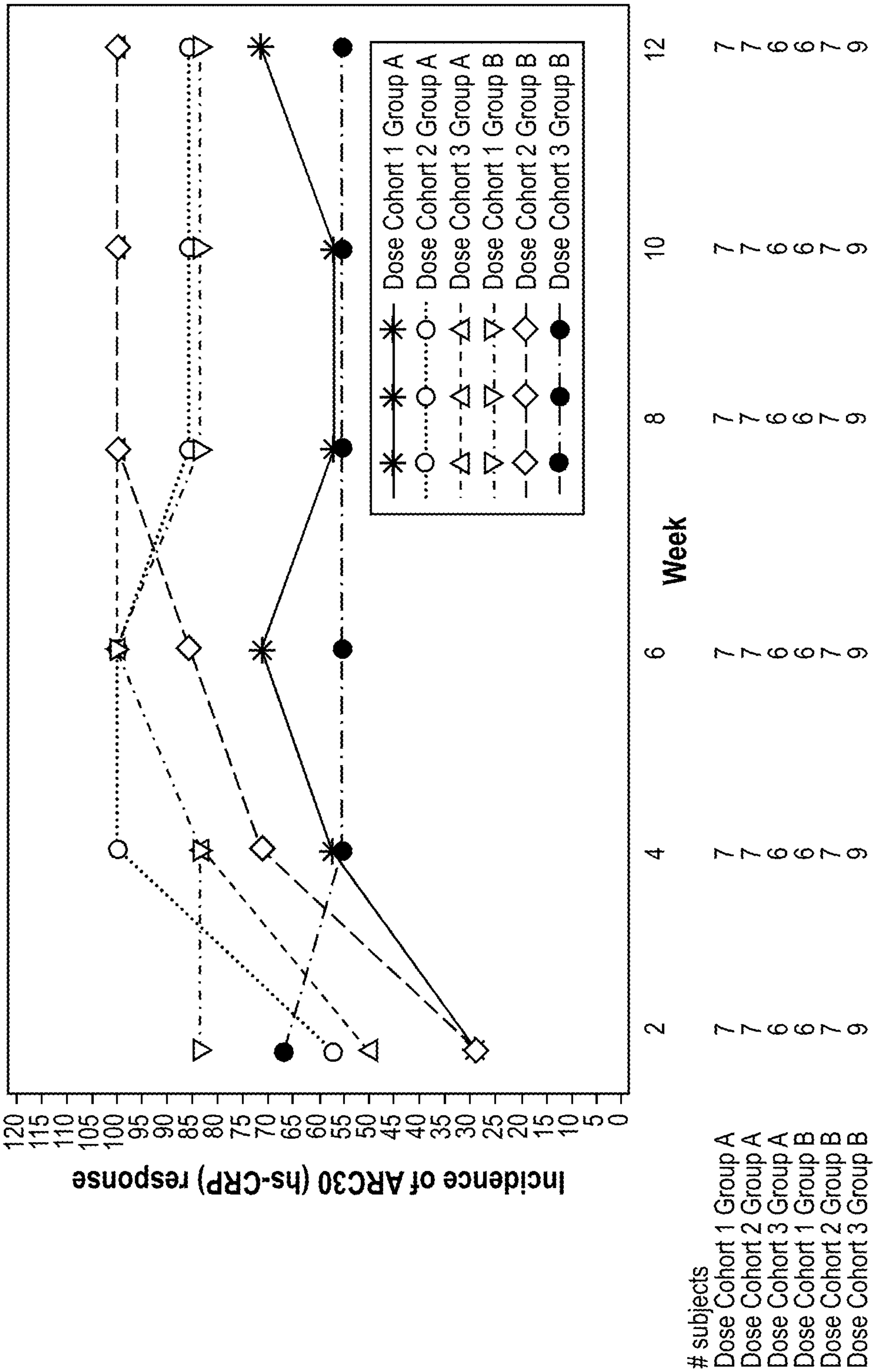

FIG. 6 is a graph showing the incidence of JIA ACR30 (hs-CRP) response (nonresponder imputation approach) during the 12-week core treatment phase.

Figure 7:
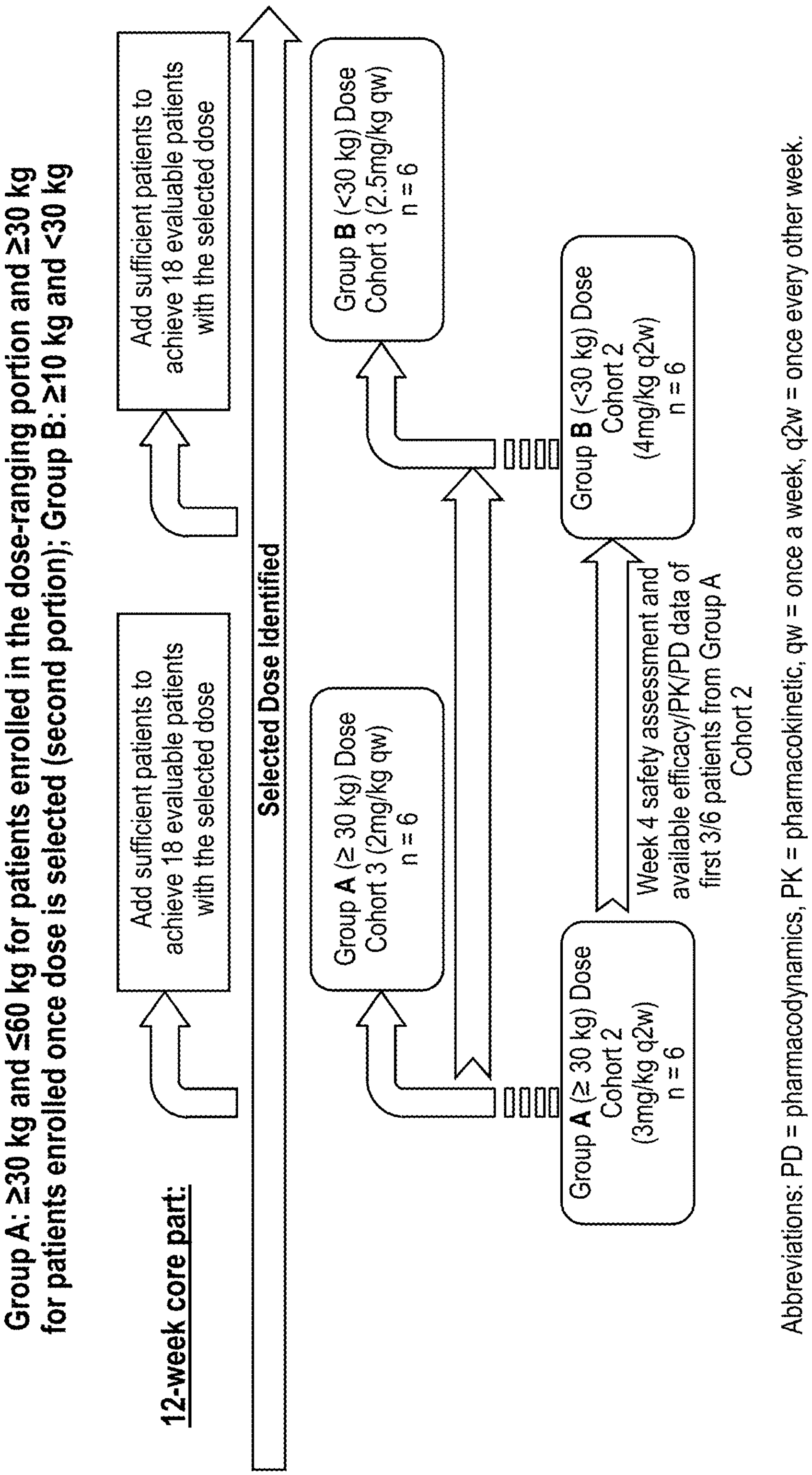

FIG. 7 is a drawing of a study flow chart for the two dose cohorts for a multinational, multicenter, open-label, sequential, 2-phase, study in children and adolescents, aged 1 to 17 years (or country specified age requirement), with sJIA who have inadequate response to or who are intolerant to standard therapy and who will receive SC injections of sarilumab administrated q2w or qw.

Figure 8:
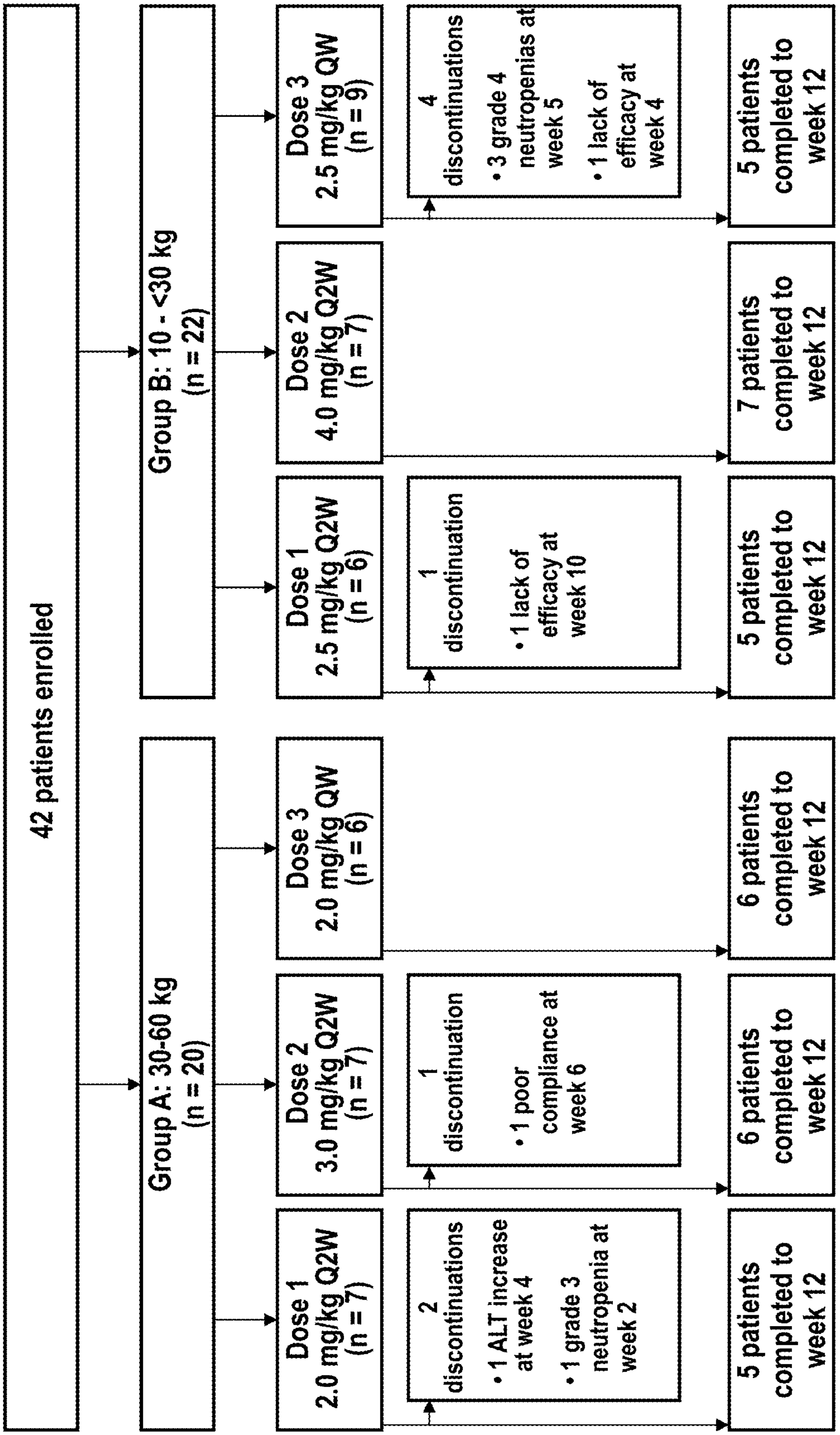

FIG. 8 is a drawing of a study flow chart showing patient disposition. ALT=alanine aminotransferase; QW=every week; Q2W=every 2 weeks.

FIGS. 9A-9D are graphs showing proportions of patients achieving JIA ACR response thresholds and mean change from baseline to week 12 in JADAS-27-CRP, as observed while on-treatment. CRP=C-reactive protein; JADAS-27-CRP=juvenile arthritis disease activity score with 27-joint count and CRP; JIA ACR30/70/90=juvenile idiopathic arthritis American College of Rheumatology 30/70/90% response; SE=standard error.

Figure 10A:
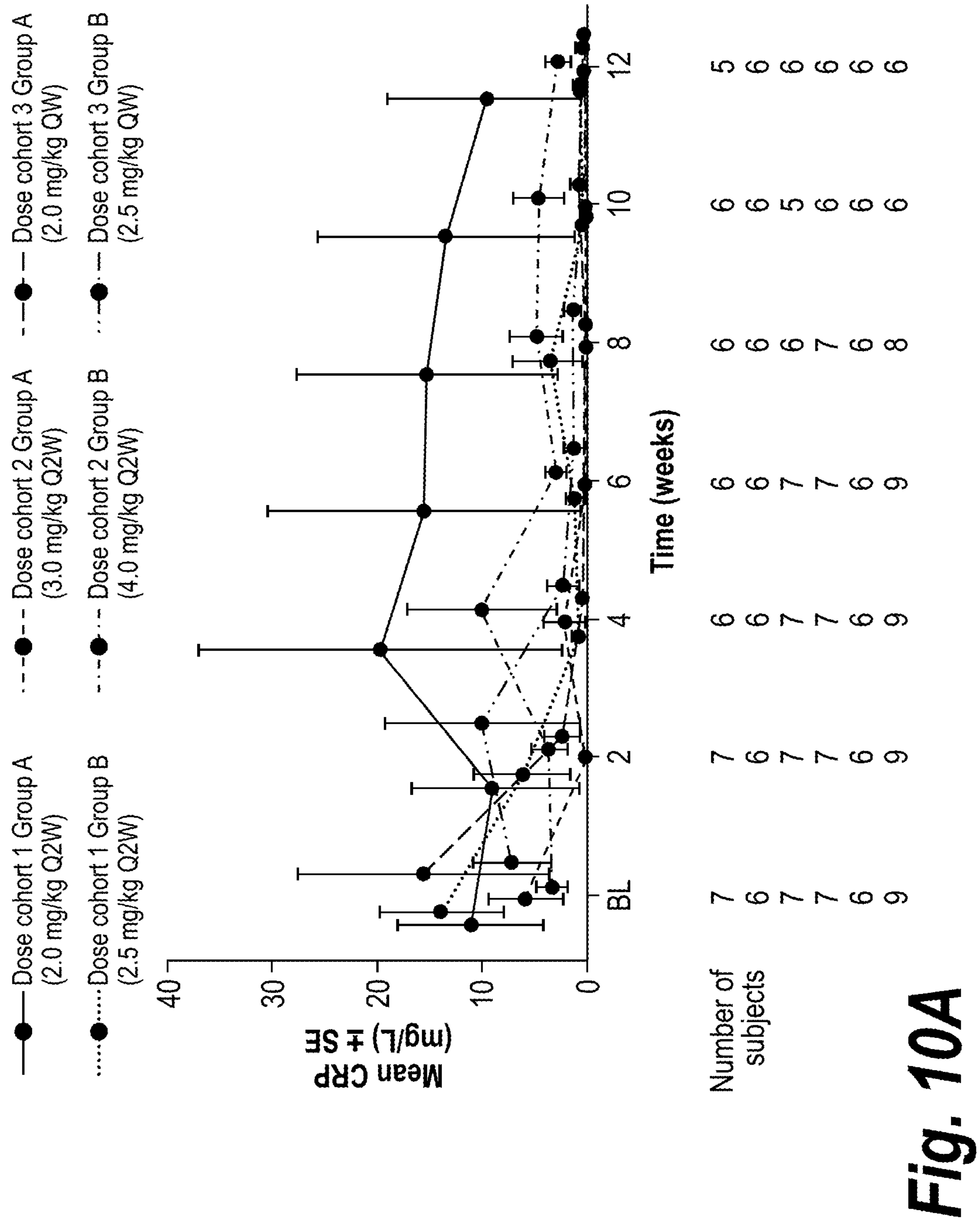
Figure 10B:
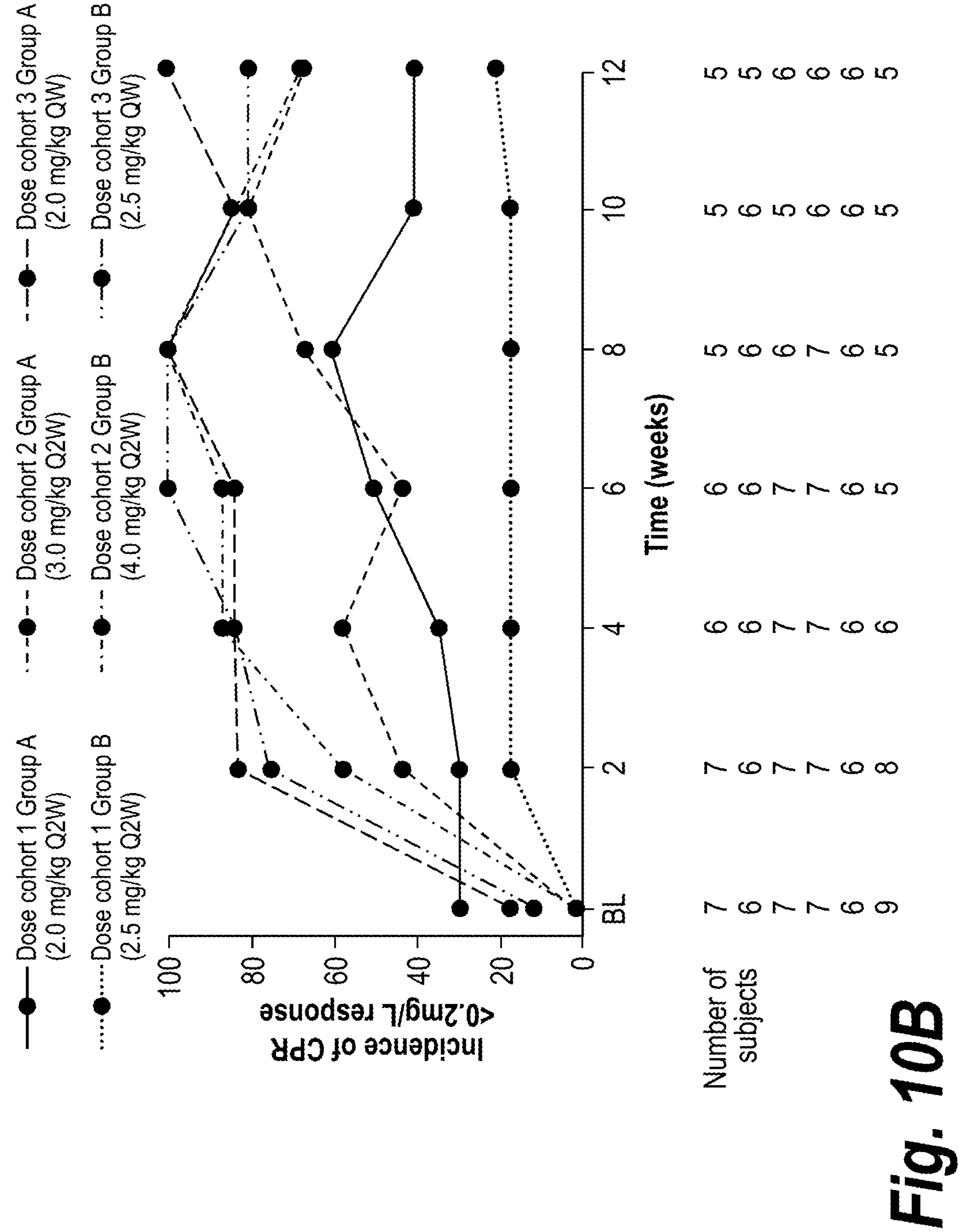

FIGS. 10A-10B are graphs of the mean CRP concentration and proportion of patients with undetectable CRP (<0.2 mg/L) in core treatment phase, as observed while on-treatment. BL=baseline; CRP=C-reactive protein; SE=standard error.

Figure 11A:
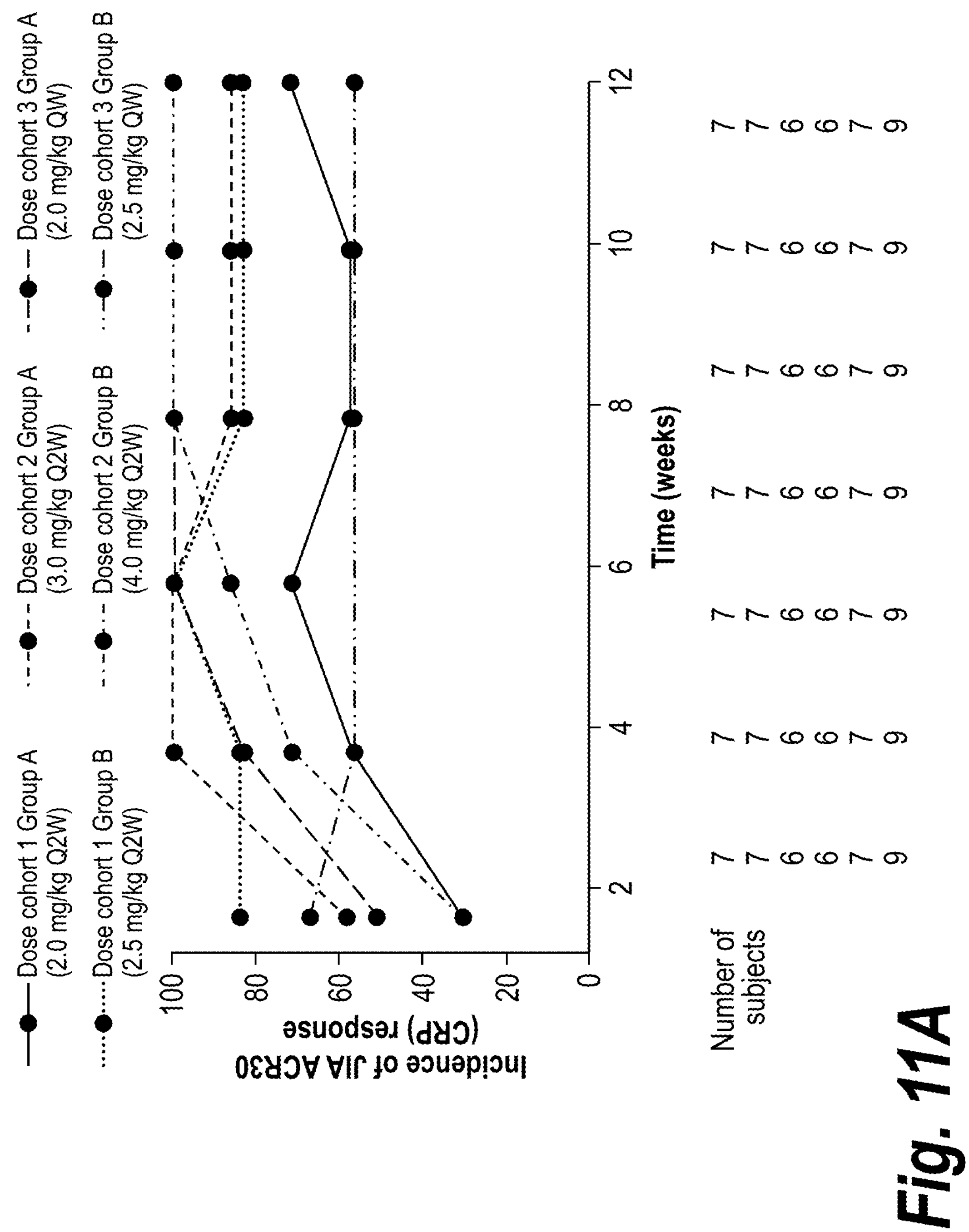
Figure 11B:
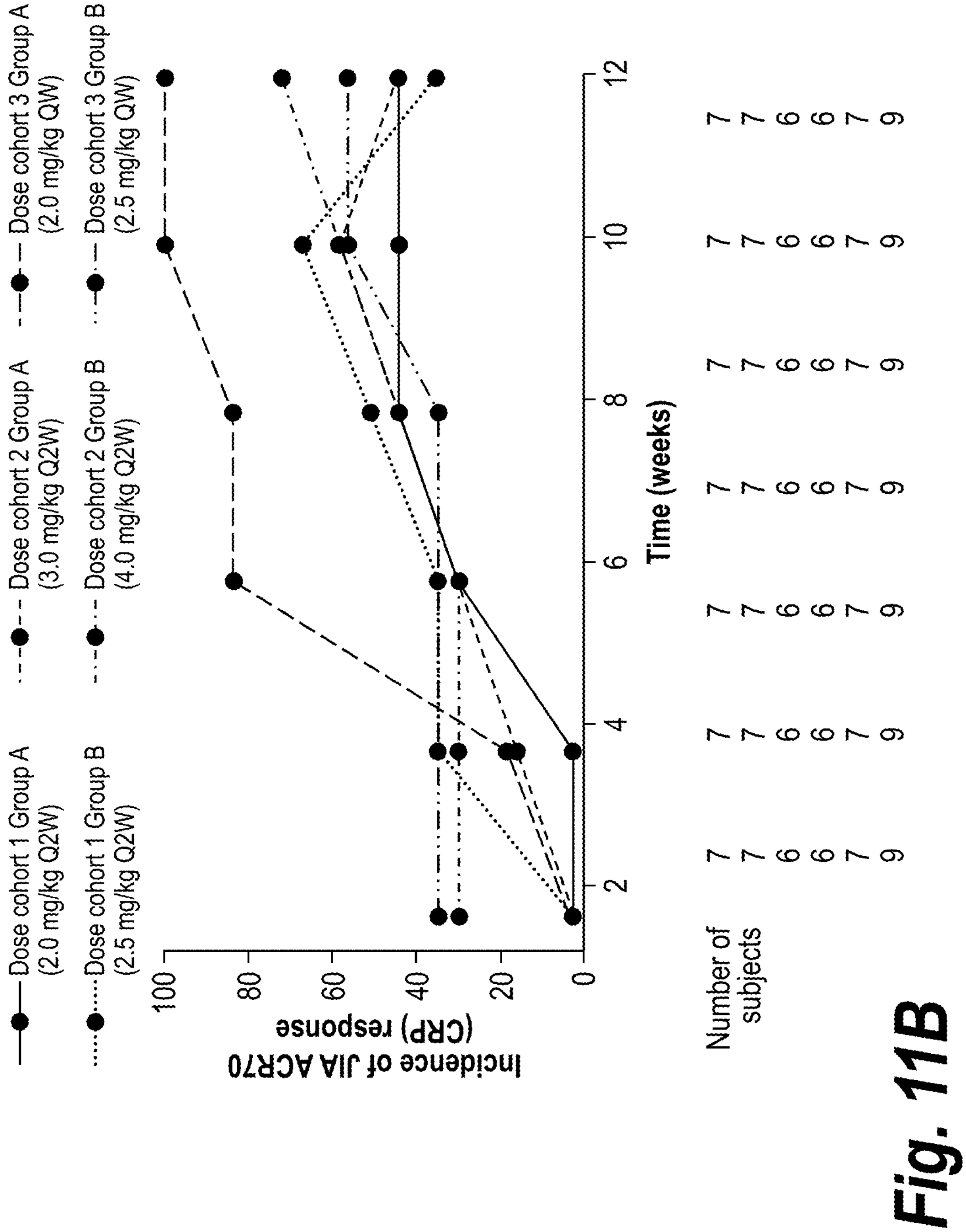
Figure 11C:
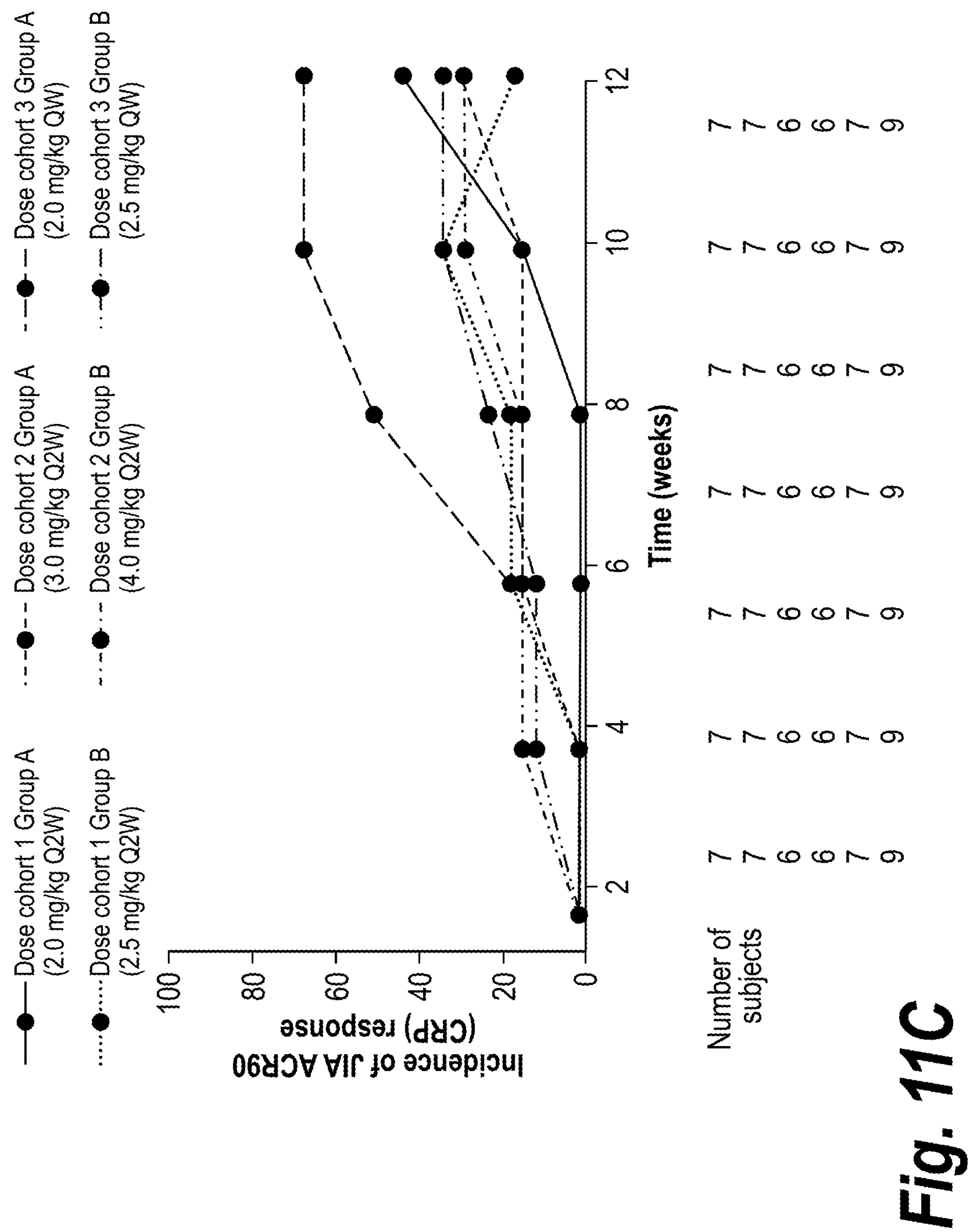

FIGS. 11A-11C are graphs of the proportions of patients achieving JIA ACR responses, calculated by nonresponder imputation. CRP=C-reactive protein. JIA ACR30/70/90=juvenile idiopathic arthritis American College of Rheumatology 30/70/90% response.

DETAILED DESCRIPTION

The disclosure provides pharmaceutical compositions and methods of using these compositions for the treatment of JIA (e.g., sJIA and pcJIA), and the improvement of at least one symptom of the disorder. These compositions include at least one antibody that specifically binds human interleukin-6 receptor (hIL-6R).

The efficacy of the antibody for treating JIA is typically measured using the standard methods in the field, commonly used by the clinicians and the rheumatologists, for example Juvenile idiopathic arthritis ACR30/50/70/90/100, an ACR component, change in glucocorticoid use (for sJIA), and Juvenile Arthritis Disease Activity Score-27 (JADAS) See Consolaro et al. Development and Validation of a Composite Disease Activity Score for Juvenile Idiopathic Arthritis. *Arthritis & Rheumatism.* 2009 May; 61(5):658-666) incorporated by reference herein in its entirety. JIA ACR is well known to clinicians and can readily be determined by those of ordinary skill in the art of JIA diagnosis and treatment. JIA ACR is also known as (and is synonymous with) pediatric ACR. Non-limiting descriptions relating to JIA ACR are provided in Giannini et al. (1994) "Preliminary core of set of outcome variables for use in JRA clinical trials" *Arthritis Rheum.* 37 Suppl 9:S428, which is incorporated herein by reference for all purposes.

As used within the claims the Summary, and the Detailed Description herein, the term "about" in quantitative terms refers to plus or minus 10% of the value it modifies (rounded up to the nearest whole number if the value is not subdividable, such as a number of molecules or nucleotides). For example, the phrase "about 100 mg" would encompass 90 mg to 110 mg, inclusive; the phrase "about 2500 mg" would encompass 2250 mg to 2750 mg. When applied to a percentage, the term "about" refers to plus or minus 10% relative to that percentage. For example, the phrase "about 20%" would encompass 18-22% and "about 80%" would encompass 72-88%, inclusive. Moreover, where "about" is used herein in conjunction with a quantitative term it is understood that in addition to the value plus or minus 10%, the exact value of the quantitative term is also contemplated and described. For example, the term "about 23%" expressly contemplates, describes, and includes exactly 23%.

It is to be noted that the term "a" or "an" entity refers to one or more of that entity; for example, "a symptom," is understood to represent one or more symptoms. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

JIA

Arthritis is swelling within a joint, or limitation in the range of joint movement with joint pain or tenderness, which persists for at least 6 weeks, is observed by a physician, and is not due to primarily mechanical disorders. (Petty R E, et al. International League of Associations for Rheumatology Classification of Juvenile Idiopathic Arthritis: Second Revision, Edmonton, 2001. J Rheumatol. 2004 February; 31(2): 390-2), incorporated by reference herein in its entirety).

JIA is an autoimmune disorder involving joint inflammation. The disorder typically presents in patients before their $16^{th}$ birthday, and can continue into adulthood. JIA affects 1 child in every 1000. Typical symptoms include limping, stiffness when awakening, reluctance of the child to use an arm or leg, reduced activity level, persistent fever, joint swelling, and difficulty with fine motor activities. JIA comprises 7 subtypes (e.g., systemic JIA RF-positive polyarticular JIA, and RF-negative polyarticular JIA) categorized by age of onset, range, and disease characteristics in the first 6 months after onset as defined by the ILAR in 2001.

In sJIA, joint inflammation may not manifest at the onset of the illness when prominent signs are extra-articular, delaying the diagnosis, but eventually develops in most patients in a polyarticular pattern. Clinical features (defined by the ILAR classification) include arthritis with/proceeded by daily fever for at least 2 weeks and ≥one of: evanescent salmon-colored erythematous rash, generalized lymphadenopathy, hepato/splenomegaly and serositis. In certain embodiments, exclusion criteria for sJIA include psoriasis or psoriasis in a first grade relative; presence of human leukocyte antigen-B27 (HLA-B27); ankylosing spondylitis, enthesitis-associated arthritis, sacroiliitis accompanied by chronic inflammatory bowel disease, Reiter's disease in a first grade relative; and presence of rheumatoid factors (RFs) on at least 2 occasions at least 3 months apart. sJIA represents 10% of JIA cases and is known to occur at any age during childhood and adolescence. In terms of outcomes, patients with sJIA are known: to have a 50% remittance in year 1; 25% have severe destructive joint disease; general growth abnormalities; and macrophage activation syndrome.

sJIA fever is classically a quotidian spiking fever and may be accompanied by one or more of the following: evanescent (nonfixed) erythematous rash, generalized lymph node enlargement, hepatomegaly and/or splenomegaly, and serositis. (Petty R E, et al. International League of Associations for Rheumatology Classification of Juvenile Idiopathic Arthritis: Second Revision, Edmonton, 2001. J Rheumatol.

2004 February; 31(2):390-2). Onset of sJIA has a peak in patients 4 to 6 years of age and can occasionally occur in adolescence in patients 12 to 18 years of age.

As used herein the term "polyarticular-course juvenile idiopathic arthritis" or "pcJIA" includes RF-positive polyarticular JIA, RF-negative polyarticular JIA, and extended oligoarticular JIA.

Polyarticular JIA, a subtype of pcJIA, affects at least 5 joints. Both large and small joints can be involved, and often in symmetric bilateral distribution, and often involving weight-bearing joints and small joints in the hands. Low grade fevers can accompany the arthritis.

Presence of rheumatoid factor (RF) differentiates the 2 forms of polyarticular JIA: RF-positive and RF-negative polyarticular JIA: Rheumatoid factor (RF)-positive polyarticular JIA represents a relatively small proportion of all children and adolescents with JIA (3%-5%) but it is the only JIA subgroup resembling adult rheumatoid arthritis (RA), a deforming symmetrical polyarthritis, due to chronic synovial inflammation, articular cartilage loss and erosion of juxta-articular bone. Features of RF-positive pcJIA are the mean onset at age of 12 to 14 years, the marked female gender predominance (13:1 female/male ratio), symmetrical involvement of small and large joints, production of polyclonal IgM RF or anti-CCP antibodies, genetic susceptibility (association with the HLA-DR4 allele), a clinical course marked by normocytic chronic anemia (reticuloendothelial block), and acute phase proteins (elevated ESR and C-reactive protein) that rarely remits spontaneously, as well as elevated white blood cell count. The association with firm, mobile and nonpainful rheumatoid nodule formation is possible but rare. Laboratory findings are expected to be more severe than those associated with oligoarthritis. Long-term sequelae include joint subluxation (wrists and thumbs), joint contractures (proximal and distal interphalangeals, bone overgrowth of proximal interphalangeals, and finger deformities (e.g., swan-neck or boutonniere deformities). Asymptomatic arthritis of the cervical spine, associated with decreased extension, can lead to subluxation, typically of C2 vertebrae on C3 and fusion of the posterior vertebral elements. Arthritis of the temporal-mandibular joint may also be asymptomatic and lead to micrognathia (Petty, R. E. et al., 2004. J Rheumatol. 31(2):390-2).

RF-negative polyarticular JIA presents at a younger age (in late childhood, 7 to 9 years) than RF-positive polyarticular JIA and represents 11 to 28% of all children and adolescents with JIA. It may not be as destructive and persistent as RF-positive disease but does, by definition, involve 5 or more joints. Radiologic changes in RF-negative disease occur later than in RF-positive disease. Severe limitations in motion are usually accompanied by muscle weakness and decreased physical function.

Oligoarticular JIA (oJIA), another subtype of pcJIA, is the most common subtype of juvenile arthritis, representing approximately 50% of all patients with JIA in the US and Western Europe. Onset ranges from 1 to 5 years and peaks at 2 to 3 years. It is defined as an aseptic inflammatory synovitis that affects generally up to 4 joints (typically larger joints, such as knees, ankles, wrists) and is not associated with constitutional findings such as fever, weight loss, fatigue or systemic signs of inflammation. Nevertheless, if greater than 4 joints become affected after the first 6 months of disease, it is designated as extended oligoarthritis in contrast to persistent oJIA that features only up to 4 joints throughout the course of the disease. Children are often well-appearing despite ambulating with a limp. oJIA carries a risk for developing chronic anterior uveitis, especially when antinuclear antibodies (ANA) are present and disease onset is in early childhood. It is typically asymptomatic at onset and requires screening by ophthalmologic slit lamp examination. Chronic arthritis in a knee or ankle may lead to overgrowth of that limb with subsequent leg length discrepancy. Muscle atrophy, often of extensor muscles (e.g., vastus lateralis, quadriceps when knee affected) and/or flexion contractures in the knees and, less commonly, the wrists are found.

Current treatments of JIA include steroids, e.g., conventional synthetic DMARDs and biologic DMARDs. The development of new drugs that are capable of selectively inhibiting single molecules and pathways offers the hope of improving remission rates while minimizing disease damage and treatment-related side effects (Giancane, et al. Juvenile Idiopathic Arthritis: Diagnosis and Treatment. Rheumatology and Therapy. 2016; 3(2):187-207).

One candidate for treatment of JIA is interleukin-6 (IL-6) inhibition. IL-6 is a key cytokine with a wide range of biological activities, including regulation of immune reactivity, the acute-phase response, inflammation, oncogenesis and hematopoiesis (Kishimoto, et al. The Cytokine Handbook (London: Academic Press). 2003, pp. 281-304). Overproduction of IL-6 has been found to play pathological roles in chronic inflammatory diseases.

IL-6 interacts directly with the IL-6Rα subunit and the IL-6/IL-6Rα pair forms a high affinity complex with the glycoprotein 130 (gp130) subunit. IL-6Rα also exists in a soluble form, which is involved in trans-signaling and allows IL-6 to affect cells that do not express IL-6Rα including synovial cells in the joint (Rose-John et al., J Leukoc Biol. 2006; 80(2), 227-36).

Sarilumab, also designated as SAR153191 or REGN88, is a recombinant IgG1 kappa monoclonal antibody of fully human sequence directed against the alpha subunit of the IL-6 receptor complex (IL-6Rα). Sarilumab is a potent and specific inhibitor of IL-6 signaling. By binding to IL-6Rα with high affinity, sarilumab blocks the binding of IL-6 and interrupts the cytokine-mediated signaling cascade. In certain embodiments, interleukin-6 is a key element in the etiology of rheumatic conditions and inhibition of its signaling is a critical part of the mechanism of action of sarilumab. In ex vivo assays, sarilumab did not demonstrate antibody-dependent cellular cytotoxicity (ADCC) or complement-dependent cytotoxicity (CDC) on relevant cell types where sarilumab binding was verified by fluorescence-activated cell sorter (FACS) analysis (Committee for Medicinal Products for Human Use, Assessment Report, Apr. 27, 2017 EMA/292840/2017, available at ema.europa.eu/documents/assessment-report/kevzara-epar-public-assessment-report_en.pdf).

Antibodies

The present disclosure includes methods that comprise administering to a subject an antibody, or an antigen-binding fragment thereof, that binds specifically to hIL-6R. As used herein, the term "hIL-6R" means a human cytokine receptor that specifically binds human IL-6. In certain embodiments, the antibody that is administered to the patient binds specifically to the extracellular domain of hIL-6R.

The term "antibody"; as used herein, refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed CDRs, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries); or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, and bivalent nanobodies), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may in various embodiments consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may in various embodiments comprise a homo-dimer or hetero-dimer (or other multimer) of any of the variable and constant domain configurations listed above in non-covalent association with one another and/or with one or more monomeric VH or VL domain (e.g., by disulfide bond(s)).

In specific embodiments, the antibody or antibody fragment for use in the method of the invention may be a multispecific antibody, which may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bispecific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second CH3 may further comprise an Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention. Any multispecific antibody format, including the exemplary bispecific antibody formats disclosed herein, may in various embodiments be adapted for use in the context of an antigen-binding fragment of ananti-IL-6R antibody using routine techniques available in the art.

The fully-human anti-IL-6R antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework residues and/or CDR residues within the VH and/or VL domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies featured in the disclosure may in various embodiments nonetheless include amino acid residues not encoded by human germline immunoglobulin sequences (e.g., mutations introduced by random or site-specific mutagenesis in vitro or by somatic mutation in vivo), for example in the CDRs and in some embodiments CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., (1992) Nucl. Acids Res. 20:6287-6295, incorporated herein by reference in its entirety,) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In an embodiment, an immunoglobulin molecule comprises a stable four chain construct of approximately 150-160 kDa in which the dimers are held together by an interchain heavy chain disulfide bond. In another embodiment, the dimers are not linked via inter-chain disulfide bonds and a molecule of about 75-80 kDa is formed composed of a covalently coupled light and heavy chain (half-antibody). These embodiments/forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al., (1993) Molecular Immunology 30:105, incorporated by reference in its entirety) to levels typically observed using a human IgG1 hinge. The instant disclosure encompasses in various embodiments antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." In various embodiments, the isolated antibody also includes an antibody in situ within a recombinant cell. In other embodiments, isolated antibodies are antibodies that have been subjected to at least one purification or isolation step. In various embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-6R, as used herein, includes antibodies that bind IL-6R or portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured in a surface plasmon resonance assay. Specific binding can also be characterized by a dissociation constant of at least about $1\times10^{-6}$ M or smaller. In other embodiments, the dissociation constant is at least about $1\times10^{-7}$ M, $1\times10^{-8}$ M, or $1\times10^{-9}$ M. An isolated antibody that specifically binds human IL-6R may, however, have cross-reactivity to other antigens, such as IL-6R molecules from other (non-human) species.

The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, NJ).

The term "KD", as used herein, is intended to refer to the equilibrium dissociation constant of an antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The anti-IL-6R antibodies useful for the methods described herein may in various embodiments include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes in various embodiments methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). Numerous antibodies and antigen-binding fragments may be constructed which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a certain germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present disclosure.

The present disclosure also includes methods involving the use of anti-IL-6R antibodies comprising variants of any of the HCVR, LCVR, and/or CDR amino acid sequences disclosed herein having one or more conservative substitutions. For example, the present disclosure includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

According to the present disclosure, the anti-IL-6R antibody, or antigen-binding fragment thereof, in various embodiments comprises a HCVR, LCVR, and/or CDRs comprising any of the amino acid sequences of the anti-IL-6R antibodies described in U.S. Pat. No. 7,582,298, incorporated herein by reference in its entirety. In certain embodiments, the anti-IL-6R antibody or antigen-binding fragment thereof comprises the HCDRs of a HCVR comprising the amino acid sequence of SEQ ID NO: 1 and the LCDRs of a LCVR comprising the amino acid sequence of SEQ ID NO: 2. According to certain embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-6R antibody or antigen-binding fragment thereof comprises an HCVR comprising the amino acid sequence of SEQ ID NO: 1 and an LCVR comprising the amino acid sequence of SEQ ID NO: 2.

In another embodiment, the anti-IL-6R antibody or antigen-binding fragment thereof comprises a heavy chain comprising the amino acid sequence of SEQ ID NO: 9 and a light chain comprising the amino acid sequence of SEQ ID NO: 10. In some embodiments, the extracellular domain of hIL-6R comprises the amino acid sequence of SEQ ID NO: 11. According to certain exemplary embodiments, the methods of the present disclosure comprise the use of the anti-IL-6R antibody referred to and known in the art as sarilumab, or a bioequivalent thereof.

```
The amino acid sequence of SEQ ID NO: 1 is
EVQLVESGGGLVQPGRSLRLSCAASRFTFDDYAMHWVRQAPGKGLEWVSG

ISWNSGRIGYADSVKGRFTISRDNAENSLFLQMNGLRAEDTALYYCAKGR

DSFDIWGQGTMVTVSS
```

-continued

The amino acid sequence of SEQ ID NO: 2 is
DIQMTQSPSSVSASVGDRVTITCRASQGISSWLAWYQQKPGKAPKLLIYG
ASSLESGVPSRFSGSGSGTDFTLTISSLQPEDFASYYCQQANSFPYTFGQ
GTKLEIK.

The amino acid sequence of SEQ ID NO: 3 is
RFTFDDYA.

The amino acid sequence of SEQ ID NO: 4 is
ISWNSGRI.

The amino acid sequence of SEQ ID NO: 5 is
AKGRDSFDI.

The amino acid sequence of SEQ ID NO: 6 is
QGISSW.

The amino acid sequence of SEQ ID NO: 7 is
GAS.

The amino acid sequence of SEQ ID NO: 8 is
QQANSFPYT.

The amino acid sequence of SEQ ID NO: 9 is
EVQLVESGGGLVQPGRSLRLSCAASRFTFDDYAMHWVRQAPGKGLEWVSG
ISWNSGRIGYADSVKGRFTISRDNAENSLFLQMNGLRAEDTALYYCAKGR
DSFDIWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK.

The amino acid sequence of SEQ ID NO: 10 is
DIQMTQSPSSVSASVGDRVTITCRASQGISSWLAWYQQKPGKAPKLLIYG
ASSLESGVPSRFSGSGSGTDFTLTISSLQPEDFASYYCQQANSFPYTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.

The sequence of SEQ ID NO: 11 is
MVAVGCALLAALLAAPGAALAPRRCPAQEVARGVLTSLPGDSVTLTCPGV
EPEDNATVHWVLRKPAAGSHPSRWAGMGRRLLLRSVQLHDSGNYSCYRAG
RPAGTVHLLVDVPPEEPQLSCFRKSPLSNVVCEWGPRSTPSLTTKAVLLV
RKFQNSPAEDFQEPCQYSQESQKFSCQLAVPEGDSSFYIVSMCVASSVGS
KFSKTQTFQGCGILQPDPPANITVTAVARNPRWLSVTWQDPHSWNSSFYR
LRFELRYRAERSKTFTTWMVKDLQHHCVIHDAWSGLRHVVQLRAQEEFGQ
GEWSEWSPEAMGTPWTESRSPPAENEVSTPMQALTTNKDDDNILFRDSAN
ATSLPVQD.

The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an anti-IL-6R antibody are bioequivalent if they are pharmaceutically equivalent, meaning they contain the same amount of active ingredient (e.g., IL-6R antibody), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration (Cmax) and area under the plasma drug concentration time curve (AUC).

The disclosure in certain embodiments relates to methods comprising administering to the subject an antibody which comprises the heavy chain variable region comprising sequence SEQ ID NO: 1 and the light chain variable region comprising sequence SEQ ID NO: 2.

The disclosure provides pharmaceutical compositions comprising such antibody, and methods of using these compositions.

The antibody in various embodiments comprises the heavy chain variable region comprising sequence SEQ ID NO: 1 and the light chain variable region comprising sequence SEQ ID NO: 2 is an antibody that specifically binds hIL-6R. See international publication number WO2007/143168, incorporated herein by reference in its entirety. In one embodiment, the antibody comprises the heavy chain variable region comprising sequence SEQ ID NO: 9 and the light chain variable region comprising sequence SEQ ID NO: 10. In various embodiments, the antibody is sarilumab.

DMARDs

DMARDs are drugs defined by their use in rheumatoid arthritis and JIA to slow down disease progression.

DMARDs have been classified as synthetic (sDMARD) and biological (bDMARD). sDMARDs include, non-exhaustively, methotrexate, sulfasalazine, leflunomide, and hydroxychloroquine. bDMARDs include, non-exhaustively, adalimumab, golimumab, etanercept, abatacept, infliximab, rituximab, and tocilizumab.

In some embodiments, no other DMARD is administered with the antibody. In some embodiments, at least one other DMARD is administered to the subject. In an embodiment, at least one other DMARD is administered to the subject concurrently with or at the same time as the antibody.

In some embodiments, the subject had an inadequate response to current treatment for JIA. In some embodiments, the subject had an inadequate response to current treatment for JIA and is considered a candidate for a bDMARD. In some embodiments, the subject's current treatment is a corticosteroid, sDMARD, and/or a bDMARD. By way of example, but not by way of limitation, in some embodiment, the corticosteroid is selected from prednisone, prednisolone, and methyl-prednisolone.

Methods of Administration and Formulations

The methods described herein comprise administering a therapeutically effective amount of an anti-IL-6R antibody to a subject. As used herein, an "effective amount" or "therapeutically effective amount" is a dose of the therapeutic that results in treatment of sJIA and/or pcJIA. As used herein, "treating" refers to causing a detectable improvement in one or more symptoms associated with sJIA and/or pcJIA or causing a biological effect (e.g., a decrease in the level of a particular biomarker) that is correlated with the underlying pathologic mechanism(s) giving rise to the condition or symptom(s). For example, a dose of anti-IL-6R antibody which causes an improvement in any of the following symptoms or conditions associated with juvenile idiopathic arthritis is deemed a "therapeutically effective amount": limping, stiffness when awakening, reluctance of the subject to use an arm or leg, reduced activity level, persistent fever, joint swelling, and difficulty with fine motor activities.

An "improvement" in an JIA-associated symptom in various embodiments refers reduction in the incidence of the JIA symptom which may correlate with an improvement in one or more JIA-associated test, score or metric (as described herein). For example, the improvement may correlate an increase from baseline of one or more of JIA ACR criteria, and/or a decrease from baseline of one or more of corticosteroid use, Juvenile Arthritis Disease Activity Score, or fever. In an embodiment, improvement may comprise a decrease in baseline of stiffness (e.g., a joint with limited motion). As used herein, the term "baseline," with regard to an JIA-associated parameter, means the numerical value of the JIA-associated parameter for a patient prior to or at the time of administration of the antibody of the present invention. A detectable "improvement" can also be detected using at least one test, score or metric described herein. In various embodiments, the improvement is detected using at least one selected from the group consisting of: Juvenile idiopathic arthritis American College of Rheumatism (ACR), (e.g., JIA ACR30, JIA ACR50, JIA ACR70, JIA ACR90, and JIA ACR100). In various embodiments, the improvement is characterized by at least one score or metric, such as physician global assessment of disease activity score, patient or parent assessment of overall well-being, childhood health assessment questionnaire, number of joints with active arthritis, number of joints with limited motion, and/or high sensitivity C-reactive protein. In certain embodiments, an improvement in a symptom of sJIA is reduced fever (e.g., in subjects with a fever when the antibody is first administered). In various embodiments, the improvement is characterized by at least one biomarker. In some embodiments, the improvement is characterized by an increase in at least one biomarker. In some embodiments, the improvement is characterized by a reduction in at least one biomarker.

In another example, a treatment has not been effective when a dose of anti-IL-6R antibody does not result in a detectable improvement in one or more parameters or symptoms associated with JIA or which does not cause a biological effect that is correlated with the underlying pathologic mechanism(s) giving rise to the condition or symptom(s) of JIA.

According to some of these embodiments, the IL-6R antibody is administered subcutaneously. According to some of these embodiments, the IL-6R antibody is sarilumab.

In accordance with the methods of the present invention, a therapeutically effective amount of anti-IL-6R antibody that is administered to the subject will vary depending upon the age and the size (e.g., body weight or body surface area) of the subject as well as the route of administration and other factors well known to those of ordinary skill in the art.

In certain embodiments, the dose of the antibody varies depending on the body weight of the subject. In various embodiments, if a subject has a body weight of at least 30 kg (e.g., up to 60 kg, 70 kg, 80 kg, 90 kg, or 100 kg), then the subject is administered a dose of 2.0 mg/kg once every 2 weeks. In other embodiments, if a subject has a body weight of at least 30 kg, and less than 40, 50, 60, 70, 80, 90 or 100 kg then the subject is administered a dose of 2.0 mg/kg once every 2 weeks. In some embodiments, if a subject has a body weight of at least 30 kg, then the subject is administered a dose of 3.0 mg/kg once every 2 weeks. In some embodiments, if a subject has a body weight of at least 30 kg, then the subject is administered a dose of 4-6 mg/kg once every 2 weeks. In other embodiments, if a subject has a body weight of at least 30 kg, and less than 40, 50, 60, 70, 80, 90 or 100 kg then the subject is administered a dose of 3.0 mg/kg once every 2 weeks. In certain embodiments, if a subject has a body weight of at least 30 kg, then the subject is administered a dose of 2.0 mg/kg once per week. In other embodiments, if a subject has a body weight of at least 30 kg, and less than 40, 50, 60, 70, 80, 90 or 100 kg then the subject is administered a dose of 2.0 mg/kg once per week. In various embodiments, if a subject has a body weight of 10-<30 kg, then the subject is administered a dose of 2.5 mg/kg every 2 weeks. In certain embodiments, if a subject has a body weight of 10-<30 kg, then the subject is administered a dose of 4 mg/kg every-2 weeks. In some embodiments, if a subject has a body weight of 10-<30 kg, then the subject is administered a dose of 2.5 mg/kg per week. In various embodiments, if a subject has a body weight of 10-<30 kg, then the subject is administered a dose of 5-7 mg/kg every 2 weeks. In various embodiments, if a subject has a body weight of 10-<30 kg, then the subject is administered a dose of 4 mg/kg every 2 weeks.

In certain embodiments, the dose of anti-IL-6R antibody administered to the subject is from about 10 mg to about 600 mg. In some embodiments, the dose of the antibody administered to the subject is from about 25 mg to about 200 mg. In various embodiments, the dose of the antibody administered to the subject is from about 60 mg to about 200 mg. For example, the present invention includes (but is not limited to) methods wherein about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300, about 325 mg, about 350 mg, about 375 mg, about 400 mg, about 425 mg, about 450 mg, about 475 mg, about 500 mg, about 525 mg, about 550 mg, about 575 mg, about 600 mg or more of anti-IL-6R antibody is administered to the patient per week or once every two weeks.

As used herein, "administered from about 2.0 to about 4.0 mg/kg" means that the referred to substance is administered at any value within the stated range including the endpoints of the range. For example, "the dose of anti-IL-6R antibody administered to the patient is from 2.0 mg/kg to 4.0 mg/kg," includes administration of 2.0 mg/kg of the anti-IL-6R antibody, 4.0 mg/kg of the anti-IL-6R antibody and all doses in between.

In various embodiments, the IL-6R antibody is administered at a dose of from about 25 to 150 mg once a week or 40 mg to 200 mg every other week. In an embodiment, the IL-6R antibody is administered at a dose of from 25 to 50 mg once per week or once every other week. In an embodiment, the IL-6R antibody is administered at a dose of from 50 to 75 mg once per week or once every other week. In an embodiment, the IL-6R antibody is administered at a dose of from 75 to 100 mg once per week or once every other week. In an embodiment, the IL-6R antibody is administered at a dose of from 100 to 125 mg once per week or once every other week. In an embodiment, the IL-6R antibody is administered at a dose of from 125 to 150 mg once per week or once every other week. In an embodiment, the IL-6R antibody is administered at a dose of from 150 to 175 mg once per week or once every other week. In an embodiment, the IL-6R antibody is administered at a dose of from 175 to 200 mg once per week or once every other week. In an embodiment, the IL-6R antibody is administered at a dose of 100 mg once a week. In an embodiment, the IL-6R antibody is administered at a dose of 150 mg once a week. In an embodiment, the IL-6R antibody is administered at a dose of 200 mg once a week. In an embodiment, the IL-6R antibody is administered at a dose of from 100 to 150 mg once a week. In an embodiment, the IL-6R antibody is administered at a dose of from 100 to 200 mg once every two weeks. In an embodiment, the IL-6R antibody is administered at a dose of from 150 to 200 mg once every two weeks. In an embodiment, the IL-6R antibody is administered at a dose of about 100 or about 150 mg once every two weeks. In an embodiment, the IL-6R antibody is administered at a dose of about 100, 150 or 200 mg once every two weeks. In an embodiment, the IL-6R antibody is administered at a dose of 100 mg once every two weeks. In an embodiment, the IL-6R antibody is administered at a dose of 150 mg once every two weeks. In an embodiment, the IL-6R antibody is administered at a dose of 200 mg once every two weeks.

In various embodiments of the method, the antibody is used at a dose listed in Tables 2-5.

The amount of anti-IL-6R antibody that is administered to the patient may be expressed in terms of milligrams of antibody per kilogram of patient body weight (i.e., mg/kg). For example, the methods of the present invention include administering an anti-IL-6R antibody to a patient at a daily dose from about 0.01 to about 100 mg/kg, from about 0.1 to about 50 mg/kg, or from about 1 to about 10 mg/kg of patient body weight. In certain embodiments, the anti-hIL6R antibody is sarilumab and is administered from about 2 mg/kg to about 4 mg/kg. In various embodiments, the anti-hIL6R antibody is sarilumab and is administered from about 2 mg/kg to about 3 mg/kg. In certain embodiments, the anti-hIL6R antibody is sarilumab and is administered from about 2.5 mg/kg to about 4 mg/kg. In various embodiments, the anti-hIL6R antibody is sarilumab and is administered from about 2 mg/kg to about 3 mg/kg at a frequency of once a week (qw) or once every two weeks (q2w). In some embodiments, the anti-hIL6R antibody is administered at a dose of about 2 mg/kg to 4 mg/kg at a frequency of once a week (qw) or once every two weeks (q2w). In some embodiments, the anti-hIL6R antibody is administered at a dose of about 2.5 mg/kg to 4 mg/kg at a frequency of once a week (qw) or once every two weeks (q2w). In various embodiments, the anti-hIL6R antibody is administered at a dose of about 1.0, 1.5, 2.0, 2.5, 3.0, 3.5, 4.0, 4.5 or 5.0 mg/kg. In some embodiments, the anti-hIL6R antibody antibody comprises a VH and a VL, wherein the VH comprises the three CDRs found within the sequence of SEQ ID NO:1 and wherein the VL comprises the three CDRs found within the sequence of SEQ ID NO:2. In other embodiments, the anti-hIL6R antibody is sarilumab.

The methods of the present invention include administering multiple doses of an anti-IL-6R antibody to a patient over a specified time course. For example, the anti-IL-6R antibody can be administered about 1 to 5 times per day, about 1 to 5 times per week, about 1 to 5 times per month or about 1 to 5 times per year. In certain embodiments, the methods of the invention include administering a first dose of anti-IL-6R antibody to a patient at a first time point, followed by administering at least a second dose of anti-IL-6R antibody to the patient at a second time point. The first and second doses, in certain embodiments, may contain the same amount of anti-IL-6R antibody. For instance, the first and second doses may each contain from about 10 mg to about 500 mg, from about 20 mg to about 300 mg, from about 100 mg to about 200 mg, or from about 100 mg to about 150 mg of the antibody. The time between the first and second doses may be from about a few hours to several weeks. For example, the second time point (i.e., the time when the second dose is administered) can be from about 1 hour to about 7 weeks after the first time point (i.e., the time when the first dose is administered). According to certain exemplary embodiments of the present invention, the second time point can be about 1 hour, about 4 hours, about 6 hours, about 8 hours, about 10 hours, about 12 hours, about 24 hours, about 2 days, about 3 days, about 4 days, about 5 days, about 6 days, about 7 days, about 2 weeks, about 4 weeks, about 6 weeks, about 8 weeks, about 10 weeks, about 12 weeks, about 14 weeks or longer after the first time point. In certain embodiments, the second time point is about 1 week or about 2 weeks. Third and subsequent doses may be similarly administered throughout the course of treatment of the patient. The invention provides methods of using therapeutic compositions comprising anti-IL-6R antibodies or antigen-binding fragments-thereof and, optionally, one or more additional therapeutic agents. The therapeutic compositions of the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA, incorporated herein by reference in its entirety. These formulations include, for example, powders, pastes, ointments, jellies, waxes, oils, lipids, lipid (cationic or anionic) containing vesicles (such as LIPOFECTIN), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311, incorporated herein by reference in its entirety.

Various delivery systems are known and can be used to administer the pharmaceutical composition of the invention, e.g., encapsulation in liposomes, microparticles, microcapsules, receptor mediated endocytosis (see, e.g., Wu et al. (1987) J. Biol. Chem. 262:4429-4432, incorporated herein by reference in its entirety). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The IL-6R antibody can be administered subcutaneously.

The pharmaceutical composition can also be delivered in a vesicle, such as a liposome (see Langer (1990) Science 249:1527-1533, incorporated herein by reference in its entirety). In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc.). As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The antibody is typically formulated as described herein and in international publication number WO2011/085158, incorporated herein by reference in its entirety.

In various embodiments, the antibody is administered as an aqueous buffered solution at about pH 6.0 containing
- about 21 mM histidine,
- about 45 mM arginine,
- about 0.2% (w/v) polysorbate 20,
- about 5% (w/v) sucrose, and
- between about 100 mg/mL and about 200 mg/mL of the antibody.

In another embodiment, the antibody is administered as an aqueous buffered solution at about pH 6.0 containing
- about 21 mM histidine,
- about 45 mM arginine,
- about 0.2% (w/v) polysorbate 20,
- about 5% (w/v) sucrose, and
- at least about 130 mg/mL of the antibody.

In another embodiment, the antibody is administered as an aqueous buffered solution at about pH 6.0 containing
- about 21 mM histidine,
- about 45 mM arginine,
- about 0.2% (w/v) polysorbate 20,
- about 5% (w/v) sucrose, and
- about 131.6 mg/mL of the antibody.

In another embodiment, the antibody is administered as an aqueous buffered solution at about pH 6.0 containing
- about 21 mM histidine,
- about 45 mM arginine,
- about 0.2% (w/v) polysorbate 20,
- about 5% (w/v) sucrose; and
- about 175 mg/mL of the antibody.

In other embodiments, the antibody is administered as an aqueous buffered solution at pH 6.0 containing
- 21 mM histidine,
- 45 mM arginine,
- 0.2% (w/v) polysorbate 20,
- 5% (w/v) sucrose, and
- between 100 mg/mL and 200 mg/mL of the antibody.

In another embodiment, the antibody is administered as an aqueous buffered solution at pH 6.0 containing
- 21 mM histidine,
- 45 mM arginine,
- 0.2% (w/v) polysorbate 20,
- 5% (w/v) sucrose, and
- at least 130 mg/mL of the antibody.

In another embodiment, the antibody is administered as an aqueous buffered solution at pH 6.0 containing
- 21 mM histidine,
- 45 mM arginine,
- 0.2% (w/v) polysorbate 20,
- 5% (w/v) sucrose, and
- 131.6 mg/mL of the antibody.

In another embodiment, the antibody is administered as an aqueous buffered solution at pH 6.0 containing
- 21 mM histidine,
- 45 mM arginine,
- 0.2% (w/v) polysorbate 20,
- 5% (w/v) sucrose; and
- 175 mg/mL of the antibody.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In accordance with the methods disclosed herein, the anti-IL-6R antibody (or pharmaceutical formulation comprising the antibody) can be administered to the patient using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer an anti-IL-6R antibody (or pharmaceutical formulation comprising the antibody). Examples of such devices include, but are not limited to AUTOPEN (Owen Mumford, Inc., Woodstock, UK), DISETRONIC pen (Disetronic Medical Systems, Bergdorf, Switzerland), HUMALOG MIX 75/25 pen, HUMALOG pen, HUMALIN 70/30 pen (Eli Lilly and Co., Indianapolis, IN), NOVOPEN I, II and III (Novo Nordisk, Copenhagen, Denmark), NOVOPEN JUNIOR (Novo Nordisk, Copenhagen, Denmark), BD pen (Becton Dickinson, Franklin Lakes, NJ), OPTIPEN, OPTIPEN PRO, OPTIPEN STARLET, and OPTICLIK (Sanofi-Aventis, Frankfurt, Germany). Examples of disposable pen and/or autoinjector delivery devices having applications in subcutaneous delivery of a pharmaceutical composition of the present invention include, but are not limited to the SOLOSTAR pen (Sanofi-Aventis), the FLEXPEN (Novo Nordisk), and the KWIKPEN (Eli Lilly), the SURECLICK Autoinjector (Amgen, Thousand Oaks, CA), the PENLET (Haselmeier, Stuttgart, Germany), the EPIPEN (Dey, L. P.), and the HUMIRA Pen (AbbVie Inc., North Chicago, IL), to name only a few.

In one embodiment, the antibody is administered with a prefilled syringe. In another embodiment, the antibody is administered with a prefilled syringe containing a safety system. For example, the safety system prevents an accidental needle-stick injury. In various embodiments, the antibody is administered with a prefilled syringe containing an ERIS safety system (West Pharmaceutical Services Inc.). See also U.S. Pat. Nos. 5,215,534 and 9,248,242, incorporated herein by reference in their entireties.

In another embodiment, the antibody is administered with an auto-injector. In various embodiments, the antibody is administered with an auto-injector featuring the PUSHCLICK technology (SHL Group). In various embodiments, the auto-injector is a device comprising a syringe that allows for administration of a dose of the composition and/or antibody to a subject. See also U.S. Pat. Nos. 9,427,531 and 9,566,395, incorporated herein by reference in their entireties.

The use of a microinfusor to deliver an anti-IL-6R antibody (or pharmaceutical formulation comprising the antibody) to a patient is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996), incorporated herein by reference in their entireties. Microinfusors are particularly useful for the delivery of large doses of therapeutic proteins contained within high concentration (e.g., about 100, 125, 150, 175, 200 mg/mL or more) and/or viscous solutions.

The antibody according to the disclosure is in various embodiments administered to subjects who are suffering from a type of JIA, for example systemic juvenile idiopathic arthritis. In certain embodiments, the methods disclosed herein comprise a step of selecting a subject suffering from a type of JIA, for example systemic juvenile idiopathic arthritis. Diagnosis of systemic juvenile idiopathic arthritis is according to the ILAR 2001 JIA classification criteria (Petty R E, et al. International League of Associations for Rheumatology Classification of Juvenile Idiopathic Arthritis: Second Revision, Edmonton, 2001. J Rheumatol. 2004 February; 31(2):390-2). In some embodiments, patients are between the ages of about 1 and about 17 years of age. In various embodiments, patients are between the ages of about 4 and about 6 years of age, between the ages of about 12 and about 18 years of age, between the ages of about 12 and about 14 years of age, or between the ages of about 7 and about 9 years of age. In various embodiments, the subject displays arthritis in 5 active joints. In some embodiments, the subject displays arthritis in 2 active joints with systemic juvenile idiopathic arthritis fever (at a temperature greater than 37.5° C.) for at least 3 out of any 7 consecutive days, despite being on glucocorticoids at a stable dose for at least 3 days. In various embodiments, the subject had an inadequate response to current treatment and is considered a candidate for a bDMARD.

The antibody according to the disclosure is in various embodiments administered to subjects who are suffering from pcJIA. In certain embodiments, the methods disclosed herein comprise a step of selecting a subject suffering from a type of JIA, for example pcJIA. Diagnosis of rheumatoid factor negative or RF positive polyarticular juvenile idiopathic arthritis subtype or oligoarticular extended juvenile idiopathic arthritis subtype is according to the ILAR 2001 JIA classification criteria (Petty R E, et al. International League of Associations for Rheumatology Classification of Juvenile Idiopathic Arthritis: Second Revision, Edmonton, 2001. J Rheumatol. 2004 February; 31(2):390-2). In some embodiments, patients are between the ages of about 2 and about 17 years of age. In various embodiments, patients are between the ages of about 4 and about 6 years of age, between the ages of about 12 and about 18 years of age, between the ages of about 12 and about 14 years of age, or between the ages of about 7 and about 9 years of age. In various embodiments, the subject displays arthritis in at least 5 active joints as per the American College of Rheumatology definition of active arthritis. In various embodiments, the subject had an inadequate response to current treatment and is considered a candidate for a bDMARD.

In certain embodiments, an inadequate response to prior treatment refers to subjects whose JIA is not well controlled after receiving the prior treatment (e.g., a glucocorticoid joint injection and/or methotrexate) at the maximum tolerated typical dose. In an embodiment, an inadequate response to prior treatment refers to subjects who have moderate or high disease activity and features of poor prognosis despite prior treatment. In various embodiments, an inadequate response to prior treatment refers to subjects with a JIA symptom (e.g., any symptom listed herein) that has not improved or that has worsened despite prior treatment.

The effectiveness of various methods of treatment for sJIA and pcJIA can be assessed using any of the methods described herein, for example the Juvenile Arthritis Disease Activity Score-27 (JADAS). (Consolaro et al. Development and Validation of a Composite Disease Activity Score for Juvenile Idiopathic Arthritis. *Arthritis & Rheumatism.* 2009 May; 61(5):658-666).

All publications mentioned herein are incorporated herein by reference in their entirety for all purposes.

LIST OF ABBREVIATIONS

ACR: American College of Rheumatology
ADA: anti-drug antibody
AE: adverse event
AESI: adverse event(s) of special interest
ALP: alkaline phosphatase
ALT: alanine aminotransferase
ANA: antinuclear antibody
ANC: absolute neutrophil count
anti-dsDNA: anti-double stranded DNA
AST: aspartate aminotransferase
BP: blood pressure
BUN: blood urea nitrogen
CHAQ: Childhood Health Assessment Questionnaire
COX-2: cyclo-oxygenase-2 inhibitors
CRF: case report form
CRP: C-reactive protein
CSR: clinical study report
CYP: cytochrome
DEC: Dose Escalation Committee
DMARD: disease modifying antirheumatic drug
DMC: Data Monitoring Committee
DNA: deoxyribonucleic acid
EBV: Epstein Barr virus
e-CRF: electronic case report form
EOS: end-of-study
EOT: end-of-treatment
ESR: erythrocyte sedimentation rate
GCP: good clinical practice
HAQ-DI: Health Assessment Questionnaire Disability Index
HBc-Ab: hepatitis B core antibody
HIV: human immunodeficiency virus
HLGT: high level group term
HR: heart rate
hs-CRP: high sensitivity C-reactive protein
ICF: informed consent form
ICH: International Council for Harmonisation
IEC: Independent ethics committee
IgG: immunoglobulin G
IL-6: Interleukin 6
IL-6R: IL-6 receptor
ILAR: international league of associations for rheumatology
IMP: investigational medicinal product IRB: Institutional Review Board
IVRS: interactive voice response system
IWRS: interactive web response system
JADAS: Juvenile Arthritis Disease Activity Score
JAK: Janus kinase
JIA: juvenile idiopathic arthritis
JIA ACR: Juvenile Idiopathic Arthritis American College of Rheumatology
LDH: lactate dehydrogenase
LDL: low density lipoprotein
LFT: Liver Function Tests, liver function test
LLOQ: lower limit of quantification
mAB: monoclonal antibody
MAS: macrophage activation syndrome
mTSS: modified total sharp score
MTX: methotrexate
NIMP: noninvestigational medicinal product
NSAID: Non-steroidal anti-inflammatory drugs
oJIA: oligoarticular juvenile idiopathic arthritis
pcJIA: polyarticular course of juvenile idiopathic arthritis
PCSA: potentially clinically significant abnormality
PD: pharmacodynamic
PK: pharmacokinetic
PopPK: Population pharmacokinetic
PPD: Purified Protein Derivative
PT: preferred term
q2w: once every other week
qw: once a week
RA: rheumatoid arthritis
RF: rheumatoid factor
SAE: serious adverse event
SC: subcutaneous
SD: standard deviation
sJIA: systemic juvenile idiopathic arthritis
SOC: system organ class
SUSAR: suspected unexpected serious adverse reaction
TB: tuberculosis
TEAE: treatment-emergent adverse event
ULN: upper limit of normal
VAS: visual analogue scale
WBC: white blood cell

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for.

Example 1: An Open-label, Sequential, Ascending, Repeated Dose-finding Study of Sarilumab, Administered with Subcutaneous (SC) Injection, in Children and Adolescents, Aged 2 to 17 Years, With pcJIA Followed by an Extension Phase. (Study No. DRI13925, Study Title: An Open-label, Ascending, Repeated Dose-finding Study of Sarilumab in Children and Adolescents with pcJIA)

A phase 2 controlled trial (number NCT02776735) was commenced to test the human IgG1 anti-IL-6Rα monoclonal antibody sarilumab administered subcutaneously in treating pcJIA. This study was a multinational, multicenter, open-label, 2-phase, and 2-portion study in children and adolescents aged 2 to 17 years (or country specified age requirement), with pcJIA who had inadequate response to or who were intolerant to current therapy or who were considered as a candidate for a biologic disease modifying anti-rheumatic drug (DMARD). The 2 phases of the study were an initial 12-week core treatment phase followed by a 144-week extension phase (See FIG. 1 and FIG. 2).

Overall Study Design and Plan:

12-Week Core Treatment Phase

This multinational, multicenter, open-label study enrolled patients aged 2-17 years with a diagnosis of RF-positive or RF-negative pJIA or eoJIA according to the ILAR 2001 JIA classification criteria (1). Patients had ≥5 active joints, and had to be considered as candidates for bDMARDs per investigators' judgment.

Patients received sarilumab via subcutaneous (SC) injection, provided by a professional caregiver at the investigative site. Dose regimens were tested in 2 weight groups (Group A, ≥30-60 kg and Group B, 10-≤30 kg) in a stepwise approach, starting with the lowest sarilumab dose regimen in the higher weight group, Group A (FIG. 2). Dose regimens in Groups A/B were 2.0/2.5 mg/kg Q2W, 3.0/4.0 mg/kg Q2W, and 2.0/2.5 mg/kg QW for dose regimens 1, 2, and 3, respectively. Initiation of dose regimen 1 in Group B was permitted after data review from the first 3 patients enrolled within the same dose regimen in Group A, following at least 4 weeks of treatment. Escalation to higher dose regimens within each weight group was permitted following review of safety, efficacy, pharmacokinetic (PK) and pharmacodynamic (PD) data, once the first 3 patients enrolled in the current weight and dose group had completed 6 weeks of treatment. Enrollment in dose 3, Group B was permissible after review of data from all other weight and dose groups. Dose escalation decisions were made by the Dose Escalation Committee (DEC). The DEC could declare a dosage ineffective if the first 3 patients enrolled in that dose and weight group did not reach JIA ACR30 response by week 6, halting enrollment in that dose and weight group and discontinuing patients in that regimen to an investigator-approved standard of care. The safety of sarilumab was formally monitored throughout the study by the independent Data Monitoring Committee, comprising 3 pediatric rheumatologists.

The primary objective of the study was to investigate the PK profile of 3 dose regimens of sarilumab administered for 12 weeks in order to select one regimen for further investigation. Dose regimens were selected based on modeling and simulation to provide similar exposures to dose regimens evaluated in adult RA. Dose regimen 1 corresponded to 150 mg every 2 weeks (Q2W), the lowest approved adult dosage; dose regimen 2 to 200 mg Q2W, the recommended approved adult dosage; and dose regimen 3 to 150 mg every week (QW), the highest dosage tested in adults that demonstrated greater efficacy than placebo with an acceptable safety profile (20).

The 12-week core treatment phase (illustrated in FIG. 2) was split into 3 portions. A first sequential, ascending dose-finding portion in which 3 dose regimens (Table 1) were investigated in each of 2 weight groups: patients ≥30 kg and ≤60 kg (Group A) and patients <30 kg and ≥10 kg (Group B) in 6 evaluable patients per dose and weight group (around 36 patients in total) beginning with Group A and Dose Cohort 1. A second subsequent portion where approximately 24 additional patients (12 in each weight group, ≥30 kg (Group A) and <30 kg and ≥10 kg (Group) are enrolled directly to the selected dose regimen to achieve a total of 18 evaluatable patients per weight group at this selected dose regimen. A third portion where approximately 28 additional patients (a cap of 70% in each weight group: patients ≥30 kg [Group A] and patients <30 kg and ≥10 kg [Group B]) will be enrolled directly to the selected dose regimen to achieve a total of approximately 100 treated patients for the entire study. These patients will undergo the same on-site visits during the 12-week core treatment phase as patients recruited in the dose-finding and second portions; however, the patients in the third portion will not have the sarilumab PK sampling visits between Baseline and Week 2.

The 12-week core treatment phase was from Visit 2 (Baseline-Week 0) to the time that Visit 12 investigational medicinal product (IMP) is administrated. During the 12-week core treatment phase, in patients in the lower weight group (Group B: <30 kg and ≥10 kg) were randomly assigned to the following sarilumab PK sampling Schedule 1 or 2 in order to minimize the amount of blood withdrawn and the number of visits while maintaining the evaluation of the primary endpoint:

Schedule 1: Baseline, Day 3, Day 8, Week 2, Week 4, Week 8, and Week 12

Schedule 2: Baseline, Day 5, Day 12, Week 2, Week 4, Week 8, and Week 12.

Assessments. Data are presented for the 3 dose regimens in both weight groups and are reported from the study baseline through week 12.

The primary endpoint was PK exposure, including maximum serum concentration, area under serum concentration versus time curve calculated using the trapezoidal method during a dose interval, and serum concentration observed before treatment administration during repeated dosing. Secondary endpoints were PD, including high-sensitivity C-reactive protein (CRP) concentration, safety, and clinical efficacy. Efficacy was determined by the proportions of patients achieving a JIA ACR30/70/90 response, change from baseline in the components of the JIA ACR response, and mean change in juvenile arthritis disease activity score with 27-joint count and CRP assessment (JADAS-27-CRP), all at week 12.

Additionally, after completing the enrollment of dose-finding and second portions, a third portion where approximately 28 additional patients will be enrolled directly to the selected dose regimen to achieve a total of approximately 100 treated patients for the entire study as per a health authority recommendation. These patients will undergo the same on-site visits during the 12-week core treatment phase as patients recruited in the dose-finding and second portions; however, the patients in the third portion will not have the sarilumab PK sampling visits between Baseline and Week 2.

An additional treatment period in the extension phase will allow collection of long-term safety and clinical response data for sarilumab in pcJIA patients. This extension phase is up to 144 weeks for patients enrolled in the dose-finding and second portions and up to 84 weeks for patients enrolled in the third portion. Patients enrolled in the dose-finding portion who are already in the extension phase at time of dose regimen selection and who did not receive the selected dose regimen will have their dose regimen adjusted to the selected dose.

To minimize the amount of blood collected, Group B patients (<30 kg and ≥10 kg) in the dose-finding and second portions will be randomized to 1 of 2 different sarilumab PK sample collection schedules. The PK analyses will integrate these sampling schedules to describe the PK profile of sarilumab. No PK sample collection is planned between Baseline and Week 2 for patients enrolled in the third portion. Total volume of blood withdraw for the study will not exceed 3% of the total blood volume during a period of 4 weeks and not exceed 1% of the total blood volume at any single time (39). Furthermore, the planned frequent assessments control risk to study participants.

Lastly, the post-treatment follow-up period of 6 weeks after the last treatment visit for TEAEs, sarilumab PK and PD assessments is appropriate, taking into account the observed PK profiles in the adult RA program.

Statistical Analysis.

A population PK model of pooled data was developed using nonlinear mixed effect modeling to describe the PK profile of sarilumab. PD, safety, and efficacy data were analyzed using descriptive statistics only. Efficacy endpoints were analyzed based on a data as observed while on-treatment approach (no imputation of missing data). In addition, JIA ACR30/70/90 results were also presented using a nonresponder imputation approach (nonresponder status automatically assigned to patients with insufficient data or following discontinuation).

144-Week/84-Week Extension Phase:

The IMP at Visit 12 was considered as the first IMP for the extension phase. Only patients who have reached a JIA ACR30 response at Visit 12 (Week 12) were permitted to continue in the extension phase. Patients continued on the same dose regimen of sarilumab they were assigned to receive in the 12-week core treatment phase of the study until the selected dose regimen was determined. Once the dose regimen was selected, patients who were not already on this dose regimen had their dose regimen adjusted to the selected dose regimen and followed a new visit schedule with more frequent monitoring (for PK, safety, and efficacy) for the first 12 weeks compared to those patients who did not have dose regimen adjusted.

Patients who discontinued the study treatment prematurely were assessed using the procedure for the EOT at Visit 27. These patients were asked to return for the end-of-study (EOS) assessment 6 weeks after the EOT visit (EOT+6 weeks). For patients who discontinued the study treatment during the 12-week core treatment phase, there was an additional sarilumab PK assessment 2 weeks after the EOT visit (EOT+2 weeks) and IL-6 and sIL6R were measured at EOT visit. These patients were asked to perform all the protocol scheduled visits and assessments except sarilumab administration until Visit 12.

An 84-week extension phase is scheduled for patients enrolled in the third portion. The IMP at Visit 12 is considered as the first IMP for the extension phase. Patients who are enrolled in the third portion with the selected dose regimen will be followed-up as noted in Table 32.

Tested Dose Regimens

For each weight group, to the 3 sequential ascending dose regimens to be tested were defined based on PK modeling with the following rationale:

Dose Cohort 1: dose targeting PK exposures similar to sarilumab 150 mg q2w, the lowest effective dose regimen in adult patients with RA.

Dose Cohort 2: dose with targeted PK exposures similar to sarilumab 200 mg q2w, the recommended dose regimen in adult patients with RA.

Dose Cohort 3: dose targeting PK exposures similar to sarilumab 150 mg qw, which yielded the highest exposures in chronic dosing studies in adult patients with RA.

TABLE 1

| Dose by body weight and dose cohort | | | |
|---|---|---|---|
| Body weight | Dose Cohort 1 | Dose Cohort 2 | Dose Cohort 3 |
| Group A<br>≥30 kg and ≤60 kg | 2 mg/kg q2w<br>(6 patients) | 3 mg/kg q2w<br>(6 patients) | 2 mg/kg qw<br>(6 patients) |
| Group B<br><30 kg and ≥10 kg | 2.5 mg/kg q2w<br>(6 patients) | 4 mg/kg q2w<br>(6 patients) | 2.5 mg/kg qw<br>(6 patients) |

Abbreviations:
qw = once every week,
q2w = once every other week

The dose (mg) administered to patients was calculated at the Baseline. The dose and corresponding volume of drug product remained the same throughout the course of the 12-week core treatment phase of the trial regardless of change in patient's body weight. In the extension phase, the patient's weight was measured at each visit and the dose was adapted to the increase of weight only if the calculation shows a need for dose increase. The dose was capped at 150 mg for Dose Cohort 1 and 3, and 200 mg for Dose Cohort 2, respectively. Volumes of sarilumab to be injected for Dose Cohorts 1 to 3 are presented in Tables 2-5 below.

Tables 2 and 3 show dose information for a patient in a high weight group (Group A). The high weight patients are those who weigh ≥30 kg and ≤60 kg for dose-finding portion and ≥30 kg for additional patients in the second portion. Tables 4 and 5 show dose information for a patient in a low weight group (Group B): <30 kg and ≥10 kg.

TABLE 2

Dose information for the high weight group (Group A) Cohorts 1 and 3
Dose Cohort 1 (2 mg/kg q2w) and Cohort 3 (2 mg/kg qw)

| Body weight (kg) | Volume per injection (mL) | Corresponding dose (mg) |
|---|---|---|
| ≥30 and <33 | 0.35 | 61.25 |
| ≥33 and <37.5 | 0.40 | 70 |
| ≥37.5 and <42 | 0.45 | 78.75 |
| ≥42 and <46.5 | 0.50 | 87.5 |
| ≥46.5 and <50.5 | 0.55 | 96.25 |
| ≥50.5 and <55 | 0.60 | 105 |
| ≥55 and <59.5 | 0.65 | 113.75 |
| ≥59.5 and <64 | 0.70 | 122.5 |
| ≥64 and <68 | 0.75 | 131.25 |
| ≥68 and <72.5 | 0.80 | 140 |
| ≥72.5 | 0.85<br>(cap injection volume) | 148.75<br>(cap under 150 mg) |

TABLE 3

Dose information for the high weight group (Group A) Cohort 2
Dose Cohort 2 (3 mg/kg q2w)

| Body weight (kg) | Volume per injection (mL) | Corresponding dose (mg) |
|---|---|---|
| ≥30 and <31 | 0.50 | 87.5 |
| ≥31 and <34 | 0.55 | 96.25 |
| ≥34 and <37 | 0.60 | 105 |
| ≥37 and <39.5 | 0.65 | 113.75 |
| ≥39.5 and <42.5 | 0.70 | 122.5 |
| ≥42.5 and <45 | 0.75 | 131.25 |
| ≥45 and <48.5 | 0.80 | 140 |
| ≥48.5 and <51.5 | 0.85 | 148.75 |
| ≥51.5 and <54.5 | 0.90 | 157.5 |
| ≥54.5 and <57 | 0.95 | 166.25 |
| ≥57 and <63 | 1.00 | 175 |
| ≥63 | 1.1 | 192.5 |

TABLE 3-continued

Dose information for the high weight group (Group A) Cohort 2
Dose Cohort 2 (3 mg/kg q2w)

| Body weight (kg) | Volume per injection (mL) | Corresponding dose (mg) |
|---|---|---|
| | (cap injection volume) | (cap under 200 mg) |

Tables 3 and 4 show dose information for a patient in a low weight group (Group B): <30 kg and ≥10 kg.

TABLE 4

Dose information for the low weight group (Group B) Cohorts 1 and 3

| Body weight (kg) | Volume per injection (mL) | Corresponding dose (mg) |
|---|---|---|
| Dose Cohort 1 (2.5 mg/kg q2w) and Cohort 3 (2.5 mg/kg qw) | | |
| ≥10 and <12.5 | 0.15 | 26.25 |
| ≥12.5 and <16 | 0.20 | 35 |
| ≥16 and <19.5 | 0.25 | 43.75 |
| ≥19.5 and <23 | 0.30 | 52.5 |
| ≥23 and <26.5 | 0.35 | 61.25 |
| ≥26.5 and <30 | 0.40 | 70 |
| For patients who grow over 30 kg, the following injection volume will be followed | | |
| ≥30 and <37.5 | 0.40 | 70 |
| ≥37.5 and <42 | 0.45 | 78.75 |
| ≥42 and <46.5 | 0.50 | 87.5 |
| ≥46.5 and <50.5 | 0.55 | 96.25 |
| ≥50.5 and <55 | 0.60 | 105 |
| ≥55 and <59.5 | 0.65 | 113.75 |
| ≥59.5 and <64 | 0.70 | 122.5 |
| ≥64 and <68 | 0.75 | 131.25 |
| ≥68 and <72.5 | 0.80 | 140 |
| ≥72.5 | 0.85<br>(cap injection volume) | 148.75<br>(cap under 150 mg) |

TABLE 5

Dose information for the low weight group (Group B) Cohort 2

| Body weight (kg) | Volume per injection (mL) | Corresponding dose (mg) |
|---|---|---|
| Dose Cohort 2 (4 mg/kg q2w) | | |
| ≥10 and <12.5 | 0.25 | 43.75 |
| ≥12.5 and <14.5 | 0.30 | 52.5 |
| ≥14.5 and <16.5 | 0.35 | 61.25 |
| ≥16.5 and <19 | 0.40 | 70 |
| ≥19 and <21 | 0.45 | 78.75 |
| ≥21 and <23.5 | 0.50 | 87.5 |
| ≥23.5 and <25.5 | 0.55 | 96.25 |
| ≥25.5 and <27.5 | 0.60 | 105 |
| ≥27.5 and <30 | 0.65 | 113.75 |
| For patients who grow over 30 kg, the following injection volume will be followed | | |
| ≥30 and <39.5 | 0.65 | 113.75 |
| ≥39.5 and <42.5 | 0.70 | 122.5 |
| ≥42.5 and <45 | 0.75 | 131.25 |
| ≥45 and <48.5 | 0.80 | 140 |
| ≥48.5 and <51.5 | 0.85 | 148.75 |
| ≥51.5 and <54.5 | 0.90 | 157.5 |

TABLE 5-continued

| Dose information for the low weight group (Group B) Cohort 2 | | |
|---|---|---|
| Body weight (kg) | Volume per injection (mL) | Corresponding dose (mg) |
| ≥54.5 and <57 | 0.95 | 166.25 |
| ≥57 and <60.5 | 1.00 | 175 |
| ≥60.5 and <63 | 1.00 | 175 |
| ≥63 | 1.1 (cap injection volume) | 192.5 (cap under 200 mg) |

The volume to be administrated at each injection during 12-week core treatment phase was calculated based on Baseline (Visit 2) body weight and was maintained during all 12-week core treatment phase. The volume to be administrated during the extension treatment phase was adjustable by body weight measured at each visit in case of weight increase and if the calculation showed a need for dose increase. If the selected dose regimen is one from the 3 predefined dose cohorts, the patients subsequently enrolled at or changed to the selected dose regimen used the corresponding dose in Tables 2-5.

Duration of Study Participation for Each Patient

Total duration of study (per patient) was up to 166 weeks for patients enrolled in the dose-finding and second portions and up to 106 weeks for patients enrolled in the third portion:

Up to 4 weeks+3 days screening (up to 31 days)

12-week core treatment phase

Up to 144-week extension phase for patients enrolled in the dose-finding and second portions and up to 84-week extension phase for patients enrolled in the third portion 6-week post-treatment follow-up.

For all visits, a time frame of 3 days for dose Cohorts 1 and 2 and ±1 day for dose Cohort 3 was acceptable using Day 1 as reference except for For Visit 3 (Day 3), Visit 4 (Day 5) and Visit 5 (Day 8), no visit window is allowed where PK sampling occurs. For patients enrolled in the third portion, the PK sampling visits, ie, Visits 3, 4, 5, and 6 are not applicable during the core treatment phase.

Visit 6 (Day 12)±1 day for all 3 dose cohorts

Visit 7 (Week 2)±1 day for all 3 dose cohorts

Visit 8 (Week 4)±2 days for dose Cohort 1 and 2 and ±1 day for dose Cohort 3.

Inclusion Criteria

The inclusion criteria for the study are shown below:

1. Male and female patients aged ≥2 and ≤17 years (or country specified age requirement) at the time of the Screening visit
2. Diagnosis of RF-negative or RF-positive polyarticular JIA subtype or oJIA subtype according to the ILAR 2001 JIA Classification Criteria (2) with at least 5 active joints per ACR definition for "active arthritis" at Screening (Table 6)
3. Patient with an inadequate response to current treatment and considered as a candidate for a bDMARD as per Investigator's judgment
4. The patient who has reached the legal age of consent, or the parent(s) or the legal guardian(s) sign and date the Ethic Committee approved written informed consent. The patient's assent should be obtained based on local guidelines and the patient's maturity and intellectual capabilities of understanding the study associated information. In cases involving emancipated or mature minors with adequate decision-making capacity, or when otherwise permitted by law, a signed informed consent will be obtained directly from the parent(s) or the legal guardian(s).

Exclusion Criteria

Patients were excluded from the study for the following reasons: body weight <10 kg or >60 kg; JIA subtype other than RF-positive, RF-negative, or eoJIA; prior treatment with an anti-IL-6 or -IL-6R antagonist; treatment with any other biologic within 5 half-lives of first sarilumab dose; use of parenteral or intra-articular glucocorticoid injection within 4 weeks prior to study baseline; active or past history of opportunistic infection, including tuberculosis; live, attenuated vaccination within 4 weeks prior to baseline; or any condition that would adversely affect the patient's participation in the study. Patients receiving nonsteroidal anti-inflammatory drugs (NSAIDs), oral glucocorticoids, or conventional synthetic disease-modifying antirheumatic drug (csDMARD) treatment were excluded if the dose of NSAIDs or oral glucocorticoids was unstable within 2 weeks prior to baseline or if the oral glucocorticoid dosage exceeded the equivalent prednisone dosage of 0.5 mg/kg/day (or 30 mg/day), if the dose of csDMARDs was unstable within 6 weeks prior to baseline, or if csDMARD dosage exceeded the recommended dosage from local labeling. Written informed consent was required and obtained from all patients/guardians, based on local regulation guidelines.

TABLE 6

| Subclassification of rheumatoid factor (RF)-negative, rheumatoid factor (RF)-positive polyarticular and (oJIA) | | | | | |
|---|---|---|---|---|---|
| JIA subtypes | Clinical features defined by ILAR Classification | Exclusion Criteria (footnote a) | Frequency (% of total JIA)* | Onset (yrs) Mean-range | Outcome |
| RF-negative pcJIA (5, 7, 6) | Affects 5 or more joints in the first 6 months of disease. Tests for RF negative Tendosynovitis, uveitis, vasculitis | a, b, c, d, e | 15% | 7-9 yrs Two peaks: early: 1-3 yrs later: 6-12 yrs | 10% destructive joint disease |
| RF-positive pcJIA (5) ANA | ILAR Affects oJIA5 pcJIA or more joints in the first 6 months of disease. Tests for RF positive twice at least 2 months apart | a, b, c, e | 5% | 12-14 yrs 10-18 yrs | Like adult RA Seen in late childhood Severe destructive joint disease |

TABLE 6-continued

Subclassification of rheumatoid factor (RF)-negative, rheumatoid factor (RF)-positive polyarticular and (oJIA)

| JIA subtypes | Clinical features defined by ILAR Classification | Exclusion Criteria (footnote a) | Frequency (% of total JIA)* | Onset (yrs) Mean-range | Outcome |
|---|---|---|---|---|---|
| | Tenosynovitis, rheumatoid nodules, vasculitis, Sjögren's syndrome | | | | |
| oJIA (5, 7, 6) Persistent | Affects no more than 4 joints throughout the disease course | a, b, c, d, e | 50% | 2-3 yrs 1-5 yrs | Young age onset Chronic uveitis, especially ANA+ Leg length discrepancy |
| Extended | Affects more than 4 joints throughout the disease course | | | | Destructive joint disease Therapy as for pcJIA |

a Psoriasis or history of psoriasis in patients or first-degree relatives.
b Arthritis in HLA B27 positive males beginning after the age of 6 years;
c Ankylosing spondylitis, enthesitis-related arthritis, sacroiliitis with inflammatory bowel disease, Reiter's syndrome, acute anterior uveitis, or history of 1 of these disorders in first-degree relatives;
d Presence of IgM rheumatoid factor on at least 2 occasions at least 3 months apart;
e Presence of systemic JIA in patients.

Study Treatments

Investigational Medicinal Product (IMP)

Sarilumab, anti-IL-6R mAb (anti-interleukin 6 receptor alpha subunit monoclonal antibody).

Formulation

Sarilumab drug product was provided at 175 mg/mL in an aqueous buffered vehicle, pH 6.0. It was supplied in a 5 mL vial filled by 2.7 mL of sarilumab with an extractable volume of 2.0 mL.

Route(s) of Administration:

Sarilumab was administered subcutaneously in the abdomen or thigh when self-injected or also in upper arm (lateral side) by a professional or a non-professional caregiver. It is preferred that SC injection sites be alternated between the 4 quadrants of the abdomen (except the navel or waist area) or the thigh (front and side).

For patients receiving dose regimens 1 or 2 (q2w), injections were performed by a professional caregiver at the site during the 12-week core treatment phase of the study. For patients receiving dose regimen 3 (weekly injections), arrangements were made for qualified site personnel or home nurse to administer IMP for the doses that are not scheduled to be given at the study site. For the extension phase of the study, if the patients or the parent(s) or the legal guardian(s) or the caregiver(s) were willing and able to perform the injections, the home injection was permitted. In those cases, the training was required and provided to prepare and administer IMP starting at Visit 10 (Week 8) at the core treatment phase. This training was documented in the patients' study file. The patients or the parent(s) or the legal guardian(s) or the caregiver(s) were allowed to administer the injections under observation/supervision by the Investigator(s) or the delegate(s) at Visit 10 (Week 8), Visit 11 (Week 10), and Visit 12 (Week 12) before the allowance for home injection at the extension treatment phase.

On days when the patient has a study visit, the IMP was administered following clinical procedures and blood collection. Diaries were provided to record information pertaining to these injections; these diaries were kept as source data in the patients' study file. If the caregiver was unable or unwilling to administer IMP, arrangements were made for qualified site personnel to administer IMP for the doses that are not scheduled to be given at the study site.

Dose Regimen

Sarilumab was administered q2w or qw. However, the sarilumab administration window of ±3 days for dose Cohort 1 and 2, and 1 day for dose Cohort 3 was permitted per protocol to accommodate exceptional circumstances, e.g., laboratory test result pending, ongoing adverse event (AE), patient scheduling difficulty except the Visit 5 (Day 8). There was no administration window at Visit 5 (Day 8). There was only ±1 day of administration window for dose Cohort 1, 2 and 3 patients at Visit 7 (Week 2) and ±1 day of administration window for dose Cohort 3 or ±2 for dose Cohort 1 and 2 at Visit 8 (Week 4).

Note that an overdose (accidental or intentional) with the IMP was defined as at least twice the dose during an interval of less than 11 days for q2w administrations and less than 6 days for weekly administration The following sarilumab dose was administered q2w or qw:

Dose Cohort 1:
- Group A (≥30 kg and ≤60 kg): 2 mg/kg q2w
- Group B (≤30 kg and ≥10 kg): 2.5 mg/kg q2w.

Dose Cohort 2:
- Group A (≥30 kg and ≤60 kg): 3 mg/kg q2w
- Group B (≤30 kg and ≥10 kg): 4 mg/kg q2w.

Dose Cohort 3:
- Group A (≥30 kg and ≤60 kg): 2 mg/kg qw
- Group B (≤30 kg and ≥10 kg): 2.5 mg/kg qw.

Dose Modification

The dose (mg) administered to patients was calculated at Baseline. The dose and corresponding volume of drug product remained the same throughout the course of the 12-week core treatment phase of the trial regardless of change in patient's body weight. In the extension phase, the patient's weight was measured at each visit and the dose was adapted to the increase of weight only if the calculation showed a need for dose increase. The dose was capped at 150 mg and 200 mg for dose Cohorts 1 and 3 and dose Cohort 2, respectively. Volumes injected depending on patient's weight are further detailed in Tables 2-5.

Method of Assigning Patients to the Treatment Group

The list of randomized treatment kit numbers was generated centrally. The IMPs were packaged in accordance with this list. Patients were assigned a treatment kit by an interactive voice response system (IVRS) or an interactive web response system (IWRS).

Patients who meet the entry criteria will be included and will be dispensed the treatment kits within 2 weight groups (Group A: ≥30 kg and ≤60 kg for patients enrolled during the dose-finding portion and ≥30 kg for patients enrolled during the second and the third portions; Group B: <30 kg and ≥10 kg for all 3 portions).

For the dose-finding and second portions, the planned ratio of enrollments for the 2 weight groups is 1:1.

For the third portion, there is no pre-specified enrollment ratio for the 2 weight groups, but each weight group will be capped at 70% (ie, 20 patients). As a result, the most unbalanced enrollments by weight group possible would be 20 versus 8 patients in the third portion.

Packaging and Labeling

The IMP was provided in patient treatment kits containing labeled vials.

Storage Conditions

The study medication was kept refrigerated between 2° C. and 8° C. at the site or at home.

Pharmacokinetics, Efficacy, and Safety Assessments

Patients had planned to undergo the 12-week core treatment phase assessments according to the flowchart below (Table 7).

Pharmacokinetic Measurements and Timing

The sampling schedule for blood collection in the 12-week core treatment phase can be found in Table 7. If a SAE occurred in a patient, blood samples were collected for determination of sarilumab concentration at or near the onset and completion of the occurrence of the event, if possible. For patients who discontinued the study treatment prematurely during the core treatment phase (at or before Visit 12) an additional sarilumab PK assessment was collected 2 weeks after the planned EOT assessment (3 weeks after the last IMP injection for Dose Cohort 3 patients or 4 weeks after the last IMP injection [for Dose Cohort 1 and 2 patients]). These patients were asked to return for the end of study (EOS) assessment 6 weeks after the EOT assessment. The date of the sample collection should have been recorded. For early treatment discontinuation patients, blood samples should have been collected at the EOS Visit if possible. Serum samples were analyzed for functional sarilumab concentrations using a validated enzyme-linked immunosorbent assay (ELISA) method.

TABLE 7

12-week core treatment phase flowchart

| | Screening (4 weeks) | Baseline visit | Core treatment phase (12 weeks) | | | | | |
|---|---|---|---|---|---|---|---|---|
| | Visit | | | | | | | |
| | V1 | V2 | V3 | V4 | V5 | V6 | V7 | V8 |
| | Day | | | | | | | |
| | D 28 to D 1 (+3) (Maximum 31 days) | D 1 | D 3 [b] | D 5 [b] | D 8 [b] | D 12 [b] (±1) | D 15 (±1) | D 29 (±1 or 2) |
| | Week | | | | | | | |
| | | Wk 0 | | | | | Wk 2 | Wk 4 |
| Eligibility [c] | | | | | | | | |
| Written informed consent and patient assent form [d] | X | | | | | | | |
| Inclusion/exclusion criteria [c] | X | X | | | | | | |
| Ethnicity and race | X | | | | | | | |
| Patient demography | X | | | | | | | |
| Tanner stage and menstruation status | X | | | | | | | |
| Medical/surgical history | X | | | | | | | |
| Prior medications/ vaccination history | X | | | | | | | |
| Concomitant medication | X | X | X | X | X | X | X | X |
| Home diary/compliance [e] | | X | | | | | X | X |
| Physical examination [f] | X | X | | | | | | X |
| Optional: EBV, Hepatitis B and C and HIV [g] | X | | | | | | | |
| PPD tuberculin skin test for patients ≤5 yrs; QuantiFERON-TB test for patients >5 yrs [h] | X | | | | | | | |
| Chest X-ray [i] | X | | | | | | | |
| Confirm eligibility | | X | | | | | | |
| Call IVRS | X | X | | | | | X | X |

TABLE 7-continued 12-week core treatment phase flowchart

| | | | | | | | | |
|---|---|---|---|---|---|---|---|---|
| **IMP administration** | | | | | | | | |
| IMP administration [j] | | X | | | X [j] | | X | X |
| IMP dispense [k] | | X | | | | | X | X |
| **Vital signs and body measurement** | | | | | | | | |
| Temperature, heart rate, BP (2 measurements for BP at each scheduled time point) | X | X | | | | | | X |
| Weight | X | X | | | | | | |
| Height (stadiometer) [l] | X | X | | | | | | |
| **Efficacy assessment** | | | | | | | | |
| JIA ACR disease core set [m] | X | X | | | | | X | X |
| JADAS-27 [n] | | X | | | | | | |
| **Safety assessments** | | | | | | | | |
| AE/SAE recording | ----- | ----- | ----- | ----- | ----- | ----- | ----- | |
| TB risk assessment | X | X | | | | | X | X |
| Local tolerability | | X | | | X | | X | X |
| **Laboratory testing** | | | | | | | | |
| Hematology [o] | X | X [o] | | X [o] | | X [o] | X | X |
| Chemistry [p] | X [p] | X [p] | | | | | X | X |
| Fasting lipids [q] | X | | | | | | | X |
| Optional: HbA1c [r] | X | | | | | | | |
| hs-CRP | X | X | | | | | X | X |
| ESR | | X | | | | | | |
| RF | | X | | | | | | |
| ANA/anti dsDNA antibody | | X | | | | | | |
| Urinalysis [s] | X | | | | | | | |
| Serum pregnancy for females who are menstruating [t] | X | | | | | | | |
| Local urine pregnancy test for females who are menstruating [u] | | X | | | | | | X |
| **PK and PD** | | | | | | | | |
| Serum sarilumab PK [v] Group A (≥30 kg and ≤60 kg) | | X | X | X | X | X | X | X |
| Serum sarilumab PK [v] Group B (<30 kg and ≥10 kg) Schedule 1 | | X | X | | X | | X | X |
| Serum sarilumab PK [v] Group B (<30 kg and ≥10 kg) Schedule 2 | | X | | X | | X | X | X |
| Antibodies to sarilumab [v] | | X | | | | | | |
| IL-6 and total sIL-6Rα | | X | | | | | | |
| **Pharmacogenomics (optional)** | | | | | | | | |
| Saliva sample collection[x] | | X | | | | | | |
| | Screening (4 weeks) | Baseline visit | Core treatment phase (12 weeks) | | | | | PK Follow-up [a] V88 EOT + 2 Weeks (for patients who discontinue the study |
| | Visit | | | | | | | |
| | V9 | V10 | V11 | | V12 | | | treatment during the |
| | Day | | | | | | | |
| | D 43 (±1 or 3) | D 57 (±1 or 3) | D 71 (±1 or 3) | | D 85 (±1 or 3) | | | core treatment phase or not going to enter |

TABLE 7-continued

| 12-week core treatment phase flowchart | | | | | |
|---|---|---|---|---|---|
| | Week | | | | the extension |
| | Wk 6 | Wk 8 | Wk 10 | Wk 12 | phase |
| **Eligibility [c]** | | | | | |
| Written informed consent and patient assent form [d] | | | | | |
| Inclusion/exclusion criteria [c] | | | | | |
| Ethnicity and race | | | | | |
| Patient demography | | | | | |
| Tanner stage and menstruation status | | | | X | |
| Medical/surgical history | | | | | |
| Prior medications/ vaccination history | | | | | |
| Concomitant medication | X | X | X | X | X |
| Home diary/compliance [e] | X | X | X | X | |
| Physical examination [f] | X | | | X | |
| Optional: EBV, Hepatitis B and C and HIV [g] | | | | | |
| PPD tuberculin skin test for patients ≤5 yrs; QuantiFERON-TB test for patients >5 yrs [h] | | | | | |
| Chest X-ray [i] | | | | | |
| Confirm eligibility | | | | | |
| Call IVRS | X | X | X | X | |
| **IMP administration** | | | | | |
| IMP administration [j] | X | X | X | X | |
| IMP dispense [k] | X | X | X | X | |
| **Vital signs and body measurement** | | | | | |
| Temperature, heart rate, BP (2 measurements for BP at each scheduled time point) | | X | | X | |
| Weight | | | | X | |
| Height (stadiometer) [l] | | | | X | |
| **Efficacy assessment** | | | | | |
| JIA ACR disease core set [m] | X | X | X | X | |
| JADAS-27 [n] | | | | X | |
| **Safety assessments** | | | | | |
| AE/SAE recording | ---------- | ---------- | ---------- | ---------- | ---------- |
| TB risk assessment | X | X | X | X | |
| Local tolerability | X | X | X | X | |
| **Laboratory testing** | | | | | |
| Hematology [o] | X | X | X | X | |
| Chemistry [p] | X | X | X | X [p] | |
| Fasting lipids [q] | | | | X | |
| Optional: HbA1c [r] | | | | | |
| hs-CRP | X | X | X | X | |
| ESR | | | | X | |
| RF | | | | | |
| ANA/anti dsDNA antibody | | | | X | |
| Urinalysis [s] | | | | | |
| Serum pregnancy for females who are menstruating [t] | | | | | |
| Local urine pregnancy test for females who are menstruating [u] | | X | | X | |

TABLE 7-continued

| 12-week core treatment phase flowchart | | | |
|---|---|---|---|
| PK and PD | | | |
| Serum sarilumab PK [v] Group A (≥30 kg and ≥60 kg) | X | X | X |
| Serum sarilumab PK [v] Group B (<30 kg and ≥10 kg) Schedule 1 | X | X | X |
| Serum sarilumab PK [v] Group B (<30 kg and ≥10 kg) Schedule 2 | X | X | X |
| Antibodies to sarilumab [v] | | X | |
| IL-6 and total sIL-6Rα | | X | X [w] |
| Pharmacogenomics (optional) | | | |
| Saliva sample collection [x] | | | |

Abbreviations: ADA = anti-drug antibody, ANA = antinuclear antibodies, BP = blood pressure, DNA = deoxyribonucleic acid, D = day, EBV= Epstein-Barr virus, EC = ethics committee, EOT = End-of-Treatment, ESR = erythrocyte sedimentation rate, HbA1c = glycosylated hemoglobin, HIV = human immunodeficiency virus, hs-CRP= high sensitivity C-reactive protein, Ig = immunoglobulin, IVRS = Interactive Voice Response System, IL = interleukin, IMP = investigational medicinal product, JADAS = Juvenile Arthritis Disease Activity Score, JIA ACR = Juvenile Idiopathic Arthritis American College of Rheumatology, PK = pharmacokinetics, PPD = Purified Protein Derivative, SAE = serious adverse event, sIL-6R = soluble Interleukin-6 receptor, TB = tuberculosis, V = visit, Wk = week, yrs = years.

[a] For patients who discontinue treatment during the 12-week core treatment phase (at or before Visit 12), there will be an additional sarilumab PK assessment 2 weeks after the EOT visit (EOT+2 weeks). For patients enrolled in the third portion, Visit 88 is not applicable.

[b] Sarilumab PK sampling between Visit 2 and Visit 7 vary between patients: Visit 3 (Day 3), Visit 4 (Day 5), Visit 5 (Day 8), Visit 6 (Day 12) for Group A (≥30 kg); on visits and days of Visit 3 (Day 3), Visit 5 (Day 8) for Group B (<30 kg) schedule 1; on visits and days of visits: Visit 4 (Day 5), Visit 6 (Day 12) for Group B (<30 kg) schedule 2. Sarilumab PK sampling could be performed at home. A PK diary will be provided to capture date and time of sample collection. No sample collection window is allowed for Visit 3 (Day 3), Visit 4 (Day 5) and Visit 5 (Day 8). There is ±1 day window allowed for Visit 6 (Day 12). For patients enrolled in the third portion, Visits 3, 4, 5, and 6 are not applicable. However, an additional hematology test must be performed before the second sarilumab administration (see footnote “o” for details).

[c] At the Investigators’ discretion laboratory tests mentioned in exclusion criterion E 24 may repeated by central laboratory retesting between the Screening visit and the first IMP administration to ensure the patient meet eligibility with respect to exclusion criterion E 24. A locally approved specific consent form will be signed by patients who require Gilbert syndrome genetic testing (consent/assent must be obtained prior to performing this assessment and local regulations should be respected).

[d] Prior to all screening assessments, the patient (if he/she has reached the legal age of consent based on the local regulations), the parent(s) or the legal guardian(s) must sign and date the EC approved written informed consent form. The patient, the parent(s) and the legal guardian(s) will receive information on the study objective(s) and procedures from the Investigator. Separate written consent forms should be obtained from the parent(s) or the legal guardian(s) who allows his/her child to participate in an optional saliva sample collection for pharmacogenomic study and give permission to the Sponsor to keep their left- over/unused blood samples for future research

[e] A separate (locally approved) informed consent form will be completed by any patients requiring genetic Gilbert disease testing as per local regulations. The signed assent forms should be obtained from the patient based on local regulations and his/her maturity of understanding the study information.

[f] Home diary for IMP administration to be completed for IMP administered at home.

[g] Complete physical examinations will be performed at Visit1 (Day −28 to Day −1, up to 31 days), Visit 2 (Day 1, Week 0), Visit 8 (Week 4), Visit 9 (Week 6), and Visit 12 (Week 12) including skin, nasal cavities, eyes, ears, respiratory, cardiovascular, gastrointestinal, neurological, lymphatic, and musculoskeletal systems.

[h] Optional: Based on the Investigator’s judgment, Epstein-Barr virus (EBV) titer including IgG and IgM may be performed at the Screening; based on the patient’s family and medical history and the Investigator’s judgment, hepatitis B surface antigen (HBs-Ag), hepatitis B surface antibody (HBs-Ab), total hepatitis B core antibody (HBc-Ab), and hepatitis C antibody (HCV-Ab) may be performed at the Screening. The HIV serology will be performed only based on the Investigator’s assessment for those HIV suspected patients. For Argentina and Germany only: Serology testing for hepatitis B and C and HIV have to be performed at Screening visit for all patients in order to screen corresponding exclusion criterion E 14

[i] Purified Protein Derivative (PPD) skin test should be performed in patients ≤5 years old prior to the Baseline Visit 2 (Day 1, Week 0). Patients should be evaluated within 48 to 72 hours after placement of the PPD skin test. For patients who fail to be evaluated within 72 hours, the skin test should be repeated. An assessment of the level of risk (TB contact and/or recent immigration from a country with a high prevalence of TB) vaccination history should be taken into consideration when defining the result of the skin tests. Refer to exclusion criteria for all the details. An interferon-gamma (IFN-r) release assay, QuantiFERON-TB test will be performed for patients >5 years old. (1) After the initial TB screening, if PPD or QuantiFERON result is negative, but clinical suspicion for TB is higher than moderate, the patient should be retested for TB at any time during the study based on the Investigator’s assessment. QuantiFERON-TB test will be considered in the younger group of patients (≤5 years) based on the local PPD availability, local regulation for TB screening and the Investigator’s judgment.

[j] The chest X-ray may be performed for the patients only when deemed necessary based on the Investigator’s judgment or in line with local guideline for TB screening prior to initiating a biologic therapy for JIA patients who haven’t had a chest X-ray performed within 3 months prior to the Baseline Visit 2 (Day1, Week 0).

[k] Investigational medicinal product to be administered once every other week for patients in Dose Regimen 1 and 2 Cohorts and once every week for patients in Dose Regimen 3 Cohort. Arrangements will be made for home nurses to administer IMP for Dose Regimen 3 Cohort patients for the intermediate visits (home administration if possible). Patients should be monitored for at least 30 minutes after IMP administration for any signs or symptoms of a hypersensitivity reaction. For Germany only: After the first IMP administration the patient has to be monitored for at least 1 hour to assess local tolerability. In the dose-finding and second portions, patients who do not achieve a JIA American College of Rheumatology (ACR) 30 by the end of the 12-week core treatment period will be discontinued from the study treatment to receive standard of care as per the Investigator’s clinical judgment. Juvenile Idiopathic arthritis ACR response, including JIA ACR30 response, will be provided by the Sponsor to Investigator to evaluate this criterion only after Visit 12. For patients completing the core treatment phase at Visit 12 (Week 12), but not continuing to the extension phase for reasons other than lack of JIA ACR30 response, there will be no IMP injection at Visit 12.

[l] Investigational medicinal product will be dispensed to patients who are at the Dose Regimen 3 Cohort during the core treatment phase.

[m] Height will be measured using stadiometer at sites during the study.

[n] Juvenile Idiopathic Arthritis ACR core set includes: global assessment of the severity of disease by the physician, global assessment of overall well-being by the patient or the parent(s)/guardian(s), number of joints with active arthritis (defined as swelling not due to deformity OR limitation of motion with either pain or tenderness or both), number of joints with limitation of motion, Childhood Health Assessment Questionnaire (CHAQ), hs-CRP (2, 3, 4). At the Screening, only number of joints with active arthritis and number of joints with limitation of motion will be assessed.

[o] Juvenile Arthritis Disease Activity Score scoring was explained herein.

[p] Hematology (blood should be drawn PRIOR TO drug administration): Hemoglobin, hematocrit, red blood cell (RBC) count, and morphology (if RBC count is abnormal), white blood cell (WBC) differential (neutrophils, lymphocytes, monocytes, eosinophils, basophils), platelet count, absolute neutrophil count (ANC). An additional hematology test must be performed at Visit 6 (Day 12 ± 1 day) for Dose Regimens 1 and 2 Cohorts in order to get the results before the second dose of sarilumab administration (Visit 7: Week 2, Day 15) or prior to or at Visit 5 (Day 8) for Dose Regimen 3 Cohort (not before Visit 4 [Day 5]) in order to get the results before second dose of sarilumab administration. For patients enrolled in the dose-finding and second portions, the additional hematology test can be done at the central laboratory or at the local laboratory to confirm the neutrophil count and platelet count before the second dose of sarilumab administration. For patients enrolled in the third portion without on-site Visit 6, the additional hematology test will be done at the local laboratory before the second dose of sarilumab administration, but no earlier than Day 12. If local laboratory is used, a central laboratory sample for hematology should still be drawn pre-IMP administration at Visit 7 (Day 15, Week 2) as scheduled for Dose Regimens 1 and 2 Cohorts and Visit 5 (Day 8) for Dose Regimen 3 Cohort. For all patients, the Visit 2 (Day 1) and additional hematology laboratory assessment must be reviewed before the administration of the second dose of sarilumab at Visit 5 (Day 8) for Dose Regimen 3 Cohort patients or at Visit 7 (Week 2, Day 15) for Dose Regimens 1 and 2 Cohort patients.

TABLE 7-continued 12-week core treatment phase flowchart

[q] Chemistry (blood should be drawn BEFORE drug administration): Whole chemistry will be performed at the Screening visit, Baseline Visit 2 (Day 1, Week 0) and Visit 12 (Week 12) or EOT only: sodium, potassium, chloride, bicarbonate, blood urea nitrogen, creatinine, and creatinine clearance, glomerular filtration rate (using the modified Schwartz formula), calcium, phosphate, total protein, albumin, alanine aminotransferase (ALT), aspartate aminotransferase (AST), alkaline phosphatase (ALP), total bilirubin, conjugated bilirubin, and unconjugated bilirubin. At all other visits: only ALT, AST, ALP, total bilirubin, conjugated bilirubin, unconjugated bilirubin, and albumin will be tested.
[r] Fasting lipids (blood should be drawn BEFORE drug administration): Triglycerides (TG), total cholesterol, high density lipoprotein (HDL) cholesterol, low density lipoprotein (LDL) cholesterol. Patients are required to fast at least 8 hours before the test.
[s] Optional: HbA1c levels will be only measured based on the patient's medical history and Investigator's judgment.
[t] Urinalysis dipstick: specific gravity, pH, glucose, blood, protein, nitrates, leukocyte esterase, bilirubin. If any parameter on the dipstick is abnormal, a urine sample should be sent to the central laboratory for testing. If positive for proteins, microscopic analysis is performed by central laboratory.
[u] For females who have commenced menstruating, a serum pregnancy test is mandatory at the screening visit.
[v] For females who have commenced menstruating, a urine pregnancy local test should be performed at Visit 2 (Week 0, Day 1), Visit 8 (Week 4), Visit 10 (Week 8), and Visit 12 (Week 12). The urine pregnancy test can be performed locally. The pregnancy status should be checked by urine pregnancy testing prior to exposure to the IMP and EOT.
[w] Blood samples will be collected PRIOR TO IMP administration on the dosing days during the treatment period. If SAE occurs in a patient, blood samples should be collected for determination of sarilumab concentration and anti-drug antibody (ADA) assessment at or near the onset and completion of the occurrence of the event, if possible. In the dose-finding and second portions, if a patient discontinues study treatment prematurely during the 12-week core treatment phase, an additional PK Visit, 2 weeks after the EOT visit is required for blood sampling (Visit 88).
[x] For patients who prematurely discontinue the study treatment during the core treatment phase, the IL-6 and total siL-6R will be measured at the EOT assessment.
[y] Parent (s) or legal guardian(s) must sign a separate informed consent form prior to optional saliva sample collection for phamacogenomic study. Samples are preferred to being collected at the Baseline Visit 2 (Day 1, Week 0), but can be collected at any visit. The patient can also sign the informed consent form based on his/her age, local regulations, and his/her maturity of understanding the study information. The patient is still eligible to enroll in the study if he/she or his/her parent(s) or his/her legal guardian(s) do not wish him/her to participate in saliva sample collection.

Pharmacokinetic Variables

The sarilumab PK variables included maximum serum concentrations observed (Cmax) and area under the serum concentration versus time curve (AUC) calculated using the trapezoidal method during a dose interval (AUC0-τ), following the first dose, concentration observed before treatment administration during repeated dosing (Ctrough) from baseline to Week 12.

A population PK (PopPK) model of pooled data was developed using nonlinear mixed effect modeling to describe the PK profile of sarilumab. The following PK parameters were calculated, using the PopPK model for functional sarilumab in serum (PopPK analysis is to be reported under separate cover). The PK parameters included, but were not limited to those listed in Table 8.

TABLE 8

List of pharmacokinetic parameters and definitions

| Pharmacokinetic parameter | Definition |
|---|---|
| $C_{max}$ | Maximum serum concentration observed |
| $C_{trough}$ | Concentration observed before treatment administration during repeated dosing |
| $t_{max}$ | Time to reach $C_{max}$ |
| $AUC_{0\text{-}\tau}$ | Area under the serum concentration versus time curve calculated using the trapezoidal method during a dose interval (τ) |

Efficacy Assessments

JIA ACR Response

The JIA ACR level of response to assess signs and symptoms was used in this study (refer to Table 7). JIA ACR 30/50/70/90/100 (JIA ACR30/50/70/90/100 response was defined as a patient with 3 of 6 core set variables improved by at least 30%/50%/70%/90%/100% from baseline with no more than 1 of the remaining variables worsened by more than 30%.

JIA ACR core set included 6 variables:

1. Physician global assessment of disease activity
2. Patient/parent assessment of overall well-being
3. Functional ability determined by Childhood Health Assessment Questionnaire (CHAQ)
4. Number of joints with active arthritis (0 to 71 joints)
5. Number of joints with limitation of motion (0 to 67 joints)
6. High sensitivity C-reactive protein.

During the 12-week core treatment phase, JIA ACR disease core set will be evaluated at every site visit except Visit 3 (Day 3), Visit 4 (Day 5), Visit 5 (Day 8), and Visit 6 (Day 12). During the extension phase (for patients who remain on the current dose (selected dose regimen), the JIA ACR core set will be assessed periodically at Weeks 24, 48, 72, 96 (EOT for third portion), 120 (not applicable for third portion), 144 (not applicable for third portion), and EOT (Week 156 for dose-finding and second portions/Week 96 for third portion). For patients who change to the selected dose regimen during the extension phase.

Physician Global Assessment of Disease Activity

The Investigator was requested to rate the patient's disease activity on an anchored 100 millimeter (mm) horizontal visual analogue scale (VAS) where 0 was considered the best disease activity and 100 the worst.

Patient/Parent Assessment of Overall Well-being

Patient/parent assessment of overall well-being was measured on a 100 mm horizontal VAS. The patient or the same parent or guardian was requested to complete the form to ensure the consistency.

Childhood Health Assessment Questionnaire (CHAQ)

The CHAQ was an interview or self-administered instrument for children ≥8 years and parent/proxy administered for children younger than 8 years of age. The CHAQ was a generic measure of health status in children ages 1 to 19 years of age. The assessment consisted of 43 items in total and took approximately 10 minutes to complete. The CHAQ questionnaire was completed-before IMP dosing and at subsequent time points (as per guidance provided by the health economics and outcomes research department). The recall period was 1 week (Singh, G. et al. 1994 Arthritis Rheum. 1994 December; 37(12):1761-9).

The median CHAQ scores corresponding to mild, mild-to-moderate and moderate disability reported in the development of the CHAQ were 0.13, 0.63, and 1.75, respectively (Dempster, H. et al., 2001 Arthritis Rheum. 44(8):1768-74).

In order to eliminate discrepancies which could have been introduced by growth and development, parents were asked to note only those difficulties due to illness (e.g., if the child was unable to do an activity because he/she was too young, the response was marked as "not applicable"). Response options assessing difficulty were based on a 5 point Likert scale (0=Without Any Difficulty, 1=With Some Difficulty, 2=With Much difficulty, 3=Unable to do and 4=Not Applicable).

The CHAQ was divided into 3 parts:

1. Disability Index: 41 items assessing the ability to function in daily life further divided into 8 subscales/domains: dressing and grooming; arising; eating; walking; hygiene; reach; grip; and activities. For each domain, ratings of the degree to which daily functions were difficult to perform, required use of special aides or devices, and required assistance from another person was assessed.

To calculate the CHAQ-DI, each domain score was first calculated:

The question with the highest response determined the score for that functional area If aids or devices were used or help was needed to complete tasks in a certain area, a minimum score of 2 was recorded for the corresponding functional area The 8 subscales/domains were averaged to calculate a mean score which was the disability index (with range of 0 to 3).

Lower disability index scores indicated better than health status/better healthier related quality of life/less signs and symptoms while higher disability index scores indicated worse health status/worse HRQL/more signs and symptoms (Singh, G. et al. 1994 Arthritis Rheum. 1994 December; 37(12):1761-90; Klepper S. 2003 Arthritis Rheum. 49(3): 435-43). The minimal clinical important improvement in CHAQ disability index was a reduction in score of 0.13. The minimal clinical important deterioration in the CHAQ disability index was a median change score of 0.75 (Dempster, H. et al., 2001 Arthritis Rheum. 44(8):1768-74).

2. Discomfort Index: determined by the severity of pain in the past week, rated on a VAS (with anchors of "0 no pain" and "100 very severe pain"). To calculate the CHAQ discomfort index, the distance from the left end of the VAS in item 67 to the respondent's mark was measured and multiplied by 0.2. Range was 0 to 3.
3. Health Status: measure of the patient's or parent's global assessment of illness. To calculate the CHAQ Health Status score, the distance from the left end of the VAS in item 69 to the respondent's mark was measured and multiplied by 0.2. Range was 0 to 3.

Number of Joints with Active Arthritis and Number of Joints with Limited Motion

An active joint was defined as a joint with swelling within the joint not due to deformity, OR with limitation of motion with either pain or tenderness. Seventy-one joints were assessed for active disease by counting the number of active joints (Bazso, A. et al., 2009 J Rheumatol. 36(1):183-90; Beukelman, T. et al., 2011 Arthritis Care Res (Hoboken). 63(4):465-82).

The 71 joints included the cervical spine (counted as 1 joint), temporomandibular (2 joints, R and L side), sternoclavicular (2 joints), acromioclavicular (2 joints), shoulder (2 joints), elbow (2 joints), wrist (2 joints), metacarpophalangeal (10 joints total, 5 on each side), proximal interphalangeal (10 joints total, 5 on each side), distal interphalangeal (8 joints total, 4 on each side), hip (2 joints), knee (2 joints), ankle (2 joints), subtalar (2 joints), tarsometatarsal (2 joints), metatarsophalangeal (10 joints, 5 on each side), and foot interphalangeal (10 joints, 5 on each side).

The 67 joints examined for limitation of motion were the same as those examined for active disease except the sternoclavicular (n=2) and acromioclavicular (n=2). A formal count of the joints was performed by a trained assessor. Joint tenderness was defined as pain induced by the pressure of the joints, exerted by the assessor's thumb and index finger.

High Sensitivity C-Reactive Protein (hs-CRP)

At each visit, hs-CRP was evaluated. See Table 7. High sensitivity-C-reactive protein levels were directly correlated with IL-6R activity. It was expected that active dose regimens would have a dramatic lowering effect on C-reactive protein (CRP) levels.

Juvenile Arthritis Disease Activity Score

The JADAS score to assess disease activity was used in this study (refer to Table 7). The JADAS included 4 measures:

1. Physician global assessment of disease activity measured on a 10 centimeters (cm) VAS where 0=no activity and 10=maximum activity
2. Parent/patient global assessment of well-being, measured on a 10 cm VAS where 0=very well and 10=very poor
3. Count of joints with active disease
4. Index of inflammation: hs-CRP or ESR level:

Erythrocyte sedimentation rate normalized to a 0 to 10 scale according to the following formula: (ESR[mm/hour]−20)/10 where before making the calculation, ESR value <20 mm/hour converted to 0 and ESR values >120 mm/hour were converted to 120.

Or, hs-CRP normalized to a 0 to 10 scale according to the following formula: (CRP[mg/L]−10)/10 where before calculation, CRP values <10 mg/L were converted to 0 and CRP values >110 mg/L were converted to 110.

The JADAS was calculated as the simple linear sum of the scores of its 4 components. See Consolaro, A. et al. 2009 Arthritis Rheum. 61(5):658-66. The JADAS-27 included the following joints: cervical spine, elbows, wrists, metacarpophalangeal joints (from first to third), proximal interphalangeal joints, hips, knees, and ankles. The JADAS was found to be a valid instrument for assessment of disease activity in JIA and was potentially applicable in standard clinical care, observational studies and clinical trials (Ibid.).

Pharmacodynamic Measurement and Timing

Pharmacodynamic effects of sarilumab were assessed through measurement of the following biomarkers: hs-CRP, IL-6, and total sIL-6Rα:

N High sensitivity CRP concentrations were measured using a nephelometry (HS) assay with a LLOQ of 0.20 mg/L by Covance CLS Serum IL-6 concentrations were determined using validated quantitative sandwich enzyme immunoassay with the LLOQ of 3.12 pg/mL by Covance CLS Serum total sIL-6Rα concentrations were measured using validated an ELISA method with a LLOQ of 15 ng/mL (DOH1163) by Covance.

The sampling schedule for blood collection can be found in the study chart in Table 7.

Clinical Laboratory Evaluations

The summary statistics (including number, mean, median, SD, minimum, and maximum) of all laboratory variables (central laboratory values and changes from baseline) were calculated for each visit or study assessment (baseline, each post baseline time point, endpoint) by Dose Cohort and organized by biological function. The incidence of PCSAs and abnormal laboratory values at any time during the TEAE period were summarized by biological function and Dose Cohort. For lipids, the NCEP APTIII classification was used for baseline. The incidence of neutropenia, thrombocytopenia, and lymphopenia by maximal grade were summarized.

Analyses of Pharmacokinetic Data

Concentrations of functional sarilumab in serum were summarized using descriptive statistics. All PK analyses were performed using the PK population. This consisted of all patients in the safety population with at least 1 post dose non-missing sarilumab concentration value. Trough concentrations of functional sarilumab in serum were summarized using descriptive statistics (including number, arithmetic and geometric means, SD, SE of the mean (SEM), CV, minimum, median, and maximum) by dose, overall and by weight group, for each visit. The samples were considered non-eligible for these analyses if the previous dosing time was <11 days or >17 days before the sampling time for every other week regimens; <5 days or >9 days before the sampling time for every week regimens. Concentrations below the LLOQ were set to zero for samples at pre-dose (Week 0). Other concentrations below LLOQ were replaced by LLOQ/2. A PopPK model was developed using nonlinear mixed-effects modeling to describe the PK profile of sarilumab. The PopPK model was presented in a separate document from CSR.

Analyses of Pharmacodynamics Data

Concentrations of IL-6, total sIL-6Rα and hs-CRP in serum from baseline to Week 12 were summarized using descriptive statistics (including number, arithmetic and geometric means, SD, SEM, CV, minimum, median and maximum) by dose and weight group for each.

Analysis of Pharmacokinetic-Pharmacodynamic Data

Exploratory analyses were performed to elucidate exposure-response relationships with key efficacy endpoints and/or biomarkers. Results of the exposure-response relationships with key efficacy endpoints were presented in a separate document from the CSR.

Demographic and Other Baseline Characteristics

The results herein relate to the dose-finding portion of the 12-week core phase of this study.

Demography

Demographic and patient characteristics were described for the all-treated population in Table 9 by treatment group. Overall, patients were mostly female (64.3%) and Caucasian (78.6%) with a distribution similar across the weight and dose groups. The mean weight and age were 45.0 kg and 13.0 years in Group A and 19.7 kg and 5.2 years in Group B, respectively. Nine (21.4%) patients were recruited in South American countries and 33 (78.6%) patients were enrolled in Western regions and the rest of the world. These demographic characteristics were comparable across the three Dose Cohorts within each weight group. Detailed baseline characteristics are presented in Table 9.

Medical History

There were a total of 9 [69.2%], 11 [78.6%], and 9 [60.0%] patients in Dose Cohorts 1, 2, and 3, respectively, with any medical history. The most common primary SOC was infections and infestations seen in a total of 11 patients with more than half in Dose Cohort 2 (6 [42.9%] patients). One patient in Dose Cohort 2 from Group A had a history of intestinal problems due to a surgical procedure 3.5 years before entering the study which met exclusion criteria 21 and subsequently led to permanent discontinuation.

At baseline, patients had high disease activity, with a mean JADAS-27-CRP of 20.6, mean active joint count of 13.9, and mean CRP of 9.5 mg/L. Concomitant and prior medication use was balanced between weight groups (Table 21).

TABLE 9

Demographics and patient characteristics at baseline-All-treated population

| | Dose Cohort | | | | | | |
|---|---|---|---|---|---|---|---|
| | 1 | | | 2 | | | 3 |
| Weight Group | >30 kg | <30 kg | All | >30 kg | <30 kg | All | >30 kg |
| Age (years) | | | | | | | |
| Number | 7 | 6 | 13 | 7 | 7 | 14 | 6 |
| Mean (SD) | 12.3 (3.3) | 6.5 (3.2) | 9.6 (4.3) | 13.1 (3.4) | 4.7 (1.9) | 8.9 (5.1) | 13.7 (3.0) |
| Median | 13.0 | 6.0 | 9.0 | 15.0 | 4.0 | 7.5 | 13.0 |
| Min: Max | 7:17 | 2:11 | 2:17 | 8:16 | 3:7 | 3:16 | 9:17 |
| Age Group (years) [n (%)] | | | | | | | |
| Number | 7 | 6 | 13 | 7 | 7 | 14 | 6 |
| Children (2-11) | 2 (28.6%) | 6 (100%) | 8 (61.5%) | 3 (42.9%) | 7 (100%) | 10 (71.4%) | 1 (16.7%) |
| Adolescents (12-17) | 5 (71.4%) | 0 | 5 (38.5%) | 4 (57.1%) | 0 | 4 (28.6%) | 5 (83.3%) |
| Weight (kg) | | | | | | | |
| Number | 7 | 6 | 13 | 7 | 7 | 14 | 6 |
| Mean (SD) | 47.3 (9.4) | 20.4 (6.7) | 34.9 (16.1) | 43.8 (9.9) | 20.1 (6.8) | 31.9 (14.8) | 43.8 (7.7) |
| Median | 50.7 | 21.1 | 30.1 | 44.4 | 18.2 | 29.3 | 43.8 |
| Min: Max | 30.1:59.0 | 11.5:29.5 | 11.5:59.0 | 30.0:55.5 | 12.0:28.6 | 12.0:55.5 | 34.5:52.9 |
| Number | 7 | 6 | 13 | 7 | 7 | 14 | 6 |
| ≥30 kg | 7 (100%) | 0 | 7 (53.8%) | 7 (100%) | 0 | 7 (50.0%) | 6 (100%) |
| <30 kg | 0 | 6 (100%) | 6 (46.2%) | 0 | 7 (100%) | 7 (50.0%) | 0 |
| Body mass index (BMI) (kg/m$^2$) | | | | | | | |
| Number | 7 | 6 | 13 | 7 | 7 | 14 | 6 |
| Mean (SD) | 20.3 (3.1) | 14.4 (1.4) | 17.6 (3.9) | 19.1 (3.2) | 16.0 (1.0) | 17.6 (2.8) | 18.6 (2.5) |
| Median | 19.9 | 14.7 | 16.5 | 17.6 | 15.5 | 17.1 | 19.4 |
| Min: Max | 16.5:26.2 | 11.8:15.5 | 11.8:26.2 | 15.1:24.7 | 15.3:17.5 | 15.1:24.7 | 15.1:21.3 |

TABLE 9-continued

Demographics and patient characteristics at baseline-All-treated population

| | | | | | | | |
|---|---|---|---|---|---|---|---|
| BMI group (kg/m$^2$) [n (%)] | | | | | | | |
| Number | 7 | 6 | 13 | 7 | 7 | 14 | 6 |
| Normal (<25) | 6 (85.7%) | 6 (100%) | 12 (92.3%) | 7 (100%) | 7 (100%) | 14 (100%) | 6 (100%) |
| Overweight (≥25-30) | 1 (14.3%) | 0 | 1 (7.7%) | 0 | 0 | 0 | 0 |
| Obese (≥30) | 0 | 0 | 0 | 0 | 0 | 0 | 0 |
| Height (cm) | | | | | | | |
| Number | 7 | 6 | 13 | 7 | 7 | 14 | 6 |
| Mean (SD) | 152.3 (11.4) | 117.5 (17.5) | 136.2 (22.8) | 151.0 (10.5) | 110.3 (17.0) | 130.6 (25.1) | 153.3 (11.4) |
| Median | 154.0 | 120.0 | 138.0 | 154.0 | 109.0 | 132.0 | 154.0 |
| Min: Max | 135:165 | 89:138 | 89:165 | 133:161 | 88:131 | 88:161 | 136:168 |
| Sex [n (%)] | | | | | | | |
| Number | 7 | 6 | 13 | 7 | 7 | 14 | 6 |
| Female | 5 (71.4%) | 5 (83.3%) | 10 (76.9%) | 5 (71.4%) | 3 (42.9%) | 8 (57.1%) | 3 (50.0%) |
| Male | 2 (28.6%) | 1 (16.7%) | 3 (23.1%) | 2 (28.6%) | 4 (57.1%) | 6 (42.9%) | 3 (50.0%) |
| Race [n (%)] | | | | | | | |
| Number | 7 | 6 | 13 | 7 | 7 | 14 | 6 |
| Caucasian/White | 6 (85.7%) | 3 (50.0%) | 9 (69.2%) | 7 (100%) | 5 (71.4%) | 12 (85.7%) | 4 (66.7%) |
| Black | 0 | 0 | 0 | 0 | 0 | 0 | 0 |
| Asian/Oriental | 0 | 0 | 0 | 0 | 0 | 0 | 0 |
| Unknown | 1 (14.3%) | 2 (33.3%) | 3 (23.1%) | 0 | 0 | 0 | 2 (33.3%) |
| Missing | 0 | 1 (16.7%) | 1 (7.7%) | 0 | 2 (28.6%) | 2 (14.3%) | 0 |
| Region [n (%)] | | | | | | | |
| Number | 7 | 6 | 13 | 7 | 7 | 14 | 6 |
| Western | 3 (42.9%) | 1 (16.7%) | 4 (30.8%) | 1 (14.3%) | 3 (42.9%) | 4 (28.6%) | 2 (33.3%) |
| South America | 1 (14.3%) | 3 (50.0%) | 4 (30.8%) | 2 (28.6%) | 0 | 2 (14.3%) | 2 (33.3%) |
| Rest of the World | 3 (42.9%) | 2 (33.3%) | 5 (38.5%) | 4 (57.1%) | 4 (57.1%) | 8 (57.1%) | 2 (33.3%) |
| Tanner Stage [n (%)] | | | | | | | |
| Number | 7 | 6 | 13 | 7 | 7 | 14 | 6 |
| Stage I | 2 (28.6%) | 5 (83.3%) | 7 (53.8%) | 1 (14.3%) | 7 (100%) | 8 (57.1%) | 1 (16.7%) |
| Stage II | 0 | 1 (16.7%) | 1 (7.7%) | 1 (14.3%) | 0 | 1 (7.1%) | 2 (33.3%) |
| Stage III | 1 (14.3%) | 0 | 1 (7.7%) | 2 (28.6%) | 0 | 2 (14.3%) | 1 (16.7%) |
| Stage IV | 2 (28.6%) | 0 | 2 (15.4%) | 1 (14.3%) | 0 | 1 (7.1%) | 0 |
| Stage V | 2 (28.6%) | 0 | 2 (15.4%) | 2 (28.6%) | 0 | 2 (14.3%) | 2 (33.3%) |

| | Dose Cohort | | | | |
|---|---|---|---|---|---|
| | 3 | | All Doses Combined | | |
| Weight Group | <30 kg | All | >30 kg | <30 kg | All |
| Age (years) | | | | | |
| Number | 9 | 15 | 20 | 22 | 42 |
| Mean (SD) | 4.7 (2.4) | 8.3 (5.2) | 13.0 (3.1) | 5.2 (2.5) | 8.9 (4.8) |
| Median | 4.0 | 8.0 | 13.0 | 4.5 | 8.5 |
| Min: Max | 2:9 | 2:17 | 7:17 | 2:11 | 2:17 |
| Age Group (years) [n (%)] | | | | | |
| Number | 9 | 15 | 20 | 22 | 42 |
| Children (2-11) | 9 (100%) | 10 (66.7%) | 6 (30.0%) | 22 (100%) | 28 (66.7%) |
| Adolescents (12-17) | 0 | 5 (33.3%) | 14 (70.0%) | 0 | 14 (33.3%) |
| Weight (kg) | | | | | |
| Number | 9 | 15 | 20 | 22 | 42 |
| Mean (SD) | 18.9 (6.0) | 28.8 (14.2) | 45.0 (8.8) | 19.7 (6.1) | 31.7 (14.8) |
| Median | 16.7 | 27.2 | 46.3 | 18.4 | 29.1 |
| Min: Max | 12.4:28.7 | 12.4:52.9 | 30.0:59.0 | 11.5:29.5 | 11.5:59.0 |
| Number | 9 | 15 | 20 | 22 | 42 |
| ≥30 kg | 0 | 6 (40.0%) | 20 (100%) | 0 | 20 (47.6%) |
| <30 kg | 9 (100%) | 9 (60.0%) | 0 | 22 (100%) | 22 (52.4%) |
| Body mass index (BMI) (kg/m$^2$) | | | | | |
| Number | 9 | 15 | 20 | 22 | 42 |
| Mean (SD) | 15.7 (1.2) | 16.9 (2.3) | 19.4 (2.9) | 15.5 (1.3) | 17.3 (3.0) |
| Median | 15.4 | 15.7 | 19.3 | 15.4 | 16.3 |
| Min: Max | 14.3:18.3 | 14.3:21.3 | 15.1:26.2 | 11.8:18.3 | 11.8:26.2 |

TABLE 9-continued

Demographics and patient characteristics at baseline-All-treated population

| | | | | | |
|---|---|---|---|---|---|
| BMI group (kg/m$^2$) [n (%)] | | | | | |
| Number | 9 | 15 | 20 | 22 | 42 |
| Normal (<25) | 9 (100%) | 15 (100%) | 19 (95.0%) | 22 (100%) | 41 (97.6%) |
| Overweight (≥25-30) | 0 | 0 | 1 (5.0%) | 0 | 1 (2.4%) |
| Obese (≥30) | 0 | 0 | 0 | 0 | 0 |
| Height (cm) | | | | | |
| Number | 9 | 15 | 20 | 22 | 42 |
| Mean (SD) | 108.6 (16.4) | 126.5 (26.7) | 152.2 (10.5) | 111.5 (16.5) | 130.9 (24.7) |
| Median | 103.0 | 133.0 | 154.0 | 109.5 | 134.0 |
| Min: Max | 92:135 | 92:168 | 133:168 | 88:138 | 88:168 |
| Sex [n (%)] | | | | | |
| Number | 9 | 15 | 20 | 22 | 42 |
| Female | 6 (66.7%) | 9 (60.0%) | 13 (65.0%) | 14 (63.6%) | 27 (64.3%) |
| Male | 3 (33.3%) | 6 (40.0%) | 7 (35.0%) | 8 (36.4%) | 15 (35.7%) |
| Race [n (%)] | | | | | |
| Number | 9 | 15 | 20 | 22 | 42 |
| Caucasian/White | 8 (88.9%) | 12 (80.0%) | 17 (85.0%) | 16 (72.7%) | 33 (78.6%) |
| Black | 0 | 0 | 0 | 0 | 0 |
| Asian/Oriental | 0 | 0 | 0 | 0 | 0 |
| Unknown | 0 | 2 (13.3%) | 3 (15.0%) | 2 (9.1%) | 5 (11.9%) |
| Missing | 1 (11.1%) | 1 (6.7%) | 0 | 4 (18.2%) | 4 (9.5%) |
| Region [n (%)] | | | | | |
| Number | 9 | 15 | 20 | 22 | 42 |
| Western | 6 (66.7%) | 8 (53.3%) | 6 (30.0%) | 10 (45.5%) | 16 (38.1%) |
| South America | 1 (11.1%) | 3 (20.0%) | 5 (25.0%) | 4 (18.2%) | 9 (21.4%) |
| Rest of the World | 2 (22.2%) | 4 (26.7%) | 9 (45.0%) | 8 (36.4%) | 17 (40.5%) |
| Tanner Stage [n (%)] | | | | | |
| Number | 9 | 15 | 20 | 22 | 42 |
| Stage I | 9 (100%) | 10 (66.7%) | 4 (20.0%) | 21 (95.5%) | 25 (59.5%) |
| Stage II | 0 | 2 (13.3%) | 3 (15.0%) | 1 (4.5%) | 4 (9.5%) |
| Stage III | 0 | 1 (6.7%) | 4 (20.0%) | 0 | 4 (9.5%) |
| Stage IV | 0 | 0 | 3 (15.0%) | 0 | 3 (7.1%) |
| Stage V | 0 | 2 (13.3%) | 6 (30.0%) | 0 | 6 (14.3%) |

Abbreviations: BMI = body mass index.

Region 1 (Western countries): Czech Republic, Germany, Spain, Netherlands, United Kingdom, Finland, France, and Italy.

Region 2 (South America): Argentina, Chile, and Mexico

Region 3 (Rest of the world): Poland and Russia

Percentages are calculated using number of patients assessed as denominator.

Disease Characteristics at Baseline

Baseline disease characteristics are described for the all-treated. population in Table 10 by treatment group. The disease characteristics at baseline were comparable across the three Dose Cohorts within each weight group. The distribution of patients with RF-negative pcJIA, RF-positive pcJIA, and e-oJIA subtypes was 64.3%, 21.4%, and 14.3%, respectively. The distribution of RF-negative pcJIA was similar across the 2 weight groups while there were about twice as many patients with RF-positive pcJIA and half as many patients with e-oJIA in Group A compared to Group B.

As expected and resulting from the age of the Dose Cohorts, the median duration of JIA since diagnosis was higher in Group A (2.6 years [range: 0.3 to 15.1 years]) than Group B (1.1 years [range: 0.1 to 7.2 years]) across the Dose Cohorts. The median number of active joints and of joints with limited motion were 10.0 (range: 5.0 to 45.0) and 8.0 (range: 1.0 to 46.0), respectively, with a breakdown of 15.5 (range: 5.0 to 45.0) and 8.5 (range: 1.0 to 46.0) in Group A and 8.5 (5.0 to 32.0) and 7.0 (range: 1.0 to 34.0) in Group B. Baseline median JADAS-27-CRP was 19.3 (range: 8.5 to 35.5) (23.2 [range: 9.2 to 33.8] and 16.8 [range: 8.5 to 35.5] in Group A and B, respectively), reflecting a population with highly active disease. Baseline median hs-CRP was 1.1 mg/L (range: 0.1 to 86.5) (1.0 mg/L [range: 0.1 to 45.9] and 1.6 mg/L [range: 0.1 to 86.5] in Groups A and B, respectively). The distribution of ANC was similar across the weight and dose group.

Overall, 76.2% of patients who entered the study were receiving concomitant csDMARD treatment and 31.0% concomitant oral glucocorticoids; 28.6% of patients had received ≥1 bDMARD treatment that was halted prior to the study. Other patient and disease characteristics were comparable across weight groups.

TABLE 10

Disease characteristics at baseline - All-treated population

| | Dose Cohort | | | | | | |
|---|---|---|---|---|---|---|---|
| | 1 | | | 2 | | | 3 |
| Weight Group | ≥30 kg | <30 kg | All | ≥30 kg | <30 kg | All | ≥30 kg |
| JIA subtype [n (%)] | | | | | | | |
| Number | 7 | 6 | 13 | 7 | 7 | 14 | 6 |
| RF-positive | 2 (28.6%) | 2 (33.3%) | 4 (30.8%) | 3 (42.9%) | 0 | 3 (21.4%) | 1 (16.7%) |
| RF-negative | 5 (71.4%) | 4 (66.7%) | 9 (69.2%) | 3 (42.9%) | 5 (71.4%) | 8 (57.1%) | 4 (66.7%) |
| Extended oligoarticular | 0 | 0 | 0 | 1 (14.3%) | 2 (28.6%) | 3 (21.4%) | 1 (16.7%) |
| Duration of JIA since diagnosis (Years) | | | | | | | |
| Number | 7 | 6 | 13 | 7 | 7 | 14 | 6 |
| Mean (SD) | 4.3 (5.7) | 2.2 (2.7) | 3.4 (4.5) | 5.3 (6.2) | 1.5 (2.2) | 3.4 (4.9) | 4.1 (4.0) |
| Median | 0.8 | 1.1 | 0.9 | 1.6 | 0.5 | 1.1 | 3.8 |
| Min: Max | 0.3:15.1 | 0.3:7.2 | 0.3:15.1 | 0.6:15.1 | 0.2:6.3 | 0.2:15.1 | 0.3:11.2 |
| Rheumatoid factor [n (%)] | | | | | | | |
| Number | 6 | 6 | 12 | 7 | 7 | 14 | 6 |
| Positive (≥15 IU/mL) | 0 | 0 | 0 | 3 (42.9%) | 0 | 3 (21.4%) | 1 (16.7%) |
| Negative (<15 IU/mL) | 6 (100%) | 6 (100%) | 12 (100%) | 4 (57.1%) | 7 (100%) | 11 (78.6%) | 5 (83.3%) |
| Active arthritis joint count (0-71) | | | | | | | |
| Number | 7 | 6 | 13 | 7 | 7 | 14 | 6 |
| Mean (SD) | 19.3 (12.9) | 11.7 (5.3) | 15.8 (10.5) | 14.6 (8.9) | 8.3 (3.5) | 11.4 (7.3) | 17.7 (10.1) |
| Median | 18.0 | 10.5 | 14.0 | 12.0 | 8.0 | 9.0 | 17.0 |
| Min: Max | 6.0:45.0 | 7.0:21.0 | 6.0:45.0 | 6.0:32.0 | 5.0:15.0 | 5.0:32.0 | 5.0:30.0 |
| Limited motion joint count (0-67) | | | | | | | |
| Number | 7 | 6 | 13 | 7 | 7 | 14 | 6 |
| Mean (SD) | 10.3 (6.3) | 10.5 (12.0) | 10.4 (9.0) | 9.3 (11.1) | 7.6 (4.4) | 8.4 (8.2) | 16.5 (15.4) |
| Median | 10.0 | 7.0 | 7.0 | 6.0 | 8.0 | 7.0 | 11.5 |
| Min: Max | 2.0:21.0 | 1.0:34.0 | 1.0:34.0 | 1.0:33.0 | 2.0:15.0 | 1.0:33.0 | 3.0:46.0 |
| JADAS-27 CRP | | | | | | | |
| Number | 7 | 6 | 13 | 7 | 7 | 14 | 6 |
| Mean (SD) | 22.9 (7.8) | 21.3 (6.0) | 22.1 (6.8) | 22.5 (7.0) | 17.0 (8.4) | 19.8 (8.0) | 21.1 (8.0) |
| Median | 25.0 | 20.7 | 22.5 | 22.9 | 14.4 | 17.1 | 20.5 |
| Min: Max | 9.2:30.5 | 14.3:29.4 | 9.2:30.5 | 14.8:33.8 | 8.6:33.5 | 8.6:33.8 | 10.0:31.2 |
| CHAQ-DI | | | | | | | |
| Number | 7 | 6 | 13 | 7 | 7 | 14 | 6 |
| Mean (SD) | 1.1 (0.6) | 1.5 (0.9) | 1.3 (0.8) | 0.9 (0.8) | 1.3 (0.7) | 1.1 (0.7) | 0.7 (0.9) |
| Median | 0.9 | 1.1 | 1.0 | 0.9 | 1.1 | 1.0 | 0.3 |
| Min: Max | 0.4:1.9 | 0.5:2.9 | 0.4:2.9 | 0.0:2.3 | 0.4:2.1 | 0.0:2.3 | 0.0:2.1 |
| hs-CRP (mg/L) | | | | | | | |
| Number | 7 | 6 | 13 | 7 | 7 | 14 | 6 |
| Mean (SD) | 10.9 (18.5) | 3.2 (3.6) | 7.4 (13.9) | 13.7 (15.7) | 15.4 (31.7) | 14.6 (24.1) | 5.8 (8.9) |
| Median | 0.8 | 1.6 | 0.9 | 5.6 | 0.8 | 2.9 | 1.5 |
| Min: Max | 0.1:45.9 | 0.3:9.4 | 0.1:45.9 | 0.2:38.2 | 0.3:86.5 | 0.2:86.5 | 0.1:22.8 |
| ESR (mm/h) | | | | | | | |
| Number | 7 | 6 | 13 | 7 | 5 | 12 | 6 |
| Mean (SD) | 20.7 (29.7) | 23.8 (19.5) | 22.2 (24.5) | 30.1 (31.7) | 9.2 (5.1) | 21.4 (25.9) | 33.8 (25.9) |
| Median | 9.0 | 18.5 | 12.0 | 15.0 | 8.0 | 10.5 | 30.0 |
| Min: Max | 2:85 | 2:50 | 2:85 | 8:93 | 4:17 | 4:93 | 2:73 |
| Absolute neutrophil count (Giga/L) | | | | | | | |
| Number | 7 | 6 | 13 | 7 | 7 | 14 | 6 |
| Mean (SD) | 3.7 (1.9) | 4.4 (2.4) | 4.1 (2.1) | 4.4 (1.6) | 5.4 (1.6) | 4.9 (1.6) | 4.6 (1.3) |
| Median | 3.6 | 4.3 | 3.6 | 3.8 | 5.1 | 4.7 | 4.8 |
| Min: Max | 1.7:7.3 | 2.1:7.8 | 1.7:7.8 | 3.1:7.7 | 3.3:8.0 | 3.1:8.0 | 3.0:6.4 |
| Absolute neutrophil count [n (%)] | | | | | | | |
| Number | 7 | 6 | 13 | 7 | 7 | 14 | 6 |
| ≥5.99 x $10_9$/L | 1 (14.3%) | 1 (16.7%) | 2 (15.4%) | 1 (14.3%) | 2 (28.6%) | 3 (21.4%) | 1 (16.7%) |
| <5.99 x $10_9$/L | 6 (85.7%) | 5 (83.3%) | 11 (84.6%) | 6 (85.7%) | 5 (71.4%) | 11 (78.6%) | 5 (83.3%) |

TABLE 10-continued

Disease characteristics at baseline - All-treated population

| | Dose Cohort 3 | | All Doses Combined | | |
|---|---|---|---|---|---|
| Weight Group | <30 kg | All | ≥30 kg | <30 kg | All |
| JIA subtype [n (%)] | | | | | |
| Number | 9 | 15 | 20 | 22 | 42 |
| RF-positive | 1 (11.1%) | 2 (13.3%) | 6 (30.0%) | 3 (13.6%) | 9 (21.4%) |
| RF-negative | 6 (66.7%) | 10 (66.7%) | 12 (60.0%) | 15 (68.2%) | 27 (64.3%) |
| Extended oligoarticular | 2 (22.2%) | 3 (20.0%) | 2 (10.0%) | 4 (18.2%) | 6 (14.3%) |
| Duration of JIA since diagnosis (Years) | | | | | |
| Number | 9 | 15 | 20 | 22 | 42 |
| Mean (SD) | 1.4 (0.9) | 2.5 (2.8) | 4.6 (5.2) | 1.7 (1.9) | 3.1 (4.1) |
| Median | 1.9 | 1.9 | 2.6 | 1.1 | 1.2 |
| Min: Max | 0.1:2.6 | 0.1:11.2 | 0.3:15.1 | 0.1:7.2 | 0.1:15.1 |
| Rheumatoid factor [n (%)] | | | | | |
| Number | 9 | 15 | 19 | 22 | 41 |
| Positive (≥15 IU/mL) | 1 (11.1%) | 2 (13.3%) | 4 (21.1%) | 1 (4.5%) | 5 (12.2%) |
| Negative (<15 IU/mL) | 8 (88.9%) | 13 (86.7%) | 15 (78.9%) | 21 (95.5%) | 36 (87.8%) |
| Active arthritis joint count (0-71) | | | | | |
| Number | 9 | 15 | 20 | 22 | 42 |
| Mean (SD) | 12.7 (9.3) | 14.7 (9.6) | 17.2 (10.4) | 11.0 (6.9) | 13.9 (9.2) |
| Median | 8.0 | 10.0 | 15.5 | 8.5 | 10.0 |
| Min: Max | 5.0:32.0 | 5.0:32.0 | 5.0:45.0 | 5.0:32.0 | 5.0:45.0 |
| Limited motion joint count (0-67) | | | | | |
| Number | 9 | 15 | 20 | 22 | 42 |
| Mean (SD) | 10.6 (8.5) | 12.9 (11.6) | 11.8 (11.2) | 9.6 (8.3) | 10.6 (9.7) |
| Median | 7.0 | 9.0 | 8.5 | 7.0 | 8.0 |
| Min: Max | 2.0:25.0 | 2.0:46.0 | 1.0:46.0 | 1.0:34.0 | 1.0:46.0 |
| JADAS-27 CRP | | | | | |
| Number | 9 | 15 | 20 | 22 | 42 |
| Mean (SD) | 19.3 (8.5) | 20.0 (8.1) | 22.2 (7.2) | 19.1 (7.7) | 20.6 (7.6) |
| Median | 17.4 | 17.5 | 23.2 | 16.8 | 19.3 |
| Min: Max | 8.5:35.5 | 8.5:35.5 | 9.2:13.8 | 8.5:35.5 | 8.5:35.5 |
| CHAQ-DI | | | | | |
| Number | 9 | 15 | 20 | 22 | 42 |
| Mean (SD) | 0.9 (0.8) | 0.8 (0.8) | 0.9 (0.8) | 1.2 (0.8) | 1.1 (0.8) |
| Median | 0.6 | 0.4 | 0.9 | 1.1 | 0.9 |
| Min:Max | 0.0:2.3 | 0.0:2.3 | 0.0:2.3 | 0.0:2.9 | 0.0:2.9 |
| hs-CRP (mg/L) | | | | | |
| Number | 9 | 15 | 20 | 22 | 42 |
| Mean (SD) | 7.0 (11.8) | 6.5 (10.4) | 10.4 (14.7) | 8.7 (19.2) | 9.5 (17.0) |
| Median | 2.9 | 2.6 | 1.0 | 1.6 | 1.1 |
| Min: Max | 0.1:36.8 | 0.1:36.8 | 0.1:45.9 | 0.1:86.5 | 0.1:86.5 |
| ESR (mm/h) | | | | | |
| Number | 8 | 14 | 20 | 19 | 39 |
| Mean (SD) | 13.0 (7.7) | 21.9 (20.1) | 28.0 (28.3) | 15.4 (13.1) | 21.8 (22.9) |
| Median | 11.5 | 16.0 | 17.5 | 11.0 | 12.0 |
| Min: Max | 3:26 | 2:73 | 2:93 | 2:50 | 2:93 |
| Absolute neutrophil count (Giga/L) | | | | | |
| Number | 9 | 15 | 20 | 22 | 42 |
| Mean (SD) | 5.4 (2.1) | 5.1 (1.8) | 4.2 (1.6) | 5.2 (2.0) | 4.7 (1.8) |
| Median | 5.5 | 5.2 | 3.9 | 5.2 | 4.7 |
| Min: Max | 2.4:8.2 | 2.4:8.2 | 1.7:7.7 | 2.1:8.2 | 1.7:8.2 |
| Absolute neutrophil count [n (%)] | | | | | |
| Number | 9 | 15 | 20 | 22 | 42 |
| ≥5.99 x $10_9$/L | 3 (33.3%) | 4 (26.7%) | 3 (15.0%) | 6 (27.3%) | 9 (21.4%) |
| <5.99 x $10_9$/L | 6 (66.7%) | 11 (73.3%) | 17 (85.0%) | 16 (72.7%) | 33 (78.6%) |

Abbreviations: CHAQ-DI = Childhood Health Assessment Questionnaire-Disability Index, hs-CRP = high sensitivity C-reactive protein, JADAS = juvenile arthritis disease activity score, JIA = juvenile idiopathic arthritis, ESR = erythrocyte sedimentation rate, RF = rheumatoid factor, SD = standard deviation.

Measurement of Treatment Compliance

A given administration was considered noncompliant if the patient did not take the planned dose of IMP as required by the protocol. Percentage of compliance for a patient was defined as the number of administrations that the patient was compliant divided by the total number of administrations that the patient was scheduled to take on or before the last dose date.

Overall compliance was 97.6%. Compliance to IMP intake was 96.4%. The compliance rates were similar across the dose weight groups. One patient in Dose Cohort 2, Group B had <80% compliance due to dose interruptions caused by neutropenia. No patients received the wrong dose or overdosed.

Of the 42 patients enrolled (Group A=20, Group B=22), 34 completed the 12-week core treatment phase (Group A=17; Group B=17) and 8 patients discontinued: 5 for treatment-emergent adverse events (AEs), 2 for lack of efficacy per investigator's judgment, and 1 for poor compliance (FIG. 8).

Pharmacokinetic and Pharmacodynamic Evaluation

Concentration of Functional Sarilumab in Serum

All predose concentrations of functional sarilumab in serum were below the LLOQ (0.3125 mg/L). Individual functional concentrations in serum in the 12-week core treatment phase with descriptive statistics were analyzed for each treatment group. Mean (SD) observed concentrations of sarilumab after first SC administration are shown in FIG. 3. The mean (SD) observed trough concentration of sarilumab over time profiles are shown in FIG. 4.

Pharmacokinetic Parameters

Descriptive statistics for PK parameters of sarilumab estimated from the population PK model (POH0516) are shown in Table 11A after first dose and in Table 11B after repeated dosing. Sarilumab exhibited nonlinear PK with target mediated drug disposition in patients with pcJIA (FIG. 3). AUC0-τ is AUC with a dose interval of 2 weeks for q2w regimen or one week for qw regimen. Following repeated SC doses of sarilumab at Week 10 to 12, AUC0-14 days was used to compare exposure of different q2w and qw regimens (AUC0-14 days=2×AUC0-τ for the qw regimen and AUC0-14 days=AUC0-τ for the q2w regimen).

TABLE 11A

Mean (CV %) [median] of individual sarilumab exposure following first SC administration in pediatric patients with pcJIA

| Dose Cohort | Weight Group | Dose mg/kg | N | Cmax mg/L | AUCO-τ day*mg/L | Ctrough mg/L |
|---|---|---|---|---|---|---|
| 1 | Group A | 2 mg/kg | 7 | 7.69 (46.8) | 53.2 (45.6) | 0.626 (63.0) |
| | ≥30 kg | q2w | | [8.63] | [57.7] | [0.620] |
| | Group B | 2.5 mg/kg | 6 | 9.08 (21.2) | 63.4 (30.2) | 0.537 (47.7) |
| | <30 kg | q2w | | [9.68] | [66.2] | [0.470] |
| 2 | Group A | 3 mg/kg | 7 | 14.5 (19.4) | 123 (24.0) | 1.84 (68.7) |
| | ≥30 kg | q2w | | [15.2] | [133] | [1.69] |
| | Group B | 4 mg/kg | 7 | 18.7 (21.0) | 167 (25.7) | 3.77 (42.5) |
| | <30 kg | q2w | | [17.5] | [158] | [4.34] |
| 3 | Group A | 2 mg/kg | 6 | 11.0 (21.2) | 61.3 (21.7) | 8.07 (31.9) |
| | ≥30 kg | qw | | [10.8] | [60.8] | [7.87] |
| | Group B | 2.5 mg/kg | 9 | 8.29 (34.6) | 45.3 (36.4) | 5.22 (38.9) |
| | <30 kg | qw | | [8.63] | [48.2] | [5.96] |

TABLE 11B

Mean (CV %) [median] of individual sarilumab exposure following repeated SC administration at Week 10 to 12 or Week 11 to 12 in pediatric patients with pcJIA

| Dose Cohort | Weight Group | Dose mg/kg | N | Cmax mg/L | AUCO-τ day*mg/L | Ctrough mg/L |
|---|---|---|---|---|---|---|
| 1 | Group A | 2 mg/kg | 5 | 13.2 (13.6) | 114 (17.5) | 1.99 (85.6) |
| | ≥30 kg | q2w | | [12.6] | [116] | [1.40] |
| | Group B | 2.5 mg/kg | 5 | 14.1 (26.5) | 118 (36.6) | 1.83 (101) |
| | <30 kg | q2w | | [13.7] | [101] | [1.27] |
| 2 | Group A | 3 mg/kg | 6 | 26.4 (26.2) | 269 (33.6) | 8.46 (68.2) |
| | ≥30 kg | q2w | | [24.4] | [250] | [8.25] |
| | Group B | 4 mg/kg | 7 | 30.1 (19.7) | 310 (26.1) | 11.9 (41.2) |
| | <30 kg | q2w | | [31.1] | [331] | [13.1] |
| 3 | Group A | 2 mg/kg | 6 | 38.8 (22.7) | 250 (24.4) | 30.4 (28.2) |
| | ≥30 kg | qw | | [39.3] | [254] | [31.4] |
| | Group B | 2.5 mg/kg | 5 | 31.4 (22.4) | 203 (25.0) | 25.1 (29.2) |
| | <30 kg | qw | | [29.9] | [197] | [27.3] |

Abbreviations: AUC0 τ: area under the serum concentration versus time curve during a dose interval τ of 2 weeks (q2w regimen) or one week (qw regimen), Cmax = maximum serum concentration observed, Ctrough = concentrations observed before treatment administration during repeated dosing, CV = coefficient of variation, pcJIA = polyarticular-course juvenile idiopathic arthritis, q2w = once every other week, qw = once every week, SC = subcutaneous.

Population PK model derived Bayesian exposure

Following repeated q2w SC and qw administration at Week 10 to 12, sarilumab exposure increased in a greater than dose proportional manner, with AUC0-14 days increased 2.4- to 2.6-fold for a 1.5- to 1.6-fold increase in sarilumab dose from Dose Cohort 1 to Dose Cohort 2 and 3.4- to 4.4-fold for a 2-fold increase in sarilumab dose from Dose Cohort 1 to Dose Cohort 3. Compared to the first dose, there was a 1.9- to 2.2-fold accumulation for Dose Cohorts 1 and 2 and a 4.1- to 4.5-fold accumulation for Dose Cohort 3 at Week 12. (Table 22) The dose regimens tested in 2 weight groups achieved similar exposure for each Dose Cohort. The variability of Cmax and AUC0-τ after repeated SC doses in patients with pcJIA was in the range of 13.6 to 36.6%.

Analysis of the data for the 12-week dose-finding study was performed. Data were analyzed for patients divided by body weight into 2 groups: Group A (30-60 kg) and Group B (10-<30 kg). As described above, patients received sequential ascending doses of sarilumab: Dose 1 (Group A/B): 2.0/2.5 mg/kg q2w; Dose 2 (Group A/B): 3/4 mg/kg q2w; Dose 3 (Group A/B): 2.0/2.5 mg/kg qw. The pcJIA doses were targeted to achieve similar exposure to about 150 mg q2w, 200 mg q2w, and 150 mg qw in adults. As described above, the primary outcome was pharmacokinetics (PK) and the secondary outcomes were safety, PD, and efficacy of sarilumab.

Data show that 42 patients were enrolled (20/22 in Groups A/B) and the mean age was 13.0/5.2 years. At baseline, mean pcJIA duration, number of active joints, and JADAS27-CRP were 4.6/1.7 years, 17.2/11.0, and 22.2/19.1, in Groups A/B respectively. As in adult patients, sarilumab exhibited nonlinear PK with target-mediated drug disposition. Following repeated SC administrations, exposure increased in a greater than dose-proportional manner and accumulated 1.9-4.5-fold over 12 weeks. Sarilumab exposure was similar in both weight groups for each dose (Table 12), and comparable to corresponding adult doses. Treatment-emergent adverse events were reported in 36/42 (85.7%) patients (comparable across dose and weight groups); infections (28/42, 66.7%) were the most frequently reported AE. 12 grade 3/4 neutropenias were identified, mostly in Dose 3 (n=6) and in Group B (n=8). None was associated with infection; all resolved in a few days. Overall, 4 patients discontinued due to neutropenia and 1 due to alanine aminotransferase increase. There were no serious AEs, no cases of gastrointestinal perforation, and no deaths. By Week 12, as observed while on-treatment: all patients attained JIA ACR30; 50%, 62%, and 100% of patients attained JIA ACR70 with Doses 1, 2, and 3, respectively; JADAS27-CRP mean change from baseline in Doses 1, 2, and 3 was −74.6%, −73.1%, and −87.9%, respectively.

TABLE 12

Pharmacokinetic analysis of patient Group A (30-60 kg) and patient Group B (10-<30 kg) administered sarilumab Figure: Mean (CV %) individual sarilumab exposure, following first SC dose, and after repeated SC administration at Week 10-12 or Week 11-12, in patients with pcJIA

| pcJIA treatment | | First SC administration | | | Repeated SC administration (Week 10-12 or Week 11-12) | | |
|---|---|---|---|---|---|---|---|
| Patient weight group | Sarilumab dose | N | $C_{trough}$ mg/L (CV %) | $AUC_{0\text{-}\tau}$ day mg/L (CV %) | N | $C_{trough}$ mg/L (CV %) | $AUC_{0\text{-}\tau}$ day mg/L (CV %) |
| 10-<30 kg (Group B) | 2.5 mg/kg q2w | 6 | 0.54 (48) | 63 (30) | 5 | 1.83 (101) | 118 (37) |
| | 4.0 mg/kg q2w | 7 | 3.77 (43) | 167 (26) | 7 | 11.90 (41) | 310 (26) |
| | 2.5 mg/kg qw | 9 | 5.22 (39) | 45 (36) | 5 | 25.10 (29) | 203 (25) |
| 30-60 kg (Group A) | 2.0 mg/kg q2w | 7 | 0.63 (63) | 53 (46) | 5 | 1.99 (86) | 114 (18) |
| | 3.0 mg/kg q2w | 7 | 1.84 (69) | 123 (24) | 6 | 8.46 (68) | 269 (34) |
| | 2.0 mg/kg qw | 6 | 8.07 (32) | 61 (22) | 6 | 30.40 (28) | 250 (24) |

AUC, area under the serum concentration versus time curve, calculated using trapezoidal method during a dose interval; $C_{trough}$, serum concentration observed before treatment administration during repeated dosing; CV, coefficient of variance; N, number of patients; pcJIA, polyarticular-course juvenile idiopathic arthritis; qw, every week; q2w, every two weeks; SC, subcutaneous. Dose interval (τ) was 2 weeks for q2w, or 1 week for qw regimen.

Pharmacokinetic Conclusions

Sarilumab exhibited nonlinear PK with target mediated drug disposition in patients with pcJIA. Following repeated SC administration, sarilumab exposure increased in a greater than dose proportional manner and accumulated 1.9- to 4.5-fold over 12 weeks. For each Dose Cohort, dose regimens tested in 2 weight groups achieved similar exposure. For the additional patient Group A (30-60 kg) and patient Group B (10-<30 kg) data analysis, it was observed that sarilumab exhibited nonlinear PK with target-mediated drug disposition. In addition, all dose regimens proved effective for decreasing disease activity. Safety profile was consistent with class effects; higher incidences of neutropenia were observed with Dose 3, and in patients weighing 10-<30 kg.

CRP, ESR, IL-6, and sIL-6R Concentrations

Descriptive statistics of hs-CRP, ESR, IL-6 and total sIL-6Rα concentrations from baseline to Week 12 were analyzed for each treatment group. Mean (SE) CRP, ESR, IL-6 and sIL-6Rα concentration over time profiles were obtained for each cohort. After SC administration of sarilumab, the mean suppression of CRP and the increase of sIL-6Rα were greater in Dose Cohorts 2 and 3 than that in Dose Cohort 1. Mean CRP concentrations were reduced within 2 to 4 weeks in Dose Cohorts 2 and 3, with a greater and more rapid decrease observed with Dose Cohorts 2 and 3 than with Dose Cohort 1 (FIG. 10A). Change in mean CRP concentration from baseline to week 12 was 7.4 to 5.8 mg/L, 14.6 to 0.5 mg/L, and 6.5 to 0.1 mg/L with doses 1, 2, and 3, respectively. All patients achieved a normal CRP concentration with doses 2 and 3 between weeks 2 and 6. At week 4, the majority of patients achieved a CRP level below the detection limit (<0.2 mg/L) with doses 2 and 3 (71.4% and 83.3%, respectively, as observed while on-treatment), compared with 25.0% with dose 1. This effect was sustained over time, with 66.7% and 90.9% of patients achieving CRP<0.2 mg/L at week 12 with doses 2 and 3, respectively, compared with 30.0% with dose 1 (FIG. 10B).

The high mean CRP value in Dose Cohort 1 Group A was primarily driven by one patient whose CRPs remained elevated (between 40 to 110 mg/L) during the 12-week core treatment phase.

Erythrocyte sedimentation rates at Week 12 are consistent with what was observed for CRP. In general, mean erythrocyte sedimentation rates (ESR) concentrations decreased and mean IL-6 and sIL-6Rα concentrations increased at Week 12. As with CRP levels, a greater decrease was observed with Dose Cohorts 2 and 3, with mean change from baseline to week 12 of 22.2 to 18.2 mm/h, 21.4 to 6.9 mm/h, and 21.9 to 4.4 mm/h with Dose Cohorts 1, 2, and 3, respectively.

Pharmacodynamic Pharmacokinetic Relationship of Biomarkers

Exploratory analyses were performed to elucidate exposure-response relationships with PD biomarkers. Individual CRP, ESR, IL-6, and sIL-6Rα concentrations are plotted versus trough serum concentration at Week 12. There was no obvious relationship between individual IL-6 levels and sarilumab trough concentrations. Data show total sIL-6Rα increased with increasing sarilumab trough concentrations after repeated doses in individual patients with pcJIA. C-reactive protein levels were lower (≤1 mg/L) in the individual patients with sarilumab trough concentrations of >1 mg/L compared to those with sarilumab trough concentrations of ≤1 mg/L. The suppression of CRP was greater in Dose Cohorts 2 and 3 than in Dose Cohort 1 patients. Erythrocyte sedimentation rate was lower (≤10 mm/hour) in the individual patients with sarilumab trough concentrations of >1 mg/L compared to those with sarilumab trough concentrations of ≤1 mg/L. The suppression of ESR was greater in Dose Cohorts 2 and 3 than in Dose Cohort 1 patients.

After SC administration of sarilumab, the suppression of CRP and the increase of sIL-6Rα were greater in Dose Cohorts 2 and 3 than that in Dose Cohort 1. In general, mean ESR concentrations decreased and mean IL-6 and sIL-6Rα concentrations increased, relative to baseline, at Week 12.

Safety 2-week core treatment phase. Total exposure (patient-years of treatment) was similar across the dose and weight groups, with 4.6 and 5.0 patient-years in Groups A and B, respectively.

There were no serious AEs and no deaths (Table 23). The most commonly observed AEs were infections and neutropenia (n=28 [66.7%] and n=11 [26.2%], respectively). Infection rates were similar across dose and weight groups and were mostly driven by upper respiratory tract infections (n=9 [21.4%]; Table 25). No serious infections were reported. No cases of pneumonia or tuberculosis were identified. One case of oral candidiasis occurred (Dose Cohort 3, Group A), which resolved spontaneously without corrective treatment with no interruption in sarilumab treatment. No patients discontinued due to any infection.

Prespecified laboratory monitoring identified 12 patients with transient grade 3/4 neutropenias (28.6%). Of these patients, 3 received dose 1 (2 in Group A, 1 in Group B), 3 received dose 2 (1 in Group A, 2 in Group B), and 6 received dose 3 (1 in Group A, 5 in Group B; Table 24). All patients were asymptomatic, but 3 required protocol-mandated treatment interruption (1 each in: dose 2, Group B; dose 3, Groups A and B). No events of neutropenia were associated with an infection, and all resolved within a few days. Laboratory monitoring, including red blood cell counts, platelet counts, lipids levels, and liver function assessments did not reveal any additional potentially clinically significant abnormalities. In particular, there were no cases of drug-induced liver damage as defined by Hy's Law (21).

Protocol-mandated permanent discontinuations due to AEs occurred in 5 patients (11.9%). Of these, 1 was a case of grade 3 neutropenia at week 2 in dose 1, Group A; 3 were grade 4 neutropenias in dose 3, Group B, and 1 was an alanine aminotransferase (ALT) increase in dose 1, Group A (>5×upper limit of normal [ULN] at week 4).

Seven patients reported local reactions after injection (4 in Group A and 3 in Group B). These reactions were mostly erythema and pain; all were mild to moderate in intensity; none led to treatment discontinuation. Two patients tested positive for anti-drug antibodies at week 12: one in dose 1, Group A (neutralizing antibody positive; discontinued due to ALT>5×ULN at week 4); one in dose 3, Group B (not neutralizing antibody positive; discontinued due to grade 4 neutropenia after the first injection).

Efficacy Evaluation

JIA ACR Response Rate

The JIA ACR level of response was used in this study to assess signs and symptoms. JIA ACR 30/50/70/90/100 response was defined as a patient with 3 of 6 core set variables improved by at least 30%/50%/70%/90%/100% from baseline with no more than one of the remaining variables worsened by more than 30%.

The JIA ACR response rates were calculated by a directly observed method for those on-treatment ("as observed while on-treatment") and by imputation for patients who discontinued ("non-responder imputation approach" where discontinued patients were automatically considered as non-responders at the visits after discontinuation). JIA ACR response rates in all dose and weight groups at Week 12 are summarized in Table 13. Estimates of the precision of the JIA ACR response rate are shown in Table 33.

As observed while on-treatment, at Week 12, JIA ACR30 response rates were 100% in all doses and weight groups. The JIA ACR70 response rates were 50.0%, 61.5%, and 100% in Dose Cohort 1, 2 and 3, respectively. As calculated by non-responder imputation approach, at Week 12, the JIA ACR30 rates were 76.9%, 92.9% and 73.3% in Dose Cohort 1, 2 and 3 respectively. The JIA ACR70 response rates were 38.5%, 57.1%, and 73.3% in Dose Cohort 1, 2 and 3, respectively.

Overall, with the as observed while on-treatment approach, the occurrence of JIA ACR30 response was seen from the first assessment at Week 2 in all Dose Cohorts and weight groups. It was plateaued to 100% achievement at Week 4 and 8 for Dose Cohort 2, Groups A and B, respectively, and Week 6 and 8 for Dose Cohort 3, Group A and B, respectively while response rate in Dose Cohort 1 was fluctuant up to Week 12 (FIG. 5). The results from the non-responder imputation approach is plotted in FIG. 6.

JIA ACR Components

Data for the JIA ACR components during the 12-week core treatment phase were compiled. A summary of JIA ACR components at Week 12 is shown in Table 14. At Week 12 all Dose Cohorts and weight groups showed a decrease from baseline in all JIA ACR components, which generally appeared more pronounced in Dose Cohorts 2 and 3 compared to Dose Cohort 1. The number of joints with active arthritis decreased for patients in all Dose Cohorts in both weight groups throughout the 12-week core treatment phase. The largest mean decrease at Week 12 was observed for patients in Dose Cohort 3, Group A (−16.5). The number of joints with limited motion decreased for patients in all Dose Cohorts for both weight groups throughout the 12-week core treatment phase. The largest mean decrease at Week 12 was observed for patients in Dose Cohort 3, Group B (−11.3). The physician global VAS decreased for patients in all Dose Cohorts for both weight groups throughout the 12-week core treatment phase. The largest mean decrease at Week 12 was observed for patients in Dose Cohort 3, Group B (−5.0). The patient global VAS decreased for patients in all Dose Cohorts for both weight groups throughout the 12-week core treatment phase. The largest mean decrease at Week 12 was observed for patients in Dose Cohort 3, Group B (−5.7). Overall, the CHAQ-DI scores decreased for patients in all Dose Cohorts for both weight groups throughout the 12-week core treatment phase. The largest mean decrease at Week 12 was observed for patients in Group B, Dose Cohort 2 (−1.0). Mean hs-CRP concentrations decreased in all Dose Cohorts for both weight groups at Week 12. Mean CRP concentrations were reduced within 2 to 4 weeks in Dose Cohorts 2 and 3. The high mean CRP value in Dose Cohort 1, Group A was primarily driven by one patient whose CRPs remained elevated (between 40 to 110 mg/L) during the 12-week core treatment phase. The largest mean decrease at Week 12 was observed for patients in Group B, Dose Cohort 2 (−15.2).

Juvenile Arthritis Disease Activity Score

Disease activity was assessed by JADAS-27 CRP score. The JADAS-27 CRP score over time in each Dose Cohort and weight group were analyzed. A summary of JADAS-27 (ESR) during the 12-week core treatment phase are provided in Table 15. Investigator-reported TEAEs are shown in Table 30. Data show that compared to baseline, all Dose Cohorts and weight groups showed a decrease in JADAS-27 CRP score from Week 2. At Week 12, mean percentage change from baseline was −74.6%, −73.1%, and −87.9% in Dose Cohorts 1, 2, and 3, respectively.

TABLE 13

Summary of the JIA-ACR responses rates at Week 12 - Efficacy population

| | As observed while on-treatment | | | | |
|---|---|---|---|---|---|
| | JIA-ACR30 | JIA-ACR50 | JIA-ACR70 | JIA-ACR90 | JIA-ACR100 |
| Cohort 1 Group A | 5/5 (100%) | 4/5 (80.0%) | 3/5 (60.0%) | 3/5 (60.0%) | 0/5 |
| Cohort 1 Group B | 5/5 (100%) | 5/5 (100%) | 2/5 (40.0%) | 1/5 (20.0%) | 0/5 |
| Cohort 1 Total | 10/10 (100%) | 9/10 (90.0%) | 5/10 (50.0%) | 4/10 (40.0%) | 0/10 |
| Cohort 2 Group A | 6/6 (100%) | 5/6 (83.3%) | 3/6 (50.0%) | 2/6 (33.3%) | 0/6 |
| Cohort 2 Group B | 7/7 (100%) | 7/7 (100%) | 5/7 (71.4%) | 2/7 (28.6%) | 2/7 (28.6%) |
| Cohort 2 Total | 13/13 (100%) | 12/13 (92.3%) | 8/13 (61.5%) | 4/13 (30.8%) | 2/13 (15.4%) |
| Cohort 3 Group A | 6/6 (100%) | 6/6 (100%) | 6/6 (100%) | 4/6 (66.7%) | 2/6 (33.3%) |
| Cohort 3 Group B | 5/5 (100%) | 5/5 (100%) | 5/5 (100%) | 3/5 (60.0%) | 2/5 (40.0%) |
| Cohort 3 Total | 11/11 (100%) | 11/11 (100%) | 11/11 (100%) | 7/11 (63.6%) | 4/11 (36.4%) |

| | Non-responder imputation approach[a] | | | | |
|---|---|---|---|---|---|
| | JIA-ACR30 | JIA-ACR50 | JIA-ACR70 | JIA-ACR90 | JIA-ACR100 |
| Cohort 1 Group A | 5/7 (71.4%) | 4/7 (57.1%) | 3/7 (42.9%) | 3/7 (42.9%) | 0/7 |
| Cohort 1 Group B | 5/6 (83.3%) | 5/6 (83.3%) | 2/6 (33.3%) | 1/6 (16.7%) | 0/6 |
| Cohort 1 Total | 10/13 (76.9%) | 9/13 (69.2%) | 5/13 (38.5%) | 4/13 (30.8%) | 0/13 |
| Cohort 2 Group A | 6/7 (85.7%) | 5/7 (71.4%) | 3/7 (42.9%) | 2/7 (28.6%) | 0/7 |
| Cohort 2 Group B | 7/7 (100%) | 7/7 (100%) | 5/7 (71.4%) | 2/7 (28.6%) | 2/7 (28.6%) |
| Cohort 2 Total | 13/14 (92.9%) | 12/14 (85.7%) | 8/14 (57.1%) | 4/14 (28.6%) | 2/14 (14.3%) |
| Cohort 3 Group A | 6/6 (100%) | 6/6 (100%) | 6/6 (100%) | 4/6 (66.7%) | 2/6 (33.3%) |
| Cohort 3 Group B | 5/9 (55.6%) | 5/9 (55.6%) | 5/9 (55.6%) | 3/9 (33.3%) | 2/9 (22.2%) |
| Cohort 3 Total | 11/15 (73.3%) | 11/15 (73.3%) | 11/15 (73.3%) | 7/15 (46.7%) | 4/15 (26.7%) |

[a]Discontinued patients are automatically considered as non responders at the visits after their discontinuation.

TABLE 14

Summary of JIA ACR components at Week 12 by Dose Cohort and by weight group - Efficacy population

| | Weight Group A (≥30 kg) | | | Weight Group B (<30 kg) | | | Weight Groups A & B | | |
|---|---|---|---|---|---|---|---|---|---|
| | Dose 1 | Dose 2 | Dose 3 | Dose 1 | Dose 2 | Dose 3 | Dose 1 | Dose 2 | Dose 3 |
| **Active Joint Count (0-71)** | | | | | | | | | |
| Baseline | | | | | | | | | |
| Number | 7 | 7 | 6 | 6 | 7 | 9 | 13 | 14 | 15 |
| Mean | 19.3 | 14.6 | 17.7 | 11.7 | 8.3 | 12.7 | 15.8 | 11.4 | 14.7 |
| Week 12 | | | | | | | | | |
| Number | 5 | 6 | 6 | 6 | 7 | 6 | 11 | 13 | 12 |
| Mean | 7.2 | 5.0 | 1.2 | 2.2 | 1.0 | 1.3 | 4.5 | 2.8 | 1.3 |
| Mean change | −14.4 | −10.5 | −16.5 | −9.5 | −7.3 | −12.5 | −11.7 | −8.8 | −14.5 |
| Mean % change | −78.5 | −72.6 | −91.6 | −73.2 | −86.2 | −80.9 | −75.6 | −79.9 | −86.2 |
| Active joints counts = 0 | 2/5 (40.0%) | 0/6 | 2/6 (33.3%) | 2/5 (40.0%) | 4/7 (57.1%) | 3/5 (60.0%) | 4/10 (40.0%) | 4/13 (30.8%) | 5/11 (45.5%) |
| **Limited motion Joint Count** | | | | | | | | | |
| Baseline | | | | | | | | | |
| Number | 7 | 7 | 6 | 6 | 7 | 9 | 13 | 14 | 15 |
| Mean | 10.3 | 9.3 | 16.5 | 10.5 | 7.6 | 10.6 | 10.4 | 8.4 | 12.9 |
| Week 12 | | | | | | | | | |
| Number | 5 | 6 | 6 | 6 | 7 | 6 | 11 | 13 | 12 |
| Mean | 3.4 | 2.7 | 8.7 | 5.5 | 1.6 | 0.8 | 4.5 | 2.1 | 4.8 |
| Mean change | −7.8 | −6.8 | −7.8 | −5.0 | −6.0 | −11.3 | −6.3 | −6.4 | −9.6 |
| Mean % chang | −75.5 | −52.4 | −59.1 | −45.1 | −69.8 | −89.8 | −58.9 | −61.8 | −74.5 |
| **Physician global VAS (0-10)** | | | | | | | | | |
| Baseline | | | | | | | | | |
| Number | 7 | 7 | 6 | 6 | 7 | 9 | 13 | 14 | 15 |
| Mean | 4.6 | 4.3 | 4.1 | 4.7 | 5.2 | 4.0 | 4.7 | 4.8 | 4.1 |
| Week 12 | | | | | | | | | |
| Number | 5 | 6 | 6 | 6 | 7 | 5 | 11 | 13 | 11 |
| Mean | 1.7 | 2.0 | 1.1 | 1.8 | 0.9 | 0.6 | 1.7 | 1.4 | 0.8 |
| Mean change | −3.3 | −2.7 | −3.1 | −3.0 | −4.3 | −5.0 | −3.1 | −3.5 | −3.9 |
| Mean % change | −66.3 | −48.5 | −77.5 | −61.0 | −81.4 | −87.4 | −63.4 | −66.2 | −82.5 |
| **Patient global VAS (0-10)** | | | | | | | | | |
| Baseline | | | | | | | | | |
| Number | 7 | 7 | 6 | 6 | 7 | 9 | 13 | 14 | 15 |
| Mean | 4.6 | 6.3 | 5.3 | 7.2 | 5.5 | 5.3 | 5.8 | 5.9 | 5.3 |
| Week 12 | | | | | | | | | |
| Number | 5 | 6 | 6 | 6 | 7 | 5 | 11 | 13 | 11 |
| Mean | 1.2 | 1.8 | 0.8 | 1.8 | 1.7 | 0.3 | 1.5 | 1.8 | 0.5 |
| Mean change | −3.6 | −4.9 | −4.6 | −5.4 | −3.8 | −5.7 | −4.6 | −4.3 | −5.1 |
| Mean | 66.2 | 74.7 | 85.2 | 71.9 | 65.6 | 93.3 | 69.3 | 69.8 | 88.9 |
| **CHAQ-DI (0-3)** | | | | | | | | | |
| Baseline | | | | | | | | | |
| Number | 7 | 7 | 6 | 6 | 7 | 9 | 13 | 14 | 15 |
| Mean | 1.1 | 0.9 | 0.7 | 1.5 | 1.3 | 0.9 | 1.3 | 1.1 | 0.8 |
| Week 12 | | | | | | | | | |
| Number | 5 | 6 | 6 | 6 | 7 | 5 | 11 | 13 | 11 |
| Mean | 0.5 | 0.4 | 0.3 | 0.5 | 0.3 | 0.6 | 0.5 | 0.3 | 0.4 |
| Mean change | −0.8 | −0.7 | −0.4 | −0.9 | −1.0 | −0.8 | −0.9 | −0.9 | −0.6 |
| Mean % change | −68.1 | −67.2 | −83.3 | −64.4 | −74.2 | −69.6 | −66.1 | −71.3 | −76.4 |
| **hs-CRP (mg/L)** | | | | | | | | | |
| Baseline | | | | | | | | | |
| Number | 7 | 7 | 6 | 6 | 7 | 9 | 13 | 14 | 15 |
| Mean | 10.9 | 13.7 | 5.8 | 3.2 | 15.4 | 7.0 | 7.4 | 14.6 | 6.5 |

TABLE 14-continued

Summary of JIA ACR components at Week 12 by Dose Cohort and by weight group - Efficacy population

| | Weight Group A (≥30 kg) | | | Weight Group B (<30 kg) | | | Weight Groups A & B | | |
|---|---|---|---|---|---|---|---|---|---|
| | Dose 1 | Dose 2 | Dose 3 | Dose 1 | Dose 2 | Dose 3 | Dose 1 | Dose 2 | Dose 3 |
| Week 12 | | | | | | | | | |
| Number | 5 | 6 | 6 | 6 | 6 | 6 | 11 | 12 | 12 |
| Mean | 9.6 | 0.6 | 0.1 | 2.7 | 0.4 | 0.1 | 5.8 | 0.5 | 0.1 |
| Mean change | −5.5 | −11.5 | −5.7 | −0.5 | −15.2 | −8.2 | −2.8 | −13.4 | −7.0 |

Abbreviations: CHAQ-D1 = child health assessment questionnaire disability index, hs-CRP = high sensitivity C-reactive protein, VAS = visual analogue scale.

TABLE 15

Summary of JADAS-27 CRP during the 12-week core treatment phase by Dose Cohort and by weight group - Efficacy population

| | Weight Group A (≥30 kg) | | | Weight Group B (<30 kg) | | | Weight Groups A & B | | |
|---|---|---|---|---|---|---|---|---|---|
| | Dose 1 | Dose 2 | Dose 3 | Dose 1 | Dose 2 | Dose 3 | Dose 1 | Dose 2 | Dose 3 |
| Baseline | | | | | | | | | |
| Number | 7 | 7 | 6 | 6 | 7 | 9 | 13 | 14 | 15 |
| Mean | 22.9 | 22.5 | 21.1 | 21.3 | 17.0 | 19.3 | 22.1 | 19.8 | 20.0 |
| Mean change | 0.0 | 0.0 | 0.0 | 0.0 | 0.0 | 0.0 | 0.0 | 0.0 | 0.0 |
| Mean % change | 0.0 | 0.0 | 0.0 | 0.0 | 0.0 | 0.0 | 0.0 | 0.0 | 0.0 |
| V7/Week 2 | | | | | | | | | |
| Number | 7 | 7 | 6 | 6 | 7 | 8 | 13 | 14 | 14 |
| Mean | 18.1 | 17.5 | 12.2 | 14.1 | 12.2 | 10.6 | 16.2 | 14.8 | 11.3 |
| Mean change | −4.8 | −5.1 | −8.9 | −7.2 | −4.9 | −9.9 | −5.9 | −5.0 | −9.5 |
| Mean % change | −22.4 | −21.3 | −41.8 | −34.7 | −31.5 | −48.8 | −28.1 | −26.4 | −45.8 |
| V8/Week 4 | | | | | | | | | |
| Number | 6 | 7 | 6 | 6 | 7 | 6 | 12 | 14 | 12 |
| Mean | 16.7 | 13.4 | 10.9 | 12.7 | 9.8 | 9.1 | 14.7 | 11.6 | 10.0 |
| Mean change | −8.5 | −9.1 | −10.2 | −8.6 | −7.2 | −12.8 | −8.5 | −8.2 | −11.5 |
| Mean % change | −33.2 | −41.9 | −49.9 | −34.5 | −44.0 | −57.9 | −33.9 | −42.9 | −53.9 |
| V9/Week 6 | | | | | | | | | |
| Number | 6 | 7 | 6 | 6 | 7 | 5 | 12 | 14 | 11 |
| Mean | 13.7 | 11.0 | 6.2 | 9.7 | 8.9 | 5.9 | 11.7 | 10.0 | 6.0 |
| Mean change | −11.5 | −11.5 | −15.0 | −11.6 | −8.1 | −16.8 | −11.5 | −9.8 | −15.8 |
| Mean % change | −46.7 | −52.0 | −69.7 | −55.6 | −48.4 | −73.2 | −51.1 | −50.2 | −71.3 |
| V10/Week 8 | | | | | | | | | |
| Number | 5 | 6 | 6 | 6 | 7 | 5 | 11 | 13 | 11 |
| Mean | 10.5 | 9.8 | 3.8 | 9.0 | 7.3 | 4.2 | 9.7 | 8.5 | 3.9 |
| Mean change | −13.6 | −14.0 | −17.4 | −12.3 | −9.7 | −18.6 | −12.9 | −11.7 | −17.9 |
| Mean % change | −58.9 | −60.4 | −83.1 | −54.3 | −58.2 | −78.9 | −56.4 | −59.2 | −81.2 |
| V11/Week 10 | | | | | | | | | |
| Number | 5 | 5 | 6 | 6 | 6 | 5 | 11 | 11 | 11 |
| Mean | 8.5 | 6.5 | 3.8 | 7.3 | 6.1 | 2.6 | 7.9 | 6.3 | 3.3 |
| Mean change | −15.6 | −15.3 | −17.4 | −13.9 | −11.9 | −20.1 | −14.7 | −13.5 | −18.6 |
| Mean % change | −67.6 | −72.5 | −81.4 | −59.6 | −65.6 | −86.8 | −63.2 | −68.7 | −83.9 |

TABLE 15-continued

Summary of JADAS-27 CRP during the 12-week core treatment phase by Dose Cohort and by weight group - Efficacy population

| | Weight Group A (≥30 kg) | | | Weight Group B (<30 kg) | | | Weight Groups A & B | | |
|---|---|---|---|---|---|---|---|---|---|
| | Dose 1 | Dose 2 | Dose 3 | Dose 1 | Dose 2 | Dose 3 | Dose 1 | Dose 2 | Dose 3 |
| V12/Week 12 | | | | | | | | | |
| Number | 5 | 6 | 6 | 5 | 6 | 5 | 10 | 12 | 11 |
| Mean | 7.7 | 7.6 | 2.7 | 4.6 | 4.0 | 1.7 | 6.2 | 5.8 | 2.2 |
| Mean change | −16.4 | −16.2 | −18.5 | −18.1 | −13.2 | −21.1 | −17.2 | −14.7 | −19.7 |
| Mean % change | −69.7 | −69.9 | −86.3 | −79.5 | −76.3 | −89.8 | −74.6 | −73.1 | −87.9 |

Efficacy Conclusions

Figure 9A:
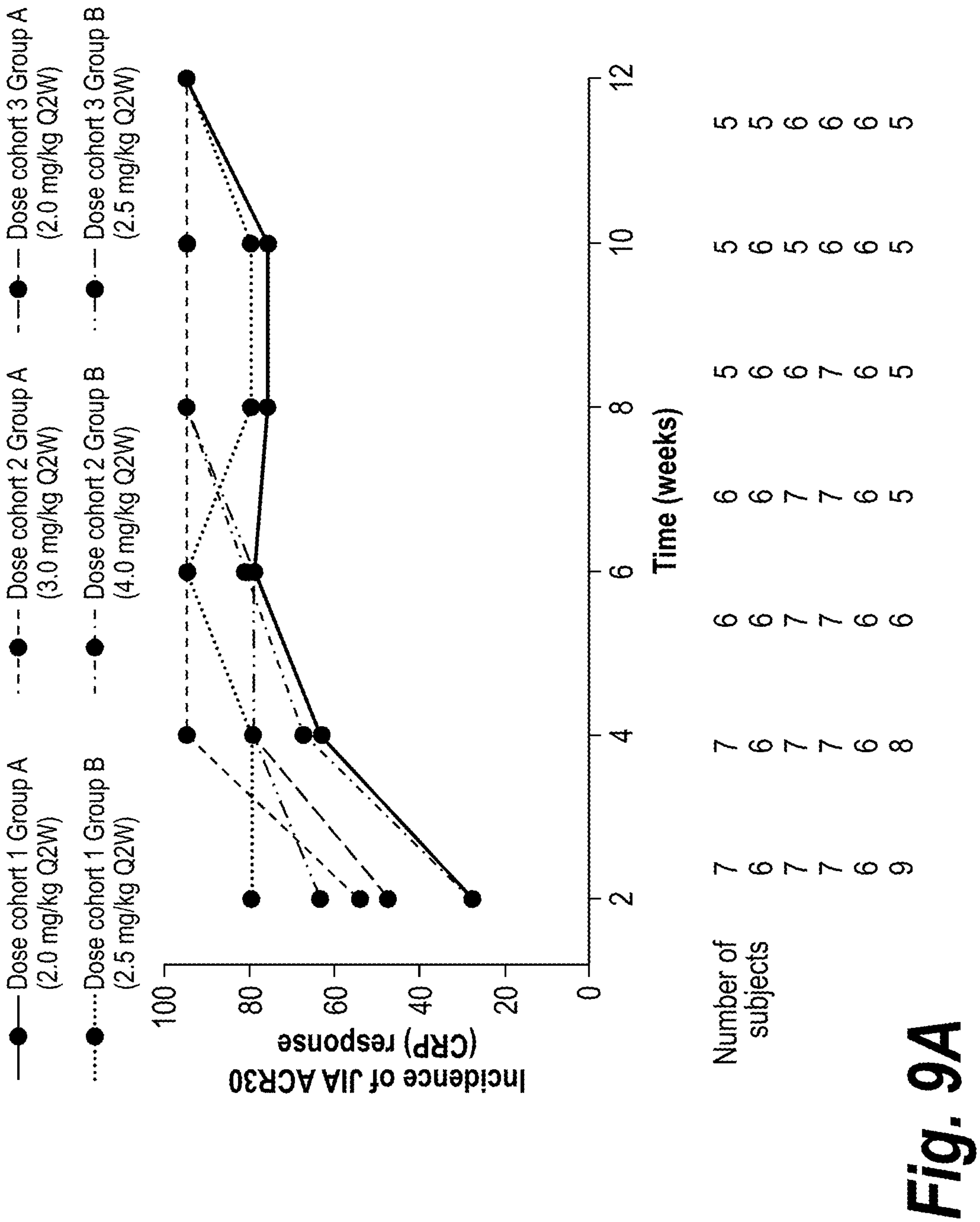
Figure 9B:
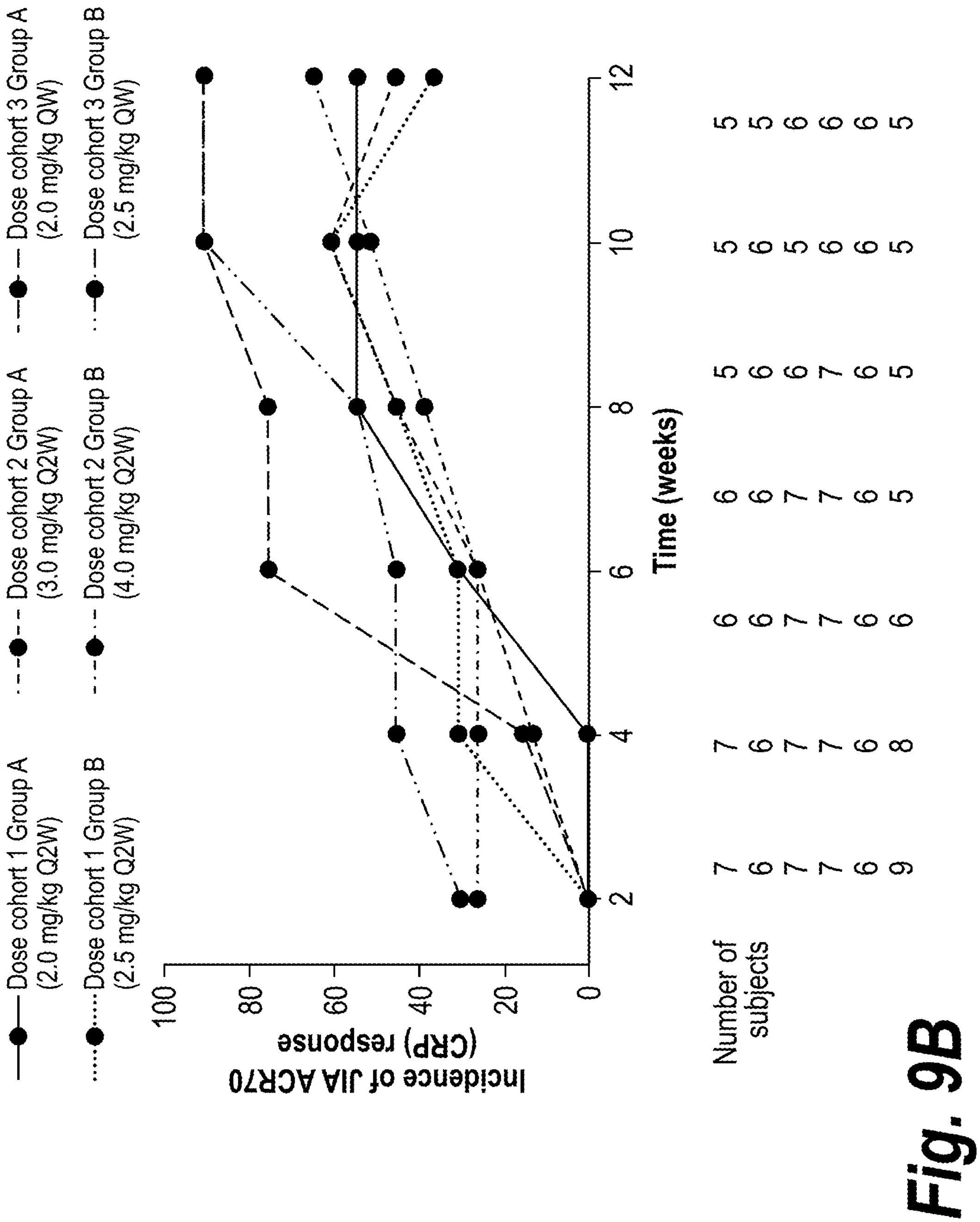
Figure 9C:
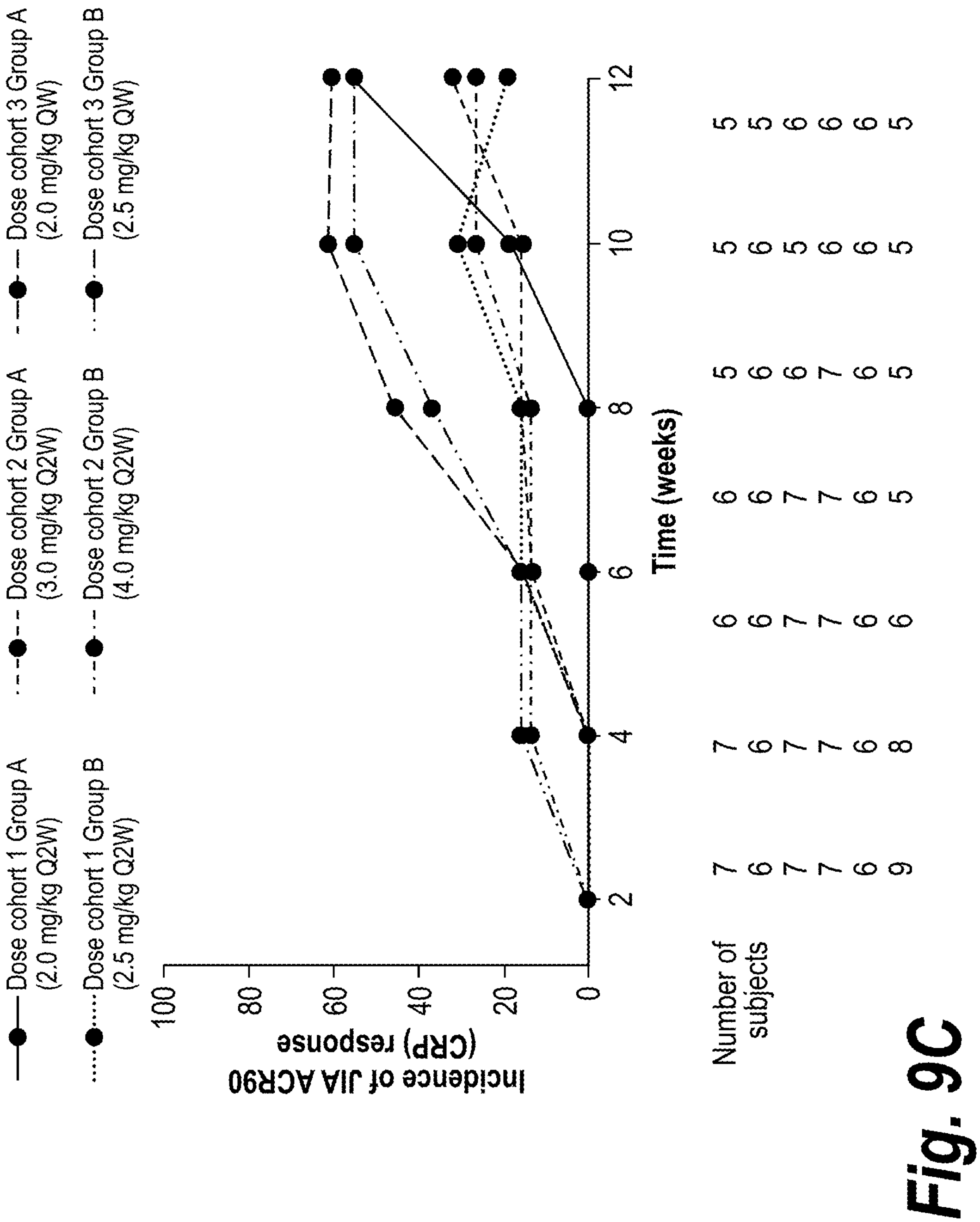

Improvement in signs and symptoms as assessed by JIA ACR response was seen in all Dose Cohorts and weight groups from Week 2 with either the as observed while on-treatment or non responder imputation approaches. No Dose Cohort was prematurely halted due to lack of efficacy. Two patients discontinued due to insufficient efficacy as judged by the investigator: 1 in Dose Cohort 1, Group B at week 10 and the other in Dose Cohort 3, Group B at week 4. Using the as observed while on-treatment approach, at Week 12, JIA ACR30 response rate was 100% (34/34) in all dose and weight groups, with Dose Cohorts 2 and 3 producing a more rapid and sustained JIA ACR30 response compared with Dose Cohort 1 (FIG. 9A). At week 12, as calculated by a nonresponder imputation approach, 77%, 93%, and 73% of patients achieved JIA ACR30 (Dose Cohorts 1, 2, and 3, respectively; FIG. 11). A large proportion of patients also reached higher response thresholds, with 50%, 62%, and 100% of patients achieving JIA ACR70 and 40%, 31%, and 64% achieving JIA ACR90 with Dose Cohorts 1, 2, and 3, respectively, at week 12 as observed while on-treatment (FIGS. 9B, 9C; results according to nonresponder imputation approach shown in FIG. 11B, 11C). All JIA ACR components were reduced by each of the 3 sarilumab dose regimens (Table 26).

There was a tendency for a more rapid JIA ACR response in Dose Cohorts 2 and 3 compared to Dose Cohort 1. With the as observed while on-treatment approach, the incidence JIA ACR30 response was plateaued to 100% achievement within the first 2 months of sarilumab treatment for Dose Cohorts 2 and 3, Group A and B, while response rate in Dose Cohort 1 was fluctuant up to Week 12.

Figure 9D:
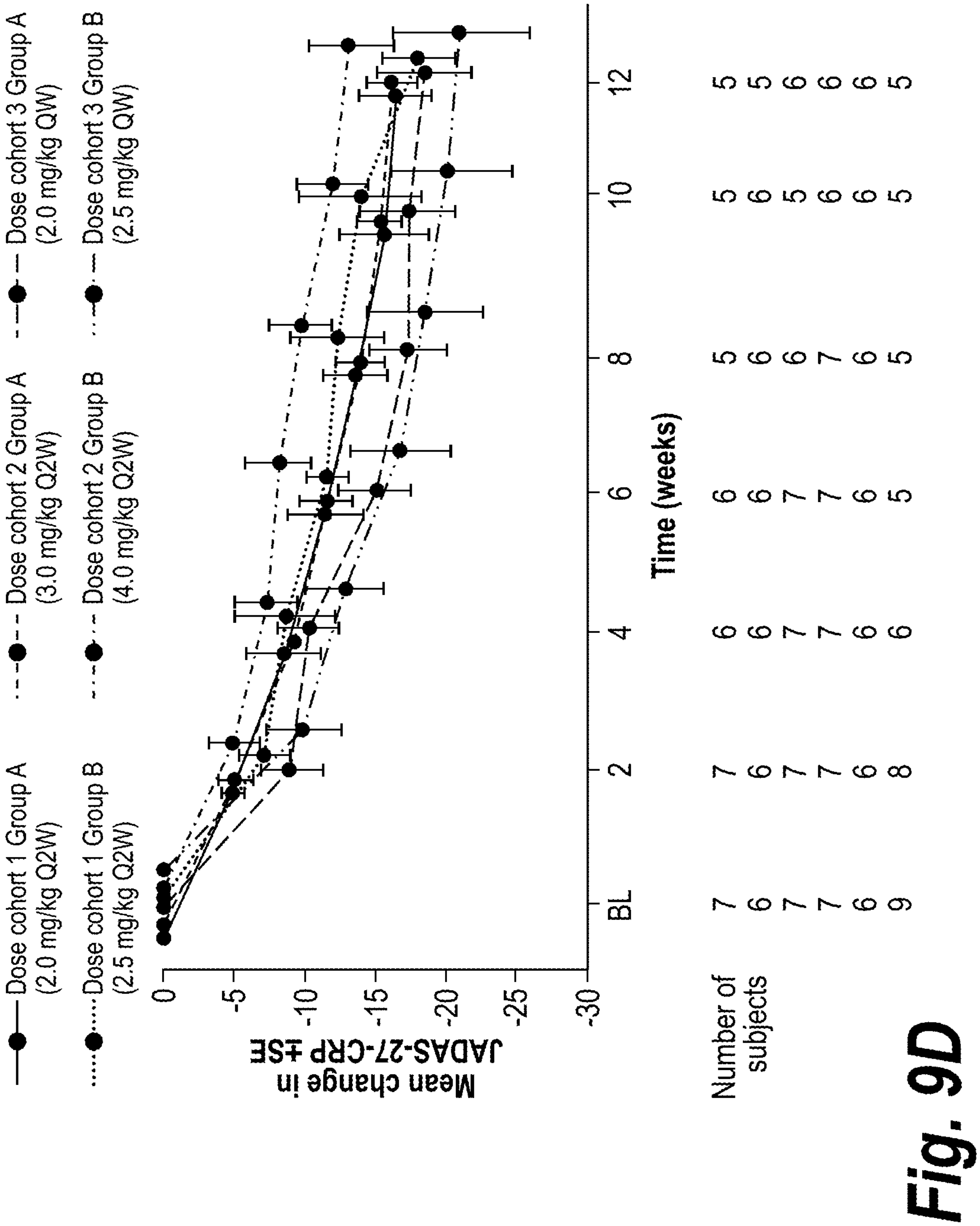

Decreases in disease activity assessed by JADAS-27 CRP was seen in patients in all Dose Cohorts and weight groups at Week 12 with a mean percentage change from baseline of −74.6%, −73.1%, and −87.9% in Dose Cohorts 1, 2, and 3, respectively, also seen from Week 2 onwards (FIG. 9D). In a post hoc analysis, at week 12, 20 patients achieved low disease activity (LDA; JADAS-27-CRP≤3.8): 6, 5, and 9 patients with Dose Cohorts 1, 2, and 3, respectively. Clinically inactive disease (CID) as defined by JADAS-27-CRP≤1 was achieved by 3 patients (1 with Dose Cohort 2 and 2 with Dose Cohort 3). CID as defined by Wallace criteria was achieved by 9 patients (3, 2, and 4 patients with doses 1, 2, and 3, respectively) (22). Thirteen patients had no active joints at week 12, 4 each with Dose Cohorts 1 and 2, and 5 with Dose Cohort 3 (Table 27).

DISCUSSION

The experimental dose regimens of sarilumab tested in the study were selected based on modeling and simulation of sarilumab PK data from adult RA patients. The weight range, body composition, and drug metabolism of pediatric patients are different from those of adults, and response to treatment and side effects can vary depending on age. As a result, the direct extrapolation of pediatric dosages from adult dosages without testing in a pediatric clinical trial may not be recommended (23, 24). The clearance of monoclonal antibodies often increases in a nonlinear manner relative to increasing body weight (25), so given the range of body weights and ages in the pcJIA population weight-adjusted dosages were considered appropriate for this study. The dose regimens tested in patients with pcJIA were chosen based on population PK simulations to achieve a similar exposure in both weight groups that would be comparable with dose regimen exposures studied in adult patients with RA. The study results supported the accuracy of the original model design based on body weight. Sarilumab exhibited nonlinear PK with target-mediated drug disposition. Body weight-adjusted dose regimens yielded comparable exposure in two body weight groups, with the exposures achieved comparable to the fixed-dose regimens tested in adults with RA.

In this study, sarilumab treatment was associated with a reduction in mean CRP values and decreased ESR, demonstrating functional inhibition of IL-6 in patients with pcJIA (20). In particular, a reduction in CRP level is known to be a direct consequence of IL-6 neutralization and indicates the effectiveness of IL-6 neutralization in patients with RA (26-28). Mean CRP reduction was more pronounced with Dose Cohorts 2 and 3, with higher numbers of these patients achieving and maintaining CRP levels below the limit of detection (<0.2 mg/L) of the high-sensitivity method utilized in this study.

JIA ACR response was seen from week 2 onward with all dose regimens of sarilumab. Based on JIA ACR70, reduction in disease signs and symptoms appeared to be more pronounced and sustained with Dose Cohort 2 and 3 compared with Dose Cohort 1. More patients achieved CID or LDA, as assessed by JADAS-27-CRP, with Dose Cohort 3 than with Dose Cohorts 1 or 2. These efficacy results paralleled the clear trends observed in the PD results (i.e. CRP concentrations), further supporting the relationship between IL-6 neutralization and therapeutic response (20, 29). Together, with the less sustained effect on CRP with Dose Cohort 1, these results supported the exclusion of Dose Cohort 1 for further study.

Treatment response rates observed in this study compared favorably with data published for a larger cohort of patients with pcJIA treated with the IL-6R blocker tocilizumab (18). The current results suggested that treatment with sarilumab may meet the goals of recent guidelines published by an international taskforce, which established the ultimate goal of treatment as disease remission and recommended that ≥50% improvement in disease activity be reached within 3 months and that treatment targets should be sustained once achieved (11). The study described herein enrolled patients with established disease, a third of whom had already failed ≥1 biologic. Nevertheless, of the 24 patients receiving Dose Cohorts 2 or 3, at 3 months, 23 and 19 achieved JIA ACR50 and JIA ACR70, respectively, 14 achieved JADAS-27-CRP LDA, and 9 had no active joints. Long-term follow-up during the extension phase of the study will provide greater insight into the ability of sarilumab to meet longer-term treatment targets and to sustain persistent clinical remission once achieved.

The types of AEs observed with sarilumab in the study were consistent with those observed with sarilumab treatment in adult patients and with anti-IL-6 class effects in pediatric patients (18, 30-32). Few local injection-site reactions were reported, and all were mild to moderate in intensity, demonstrating good local tolerability; this is important in pediatric patients given that fear of pain resulting from injection with syringes is common. The most commonly reported AEs were infections and neutropenias. Infection rates were mainly driven by upper airway infections, which are common in pediatric populations, and were balanced across weight and dose groups. No serious infections, no infections leading to discontinuations, and no opportunistic infections were reported.

Per the study protocol, absolute neutrophil count (ANC) was periodically assessed throughout the on-treatment period, including after the first sarilumab dose and before the administration of the second. This thorough hematologic monitoring, with the first post-dose assessment at day 12 for the Q2W regimens and at day 5-8 for the QW regimen, led to the detection of 12 cases of grade 3/4 neutropenia. In adult patients treated with sarilumab or with tocilizumab, ANC nadir occurred a few days (before day 7) after first treatment administration, after which ANC values recovered, consistent with class effects (33). Based on these data from studies in adults, the timing of assessments in this study helped to explain the numerical imbalance of events in Dose Cohort 3 (n=6, including 4 cases discovered at day 5) compared with the other 2 dose regimens (n=3 in both doses 1 and 2).

Of the 12 cases of grade 3/4 neutropenia, 8 occurred in Group B. An evident trend toward increased rates of neutropenia in younger, lower-weight patients was also seen in patients with pcJIA treated with tocilizumab (34, 35). There is no definitive mechanism to explain why younger patients are more prone to neutropenia than older pediatric patients or adults, but in general, a greater prevalence of neutropenia has been reported in children (36). Neutropenias were responsible for the majority of AE-driven discontinuations in the study (n=4/5): 3 cases were grade 4 neutropenia that led to discontinuation per protocol-defined criteria, and 1 was a patient with grade 3 neutropenia in whom baseline ANC was below 2,000/mm$^3$. Importantly, none of the cases of grade 3/4 neutropenia identified during this study was associated with infection, and the majority of cases resolved within a few days. This observation is consistent with data obtained from children and adults treated with tocilizumab or sarilumab, adding further data to support the conclusion that neutropenia induced by IL-6 inhibition does not drive an increased risk of infection (18, 32-34, 37). Although all available data support the conclusion that neutropenia caused by IL-6 inhibition is not associated with an increased risk of infections, the neutropenia data obtained in the study, together with the dynamics of ANC in adults following tocilizumab or sarilumab administration, argue against the selection of Dose Cohort 3 (32, 33, 37). This cautionary choice reduces the risk of neutropenia, particularly in younger children who are at higher risk. Furthermore, the use of a 2-weekly dosing regimen in dose 2 allows for a longer time for ANC recovery.

Following review of all data from the 12-week dose-finding portion of the study, Dose Cohort 2 was selected as the optimal sarilumab regimen for enrollment of additional patients in the second portion of the core treatment phase of the study, and for patients already enrolled in Dose Cohorts 1 or 3 continuing into the second portion. The Dose Cohort 2 regimen displayed a favorable balance between efficacy and safety compared with Cohorts 1 and 3. This dose regimen achieved similar exposure to, and mirrored the efficacy profile of, the equivalent adult dose regimen of 200 mg Q2W, the recommended approved dosage in adults with RA (20, 30, 31). Dose Cohort 2 also followed a 2-weekly dosing schedule (compared with the weekly regimen of Dose Cohort 3) that reduces injection stress, which is particularly relevant in children, and as mentioned above, increases ANC recovery time.

Additional data regarding the safety and efficacy of sarilumab in patients with pcJIA over time in a larger patient cohort will be provided through the enrollment of additional patients who will receive the selected dose regimen and will be followed in the extension phase of the study. As noted, this study was not blinded, and it did not include placebo or an active comparator. This was due to the ethical concerns of exposing children to a noneffective treatment, given the potential chronic and severe nature of the disease and the presence of available data on IL-6 inhibition in adults and children with arthritis (18, 38). These issues were reflected in the study design, with a sequential approach for the tested doses and frequent monitoring, the use of the independent Data Monitoring Committee to formally assess the safety of sarilumab throughout the study, in the use of the DEC to monitor patient response to treatment, and in the ability of the DEC to discontinue patients from any dose deemed noneffective and to return them to an investigator-approved standard treatment.

In conclusion, in patients with pcJIA, sarilumab exhibited nonlinear PK with target-mediated drug disposition, displayed a safety profile consistent with anti-IL-6 class effects, and decreased disease activity. This 12-week dose-finding portion of the core treatment phase of the study showed that Dose Cohort 2 (3.0 mg/kg Q2W in patients 30-60 kg, and 4.0 mg/kg Q2W in patients 10-<30 kg) achieved an exposure similar to the approved dosage of 200 mg Q2W in adults with RA. Dose Cohort 2 provides a good balance between safety/tolerability and efficacy in patients with pcJIA, and will be studied further as the optimal sarilumab dose regimen in pcJIA.

Example 2: An Open-label, Sequential, Ascending, Repeated Dose-finding Study of Sarilumab, Administered with Subcutaneous (SC) Injection, in Children and Adolescents, Aged 1 to 17 Years, With Systemic Juvenile Idiopathic Arthritis (sJIA), Followed by an Extension Phase. (Study No. DRI13926, Study Title: A Repeated Dose-finding Study of Sarilumab in Children and Adolescents with Systemic Juvenile Idiopathic Arthritis)

A phase 2 controlled trial [NCT02991469] is planned to test the human IgG1 anti-IL-6Rα monoclonal antibody sarilumab administered subcutaneously for treating sJIA.

This study targets children and adolescents aged 1 to 17 with sJIA, a JIA subset that resembles adult onset Still's, a relatively rare inflammatory disease (an estimated worldwide incidence of 0.22 and 0.34 per 100 000 for men and women, respectively; Bennett, A. N. et al., Adult onset Still's disease and collapsing glomerulopathy: successful treatment with intravenous immunoglobulins and mycophenolate mofetil. Rheumatology (Oxford). 2004; 43(6):795-9). In this pediatric population, 3 dose regimens of sarilumab are planned to be tested.

Study Design

Description of the Protocol

Study DRI13926 is a multinational, multicenter, open-label, sequential, 2-phase, study in children and adolescents, aged 1 to 17 years (or country specified age requirement), with sJIA who have inadequate response to or who are intolerant to standard therapy and who will receive SC injections of sarilumab administrated q2w or qw. The 2 phases are as follows:

1. a 12-Week Core Treatment Phase, Split into 2 Portions:

A first sequential, ascending dose-cohort, dose finding portion in which at least 2-dose regimens will be investigated in 2 weight groups: ≥30 kg and ≤60 kg patients (Group A) and <30 kg and ≥10 kg patients (Group B), in 6 evaluable patients per dose regimen weight group (at least 24 patients in total). Patient enrollment will be staggered by weight group and dose regimen, starting with Group A (≥30 kg and ≤60 kg) and Dose Cohort 2.

A subsequent portion where approximately 24 additional patients (12 in each weight group: ≥30 kg [Group A] and patients <30 kg and ≥10 kg [Group B]) will be enrolled directly to the selected dose regimen (identified based on the aggregate data from patients enrolled in the first portion) to achieve a total of 18 evaluable patients per weight group at this selected dose regimen.

The 12-week core treatment phase is from Visit 2 (baseline-Week 0) to the time that Visit 12 (Week 12) investigational medicinal product (IMP) is administrated. During the 12-week core treatment phase, in order to minimize the amount of blood withdrawn and the number of visits while maintaining the evaluation of the primary endpoint, patients of Group B (<30 kg and 210 kg) will be randomly assigned to the following sarilumab PK sampling Schedule 1 or 2:

Schedule 1: Baseline, Day 3, Day 8, Week 2, Week 4, Week 8, and Week 12

Schedule 2: Baseline, Day 5, Day 12, Week 2, Week 4, Week 8, and Week 12

2. a 144-Week Extension Phase:

The IMP at Visit 12 is considered as the first IMP for the extension phase.

Only patients who have reached a JIA ACR 30 (in the absence of fever) response at Visit 12 (Week 12) will be permitted to continue in the extension phase. Patients will continue on the same dose regimen of sarilumab they were assigned to receive in the 12-week core treatment phase of the study until the selected dose regimen is determined. Once the dose regimen is selected, patients who were not already on this dose regimen will have their dose regimen adjusted to the selected dose regimen and will follow a new visit schedule with more frequent monitoring (for PK, safety, and efficacy) for the first 12 weeks compared to those patients who do not have dose regimen adjusted.

Patients who discontinue the study treatment prematurely will be assessed using the procedure for the EOT at Visit 27. These patients will be asked to return for the end-of-study (EOS) assessment 6 weeks after the EOT visit (EOT+6 weeks). For patients who discontinue the study treatment during the 12-week core treatment phase, there will be an additional sarilumab PK assessment 2 weeks after the EOT visit (EOT+2 weeks) and IL-6 and sIL-6R will be measured at EOT visit. These patients will be asked to perform all the protocol scheduled visits and assessments except sarilumab administration until Visit 12.

Tested Dose Regimens

For each weight group, the 3 sequential ascending dose regimens initially planned to be tested were defined based on PK modeling with the following rationale:

Dose Cohort 1: dose targeting PK exposures similar to sarilumab 150 mg q2w, the lowest effective dose in adult patients with RA Dose Cohort 2: dose with targeted PK exposures similar to sarilumab 200 mg q2w, the recommended dose regimen in adult patients with RA Dose Cohort 3: dose targeting PK exposures similar to sarilumab 150 mg qw, which yielded the highest exposures in chronic dosing studies in adult patients with RA. See Table 1 for information regarding the dose by body weight and dose cohort to be utilized for this study. See also FIG. 7.

The dose (mg) to be administered to patients will be calculated at the baseline. The dose and corresponding volume of drug product will remain the same throughout the course of the 12-week core treatment phase of the trial regardless of change in patient's body weight. In the extension phase, the patient's weight will be measured at each visit and the dose will be adapted to the increase of weight only if the calculation shows a need for dose increase. The dose will be capped at 200 mg for Dose Cohort 2 and 150 mg for Dose Cohort 3, respectively. Volumes of sarilumab to be injected for the Dose Cohorts are presented in Tables 2-5.

Even though the 12-week core treatment phase starts from Visit 2 (baseline-Week 0) up to Visit 12 (Week 12) inclusive, the IMP at Visit 12 will be administered only for patients who are going to enter the extension treatment phase and after Visit 12 assessments including efficacy, safety, and PK/PD are completed.

Duration of Study Participation for Each Patient

Total duration of study (per patient) is expected to be up to 166 weeks:

Up to 4 weeks ±3 days screening (up to 31 days)

12-week core treatment period

Up to 144-week extension phase 6-week post-treatment follow-up

For all visits, a time frame of ±3 days for Dose Cohort 2 (including any potential q2w intermediate dose) and ±1 day for Dose Cohort 3 (including any potential qw intermediate dose) is acceptable using Day 1 as reference except for Visit 3 (Day 3), Visit 4 (Day 5), and Visit 5 (Day 8), no visit window is allowed where PK sampling occurs.

Visit 6 (Day 12)±1 day for all dose cohorts

Visit 7 (Week 2) ±1 day for all dose cohorts

Visit 8 (Week 4) ±2 days for Dose Cohort 2 and ±1 day for Dose Cohort 3

Stopping Rules for Grade 3/4 Neutropenia for sJIA

In grade 4 neutropenia without signs of infection, temporary termination of Sarilumab treatment was recommended, which can be resumed based on thorough assessment of the benefit versus risk by the Investigator once ANC is greater than 1000/mm$^3$. Decrease in ANC is a pharmacodynamic anti-interleukin 6 (IL-6) class effect seen in both adults and pediatric patients treated with anti-IL-6 antibodies. Following repeated dosing of sarilumab in the long-term studies of adults with rheumatoid arthritis (RA), the decrease in ANC was generally transient and not associated with an increased risk for infections. In pediatric patients, even though there is currently limited published data, the use of an anti-IL-6 was not associated with an increased risk of infections in those patients with Grade 3/4 neutropenia. Table 31 shows occurrence of Grade 3 and Grade 4 neutropenia by lowest value neutrophil count recorded on study.

Selection of Patients

Inclusion Criteria

1. Male and female patients aged ≥1 and ≤17 years at the time of the Screening visit
2. Diagnosis of sJIA subtype according to the ILAR 2001 JIA Classification Criteria Petty, R. E. et al. 2001. J Rheumatol. 2004; 31(2):390-2) with the following features at Screening
   - ≥5 active joints or
   - ≥2 active joints at Screening with systemic JIA fever >37.5° C. in the 3 days preceding baseline or for at least 3 out of any 7 consecutive days during screening despite glucocorticoids at a stable dose for at least 3 days
3. Patient with an inadequate response to current treatment and considered as a candidate for a bDMARD as per Investigator's judgment
4. The patient who has reached the legal age of consent, or the parent(s) or the legal guardian(s) sign and date the Ethics Committee (EC) approved written informed consent. The patient's assent should be obtained based on local guidelines and the patient's maturity and intellectual capabilities of understanding the study associated information. In cases involving emancipated or mature minors with adequate decision-making capacity, or when otherwise permitted by law, a signed informed consent will be obtained directly from the parent (s) or the legal guardian(s).

Study Treatments

Investigational Medicinal Product

Sarilumab, anti-IL-6R mAb.

Formulation

Sarilumab drug product will be provided at 175 mg/mL in an aqueous buffered vehicle, pH 6.0. The drug product will be supplied in a 5 mL vial filled by 2.7 mL of sarilumab with an extractable volume of 2.0 mL.

Route(s) of Administration:

Sarilumab will be administered subcutaneously in the abdomen or thigh when self-injections or also in upper arm (lateral side) by a professional or a non-professional caregiver. It is preferred that SC injection sites be alternated between the 4 quadrants of the abdomen (except the navel or waist area) or the thigh (front and side).

For patients receiving Dose Regimen 2 (q2w), injections will be performed by a professional caregiver at the site during the 12-week core treatment phase of the study. See FIG. 1. For patients receiving Dose Regimen 3 (weekly injections), arrangements must be made for qualified site personnel or home nurse to administer IMP for the doses that are not scheduled to be given at the study site. For the extension phase of the study, if the patients or the parent(s) or the legal guardian(s) or the caregiver(s) are willing and able to perform the injections, the home injection will be permitted. In those cases, the training will be required, and provided to prepare and administer IMP starting at Visit 10 (Week 8) at the core treatment phase. This training must be documented in the patients' study file. The patients or the parent(s) or the legal guardian(s) or the caregiver(s) are allowed to administer the injections under observation/supervision by the Investigator(s) or the delegate(s) at Visit 10 (Week 8), Visit 11 (Week 10), and Visit 12 (Week 12) before the allowance for home injection at the extension treatment phase.

On days when the patient has a study visit, the IMP will be administered following clinical procedures and blood collection. Diaries will be provided to record information pertaining to these injections; these diaries will be kept as source data in the patients' study file. If the caregiver is unable or unwilling to administer IMP, arrangements must be made for qualified site personnel to administer IMP for the doses that are not scheduled to be given at the study site.

Dose Regimen

Sarilumab should be administered q2w or qw. However, the sarilumab administration window of ±3 days for Dose Cohort 2 (including any potential q2w intermediate dose) and ±1 day for Dose Cohort 3 (including any potential qw intermediate dose) is permitted per protocol to accommodate exceptional circumstances, e.g., laboratory test result pending, ongoing adverse event (AE), patient scheduling difficulty except the Visit 5 (Day 8). There is no administration window at Visit 5 (Day 8). There will be only ±1 day of administration window for Dose Cohort 2 and 3 patients at Visit 7 (Week 2) and ±1 day of administration window for Dose Cohort 3 or ±2 for Dose Cohort 2 at Visit 8 (Week 4). Note that an overdose (accidental or intentional) with the IMP is defined as at least twice the dose during an interval of less than 11 days for q2w administrations and less than 6 days for weekly administration.

The following sarilumab dose is to be administered q2w or qw.

Dose Cohort 2:

- Group A (>30 kg and ≤60 kg): 3 mg/kg q2w
- Group B (<30 kg and 210 kg): 4 mg/kg q2w.

Dose Cohort 3:

- Group A (>30 kg and ≤60 kg): 2 mg/kg qw
- Group B (<30 kg and 210 kg): 2.5 mg/kg qw.

Dose Cohort 3 is also being tested as a bi-weekly regimen but keeping the same PK exposure. Therefore the range is the following:

- Patients less than 30 kg: from 5 to 7 mg/kg q2w (dose 2 is 4 mg/kg q2w)
- Patients 30 kg or more: from 4 to 6 mg/kg q2w (dose 2 is 3 mg/kg q2w)

Dose Modification

The dose (mg) to be administered to patients will be calculated at baseline. The dose and corresponding volume of drug product will remain the same throughout the course of the 12-week core treatment phase of the trial regardless of change in patient's body weight. In the extension phase, the patient's weight will be measured at each visit and the dose will be adapted to the increase of weight only if the calculation shows a need for dose increase. The dose will be capped at 200 mg for Dose Cohort 2 and 150 mg for Dose Cohort 3, respectively. Volumes for Dose Cohort 2 to 3 to be injected depending on patient's weight are described herein. See Tables 2-5.

Packaging and Labeling

The IMP will be provided in patient treatment kits containing labeled vials. The content of the labeling is in accordance with the local regulatory specifications and requirements. One kit contains one vial.

Storage Conditions and Shelf Life

The study medication should be kept refrigerated between 2° C. and 8° C. at the site or at home.

TABLE 17

| 12-week core treatment phase for sJIA | | | | | | | | |
|---|---|---|---|---|---|---|---|---|
| | Screening (4 weeks) | Baseline Visit | Core Treatment Phase (12 weeks) | | | | | |
| Visit | V1 | V2 | V3 | V4 | V5 | V6 | V7 | V8 |
| Day | D −28 to D −1 (+3) (Maximum 31 days) | D 1 | D 3 b | D 5 b | D 8 b | D 12 b (±1) | D 15 (±1) | D 29 (±1 or 2) |
| Week | | Wk 0 | | | | | Wk 2 | Wk 4 |
| **Eligibility c** | | | | | | | | |
| Written informed consent and patient assent form d | X | | | | | | | |
| Inclusion/exclusion criteria c | X | X | | | | | | |
| Ethnicity and race | X | | | | | | | |
| Patient demography | X | | | | | | | |
| Tanner stage and menstruation status | X | | | | | | | |
| Medical/surgical history | X | | | | | | | |
| Prior medications/ vaccination history | X | | | | | | | |
| Concomitant medication | X | X | X | X | X | X | X | X |
| Patient diary for IMP/compliance e | | X | | | | | X | X |
| Physical examination f | X | X | | | | | | X |
| Optional EBV, Hepatitis B & C, and HIV g | X | | | | | | | |
| PPD tuberculin skin test for patients ≤5 years; QuantiFERON-TB test for patients >5 years h | X | | | | | | | |
| Chest X-ray i | X | | | | | | | |
| Confirm eligibility | | X | | | | | | |
| Call IVRS | X | X | | | | | X | X |
| **IMP administration** | | | | | | | | |
| Investigational medicinal product (IMP) administration j | | X | | | X j | | X | X |
| IMP dispense k | | X | | | | | X | X |
| **Vital signs and body measurement** | | | | | | | | |
| Patient temperature/ rash diary l | X | X | | | | | X | X |
| Temperature, heart rate, blood pressure (2 measurements for BP at each scheduled time point) | X | X | | | | | | X |
| Weight | X | X | | | | | | |
| Height (stadiometer) m | X | X | | | | | | |
| **Efficacy assessment** | | | | | | | | |
| JIA ACR disease core set/JADAS-27 n | X | X | | | | | X | X |
| sJIA systemic features o | X | X | | | | | X | X |
| **Safety assessment** | | | | | | | | |
| Adverse event/SAE recording | \|-----------------------------------\| | | | | | | | |
| Tuberculosis risk assessment | X | X | | | | | X | X |
| Local tolerability | | X | | | X | | X | X |
| **Laboratory testing** | | | | | | | | |
| Hematology p | X | X | | X p | | X p | X | X |
| Chemistry q | X | X | | | | | X | X |
| Fasting lipids r | X | | | | | | | X |

TABLE 17-continued

| 12-week core treatment phase for sJIA | | | | | | | | |
|---|---|---|---|---|---|---|---|---|
| Optional: glycosylated hemoglobin (HbA1c) s | X | | | | | | | |
| hs-CRP | X | X | x[t] | x[t] | x[t] | x[t] | X | X |
| ESR | | X | | | | | | X |
| ANA/Anti-ds DNA antibody | | x | | | | | | |
| Fibrinogen/D-Dimer u | | | | | | | | |
| Ferritin u | | x | | | | | x | x |
| Urinalysis) v | X | | | | | | | |
| Serum pregnancy for females who are menstruating w | X | | | | | | | |
| Urine pregnancy test for females who are menstruating x | | X | | | | | | X |
| Glucocorticoid tapering | | | | | | | | X |
| Pharmacodinetics and pharmacodynamics | | | | | | | | |
| Serum sarilumab (PK) Group A (≥30 kg and <60 kg) | | X | X | X | X | X | X | X |
| Serum sarilumab (PK) y Group B (<30 kg and ≥10 kg) Schedule 1 | | X | X | | X | | X | X |
| Serum sarilumab (PK) y Group B (<30 kg and ≥10 kg) Schedule 2 | | X | | X | | X | X | X |
| Antibodies to sarilumab y | | X | | | | | | |
| IL-6 and total sIL-6R | | X | | | | | | |
| Pharmacogenomics | | | | | | | | |
| Saliva sample collection aa | | X | | | | | | |

| | Core Treatment Phase (12 weeks) Visit | | | | PK Follow-up a |
|---|---|---|---|---|---|
| | V9 | V10 | V11 | V12 | EOT + 2 Weeks (for patients who discontinue the study treatment during the |
| | Day | | | | |
| | D 43 (±1 or 3) | D 57 (±1 or 3) | D 71 (±1 or 3) | D 85 (±1 or 3) | Core Treatment Phase or not going to enter the Extension |
| | Week | | | | |
| | Wk 6 | Wk 8 | Wk 10 | Wk 12 | Phase |
| Eligibility c | | | | | |
| Written informed consent and patient assent form d | | | | | |
| Inclusion/exclusion criteria c | | | | | |
| Ethnicity and race | | | | | |
| Patient demography | | | | | |
| Tanner stage and menstruation status | | | | X | |
| Medical/surgical history | | | | | |
| Prior medications/ vaccination history | | | | | |
| Concomitant medication | X | X | X | X | X |
| Patient diary for IMP/compliance e | X | X | X | X | |
| Physical examination f | X | | | X | |
| Optional EBV, Hepatitis B & C, and HIV g | | | | | |
| PPD tuberculin skin test for patients ≤5 years; QuantiFERON-TB test for patients >5 | | | | | |

TABLE 17-continued

| 12-week core treatment phase for sJIA | | | | | |
|---|---|---|---|---|---|
| years h | | | | | |
| Chest X-ray i | | | | | |
| Confirm eligibility | | | | | |
| Call IVRS | X | X | X | X | |
| IMP administration | | | | | |
| Investigational medicinal product (IMP) administration j | X | X | X | X | |
| IMP dispense k | X | X | X | | |
| Vital signs and body measurement | | | | | |
| Patient temperature/ rash diary l | X | X | X | X | X |
| Temperature, heart rate, blood pressure (2 measurements for BP at each scheduled time point) | | X | | X | |
| Weight | | | | X | |
| Height (stadiometer) m | | | | X | |
| Efficacy assessment | | | | | |
| JIA ACR disease core set/JADAS-27 n | X | X | X | X | |
| sJIA systemic features o | X | X | X | X | X |
| Safety assessment | | | | | |
| Adverse event/SAE recording | \|-------------------------------------------------------------------------------------------------\| | | | | |
| Tuberculosis risk assessment | X | X | X | X | |
| Local tolerability | X | X | X | X | |
| Laboratory testing | | | | | |
| Hematology p | X | X | X | X | |
| Chemistry q | X | X | X | X q | |
| Fasting lipids r | | | | X | |
| Optional: glycosylated hemoglobin (HbA1c) s | | | | | |
| hs-CRP | X | X | X | X | |
| ESR | X | X | | X | |
| ANA/Anti-ds DNA antibody | | | | X | |
| Fibrinogen/D-Dimer u | X | | | | |
| Ferritin u | x | x | x | x | |
| Urinalysis v | | | | | |
| Serum pregnancy for females who are menstruatingw | | | | | |
| Urine pregnancy test for females who are menstruating x | | X | | X | |
| Glucocorticoid tapering | X | X | | X | |
| Pharmacodinetics and pharmacodynamics | | | | | |
| Serum sarilumab (PK) Group A (≥30 kg and <60 kg) | | X | | X | X |
| Serum sarilumab (PK) y Group B (<30 kg and ≥10 kg) Schedule 1 | | X | | X | X |
| Serum sarilumab (PK) y Group B (<30 kg and ≥10 kg) Schedule 2 | | X | | X | X |
| Antibodies to sarilumaby | | | | X | |
| IL-6 and total sIL-6R | | | | X | X z |

TABLE 17-continued

| 12-week core treatment phase for sJIA |
| --- |
| Pharmacogenomics |
| Saliva sample collection aa |

Abbreviations: ALP = alkaline phosphatase, ANA = anti nuclear anti bodies, ANC = absolute neutrophil counts, BP = blood pressure, DNA = Deoxyribonucleic acid, D = day, EBV = Epstein-Barr virus, EOT = end-of-treatment, ESR = erythrocyte sedimentation rate, HIV = human immunodeficiency virus, hs-CRP = high sensitivity C-reactive protein, Ig = immunoglobuline, IVRS = Interactive voice response system, IL = Interleukin, IMP = investigational medicinal product, JADAS = Juvenile Arthritis Disease Activity Score, JIA ACR = Juvenile Idiopathic Arthritis American College of Rheumatology, PK = pharmacokinetics, PPD = Purified Protein Derivative, q2w = once every other week, SAE = serious adverse event, sIL-6R = soluble Interleukin-6 receptor, sJIA = Systemic Juvenile Idiopathic Arthritis, TB = tuberculosis, V = visit, Wk = week.

a For patients who discontinue the study treatment during the 12-week core treatment phase (at or before Visit 12), there will be an additional PK assessment 2 weeks after the EOT visit (EOT + 2 weeks).

b Pharmacokinetic sampling on visits and days of visits: Visit 3 (D 3), Visit 4 (D 5), Visit 5 (D 8), Visit 6 (D 12) for Group A (≥30 kg); on visits and days of Visit 3 (D 3), Visit 5 (D 8) for Group B (<30 kg) schedule 1; on visits and days of visits: Visit 4 (D 5), Visit 6 (D 12) for Group B (<30 kg) Schedule 2. PK sampling could be performed at home. No sample collection window is allowed for Visit 3 (D 3), Visit 4 (D 5), and Visit 5 (D 8). There is ±1 day window allowed for Visit 6 (D 12). Please refer to the additional hematology test during the PK sampling period.

c At the Investigators' discretion laboratory tests mentioned in exclusion criterion 27 may be repeated by central laboratory retesting between the Screening visit and the first IMP administration to ensure the patient meet eligibility with respect to exclusion criterion 27. A locally approved specific consent form will be signed by patients who require Gilbert syndrome genetic testing (consent/assent must be obtained prior to performing this assessment and local regulations should be respected).

d Prior to all screening assessments, the patient (if he/she has reached the legal age of consent based on the local regulations), the parent(s) or the legal guardian(s) must sign and date the EC approved written informed consent form. The patient, the parent(s), and the legal guardian(s) will receive information on the study objective (s) and procedures from the Investigator. Separate written consent forms should be obtained from the parent(s) or the legal guardian(s) who allow his/her child to participate in an optional saliva sample collection for pharmacogenomic study and give permission to the Sponsor to keep their left- over/unused blood samples for future research. A separate (locally approved) informed consent form will be completed by any patients requiring genetic Gilbert disease testing as per local regulations. The signed assent forms should be obtained from the patient based on local regulations and his/her maturity of understanding the study information.

e Patient diary for IMP administration to be completed for IMP administered at home.

f Complete physical examinations will be performed at Visit 1 (D −28 to D −1, up to 31 days), Visit 2 (D 1, Week 0), Visit 8 (Week 4), Visit 9 (Week 6), and Visit 12 (Week 12) including skin, nasal cavities, eyes, ears, respiratory, cardiovascular, gastrointestinal, neurological, lymphatic, and musculoskeletal systems.

g Optional: Based on the Investigator's judgment, Epstein Barr virus (EBV) titer including IgG, and IgM may be performed at the Screening; based on the patient's family and medical history and the Investigator's judgment, hepatitis B surface antigen (HBs-Ag), hepatitis B surface antibody (HBs-Ab), total hepatitis B core antibody (HBc-Ab), and hepatitis C antibody (HCV-Ab) may be performed at the Screening. HIV serology will be performed only based on the Investigator's assessment for those HIV suspected patients.

For Germany only: Serology testing for hepatitis B & C and HIV have to be performed at Screening visit for all patients in order to screen corresponding exclusion criterion 18 h Purified Protein Derivative (PPD) Skin Test should be performed in patients ≤5 years old prior to the Baseline Visit 2 (D1, Week 0). Patients should be evaluated within 48-72 hours after placement of the PPD skin test. For patients who fail to be evaluated within 72 hours, the skin test should be repeated. An assessment of the level of risk (TB contact and/or recent immigration from a country with a high prevalence of TB) should be taken into consideration when defining the result of the skin tests. Refer to exclusion criterion 17 for all the details. An interferon-gamma (IFN-r) release assay, QuantiFERON-TB test will be performed for patients >5 years old (1). After the initial TB screening, if PPD orQuantiFERON result is negative, but clinical suspicion forTB is higher than moderate, the patient should be rescreened for TB at any time during the study based on the Investigator's assessment. Quantiferon TB test will be considered in the younger group of patients (<5 years) based on the local PPD availability, local regulation for TB screening, and the Investigator's judgment.

i The chest X-ray may be performed for the patients only when deemed necessary based on the Investigator's judgment or in line with local guideline for TB screening prior to initiating a biologic therapy for JIA patients who haven't had chest X-ray performed within 3 months prior to the Baseline Visit 2 (D1, Week 0).

j Investigational medicinal product to be administered q2w for patients in Dose Cohort 2 and once every week for patients in Dose Cohort 3. Arrangements will be made for home nurses to administer IMP for Dose Cohort 3 patients for the intermediate visits (home administration if possible). Patients should be monitored for at least 30 minutes after IMP administration for any signs or symptoms of a hypersensitivity reaction. Patients who do not achieve a Juvenile Idiopathic Arthritis American College of Rheumatology (JIA ACR) 30 by the end of the 12-week core treatment period will be discontinued from the study treatment to receive standard of care as per the Investigator's clinical judgment. JIA ACR response, including JIA ACR30 response, will be provided by the Sponsor to Investigator to evaluate this criterion only after V12. For patients completing the core treatment phase at V12, but not continuing the extension phase for reasons other than lack of JIA ACR30 response, there will be no IMP injection at visit 12.

For Germany only: After the first IMP administration the patient has to be monitored for at least 1 hour to assess local tolerability.

k Investigational medicinal product will be dispensed to patients who are at the Dose Cohort 3 during the core treatment phase.

l Patient temperature/rash diary will include recording tympanic temperatures and reporting rash (if occur) at home every day between screening and baseline visits and for at least 7 days prior to each subsequent scheduled visit with ACR JIA efficacy core set assessment. Temperature should be measured a minimum of twice daily at fixed points, upon arising and prior to bedtime, as well as anytime if fever is suspected.

m Collect an additional height measured closest to 1 year before baseline. Height will be measured using stadiometer at sites during the study.

n Juvenile Idiopathic Arthritis ACR core setincludes: global assessment of the severity of disease by the physician, global assessment of overall well-being by the patient or parent(s)/legal guardian(s), numberof joints with active arthritis (defined as swelling within the joint not due to deformity, OR limitation of motion with either pain or tenderness, or both), number of joints with limitation of motion, Childhood Health Assessment Questionnaire (CHAQ), hs-CRP and fever (Petty, R. E. et al., International League of Associations for Rheumatology classification of juvenile idiopathic arthritis: second revision, Edmonton, 2001. J Rheumatol. 2004; 31 (2): 390-2; Giannini, E. H. et al. Preliminary definition of improvement in juvenile arthritis. Arthritis Rheum. 1997; 40 (7): 1202-9; 4. Beukelman, T. et al.,, 2011 American College of Rheumatology recommendations for the treatment of juvenile idiopathic arthritis: initiation and safety monitoring of therapeutic agents for the treatment of arthritis and systemic features. Arthritis Care Res (Hoboken). 2011; 63 (4): 465-82. At the Screening, only the fever, the number of joints with active arthritis, and the number of joints with limitation of motion will be assessed. JADAS scoring is explained herein.

o Systemic features of sJIA include fever, evanescent salmon-colored erythematous rash, generalized lymph node enlargement, hepatomegaly, splenomegaly, and serositis and other complications at Screening, Baseline, and Visit 12. Only fever and evanescent salmon-colorederythematous rash will be assessed at Week 2, Week 4, Week 6, Week 8, and Week 10.

p Hematology (blood should be drawn PRIOR TO drug administration): Hemoglobin, hematocrit, red blood cell (RBC) count, and morphology (if RBC count is abnormal), white blood cell (WBC), white blood cell differential (neutrophils, lymphocytes, monocytes, eosinophils, basophils), platelet count, absolute neutrophil count (ANC). An additional hematology test must be performed at Visit 6 (Day 12 ±1 day) for Cohort 2 patients in order to get results prior to Visit 7 (Day 15, Week 2), the second dose of sarilumab injection. For dose cohort 3 patients, an additional hematology test should be performed prior to or at Visit 5 (Day 8) but no earlier than Visit 4 (Day 5) and the results need to be reviewed prior to the second sarilumab injection at Visit 5 (Day 8). The additional hematology test can be done at the central laboratory or at the local laboratory to confirm if the ANC and platelet count are not within the protocol-defined limits for temporary or permanent discontinuation of study drug. If local laboratory is used, a central laboratory sample for hematology should still be drawn pre-IMP administration at Visit 7 (Day 15, Week 2) as scheduled for Cohort 2 and Visit 5 (Day 8) for Cohort 3. For all patients, the Visit 2 (Day 1) hematology laboratory assessment must be reviewed before the administration of the second dose of sarilumab at Visit 5 (Day 8) for Dose Cohort 3 patients or at Visit 7 (Week2, Day 15) for Dose Cohort 2 patients.

q Chemistry (blood should be drawn PRIOR TO drug administration): Whole chemistry will be performed at the Screening visit, Baseline Visit 2 (Day 1, Week 0), and Visit12 (Week 12) or EOT only: sodium, potassium, chloride, bicarbonate, blood urea nitrogen, creatinine, and creatinine clearance, glomerular filtration rate, calcium, phosphate, total protein, albumin, alanine aminotransferase (ALT), aspartate aminotransferase (AST), alkaline phosphatase (ALP), lactate dehydrogenase (LDH), total bilirubin, conjugated bilirubin, and unconjugated bilirubin. At all other visits: only ALT, AST, ALP, LDH, total bilirubin, conjugated bilirubin, unconjugated bilirubin, and albumin will be tested.

r Fasting lipids (blood should be drawn PRIOR TO drug administration): Triglycerides (TG), total cholesterol, high density lipoprotein (HDL) cholesterol, low density lipoprotein (LDL) cholesterol. Patients are required to fast at least 8 hours before the test.

s Optional: HbA1c levels will be only measured based on the patient's medical history and the Investigator's judgment.

TABLE 17-continued

| 12-week core treatment phase for sJIA |
| --- |

[t]hs-CRP will be measured on Day 3 and 8 for patients ≥30 kg (Group A). For patients <30 kg (Group B) in PK Schedule 1 group, hs-CRP will be measured on Day 3 and 8. For patients <30 kg (Group B) in PK Schedule 2 group, hs-CRP will be measured on Days 5 and 12.

u When macrophage activation syndrome (MAS) suspected, ferritin, blood cell accounts (red blood cell, while blood cell, platelet, and hemoglobin), AST/ALT, triglycerides, and fibrinogen tests need to be ordered if necessary based on the Investigator's judgment. Described herein are clinical and laboratory features for MAS diagnosis.

v Urinalysis dipstick: specific gravity, pH, glucose, blood, protein, nitrites, leukocyte esterase, bilirubin. If any parameter on the dipstick is abnormal, a urine sample should be sent to the central laboratory for testing. If positive for proteins, microscopic analysis is performed by central laboratory.

w For females who have commenced menstruating, a serum pregnancy test is mandatory at the Screening visit.

x For females who have commenced menstruating, a serum pregnancy test should be performed at Screening and a urine pregnancy test should be performed at Visit 2 (Week 0, Day 1), Visit 8 (Week 4), Visit 10 (Week 8), and Visit 12 (Week 12). The urine pregnancy test could be performed locally. The pregnancy status should be checked by urine pregnancy testing prior to exposure to the IMP and EOT.

y Blood samples will be collected PRIOR TO IMP administration on the dosing days during the treatment period. If an SAE occurs in a patient, blood samples should be collected for determination of sarilumab concentration and antidrug antibody (ADA) assessment at or near the onset and completion of the occurrence of the event, if possible/*98+–.

z For patients who discontinue the study treatment prematurely during the core treatment phase, the IL-6 and total sIL-6R will be measured at the EOT assessment.

aa Parent (s) or legal guardian(s) must sign a separate Written Subject Information (WSI) prior to saliva sample collection for phamacogenomic study. Samples are preferred to being collected at the Baseline Visit 2 (D1, Week 0), but can be collected at any visit. The patient can also sign the WSI based on his/her age, local regulations, and his/her maturity of understanding the study information. The patient is still eligible to enroll in the study if he/she or his/her parent(s) or his/her legal guardian(s) do not wish him/her to participate in saliva sample collection.

TABLE 18

Flow chart for patients who remain on the current dose (selected dose regimen) from the dose-finding portion or recruited directly under the selected dose regimen during the second portion

| | Extension Phase (up to 144 weeks of sarilumab exposure from V12) | | | | | |
| --- | --- | --- | --- | --- | --- | --- |
| | Visit | | | | | |
| | V13 | V14 | V15 | V16 | V17 | V18 |
| | Day | | | | | |
| | D 113 (±1 or 3) | D 141 (±1 or 3) | D 169 (±1 or 3) | D 225 (±1 or 3) | D 281 (±1 or 3) | D 337 (±1 or 3) |
| | Week | | | | | |
| | Wk 16 | Wk 20 | Wk 24 | Wk 32 | Wk 40 | Wk 48 |
| Concomitant medication | X | X | X | X | X | X |
| Patient diary/IMP compliance c | X | X | X | X | X | X |
| Physical examination d | | | X | | | X |
| Call IVRS | X | X | X | X | X | X |
| Tanner stage and menstruation status | | | X | | | X |
| **Treatment** | | | | | | |
| Investigational medicinal product (IMP) administration e | X | X | X | X | X | X |
| IMP dispense | X | X | X | X | X | X |
| **Vital signs and body measurement** | | | | | | |
| Patient temperature/rash diary f | X | X | X | X | X | X |
| Temperature, heart rate, blood pressure (2 measurements for BP at each scheduled time point) | X | X | X | X | X | X |
| Weight | X | X | X | X | X | X |
| Height (stadiometer) g | | | X | | | X |

TABLE 18-continued

Flow chart for patients who remain on the current dose (selected dose regimen) from the dose-finding portion or recruited directly under the selected dose regimen during the second portion

| | | | | | | |
|---|---|---|---|---|---|---|
| **Efficacy assessment** | | | | | | |
| JIA ACR core set/JADAS-27 h | | | X | | | X |
| sJIA systemic features i | | | X | | | X |
| **Safety assessment** | | | | | | |
| AE/SAE recording | ----- | ----- | ----- | ----- | ----- | ----- |
| Tuberculosis risk assessment | X | X | X | X | X | X |
| PPD tuberculin skin test for patients ≤5 years; QuantiFERON-TB test for patients >5 years | | | | | | X |
| Local tolerability | X | X | X | X | X | X |
| **Laboratory testing** | | | | | | |
| Hematology j | X | X | X | X | X | X |
| Chemistry k | X | X | X | X | X | X |
| Fasting lipids l | | | X | | | X |
| hs-CRP | | | X | | | X |
| ESR | | | X | | | X |
| ANA/Anti-ds DNA antibody | | | X | | | X |
| Fibrinogen/D-Dimer and Ferritin m | X | | | | | |
| Urine pregnancy test for females who are menstruating n | X | X | X | X | X | X |
| **Pharmacokinetics** | | | | | | |
| Serum sarilumab (PK) o | | | X | | | X |
| Antibodies to sarilumab o | | | X | | | X |

| | Extension Phase (up to 144 weeks of sarilumab exposure from V12) | | | | |
|---|---|---|---|---|---|
| | Visit | | | | |
| | V19 | V20 | V21 | V22 | V23 |
| | Day | | | | |
| | D 421 (±1 or 3) | D 505 (±1 or 3) | D 589 (±1 or 3) | D 673 (±1 or 3) | D 757 (±1 or 3) |
| | Week | | | | |
| | Wk 60 | Wk 72 | Wk 84 | Wk 96 | Wk 108 |
| Concomitant medication | X | X | X | X | X |
| Patient diary/IMP compliance c | X | X | X | X | X |
| Physical examination d | | X | | X | X |
| Call IVRS | X | X | X | X | X |
| Tanner stage and menstruation status | | X | | X | |
| **Treatment** | | | | | |
| Investigational medicinal product (IMP) administration e | X | X | X | X | X |
| IMP dispense | X | X | X | X | X |

TABLE 18-continued

Flow chart for patients who remain on the current dose (selected dose regimen) from the dose-finding portion or recruited directly under the selected dose regimen during the second portion

| | | | | | |
|---|---|---|---|---|---|
| **Vital signs and body measurement** | | | | | |
| Patient temperature/rash diary f | X | X | X | X | X |
| Temperature, heart rate, blood pressure (2 measurements for BP at each scheduled time point) | X | X | X | X | X |
| Weight | X | X | X | X | X |
| Height (stadiometer) g | | X | | X | |
| **Efficacy assessment** | | | | | |
| JIA ACR core set/JADAS-27 h | | X | | X | |
| sJIA systemic features i | | X | | X | |
| **Safety assessment** | | | | | |
| AE/SAE recording | \|------------ | ------------ | ------------ | ------------ | ------------\| |
| Tuberculosis risk assessment | X | X | X | X | X |
| PPD tuberculin skin test for patients ≤5 years; QuantiFERON-TB test for patients >5 years | | | | X | |
| Local tolerability | X | X | X | X | X |
| **Laboratory testing** | | | | | |
| Hematology j | X | X | X | X | X |
| Chemistry k | X | X | X | X | X |
| Fasting lipids l | | X | | X | |
| hs-CRP | | X | | X | |
| ESR | | X | | X | |
| ANA/Anti-ds DNA antibody | | X | | X | |
| Fibrinogen/D-Dimer and Ferritin m | X | | | | X |
| Urine pregnancy test for females who are menstruating n | X | X | X | X | X |
| **Pharmacokinetics** | | | | | |
| Serum sarilumab (PK) o | | X | | X | |
| Antibodies to sarilumab o | | X | | X | |

| | Extension Phase (up to 144 weeks of sarilumab exposure from V12) | | | | Post-treatment Follow-up (6 weeks) |
|---|---|---|---|---|---|
| | **Visit** | | | | |
| | V24 | V25 | V26 | V27 a | V28 b |
| | **Day** | | | | |
| | D 841 (±1 or 3) | D 925 (±1 or 3) | D 1009 (±1 or 3) | Wk 156/ | EOS: Wk 162/ |
| | **Week** | | | | |
| | Wk 120 | Wk 132 | Wk 144 | EOT | (EOT + 6 Weeks) |
| Concomitant medication | X | X | X | X | X |
| Patient diary/IMP compliance c | X | X | X | X | |
| Physical examination d | X | | X | X | X |
| Call IVRS | X | X | X | X | X |
| Tanner stage and menstruation status | X | | X | X | X |

TABLE 18-continued

Flow chart for patients who remain on the current dose (selected dose regimen) from the dose-finding portion or recruited directly under the selected dose regimen during the second portion

| | | | | | |
|---|---|---|---|---|---|
| **Treatment** | | | | | |
| Investigational medicinal product (IMP) administration e | X | X | X | | |
| IMP dispense | X | X | X | | |
| Vital signs and body measurement | | | | | |
| Patient temperature/rash diary f | X | X | X | X | |
| Temperature, heart rate, blood pressure (2 measurements for BP at each scheduled time point) | X | X | X | X | X |
| Weight | X | X | X | X | X |
| Height (stadiometer) g | X | | X | X | |
| **Efficacy assessment** | | | | | |
| JIA ACR core set/JADAS-27 h | X | | X | X | |
| sJIA systemic features i | X | | X | X | X |
| **Safety assessment** | | | | | |
| AE/SAE recording | ------------------ | ------------------ | ------------------ | ------------------ | ------------------ |
| Tuberculosis risk assessment | X | X | X | X | X |
| PPD tuberculin skin test for patients ≤5 years; QuantiFERON-TB test for patients >5 years | | | X | | |
| Local tolerability | X | X | X | X | |
| **Laboratory testing** | | | | | |
| Hematology j | X | X | X | X | |
| Chemistry k | X | X | X | X | |
| Fasting lipids l | X | | X | X | |
| hs-CRP | X | | X | X | |
| ESR | X | | X | X | |
| ANA/Anti-ds DNA antibody | X | | X | X | |
| Fibrinogen/D-Dimer and Ferritin m | | | | X | |
| Urine pregnancy test for females who are menstruating n | X | X | X | X | |
| **Pharmacokinetics** | | | | | |
| Serum sarilumab (PK) o | X | | | X | X |
| Antibodies to sarilumab o | X | | | X | X |

Abbreviations: AE = adverse event, ALP = alkaline phosphatase, ALT = alanine aminotransferase, ANU = absolute neutrophil counts, AST = aspartate aminotransferase, ANA = anti nuclear antibodies, BP = blood pressure, DNA = Deoxyribonucleic acid, D = day, EOS = end-of-study, EOT = end-of-treatment, ESR = erythrocyte sedimentation rate, EBV = Epstein-Barr virus, HIV = human immunodeficiency virus, hs-CRP = high sensitivity C-reactive protein, IMP = investigational medicinal product, IVRS = Interactive voice response system, IL = Interleukin, JADAS = Juvenile Arthritis Disease Activity Score, JIA ACR = Juvenile Idiopathic Arthritis American College of Rheumatology, PK = pharmaco kinetics, PPD = purified protein derivative, q2w = once every other week, SAE = serious adverse event, sJIA = Systemic Juvenile Idiopathic Arthritis; TB = Tuberculosis, V = visit, Wk = week.

a Visit 27 is the study planned end-of-treatment (EOT) visit. If patients discontinue the study treatment prematurely, EOT will occur 1 week after the last IMP injection for Dose Cohort 3 and 2 weeks after the last IMP injection for Dose Cohort 2.

b Visit 28 is the study planned end-of-study (EOS) visit. If patients discontinue the study treatment prematurely, these patients will be asked to return for the EOS assessment 6 weeks after the EOT visit (EOT + 6 weeks). This EOS (EOT + 6 weeks) visit will be applicable to all the patients in both Core Treatment Phase and Extension Phase.

c Patient diary for IMP administration to be completed for IMP administered at home.

d Complete physical examinations will be performed at Visit 15 (week 24), Visit 18 (Week 48), Visit 20 (Week 72), Visit 22 (Week 96,) Visit 24 (Week 120), Visit 26 (Week 144), Visit 27 EOT, and Visit 28 EOS including skin, nasal cavities, eyes, ears, respiratory, cardiovascular, gastrointestinal, neurological, lymphatic, and musculoskeletal systems.

e IMP to be administered q2w for patients in Dose Cohort 2 and weekly for patients in Dose Cohort 3. For patients who complete the extension phase, if the selected dose regimen is dosed biweekly (q2w), then the last IMP injection will occur at Week 154; if the selected dose regimen is dosed weekly (qw), then the last IMP injection will occur at Week 155. Patients will have EOT assessment at the Visit 27 (Week 156). For patients who discontinue the study treatment prematurely during the extension phase, it will be preferable to have EOT assessment 2 weeks after the last IMP injection for Dose Cohort 2 patients and 1 week after the last IMP injection for Dose Cohort 3 patients. In case the patient is unable to meet the planned schedule, the EOT visit will be used for assessment at the next protocol defined visit after the last IMP injection. Patients will be asked to return to the site for the EOS assessment 6 weeks after the EOT visit. Patients should be monitored for at least 30 minutes after IMP administration for any signs or symptoms of a hyper sensitivity reaction. There will be no IMP injection at the Visit 27 (Week 156).

TABLE 18-continued

Flow chart for patients who remain on the current dose (selected dose regimen) from the dose-finding portion or recruited directly under the selected dose regimen during the second portion f Patient temperature/rash diary will include recording tympanic temperatures and reporting rash (if occur) at home for at least 7 days prior to each subsequent scheduled visit with ACR JIA efficacy core set assessment. Temperature should be measured minimum of twice daily, at fixed points, upon arising, and prior to bedtime as well as anytime if fever is suspected.

g Collect an additional height measured closest to 1 year before baseline. Height will be measured using stadiometer at sites during the study.

h JIA ACR core set includes: global assessment of the severity of disease by the physician, global assessment of overall well-being by the patient or parent/legal guardian, number of joints with active arthritis defined as swelling within the joint not due to deformity, OR limitation of motion with either pain or tenderness, or both), number of joints with limitation of motion, Childhood Health Assessment Questionnaire (CHAQ), hs-CRP, and fever. JADAS scoring is explained herein.

i Systemic features of sJIA include fever, evanescent salmon-colored erythematous rash, generalized lymph node enlargement, hepatomegaly, splenomegaly, serositis and other complications at Week 156 (EOT Visit). Only fever and evanescent salmon-colored erythematous rash will be assessed at Week 24, Week 48, Week 72, Week 96, Week 120, Week 144, and Week 162 (EOS Visit).

j Hematology (blood should be drawn PRIOR TO drug administration): Hemoglobin, hematocrit, red blood cell (RBC), count and morphology (if RBC count is abnormal), white blood cell (WBC) differential (neutrophils, lymphocytes, monocytes, eosinophils, basophils), platelet count, absolute neutrophil count (ANC).

k Chemistry (blood should be drawn BEFORE drug administration): ALT, AST, ALP, lactate dehydrogenase (LDH), total bilirubin, conjugated bilirubin, unconjugated bilirubin, and albumin will be tested. Complete chemistry should be done at Visit 27 EOT.

l Lipids (blood should be drawn BEFORE drug administration): Triglycerides (TG), total cholesterol, high density lipoprotein (HDL) cholesterol, low density lipoprotein (LDL) cholesterol. Patients are required to fast at least 8 hours before the test.

m When MAS suspected, ferritin, blood cell accounts (red blood cell, while blood cell, platelet, and hemoglobin), AST/ALT, triglycerides, and fibrinogen tests need to be ordered if necessary based on Investigator's judgment. Refer to clinical and laboratory features for MAS diagnosis described herein.

n For females who have commenced menstruating, urine pregnancy test should be performed prior to exposure to the IMP injection at each scheduled visit and at the EOT. The urine pregnancy test could be performed locally.

o Blood samples will be collected PRIOR TO IMP administration on the dosing days during the treatment period. If an SAE occurs in a patient, blood samples should be collected for determination of sarilumab concentration and antidrug antibody (ADA) assessment at or near the onset and completion of the occurrence of the event, if possible.

TABLE 19

Flow chart for patients who change to the selected dose (during extension phase)

| | Visit (up to a total of 144 weeks of sarilumab exposure from V12) | | | | | | | | | | | |
|---|---|---|---|---|---|---|---|---|---|---|---|---|
| | Visit | | | | | | | | | | | |
| | V101 | V102 | V103 | V104 | V105 | V106 | V107 | V108 | V109 | V110 | V111 | V112 |
| | Day at this dose | | | | | | | | | | | |
| | D 1 (±1 or 3) | D 15 (±1 or 3) | D 29 (±1 or 3) | D 43 (±1 or 3) | D 57 (±1 or 3) | D 85 (±1 or 3) | D 113 (±1 or 3) | D 141 (±1 or 3) | D 169 (±1 or 3) | D 225 (±1 or 3) | D 281 (±1 or 3) | D 337 (±1 or 3) |
| | Week at this dose | | | | | | | | | | | |
| | Wk 0 | Wk 2 | Wk 4 | Wk 6 | Wk 8 | Wk 12 | Wk 16 | Wk 20 | Wk 24 | Wk 32 | Wk 40 | Wk 48 |
| Tanner stage and menstruation status | X | | | | | | | | X | | | X |
| Concomitant medication | X | X | X | X | X | X | X | X | X | X | X | X |
| Patient diary for IMP/compliance c | X | X | X | X | X | X | X | X | X | X | X | X |
| Physical examination d | X | | | X | | X | | | X | | | X |
| Call IVRS | X | X | X | X | X | X | X | X | X | X | X | X |
| IMP administration | | | | | | | | | | | | |
| Investigational medicinal product (IMP) administration e | X | X | X | X | X | X | X | X | X | X | X | X |
| IMP dispense | X | X | X | X | X | X | X | X | X | X | X | X |
| Vital signs and body measurement | | | | | | | | | | | | |
| Patient temperature/rash diary f | X | X | X | X | X | X | X | X | X | X | X | X |
| Temperature, heart rate, blood pressure (2 measurements for BP at each scheduled time point) | X | X | X | X | X | X | X | X | X | X | X | X |
| Weight | X | | X | | X | X | X | X | X | X | X | X |
| Height (stadiometer) g | X | | | | | | | | X | | | X |
| Efficacy assessment | | | | | | | | | | | | |
| JIA ACR disease core set/JADAS-27 h | X | X | X | X | X | X | | | X | | | X |
| sJIA systemic features i | X | X | X | X | X | X | | | X | | | X |

TABLE 19-continued

Flow chart for patients who change to the selected dose (during extension phase)

| | | | | | | | | | | | | |
|---|---|---|---|---|---|---|---|---|---|---|---|---|
| **Safety assessment** | | | | | | | | | | | | |
| Adverse event/SAE recording | ------ | ------ | ------ | ------ | ------ | ------ | ------ | ------ | ------ | ------ | ------ | ------ |
| Tuberculosis risk assessment | X | X | X | X | X | X | X | X | X | X | X | X |
| PPD tuberculin skin test for patients ≤5 years; QuantiFERON-TB test for patients >5 years | X | | | | | | | | | | | X |
| Local tolerability | X | X | X | X | X | X | X | X | X | X | X | X |
| **Laboratory testing** | | | | | | | | | | | | |
| Hematology j | X | X | X | | X | X | X | X | X | X | X | X |
| Chemistry k | X | X | X | | X | X | X | X | X | X | X | X |
| Fasting lipids l | X | | X | | | X | X | | X | | | X |
| hs-CRP | X | X | X | X | X | X | | | X | | | X |
| ESR | X | | | | | X | | | X | | | X |
| ANA/Anti-ds DNA antibody | X | | | | | | X | | X | | | X |
| Ferritin/Fibrinogen/D-Dimer m | X | | | | | | X | | | | | |
| Urine pregnancy test for females who are menstruating n | X | | X | | X | X | X | X | X | X | X | X |
| **Pharmacokinetics and pharmacodynamics** | | | | | | | | | | | | |
| Serum sarilumab (PK) o | X | X | X | | X | X | | | X | | | X |
| Antibodies to sarilumab o | X | | | | | | | | X | | | X |

| | Visit (up to a total of 144 weeks of sarilumab exposure from V12) | | | | |
|---|---|---|---|---|---|
| | Visit | | | | |
| | V113 | V114 | V115 | V116 | V117 |
| | Day at this dose | | | | |
| | D 421 (±1 or 3) | D 505 (±1 or 3) | D 589 (±1 or 3) | D 673 (±1 or 3) | D 757 (±1 or 3) |
| | Week at this dose | | | | |
| | Wk 60 | Wk 72 | Wk 84 | Wk 96 | Wk 108 |
| Tanner stage and menstruation status | | X | | X | |
| Concomitant medication | X | X | X | X | X |
| Patient diary for IMP/compliance c | X | X | X | X | X |
| Physical examination d | | X | | X | |
| Call IVRS | X | X | X | X | X |
| **IMP administration** | | | | | |
| Investigational medicinal product (IMP) administration e | X | X | X | X | X |
| IMP dispense | X | X | X | X | X |
| **Vital signs and body measurement** | | | | | |
| Patient temperature/rash diary f | X | X | X | X | X |
| Temperature, heart rate, blood pressure (2 measurements for BP at each scheduled time point) | X | X | X | X | X |
| Weight | X | X | X | X | X |
| Height (stadiometer) g | | X | | X | |
| **Efficacy assessment** | | | | | |
| JIA ACR disease core set/JADAS-27 h | | X | | X | |
| sJIA systemic features i | | X | | X | |

TABLE 19-continued

Flow chart for patients who change to the selected dose (during extension phase)

| | | | | | |
|---|---|---|---|---|---|
| **Safety assessment** | | | | | |
| Adverse event/SAE recording | \|------------------------------------------------------------------------\| | | | | |
| Tuberculosis risk assessment | X | X | X | X | X |
| PPD tuberculin skin test for patients ≤5 years; QuantiFERON-TB test for patients >5 years | | | | X | |
| Local tolerability | X | X | X | X | X |
| **Laboratory testing** | | | | | |
| Hematology j | X | X | X | X | X |
| Chemistry k | X | X | X | X | X |
| Fasting lipids l | | X | | X | |
| hs-CRP | | X | | X | |
| ESR | | X | | X | |
| ANA/Anti-ds DNA antibody | | X | | X | |
| Ferritin/Fibrinogen/D-Dimer m | X | | | | X |
| Urine pregnancy test for females who are menstruating n | X | X | X | X | X |
| **Pharmacokinetics and pharmacodynamics** | | | | | |
| Serum sarilumab (PK) o | | X | | X | |
| Antibodies to sarilumab o | | X | | X | |

| | Visit (up to a total of 144 weeks of sarilumab exposure from V12) | | | Post-treatment Follow-up (6 weeks) |
|---|---|---|---|---|
| | **Visit** | | | |
| | V118 | V119 | V27 a | V28 b |
| | **Day at this dose** | | | |
| | D 841 (±1 or 3) | D 925 (±1 or 3) | EOT | EOS: (EOT + 6 Weeks) |
| | **Week at this dose** | | | |
| | Wk 120 | Wk 132 | Check Table 1 for the weeks between patient's last on-treatment visit and EOT | (EOT + 6 Weeks) |
| Tanner stage and menstruation status | X | | X | X |
| Concomitant medication | X | X | X | X |
| Patient diary for IMP/compliance c | X | X | X | |
| Physical examination d | X | | X | X |
| Call IVRS | X | X | X | X |
| **IMP administration** | | | | |
| Investigational medicinal product (IMP) administration e | X | X | | |
| IMP dispense | X | X | | |
| **Vital signs and body measurement** | | | | |
| Patient temperature/rash diary f | X | X | X | X |
| Temperature, heart rate, blood pressure (2 measurements for BP at each scheduled time point) | X | X | X | X |
| Weight | X | X | X | X |
| Height (stadiometer) g | X | | X | |
| **Efficacy assessment** | | | | |
| JIA ACR disease core set/JADAS-27 h | X | | X | |
| sJIA systemic features i | X | | X | |

TABLE 19-continued

Flow chart for patients who change to the selected dose (during extension phase)

| | | | | |
|---|---|---|---|---|
| **Safety assessment** | | | | |
| Adverse event/SAE recording | \|------------------------------------------------------------------------------------\| | | | |
| Tuberculosis risk assessment PPD tuberculin skin test for patients ≤5 years; QuantiFERON-TB test for patients >5 years | X | X | X | X |
| Local tolerability | X | X | X | |
| **Laboratory testing** | | | | |
| Hematology j | X | X | X | |
| Chemistry k | X | X | X | |
| Fasting lipids l | X | | X | |
| hs-CRP | X | | X | |
| ESR | X | | X | |
| ANA/Anti-ds DNA antibody | X | | X | |
| Ferritin/Fibrinogen/D-Dimer m | | | X | |
| Urine pregnancy test for females who are menstruating n | X | X | X | |
| **Pharmacokinetics and pharmacodynamics** | | | | |
| Serum sarilumab (PK) o | X | | X | X |
| Antibodies to sarilumab o | X | | X | X |

Abbreviations: AE = adverse event, ALP = alkaline phosphatase, ANA = antinuclear antibodies, ANC = absolute neutrophil counts, BP = blood pressure, DNA = Deoxyribonucleic acid, D = day, EOT = end-of-treatment, EOS = end-of-study, ESR = erythrocyte sedimentation rate, hs-CRP = high sensitivity C-reactive protein, IMP = investigational medicinal product, IVRS = Interactive voice response system, JADAS = Juvenile Arthritis Disease Activity Score, JIA ACR = Juvenile Idiopathic Arthritis American College of Rheumatology, PK = pharmaco kinetics, PPD = Purified Protein Derivative, SAE = serious adverse event, sJIA = Systemic Juvenile Idiopathic Arthritis; TB = Tuberculosis, V = visit, Wk = week.

a Visit 27 is the study planned end-of-treatment (EOT) visit. If patients discontinue the study treatment prematurely, EOT will occur 1 week after the last IMP injection for Dose Cohort 3 and 2 weeks after the last IMP injection for Dose Cohort 2.

b Visit 28 is the study planned end-of-study (EOS) visit. If patients discontinue the study treatment prematurely, these patients will be asked to return for the EOS assessment 6 weeks after the EOT visit (EOT + 6 weeks). This EOS (EOT + 6 weeks) visit will be applicable to all the patients in both Core Treatment Phase and Extension Phase.

c Patient diary for IMP administration to be completed for IMP administered at home.

d Complete physical examinations will include skin, nasal cavities, eyes, ears, respiratory, cardiovascular, gastrointestinal, neurological, lymphatic, and musculoskeletal systems.

e Investigational medicinal product to be administered q2w for patients in Dose Cohort 2 and weekly for patients in Dose Cohort 3. For patients who complete the extension phase, if the selected dose regimen is dosed biweekly (q2w), then the last IMP injection will occur 2 weeks before EOT; if the selected dose regimen is dosed weekly (qw), then the last IMP injection will occur 1 week before EOT. Patients will have EOT assessment at the Visit 27 (Week 156). For patients who discontinue the study prematurely during the extension phase, it will be preferable to have EOT assessment 2 weeks after the last IMP injection for Dose Cohort 2 patients and 1 week after the last IMP injection for Dose Cohort 3 patients. In case the patient is unable to meet the planned schedule, the EOT visit will be used for assessment at the next protocol defined visit after the last IMP injection. Patients will be asked to return to the site for the EOS assessment 6 weeks after the EOT visit. Patients should be monitored for at least 30 minutes after IMP administration for any signs or symptoms of a hypersensitivity reaction. There will be no IMP injection at the Visit 27 (Week 156).

f Patient temperature/rash diary will include recording tympanic temperatures and report rash (if occur) at home for at least 7 days prior to each subsequent scheduled visit with ACR JIA efficacy core set assessment. Temperature should be measured minimum of twice daily, at fixed points, upon arising and prior to bedtime as well as anytime if fever is suspected.

g Collect an additional height closest to 1 year before baseline. Height will be measured using stadiometer at sites during the study.

h Juvenile Idiopathic Arthritis ACR core set includes: global assessment of the severity of disease by the physician, global assessment of overall well-being by the patient or parent/legal guardian, number of joints with active arthritis defined as swelling within the joint not due to deformity, OR limitation of motion with either pain or tenderness, or both), number of joints with limitation of motion, Childhood Health Assessment Questionnaire (CHAQ), hs-CRP, and fever. JADAS scoring is explained herein.

i Only fever and evanescent salmon-colored erythematous rash will be assessed.

j Hematology (blood should be drawn PRIOR TO drug administration): Hemoglobin, hematocrit, red blood cell (RBC) count, and morphology (if RBC count is abnormal), white blood cell (WBC) differential (neutrophils, lymphocytes, monocytes, eosinophils, basophils), platelet count, absolute neutrophil count (ANC).

k Chemistry (blood should be drawn BEFORE drug administration): ALT, AST, ALP, lactate dehydrogenase (LDH), total bilirubin, conjugated bilirubin, unconjugated bilirubin, and albumin will be tested. Complete chemistry should be done at Visit 27 EOT.

l Lipids (blood should be drawn BEFORE drug administration): Triglycerides (TG), total cholesterol, high density lipoprotein (HDL) cholesterol, low density lipoprotein (LDL) cholesterol. Patients are required to fast at least 8 hours before the test.

m When MAS suspected, ferritin, blood cell accounts (red blood cell, while blood cell, platelet, and hemoglobin), AST/ALT, triglycerides, and fibrinogen tests need to be ordered if necessary based on Investigator's judgment.

n For females who have commenced menstruating, urine pregnancy test should be performed prior to exposure to the IMP injection at scheduled visits mentioned in the above flowchart. The urine pregnancy test could be performed locally.

o Blood samples will be collected PRIOR TO IMP administration on the dosing days during the treatment period. If an SAE occurs in a patient, blood samples should be collected for determination of sarilumab concentration and antidrug antibody (ADA) assessment at or near the onset and completion of the occurrence of the event, if possible.

Pharmacokinetics Handling Procedure

It is extremely important to collect all blood samples as close to the protocol specified days as possible (see the study flow chart of Table 17 for sampling schedule). The reasons for any missed or lost blood samples should be documented. Special procedures for collection, storage and shipping of serum are described may be utilized. See Table 20.

TABLE 20

Sample handling procedure for sarilumab and antisarilumab antibody

| Sample type | Functional sarilumab | Antisarilumab antibody |
|---|---|---|
| Matrix | Serum | Serum |
| Blood sample volume | 0.5 ml* | 0.5 mL[a] |
| Anticoagulant | None | None |
| Blood handling procedures | See operation manual | See operation manual |
| Storage conditions | 9 months at −20 °C | 24 months at −20 °C |
| Serum shipment conditions | or below 80 °C (preferred) In dry ice | or below 80 °C (preferred) In dry ice |

[a]For a study visit with blood collection for both PK and anti-sarilumab antibody samples (e g., Baseline Visit 2), it is recommended to draw 1 mL of blood. The serum will be split equally into 2 aliquots to obtain one PK serum aliquot and one anti-sarilumab antibody serum aliquot.

Bioanalytical Method

The serum levels of functional sarilumab and anti-sarilumab antibodies will be determined using validated bioanalytical methods.

Pharmacokinetics Parameters

A PopPK model will be developed using nonlinear mixed effect modeling to describe the PK profile of sarilumab. The following PK parameters will be calculated, using the PopPK model for functional sarilumab in serum. The PK parameters will include, but may not be limited to the following: $C_{max}$, $C_{trough}$, $t_{max}$, and AUC0-τ.

TABLE 21

Patient and disease characteristics at study baseline*

| Dose cohort / Weight group / Patients | All Group A (30-60 kg) n = 20 | All Group B (10-<30 kg) n = 22 | All A + B n = 42 | 1 (2.0/−2.5 mg/kg Q2W)† A + B n = 13 | 2 (3.0/−4.0 mg/kg Q2W)‡ A + B n = 14 | 3 (2.0/−2.5 mg/kg QW)§ A + B n = 15 |
|---|---|---|---|---|---|---|
| Age, mean yrs (SD) | 13.0 (3.1) | 5.2 (2.5) | 8.9 (4.8) | 9.6 (4.3) | 8.9 (5.1) | 8.3 (5.2) |
| Children (2-11 yrs), n (%) | 6 (30.0) | 22 (100.0) | 28 (66.7) | 8 (61.5) | 10 (71.4) | 10 (66.7) |
| Weight, mean kg (SD) | 45.0 (8.8) | 19.7 (6.1) | 31.7 (14.8) | 34.9 (16.1) | 31.9 (14.8) | 28.8 (14.2) |
| Female, n (%) | 13 (65.0) | 14 (63.6) | 27 (64.3) | 10 (76.9) | 8 (57.1) | 9 (60.0) |
| Race, n (%) | | | | | | |
| White | 17 (85.0) | 16 (72.7) | 33 (78.6) | 9 (69.2) | 12 (85.7) | 12 (80.0) |
| Black | 0 | 0 | 0 | 0 | 0 | 0 |
| Asian | 0 | 0 | 0 | 0 | 0 | 0 |
| Unknown | 3 (15.0) | 2 (9.1) | 5 (11.9) | 3 (23.1) | 0 | 2 (13.3) |
| Region, n (%) | | | | | | |
| Western | 6 (30.0) | 10 (45.5) | 16 (38.1) | 4 (30.1) | 4 (28.6) | 8 (53.3) |
| South America | 5 (25.0) | 4 (18.2) | 9 (21.4) | 4 (30.1) | 2 (14.3) | 3 (20.0) |
| Disease characteristics | | | | | | |
| Polyarticular RF(+) JIA, n (%) | 6 (30.0) | 3 (13.6) | 9 (21.4) | 4 (30.8) | 3 (21.4) | 2 (13.3) |
| Polyarticular RF(−) JIA, n (%) | 12 (60.0) | 15 (68.2) | 27 (64.3) | 9 (69.2) | 8 (57.1) | 10 (66.7) |
| Extended oligoarticular JIA, n (%) | 2 (10.0) | 4 (18.2) | 6 (14.3) | 0 | 3 (21.4) | 3 (20.0) |
| JIA duration, mean yrs (SD) | 4.6 (5.2) | 1.7 (1.9) | 3.1 (4.1) | 3.4 (4.5) | 3.4 (4.9) | 2.5 (2.8) |
| Active joint count (0-71), mean (SD) | 17.2 (10.4) | 11.0 (6.9) | 13.9 (9.2) | 15.8 (10.5) | 11.4 (7.3) | 14.7 (9.6) |
| Limited motion joint count (0-67), mean (SD) | 11.8 (11.2) | 9.6 (8.3) | 10.6 (9.7) | 10.4 (9.0) | 8.4 (8.2) | 12.9 (11.6) |
| Physician global VAS (0-10), mean (SD) | 4.4 (2.0) | 4.6 (2.6) | 4.5 (2.3) | 4.7 (2.1) | 4.8 (2.2) | 4.1 (2.6) |
| Patient global VAS (0-10), mean (SD) | 5.4 (1.7) | 5.9 (2.1) | 5.7 (1.9) | 5.8 (2.3) | 5.9 (1.8) | 5.3 (1.7) |
| CHAQ-DI (0-3), mean (SD) | 0.9 (0.8) | 1.2 (0.8) | 1.1 (0.8) | 1.3 (0.8) | 1.1 (0.7) | 0.8 (0.8) |
| JADAS-27 CRP, mean (SD) | 22.2 (7.2) | 19.1 (7.7) | 20.6 (7.6) | 22.1 (6.8) | 19.8 (8.0) | 20.0 (8.1) |

TABLE 21-continued

| Patient and disease characteristics at study baseline* | | | | | | |
|---|---|---|---|---|---|---|
| Dose cohort | All | All | All | 1 (2.0/–2.5 mg/kg Q2W)† | 2 (3.0/–4.0 mg/kg Q2W)‡ | 3 (2.0/–2.5 mg/kg QW)§ |
| Weight group | Group A (30-60 kg) | Group B (10-<30 kg) | A + B | A + B | A + B | A + B |
| Patients | n = 20 | n = 22 | n = 42 | n = 13 | n = 14 | n = 15 |
| CRP, mean mg/L (SD) | 10.4 (14.7) | 8.7 (19.2) | 9.5 (17.0) | 7.4 (13.9) | 14.6 (24.1) | 6.5 (10.4) |
| ESR, mean mm/h (SD) | 28.0 (28.3) | 15.4 (13.1) | 21.8 (22.9) | 22.2 (24.5) | 21.4 (25.9) | 21.9 (20.1) |
| ANC, mean cells/mm$^3$ (SD) | 4,200 (1,600) | 5,200 (2,000) | 4,700 (1,800) | 4,100 (2,100) | 4,900 (1,600) | 5,100 (1,800) |
| Prior and baseline treatments, n (%) | | | | | | |
| Baseline csDMARD | 17 (85.0) | 15 (68.2) | 32 (76.2) | 8 (61.5) | 12 (85.7) | 12 (80.0) |
| Methotrexate | 15 (75.0) | 15 (68.2) | 30 (71.4) | 8 (61.5) | 10 (71.4) | 12 (80.0) |
| Baseline systemic GC | 5 (25.0) | 8 (36.4) | 13 (31.0) | 4 (30.8) | 3 (21.4) | 6 (40.0) |
| Any prior bDMARD | 6 (30.0) | 6 (27.3) | 12 (28.6) | 5 (38.5) | 3 (21.4) | 4 (26.7) |
| Etanercept | 5 (25.0) | 5 (22.7) | 10 (23.8) | 4 (30.8) | 2 (14.3) | 4 (26.7) |
| Adalimumab | 2 (10.0) | 1 (4.5) | 3 (7.1) | 1 (7.7) | 2 (14.3) | 0 |

*ANC = absolute neutrophil count; bDMARD = biologic DMARD; CHAQ-DI = Childhood Health Assessment Questionnaire-Disability Index; CRP = C-reactive protein; csDMARD = conventional synthetic DMARD; DMARD = disease-modifying antirheumatic drug; ESR = erythrocyte sedimentation rate; GC = glucocorticoid; JADAS-27 CRP = juvenile arthritis disease activity score = 27-joint count score with C-reactive protein; JIA = juvenile idiopathic arthritis; n = total number of patients who met criterion at least once during treatment; QW = every week; Q2W = every 2 weeks; RF = rheumatoid factor; SD = standard deviation; VAS = visual analog scale; yrs = years.

†Dose 1, 2.0 mg/kg Q2W in patients 30-60 kg, and 2.5 mg/kg Q2W in patients 10-<30 kg.

‡Dose 2, 3.0 mg/kg Q2W in patients 30-60 kg, and 4.0 mg/kg Q2W in patients 10-<30 kg.

§Dose 3, 2.0 mg/kg QW in patients 30-60 kg, and 2.5 mg/kg QW in patients 10-<30 kg.

TABLE 22

Sarilumab PK data at first administration and at week 12 after repeated administration*

| | n | $C_{max}$ mg/L (CV %) | $AUC_{0-\tau}$ day mg/L (CV %) | $C_{trough}$ mg/L (CV %) |
|---|---|---|---|---|
| First SC administration | | | | |
| Group A (30-60 kg) | | | | |
| 2.0 mg/kg Q2W | 7 | 7.69 (47) | 53.2 (46) | 0.63 (63) |
| 3.0 mg/kg Q2W | 7 | 14.5 (19) | 123 (24) | 1.84 (69) |
| 2.0 mg/kg QW | 6 | 11.0 (21) | 61.3 (22) | 8.07 (32) |
| Group B (10-<30 kg) | | | | |
| 2.5 mg/kg Q2W | 6 | 9.08 (21) | 63.4 (30) | 0.54 (48) |
| 4.0 mg/kg Q2W | 7 | 18.7 (21) | 167 (26) | 3.77 (43) |
| 2.5 mg/kg QW | 9 | 8.29 (35) | 45.3 (36) | 5.22 (39) |
| Repeated SC administration (weeks 10-12 or weeks 11-12)† | | | | |
| Group A (30-60 kg) | | | | |
| 2.0 mg/kg Q2W | 5 | 13.2 (14) | 114 (18) | 1.99 (86) |
| 3.0 mg/kg Q2W | 6 | 26.4 (26) | 269 (34) | 8.46 (68) |
| 2.0 mg/kg QW | 6 | 38.8 (23) | 250 (24) | 30.4 (28) |
| Group B (10-<30 kg) | | | | |
| 2.5 mg/kg Q2W | 5 | 14.1 (27) | 118 (37) | 1.83 (101) |
| 4.0 mg/kg Q2W | 7 | 30.1 (20) | 310 (26) | 11.9 (41) |
| 2.5 mg/kg QW | 5 | 31.4 (22) | 203 (25) | 25.1 (29) |

*$AUC_{0-\tau}$ = area under the serum concentration versus time curve during a dose interval τ of 2 weeks (Q2W regimen) or 1 week (QW regimen);
$C_{max}$ = maximum serum concentration observed;
$C_{trough}$ = concentration observed before treatment administration during repeated dosing;
CV % = coefficient of variation;
n = total number of patients who met criterion at least once during treatment;
QW = every week;
Q2W = every 2 weeks;
SC = subcutaneous.
†Q2W dose regimens tested at weeks 10-12;
QW dose regimens tested at weeks 11-12.

TABLE 23

Investigator-reported AEs*

| | Dose Cohort | | | | | |
|---|---|---|---|---|---|---|
| | All Doses | | | 1 (2.0/2.5 mg/kg Q2W)† | 2 (3.0/4.0 mg/kg Q2W)‡ | 3 (2.0/2.5 mg/kg QW)§ |
| | Patient weight group | | | | | |
| | Group A (30-60 kg) | Group B (10-<30 kg) | A + B | A + B | A + B | A + B |
| | Number of patients enrolled | | | | | |
| | 20 | 22 | 42 | 13 | 14 | 15 |
| Cumulative treatment exposure, PYs | 4.6 | 5.0 | 9.7 | 3.1 | 3.3 | 3.3 |
| Summary, n (%) [$n_E$/100 PYs] | | | | | | |
| AEs | 16 (80.0) [973] | 20 (90.9) [1,210] | 36 (85.7) [1,097] | 11 (84.6) [785] | 12 (85.7) [1,273] | 13 (86.7) [1,209] |
| SAEs | 0 | 0 | 0 | 0 | 0 | 0 |
| AEs leading to death | 0 | 0 | 0 | 0 | 0 | 0 |
| AEs leading to treatment discontinuation | 2 (10.0) [43.3] | 3 (13.6) [59.5] | 5 (11.9) [51.7] | 2 (15.4) [65.4] | 0 | 3 (20.0) [90.7] |
| Neutropenia | 1 (5.0) [21.6] | 3 (13.6) [59.5] | 4 (9.5) [41.4] | 1 (7.7) [32.7] | 0 | 3 (20.0) [90.7] |
| ALT increased | 1 (5.0) [21.6] | 0 | 1 (2.4) [10.3] | 1 (7.7) [32.7] | 0 | 0 |
| AEs with overall incidence ≥5%, n (%)[nE/100 PYs] | | | | | | |
| Neutropenia | 3 (15.0) [64.9] | 8 (36.4) [178.6] | 11 (26.2) [124.2] | 3 (23.1) [98.1] | 3 (21.4) [121.2] | 5 (33.3) [151.2] |
| Upper respiratory tract infection | 5 (25.0) [108.1] | 4 (18.2) [99.2] | 9 (21.4) [103.5] | 4 (30.8) [130.8] | 2 (14.3) [90.9] | 3 (20.0) [90.7] |
| Nasopharyngitis | 3 (15.0) [86.5] | 1 (4.5) [19.8] | 4 (9.5) [51.7] | 1 (7.7) [32.7] | 2 (14.3) [90.9] | 1 (6.7) [30.2] |
| Injection-site erythema | 1 (5.0) [43.2] | 2 (9.1) [59.5] | 3 (7.1) [51.7] | 0 | 3 (21.4) [151.6] | 0 |
| Rhinitis | 1 (5.0) [21.6] | 2 (9.1) [39.7] | 3 (7.1) [31.0] | 2 (15.4) [65.4] | 0 | 1 (6.7) [30.2] |
| Leukopenia | 1 (5.0) [21.6] | 2 (9.1) [39.7] | 3 (7.1) [31.0] | 1 (7.7) [32.7] | 2 (14.3) [60.6] | 0 |
| Conjunctivitis | 0 | 3 (13.6) [79.4] | 3 (7.1) [41.4] | 0 | 2 (14.3) [90.9] | 1 (6.7) [30.2] |
| Diarrhea | 1 (5.0) [21.6] | 2 (9.1) [39.7] | 3 (7.1) [31.0] | 0 | 2 (14.3) [60.6] | 1 (6.7) [30.2] |
| Bronchitis | 0 | 3 (13.6) [59.5] | 3 (7.1) [31.0] | 0 | 1 (7.1) [30.3] | 2 (13.3) [60.5] |

*AEs = treatment-emergent adverse events; ALT = alanine aminotransferase; n = total number of patients who met criterion at least once during treatment; $n_E$ = number of events; PY = patient-years; QW = every week; Q2W = every 2 weeks; SAEs = serious AEs. All terms from MedDRA 21.0.

†Dose 1, 2.0 mg/kg Q2W in patients 30-60 kg, and 2.5 mg/kg Q2W in patients 10-<30 kg.

‡Dose 2, 3.0 mg/kg Q2W in patients 30-60 kg, and 4.0 mg/kg Q2W in patients 10-<30 kg.

§Dose 3, 2.0 mg/kg QW in patients 30-60 kg, and 2.5 mg/kg QW in patients 10-<30 kg.

TABLE 24

Absolute neutrophil count by lowest value recorded on study*

| | Dose Cohort | | | | | |
|---|---|---|---|---|---|---|
| | All Doses | | | 1 (2.0/2.5 mg/kg Q2W)† | 2 (3.0/4.0 mg/kg Q2W)‡ | 3 (2.0/2.5 mg/kg QW)§ |
| | Patient weight group | | | | | |
| | Group A (30-60 kg) | Group B (10-<30 kg) | A + B | A + B | A + B | A + B |
| | Number of patients enrolled | | | | | |
| | 20 | 22 | 42 | 13 | 14 | 15 |
| | Neutropenia by lowest count observed on study, n (%) | | | | | |
| Grade 3: ≥500-1,000 cells/mm$^3$ | 4 (20.0) | 3 (13.6) | 7 (16.7) | 3 (23.1) | 2 (14.3) | 2 (13.3) |
| Grade 4: <500 cells/mm$^3$ | 0 | 5 (22.7) | 5 (11.9) | 0 | 1 (7.1) | 4 (26.7) |

*n = total number of patients who met criterion at least once during treatment; QW = every week; Q2W = every 2 weeks.

†Dose 1, 2.0 mg/kg Q2W in patients 30-60 kg, and 2.5 mg/kg Q2W in patients 10-<30 kg.

‡Dose 2, 3.0 mg/kg Q2W in patients 30-60 kg, and 4.0 mg/kg Q2W in patients 10-<30 kg.

§Dose 3, 2.0 mg/kg QW in patients 30-60 kg, and 2.5 mg/kg QW in patients 10-<30 kg.

TABLE 25

All investigator-reported infections*

| | Dose Cohort | | | | | |
|---|---|---|---|---|---|---|
| | All Doses | | | 1 (2.0/2.5 mg/kg Q2W)† | 2 (3.0/4.0 mg/kg Q2W)‡ | 3 (2.0/2.5 mg/kg QW)§ |
| | Patient weight group | | | | | |
| | Group A (30-60 kg) | Group B (10-<30 kg) | A + B | A + B | A + B | A + B |
| | Number of patients enrolled | | | | | |
| | 20 | 22 | 42 | 13 | 14 | 15 |
| | Cumulative treatment exposure, PYs | | | | | |
| | 4.6 | 5.1 | 9.7 | 3.1 | 3.3 | 3.3 |
| | Summary, n (%) [$n_E$/100 PYs] | | | | | |
| Upper respiratory tract infection | 5 (25.0) [108.1] | 4 (18.2) [99.2] | 9 (21.4) [103.5] | 4 (30.8) [130.8] | 2 (14.3) [90.9] | 3 (20.0) [90.7] |
| Rhinitis | 1 (5.0) [21.6] | 2 (9.1) [39.7] | 3 (7.1) [31.0] | 2 (15.4) [65.4] | 0 | 1 (6.7) [30.2] |
| Gastroenteritis | 1 (5.0) [21.6] | 1 (4.5) [19.8] | 2 (4.8) [20.7] | 1 (7.7) [32.7] | 1 (7.1) [30.3] | 0 |
| Nasopharyngitis | 3 (15.0) [86.5] | 1 (4.5) [19.8] | 4 (9.5) [51.7] | 1 (7.7) [32.7] | 2 (14.3) [90.9] | 1 (6.7) [30.2] |
| Pharyngotonsillitis | 1 (5.0) [21.6] | 0 | 1 (2.4) [10.3] | 1 (7.7) [32.7] | 0 | 0 |
| Upper respiratory tract infection bacterial | 0 | 1 (4.5) [19.8] | 1 (2.4) [10.3] | 1 (7.7) [32.7] | 0 | 0 |
| Bronchitis | 0 | 3 (13.6) [59.5] | 3 (7.1) [31.0] | 0 | 1 (7.1) [30.3] | 2 (13.3) [60.5] |
| Conjunctivitis | 0 | 3 (13.6) [79.4] | 3 (7.1) [41.4] | 0 | 2 (14.3) [90.9] | 1 (6.7) [30.2] |
| Cystitis | 1 (5.0) [21.6] | 0 | 1 (2.4) [10.3] | 0 | 0 | 1 (6.7) [30.2] |
| Eczema infected | 0 | 1 (4.5) [19.8] | 1 (2.4) [10.3] | 0 | 1 (7.1) [30.3] | 0 |
| Gastritis viral | 0 | 1 (4.5) [19.8] | 1 (2.4) [10.3] | 0 | 0 | 1 (6.7) [30.2] |
| Oral candidiasis | 1 (5.0) [21.6] | | 1 (2.4) [10.3] | 0 | 0 | 1 (6.7) [30.2] |
| Otitis media | 0 | 1 (4.5) [19.8] | 1 (2.4) [10.3] | 0 | 1 (7.1) [30.3] | 0 |
| Pharyngitis | 1 (5.0) [21.6] | 0 | 1 (2.4) [10.3] | 0 | 1 (7.1) [30.3] | 0 |

TABLE 25-continued

All investigator-reported infections*

| | Dose Cohort | | | | | |
|---|---|---|---|---|---|---|
| | All Doses | | | 1 (2.0/2.5 mg/kg Q2W)† | 2 (3.0/4.0 mg/kg Q2W)‡ | 3 (2.0/2.5 mg/kg QW)§ |
| | Patient weight group | | | | | |
| | Group A (30-60 kg) | Group B (10-<30 kg) | A + B | A + B | A + B | A + B |
| | Number of patients enrolled | | | | | |
| | 20 | 22 | 42 | 13 | 14 | 15 |
| | Cumulative treatment exposure, PYs | | | | | |
| | 4.6 | 5.1 | 9.7 | 3.1 | 3.3 | 3.3 |
| | Summary, n (%) [$n_E$/100 PYs] | | | | | |
| Pharyngitis bacterial | 1 (5.0) [21.6] | 0 | 1 (2.4) [10.3] | 0 | 0 | 1 (6.7) [30.2] |
| Tonsillitis | 0 | 1 (4.5) [19.8] | 1 (2.4) [10.3] | 0 | 1 (7.1) [30.3] | 0 |
| Varicella | 0 | 1 (4.5) [19.8] | 1 (2.4) [10.3] | 0 | 1 (7.1) [30.3] | 0 |
| Viral upper respiratory tract infection | 0 | 1 (4.5) [19.8] | 1 (2.4) [20.7] | 0 | 0 | 1 (6.7) |

*$n_E$ = number of events; PY = patient-years; QW = every week; Q2W = every 2 weeks. All terms from MedDRA 21.0.
†Dose 1, 2.0 mg/kg Q2W in patients 30-60 kg, and 2.5 mg/kg Q2W in patients 10-<30 kg.
‡Dose 2, 3.0 mg/kg Q2W in patients 30-60 kg, and 4.0 mg/kg Q2W in patients 10-<30 kg.
§Dose 3, 2.0 mg/kg QW in patients 30-60 kg, and 2.5 mg/kg QW in patients 10-<30 kg.

TABLE 26

Mean change in JIA ACR components from baseline, at week 12*

| Dose Cohort | 1 (2.0/2.5 mg/kg Q2W)† | 2 (3.0/4.0 mg/kg Q2W)‡ | 3 (2.0/2.5 mg/kg QW)§ |
|---|---|---|---|
| Patient weight group‖ | A + B | A + B | A + B |
| Number of patients enrolled | 13 | 14 | 15 |
| ACR component, mean (mean % change) [SE] | | | |
| Active joint count (0-71) BL | 15.8 [2.92] | 11.4 [1.95] | 14.7 [2.48] |
| Change from BL at week 12 | −11.7 (−76) [1.93] | −8.8 (−80) [1.39] | −14.5 (−86) [3.13] |
| Limited motion joint count BL | 10.4 [2.49] | 8.4 [2.18] | 12.9 [3.00] |
| Change from BL at week 12 | −6.3 (−59) [1.45] | −6.4 (−62) [1.88] | −9.6 (−75) [2.27] |
| Physician global VAS (0-10) BL | 4.7 [0.58] | 4.8 [0.61] | 4.1 [0.68] |
| Change from BL at week 12 | −3.1 (−63) [0.73] | −3.6 (−66) [0.68] | −3.9 (−83) [0.73] |
| Patient global VAS (0-10) BL | 5.8 [0.64] | 5.9 [0.48] | 5.3 [0.45] |
| Change from BL at week 12 | −4.6 (−69) [0.70] | −4.3 (−70) [0.47] | −5.1 (−89) [0.59] |
| CHAQ-DI (0-3) BL | 1.3 [0.21] | 1.1 [0.20] | 0.8 [0.21] |
| Change from BL at week 12 | −0.9 (−66) [0.17] | −0.9 (−71) [0.19] | −0.6 (−76) [0.14] |

TABLE 26-continued

Mean change in JIA ACR components from baseline, at week 12*

| Dose Cohort | 1 (2.0/2.5 mg/kg Q2W)† | 2 (3.0/4.0 mg/kg Q2W)‡ | 3 (2.0/2.5 mg/kg QW)§ |
|---|---|---|---|
| CRP (mg/L) BL | 7.4 [3.84] | 14.6 [6.43] | 6.5 [2.68] |
| Change from BL at week 12 | −2.8 [2.62] | −13.4 [7.42] | −7.0 [3.32] |

*ACR = American College of Rheumatology;
BL = baseline;
CHAQ-DI = Childhood Health Assessment Questionnaire-Disability Index;
CRP = C-reactive protein;
JIA ACR30/70/90 = juvenile idiopathic arthritis American College of Rheumatology 30/70/90% response;
QW = every week;
Q2W = every 2 weeks;
SE = standard error;
VAS = visual analog scale.
†Dose 1, 2.0 mg/kg Q2W in patients 30-60 kg, and 2.5 mg/kg Q2W in patients 10-<30 kg.
‡Dose 2, 3.0 mg/kg Q2W in patients 30-60 kg, and 4.0 mg/kg Q2W in patients 10-<30 kg.
§Dose 3, 2.0 mg/kg QW in patients 30-60 kg, and 2.5 mg/kg QW in patients 10-<30 kg.
||Weight Group A, 30-60 kg, Weight Group B, 10-<30 kg.

TABLE 27

Patients achieving clinically inactive disease or low disease activity at week 12 (observed cases)*

| | Dose cohort | | |
|---|---|---|---|
| Dose Cohort | 1 (2.0/2.5 mg/kg Q2W)† | 2 (3.0/4.0 mg/kg Q2W)‡ | 3 (2.0/2.5 mg/kg QW)§ |
| Patient weight group|| | A + B | A + B | A + B |
| Number of patients enrolled | 13 | 14 | 15 |
| Active joint count = 0, n (%) | 4/10 (40) | 4/13 (31) | 5/11 (45) |
| Clinically inactive disease by JADAS-27-CRP ≤ 1, n (%) | 0/10 (0) | 1/12 (8)** | 2/11 (18) |
| Clinically inactive or LDA by JADAS-27-CRP ≤ 3.8, n (%) | 6/10 (60) | 5/12 (42)** | 9/11 (82) |
| Clinically inactive disease by Wallace criteria††, n (%) | 3/10 (30) | 2/13 (15) | 4/11 (36) |

*CRP = C-reactive protein;
JADAS-27-CRP = juvenile arthritis disease activity score with 27-joint count and CRP;
LDA = low disease activity;
n = total number of patients who met criterion at least once during treatment;
QW = every week;
Q2W = every 2 weeks;
VAS = visual analog scale.
†Dose 1, 2.0 mg/kg Q2W in patients 30-60 kg, and 2.5 mg/kg Q2W in patients 10-<30 kg.
‡Dose 2, 3.0 mg/kg Q2W in patients 30-60 kg, and 4.0 mg/kg Q2W in patients 10-<30 kg.
§Dose 3, 2.0 mg/kg QW in patients 30-60 kg, and 2.5 mg/kg QW in patients 10-<30 kg.
||Weight Group A, 30-60 kg, Weight Group B, 10-<30 kg.
**One patient did not complete all components of the JADAS-27-CRP assessment at week 12, and was removed.
††Wallace criteria defined as physician global VAS <1/10, no active arthritis, no active uveitis, and CRP <10 mg/L.

Secondary Endpoint(s)

12-Week Core Treatment Phase

The following parameters will be analyzed in 12-week open label core treatment phase.

Safety

- Adverse events, vital signs, physical examination, laboratory values
- Acceptability assessments (local tolerability)

Efficacy

- JIA ACR30/50/70/90/100 (in the absence of fever) response rate at Week 12
- Change from baseline in individual JIA ACR components at Week 12
- Juvenile Arthritis Disease Activity Score-27 (JADAS) change from baseline at Week 12
- Changes in glucocorticoid use which will be assessed descriptively using line plot on glucocorticoid equivalent prednisone dose from baseline to the end of the 12-week core treatment period for each individual patient by dose cohort and by weight group Pharmacodynamics

- Changes in IL-6 associated biomarkers (eg, serum levels of high sensitivity C-reactive protein [hs-CRP], IL-6, sIL-6R)

Extension Phase

Safety

- Adverse events, vital signs, physical examination, laboratory values
- Acceptability assessments (local tolerability)

Efficacy

- JIA ACR 30/50/70/90/100 (in the absence of fever) response rate at Weeks 24, 48, and every 24 weeks up to the end of the study Juvenile Arthritis Disease Activity Score-27 change from baseline at Weeks 24, 48, and every 24 weeks up to the end of the visit
  - Change from baseline in individual JIA ACR components at Weeks 24 and 48, and every 24 weeks up to the end of the study
  - Proportion of patients receiving glucocorticoids by dose category (glucocorticoid equivalent prednisone dose 20.5 mg/kg, 20.2 mg/kg and <0.5 mg/kg, <0.2 mg/kg) at Weeks 24, 48, and every 24 weeks up to the end of the study compared to baseline
  - Proportion of patients free of glucocorticoids and without JIA flare at Weeks 24, 48, and every 24 following weeks up to the end of the study
  - Changes in glucocorticoid use which will be assessed descriptively using line plot on glucocorticoid equivalent prednisone dose from baseline to the end of the treatment period for each individual patient by dose cohort and by weight group Exploratory Endpoint 12-Week Core Treatment Period

- Proportion of patients with fever due to systemic JIA baseline who are free of fever at Week 12
- Proportion of patients with rash due to systemic JIA baseline who are free of rash at Week 12

Extension Phase

- Growth assessments at Years 1, 2, and 3, including height velocity and height standard deviation (SD) scores, for patients who never received growth hormone and did not reach Tanner stage 5 by the end of the first year of treatment.
- Proportion of patients with fever at Baseline who are free of fever at Weeks 24, 48, and every 24 weeks up to end of the study.
- Proportion of patients with rash due to systemic JIA at Baseline who are free of rash at Weeks 24, 48, and every 24 weeks up to end of the study.

Efficacy Endpoints

JIA ACR Response

The JIA ACR rating scale to assess signs and symptoms will be used in this study. The JIA ACR 30/50/70/90/100 will be assessed at Weeks 12, 24, 48, 72, 96, 120, 144, and 156 (EOT). The JIA ACR 30/50/70/90/100 (in the absence of fever) response is defined as a patient with 3 of 6 core set variables improved by at least 30%/50%/70%/90%/100% from baseline with no more than 1 of the remaining variables worsened by more than 30%.

The JIA ACR core set includes 6 variables plus fever for sJIA:

- Physician global assessment of disease activity
- Patient/parent assessment of overall well-being
- Functional ability determined by Childhood Health Assessment Questionnaire (CHAQ)
- Number of joints with active arthritis (0-71 joints)
- Number of joints with limitation of motion (0-67 joints)
- High sensitivity C-reactive protein
- Fever (within the prior 7 days)
- The JIA ACR core set will be evaluated at every site visit except Visit 3 (Day 3), Visit 4 (Day 5), Visit 5 (Day 8), Visit 6 (Day 12), and the EOS visit. Temperature should be measured 7 days prior ACR assessment.

JIA ACR30 core set variable scores and changes from baseline for each dose cohort and weight group will be summarized by visit using means, standard errors, and corresponding 95% CIs. JIA ACR30/50/70/90/100 response using ESR instead of hs-CRP will also be summarized using the same methods.

Physician Global Assessment of Disease Activity

Physician's global assessment of disease activity will be performed at Screening, at Baseline prior to IMP administration and at each site visit until the EOT visit. The Investigator will be requested to rate the patient's disease activity on an anchored 100 mm horizontal visual analogue scale (VAS) where 0 is considered the best disease activity and 100 the worst.

Patient/parent assessment of overall well-being Patient/parent assessment of overall well-being will be measured on a 100 mm horizontal VAS at Screening, at Baseline prior to dosing and at each site visit until the EOT visit. The patient or the same parent or the same guardian should be requested to complete the form to ensure the consistency.

Childhood Health Assessment Questionnaire (CHAQ) The CHAQ is an interview or self-administered instrument for children ≥8 and parent/proxy-administered for children younger than 8 years of age. The CHAQ is a generic measure of health status in children ages 1 to 19 years of age. The Spearman's correlation coefficient between Disability Index scores from questionnaires administered to parents and those administered to other children (>8 years) was 0.84 (n=29; P<0.001), demonstrating that parents can accurately report for their children. The face validity of the instrument was evaluated by a group of 20 health professionals and parents of 22 healthy children. The assessment consists of 43 items in total and takes approximately 10 minutes to complete. The CHAQ will be completed before IMP dosing and at subsequent time points. The recall period is 1 week (Klepper, S. E. et al., 2003 Arthritis Rheum. 49(3):435-43; Singh, G. et al., 1994 Arthritis Rheum. 37(12):1761-9). In this case, the actual date and data of the CHAQ will be recorded in the eCRF.

The median CHAQ scores corresponding to mild, mild-to-moderate, and moderate disability reported in the development of the CHAQ were 0.13, 0.63, and 1.75, respectively (Dempster, H. et al., 2001 Arthritis Rheum. 44(8):1768-7).

In order to eliminate discrepancies which could be introduced by growth and development, parents are asked to note only those difficulties due to illness (eg, if child unable to do an activity because too young, mark response as "not applicable"). Response options assessing difficulty are based on a 5 point Likert Scale (0=Without Any Difficulty, 1=With Some Difficulty, 2=With MUCH Difficulty, 3=Unable to do and 4=Not Applicable).

Part 1 of the CHAQ is the Disability Index which contains 41 items assessing ability to function in daily life. The following 8 subscales/domains: 1. Dressing and Grooming, 2. Arising, 3. Eating, 4. Walking, 5. Hygiene, 6. Reach, 7. Grip, and 8. Activities. For each domain: (a) ratings of the degree to which daily functions are difficult to perform (items 6-9, 12-13, 16-18, 21-22, 34-38, 41-44, 47-51, and 54-58); (b) require use of special aides or devices (item 24-27, 60-62) and (c) require assistance from another person (items 29-30, 64-65) are assessed.

- To calculate the Childhood Health Assessment Questionnaire Disability Index (CHAQ-DI) each domain score is first calculated:

The question with the highest response determines the score for that functional area.

If aids or devices are used or help is needed to complete tasks in a certain area, a minimum score of 2 is recorded for the corresponding functional area.

The 8 subscales/domains are averaged to calculate a mean score which is the Disability Index (with range of 0-3)

Lower Disability Index scores indicate better than health status/better healthier related quality of life/less signs and symptoms while higher disability index scores indicate worse health status/worse Health-related quality of life (HRQL)/more signs and symptoms. The minimal clinical important improvement in CHAQ Disability Index is a reduction in score of 0.13. The minimal clinical important deterioration in the CHAQ disability index is a median change score of 0.75 (20, 19).

Part 2 of the CHAQ is the Discomfort Index while Part 3 of the CHAQ is the Health Status measure; both are measured on separate 15 cm scales.

The CHAQ-Discomfort Index is determined by the severity of pain in the past week, rated on a VAS (with anchors of "0 no pain" and "100 very severe pain").

To calculate the CHAQ Discomfort Index (item 67)

Measure the distance from the left end of the VAS in item 67 to the respondent's mark and multiply by 0.2 Range is 0-3. The Discomfort Index score can be rescaled to a 0-100 scale.

The Part 3 of the CHAQ Health Status score measure the patient's or parent's global assessment of illness.

To calculate the CHAQ Health Status score (item 69)

Measure the distance from the left end of the VAS in item 69 to the respondent's mark and multiply by 0.2 Range is 0-3. The Health Status score can be rescaled to a 0-100 scale.

Number of Joints with Active Arthritis and Number of Joints with Limited Motion

An active joint is defined as joint with:

Swelling within joint not due to deformity, OR

Limitation of motion with either pain or tenderness

Seventy-one (71) joints will be assessed for active disease by counting the number of the joints with swelling not due to deformity OR limitation of motion with either pain or tenderness or both (Bazso, A. et al., 2009 J Rheumatol. 36(1):183-90; National Cholesterol Education Program (NCEP): highlights of the report of the expert panel on blood cholesterol levels in children and adolescents. Pediatrics. 1992; 89(3); 495-501).

Cervical spine (counts as 1 joint), Temporomandibular (2 joints, R and L side), Sternoclavicular (2 joints), Acromioclavicular (2 joints), Shoulder (2 joints), Elbow (2 joints), Wrist (2 joints), Metacarpophalangeal (10 joints total, 5 on each side), Proximal interphalangeal (10 joints total, 5 on each side), Distal interphalangeal (8 joints total, 4 on each side), Hip (2 joints), Knee (2 joints), Ankle (2 joints), Subtalar (2 joints), Tarsometatarsal (2 joints), Metatarsophalangeal (10 joints, 5 on each side), and Foot interphalangeal (10 joints, 5 on each side) total 71 joints.

Sixty-seven (67) joints will be examined for limitation of motion are the same as those examined for active disease except the sternoclavicular (n=2) and acromioclavicular (n=2). A formal count of the joints will be performed by a trained assessor. Joint tenderness is defined as pain induced by the pressure of the joints, exerted by the assessor's thumb and index finger.

High Sensitivity C-Reactive Protein

High sensitivity C-reactive protein will be evaluated at Visit 1 (Day-28 to Day −1, up to 31 days), the Baseline Visit 2 (Week 0, Day 1), Visit 7 (Week 2), Visit 8 (Week 4), Visit 9 (Week 6), Visit 10 (Week 8), Visit 11 (Week 10), Visit 12 (Week 12), and every visit at the extension phase from Visit 13 (Week 16) to Visit 27 EOT (Week 156) for patients remaining in selected dose; from Visit 101 (Week 0) to Visit 108 (Week 12), at Visit 109 (Week 24), Visit 112 (Week 48), Visit 114 (Week 72), Visit 116 (Week 96), Visit 118 (Week 120), and Visit 27 EOT. For patients <30 kg (Group B) in PK Schedule 1 group, hs-CRP will be measured on Day 3 and 8. For patients <30 kg (Group B) in PK Schedule 2 group, hs-CRP will be measured on Day 5 and 12. High sensitive C=reactive protein levels are directly correlated with IL-6R activity. It is expected that active dose regimens will have a dramatic lowering effect on CRP levels.

Juvenile Arthritis Disease Activity Score

The JADAS includes 4 measures:

1. Physician global assessment of disease activity measured on a 10 cm VAS where 0=no activity and 10=maximum activity
2. Parent/patient global assessment of well-being, measured on a 10 cm VAS where 0=very well and 10=very poor
3. Count of joints with active disease
4. Erythrocyte sedimentation rate normalized to a 0-10 scale according to the following formula:

$$[ESR(mm/hour)-20]/10$$

Before making the calculation, ESR value <20 mm/hour converted to 0 and ESR values >120 mm/hour were converted to 120.

The JADAS will be calculated as the simple linear sum of the scores of its 4 components (Consolaro, A. et al., 2009 Arthritis Rheum. 61(5):658-623). Overall score and change from baseline in JADAS-27 will be summarized by visit (including number, mean, standard error, SD, median, minimum, and maximum) for each dose cohort and weight group (if possible).

The JADAS-27 includes the following joints: cervical spine, elbows, wrists, metacarpophalangeal joints (from first to third), proximal interphalangeal joints, hips, knees, and ankles. The JADAS was found to be a valid instrument for assessment of disease activity in JIA and is potentially applicable in standard clinical care, observational studies, and clinical trials (23). The JADAS-27 will be calculated at Visit 12 (Week 12), Visit 15 (Week 24), Visit 18 (Week 48), Visit 20 (Week 72), Visit 22 (Week 96), Visit 24 (Week 120), Visit 26 (Week 144), and Visit 27 EOT (Week 156) for patients remaining in selected dose; from Visit 101 (Week 0) to Visit 106 (Week 12), at Visit 109 (Week 24), Visit 112 (Week 48), Visit 114 (Week 72), Visit 116 (Week 96), Visit 118 (Week 120), and Visit 27 EOT for patients who changed to selected dose.

Systemic Features of sJIA

Systemic features of sJIA including fever, evanescent salmon-colored erythematous rash, generalized lymph node enlargement, hepatomegaly, splenomegaly serositis, and other complications will be collected at the Screening Visit 1 (Day −28 to Day −1, up to 31 days) to confirm diagnosis, Visit 2 (Week 0), Visit 12 (Week 12), and Visit 27 (Week 156); only fever, evanescent salmon-colored erythematous rash will be collected at Visit 15 (Week 24), Visit 18 (Week 48), and every 24 weeks up to the end of the study.

The common systemic features, including fever and rash related to sJIA will be collected at all visits when JIA ACR core components are assessed.

Rash related to sJIA refers to evanescent, salmon-colored erythematous rash.

Free of rash is defined as no rash related to sJIA recorded in the patient diary in the 7 days prior to assessment day.

Absence of fever is defined as no temperature measurements ≥37.5° C. in the 7 days preceding the visit when JIA ACR core components are assessed.

The effect of treatment on fever and rash will be assessed at Week 12 compared to Baseline.

Proportion of patients with fever due to systemic JIA at Baseline who are free of fever for each dose cohort, overall, and by weight group (if there is sufficient data) will be summarized by visit (i.e., Week 12, 24, 48, and every 24 weeks up to the end of study).

Proportion of patients with rash due to systemic JIA at Baseline who are free of rash for each dose cohort, overall, and by weight group (if there is sufficient data) will be summarized by visit (i.e., Week 12, 24, 48, and every 24 weeks up to the end of study).

Glucocorticoid Use Assessment

The proportion of patients receiving glucocorticoids by dose category (20.5 mg/kg, 20.2 mg/kg and <0.5 mg/kg, <0.2 mg/kg), and the proportion of patients free of glucocorticoids and without JIA flare at Weeks 24, 48, 72, and 104, will be summarized for each dose cohort and weight group to compare to proportion at baseline. The glucocorticoid equivalent prednisone dose in mg/kg/day at a specific time point (i.e., Weeks 0, 24, 48, 72, or 104) will be calculated based on the glucocorticoids taken within 2 weeks prior to that time point. JIA flare at a specific time point (i.e., Weeks 24, 48, 72, or 104) is defined as JIA ACR50 response is not maintained, or fever (any temperature measurement ≥37.5° C.), or ESR 220 mm/h between the prior visit and this time point.

The glucocorticoid equivalent prednisone dose (raw value and change from baseline) will be summarized by visit (mean, SD, median, etc.) by dose cohort and weight group. In addition, the glucocorticoid equivalent prednisone dose at each visit during the treatment period (both core and extension) will be plotted for each individual patient by dose cohort and weight group.

Growth Assessments

The effect on growth will be assessed using height velocity and height SD scores for patients who never received growth hormone and did not reach Tanner stage 5 by the end of the first year of treatment.

Height velocity (centimeters per year) will be calculated based on height change and time interval between height measurements. Pretreatment height velocities will be estimated using the height measured closest to 1 year before baseline, provided that measurements were obtained between 9 and 24 months before baseline. Subsequently, height velocities in Years 1 and 2 of treatment will be calculated. Height measurements closest to the 1-year, and 2-year cutoffs will be used.

Height will be measured in a standing position using a wall mounted stadiometer. When obtaining the height measurement, children will be measured without shoes, hats or hair ornaments with a fixed right angle at the head with head, shoulders, buttocks, and heels against the wall and with feet together. Because of slight changes in a child's posture with each measurement three consecutive measurements will be obtained on each child. The average of the three measurements will be considered to be the true height of the child, providing the measurements are within 0.3 cm. If the measurements are >0.3 cm apart, they will be retaken, and averaged when they are within acceptable range. The measurements utilized for growth velocity calculations will be taken as indicated in the schedule of assessments.

Height will be measured via validated methods at site. Expected normal height velocity during an interval for a given patient will be calculated as the difference in World Health Organization (WHO; World Health Organization. Child growth standards: WHO Anthro (version 2011) and macros. URL: who.int/childgrowth/software/en/) mean height for the age and sex of the patient divided by the change in age. Height velocities will be compared to the expected normal height velocity at pretreatment and during Years 1, 2, and 3 of treatment. Height SD scores will be computed (see below) using WHO norms (Ibid.). Reference populations have mean SD scores of 0, and values between −2 and +2 are generally considered the normal range: SD score=(observed value−median value of the reference population)/SD value of reference population.

To assess the effect on growth, change from baseline in height SD scores at Years 1, 2, and 3 of treatment will be summarized descriptively using mean, SD, and 95% CI. The proportions of patients with height velocities exceeding WHO expectations will be summarized at pretreatment, and during Years 1, 2, and 3 of treatment. Mean height velocities will be compared with the expected WHO normal height velocities at pretreatment and during Years 1, 2, and 3.

Physical Examination

A complete physical examination will be performed at the Screening Visit 1 (Day −28 to Day −1, up to 31 days), Visit 2 (Day 1, Week 0), Visit 8 (Week 4), Visit 9 (Week 6), Visit 12 (Week 12), Visit 15 (Week 24), Visit 18 (Week 48), Visit 20 (Week 72), Visit 22 (Week 96), Visit 24 (Week 120), Visit 26 (Week 144), and Visit 27 EOT (Week 156) for patients remaining in selected dose; at Visit 101 (Week 0), Visit 104 (Week 6), Visit 106 (Week 12), Visit 109 (Week 24), Visit 112 (Week 48), Visit 114 (Week 72), Visit 116 (Week 96), Visit 118 (Week 120), Visit 27 EOT, and Visit 28 EOS for patients who changed to selected dose. Any clinically significant abnormalities should be reported in the patient eCRF as medical history if observed and already known at Visit 1 (Day −28 to Day −1, up to 31 days) and reported as an AE if observed at Visit 2 (Day 1, Week 0) and during subsequent visits. Any clinically significant physical examination abnormality known at the Screening visit should be reported as medical history and not an AE. Clinically significant abnormalities or worsening from baseline reported after the Screening visit should be reported as AEs.

Weight

Weight should be taken with the patient wearing undergarments or very light clothing (without outerwear or accessories) and no shoes and with an empty bladder. The same scale is recommended to be used throughout the study. Weight is to be determined to nearest 0.1 kg. The same scale is recommended to be used throughout the study. Weight will be collected at the Screening Visit 1 (Day −28 to Day −1, up to 31 days), Baseline Visit 2 (Day 1, Week 0), Visit 12 (Week 12), and every visit during the extension phase for patients remaining in selected dose; from Visit 101 (Week 0) to Visit 119 (Week 132), Visit 27 EOT, and Visit 28 EOS, except for Visit 102 (Week 2) and Visit 104 (Week 6) for patients who changed to selected dose.

Pharmacodynamics Parameters

Pharmacodynamic effects of sarilumab will be assessed through measurement of the following biomarkers: hs-CRP, IL-6, sIL-6R.

Assessment Schedule

The sampling schedule for blood collection can be found in the study flow chart (see Tables 17-19). IL-6 and total sIL-6R will be measured at the Baseline Visit 2 (week 0) and Visit 12 (Week 12). For patients who discontinue the study treatment prematurely during the core treatment phase, the IL-6, and total sIL-6R will be measured at the EOT assessment.

Pharmacogenomics

Parent(s) or legal guardian(s) will be required to sign a separate ICF for saliva sample collection. Deoxyribonucleic acid samples for the genomic research will be double-coded as defined by the International Council for Harmonisation (ICH) guideline 15. Deoxyribonucleic acid samples may be stored for up to 15 years after the final date of the clinical study report (CSR) and may be used for research purposes.

The purpose of the genomic analyses is to identify genomic associations with clinical or biomarker response to target modulation, disease prognosis, and progression, or other clinical outcome measures. These data may be used or combined with data collected from other studies to identify genomic markers that may predict response and elucidate mechanisms of disease. Analyses may include sequence determination or single nucleotide polymorphism studies of candidate genes and surrounding genomic regions. Genome wide studies, including (but not limited to) single nucleotide polymorphism analyses, genomic sequencing, and transcriptome sequencing may also be performed. If indicated, genomic analyses may also be performed to identify markers associated with toxicity. Patients are still eligible to enroll in the study if they and their parents or legal guardians do not wish to participate in the pharmacogenomic sample collection.

Any unused or left-over serum samples collected for drug concentration or ADA measurements may be stored and used for exploratory biomarker research related to sJIA, inhibition of the IL-6Rα pathway with an antibody, treatment response (PD and or predictive), to investigate unexpected AEs, or to identify markers associated with toxicity. Samples may be stored up to 15 years after the date of the CSR or based on local regulation.

TABLE 28

Last on-treatment visit prior to EOT visit (Visit 27) for patients who change from a nonselected dose to the selected dose

| Visit when the first dose adjustment occurs | Patient's last on-treatment visit prior to Visit 27 (EOT) | Weeks between patient's last on-treatment visit and EOT |
|---|---|---|
| Visit 13 (Week 16) | Visit 119 (Week 132) | 8 weeks |
| Visit 14 (Week 20) | Visit 119 (Week 132) | 4 weeks |
| Visit 15 (Week 24) | Visit 118 (Week 120) | 12 weeks |
| Visit 16 (Week 32) | Visit 118 (Week 120) | 4 weeks |
| Visit 17 (Week 40) | Visit 117 (Week 108) | 8 weeks |
| Visit 18 (Week 48) | Visit 116 (Week 96) | 12 weeks |
| Visit 19 (Week 60) | Visit 115 (Week 84) | 12 weeks |
| Visit 20 (Week 72) | Visit 114 (Week 72) | 12 weeks |
| Visit 21 (Week 84) | Visit 113 (Week 60) | 12 weeks |
| Visit 22 (Week 96) | Visit 112 (Week 48) | 12 weeks |
| Visit 23 (Week 108) | Visit 111 (Week 40) | 8 weeks |
| Visit 24 (Week 120) | Visit 109 (Week 24) | 12 weeks |
| Visit 25 (Week 132) | Visit 106 (Week 12) | 12 weeks |
| Visit 26 (Week 144) | Visit 105 (Week 8) | 4 weeks |

TABLE 29

Characteristics of sJIA

| Clinical features defined by ILAR Classifaction | Exclusion criteria[a] | Frequency (% of total JIA) | Onset (yrs) Mean-range | Outcome |
|---|---|---|---|---|
| Arthritis with/proceeded by daily fever for at least 2 weeks and ≥ one of: evanescent salmon-colored erythematous rash, generalized lymphadenopathy, hepato/splenomegaly and serositis ((8). | a, b, c, d | 10% | 4-6 Any age during childhood and adolescence | 50% remit in Year 1 25% have severe destructive joint disease General growth abnormalities Macrophage activation syndrome |

Abbreviations: HLA-B27 = human leukocyte antigen-B27, ILAR = International League of Associations for Rheumatology, JIA = juvenile idiopathic arthritis, RF = rheumatoid factor.

a Specific exclusion criteria:

a = psoriasis or psoriasis in a first grade relative;

b = presence of HLA-B27, male gender, and age above 6 years;

c = ankylosing spondylitis, enthesitis-associated arthritis, sacroiliitis accompanied by chronic inflammatory bowel disease, Reiter's disease in a first grade relative;

d = presence of RFs on at least 2 occasions at least 3 months apart.

TABLE 30

Investigator-reported TEAEs

| | Dose cohort | | | | | |
|---|---|---|---|---|---|---|
| | 1 | 2 | 3 | All doses | | |
| | Patient weight group | | | | | |
| | A + B | A + B | A + B | Group A | Group B | A + B |
| | Number of patients enrolled | | | | | |
| | 13 | 14 | 15 | 20 | 22 | 42 |
| | Cumulative treatment exposure, PY | | | | | |
| | 2.6 | 3.0 | 2.7 | 4.1 | 4.2 | 8.3 |
| Summary, n (%) | | | | | | |
| TEAEs | 11 (84.6) | 12 (85.7) | 13 (85.7) | 16 (80.0) | 20 (90.9) | 36 (85.7) |
| Serious TEAEs | 0 | 0 | 0 | 0 | 0 | 0 |
| TEAEs leading to death | 0 | 0 | 0 | 0 | 0 | 0 |
| TEAEs leading to treatment discontinuation | 2 (15.4) | 0 | 3 (20.0) | 2 (10.0) | 3 (13.6) | 5 (11.9) |
| Neutropenia | 1 (7.7) | 0 | 3 (20.0) | 1 (5.0) | 3 (13.6) | 4 (9.5) |
| ALT increased (5-10 xULN) | 1 (7.7) | 0 | 4 | 1 (5.0) | 0 | 1 (2.4) |
| TEAEs with overall incidence ≥ 5%, n (%) | | | | | | |
| Neutropenia | 3 (23.1) | 3 (21.4) | 5 (33.3) | 3 (15.0) | 8 (36.4) | 11 (26.2) |
| Upper respiratory tract infection | 4 (30.8) | 2 (14.3) | 3 (20.0) | 5 (25.0) | 4 (18.2) | 9 (21.4) |
| Nasopharyngitis | 1 (7.7) | 2 (14.3) | 1 (6.7) | 3 (15.0) | 1 (4.5) | 4 (9.5) |
| Infection-site erythema | 0 | 3 (21.4) | 0 | 1 (5.0) | 2 (9.1) | 3 (7.1) |
| Rhinitis | 2 (15.4) | 0 | 1 (6.7) | 1 (5.0) | 2 (9.1) | 3 (7.1) |
| Leukopenia | 1 (7.7) | 2 (14.3) | 0 | 1 (5.0) | 2 (9.1) | 3 (7.1) |
| Conjunctivitis | 0 | 2 (14.3) | 1 (6.7) | 0 | 3 (13.6) | 3 (7.1) |
| Diarrhea | 0 | 2 (14.3) | 1 (6.7) | 1 (5.0) | 2 (9.1) | 3 (7.1) |
| Bronchitis | 0 | 1 (7.1) | 2 (13.3) | 0 | 3 (13.6) | 3 (7.1) |

PY, patient-years; ULN, upper limit of normal.

TABLE 31

Table showing Grade 3 and Grade 4 neutropenia by lowest value neutrophil count recorded on study.

| | Dose cohort | | | All doses | | |
|---|---|---|---|---|---|---|
| | Patient weight group | | | | | |
| | 1<br>A + b | 2<br>A + B | 3<br>A + B | Group A | Group B | A + B |
| | Number of patients enrolled | | | | | |
| | 13 | 14 | 19 | 20 | 22 | 42 |
| ANC (maximum grade observed)[a], n (%) | | | | | | |
| Grade 3: ≥500-1000 cells/mm$^3$ | 3 (23.1) | 2 (14.3) | 2 (13.3) | 4 (20.0) | 3 (13.6) | 7 (16.7) |
| Grade 4: <500 cells/mm$^3$ | 0 | 1 (7.1) | 4 (26.7) | 0 | 5 (22.7) | 5 (11.9) |

[a]Prespecified laboratory monitoring.

ANC, absolute neutrophil count; LLN, lower limit of normal.

TABLE 32

Flow chart for patients enrolled directly under the selected dose regimen in the third portion

| | Extension phase (up to 84 weeks of sarilumab exposure from V12 for third portion [Portion 3]) | | | | | | | | | | Post-treatment follow-up (6 weeks) |
|---|---|---|---|---|---|---|---|---|---|---|---|---|
| | Visit | | | | | | | | | | | |
| | V13[a] | V14[a] | V15 | V16[a] | V16.1[b] | V17[a] | V18 | V19 | V20 | V21 | V27/EOT[c] | V28/EOS[d] |
| | Day | | | | | | | | | | | |
| Week | D 113 (±1 or 3) Wk 16 | D 141 (±1 or 3) Wk 20 | D 169 (±1 or 3) Wk 24 | D 225 (±1 or 3) Wk 32 | D 253 (±1 or 3) Wk 36 | D 281 (±1 or 3) Wk 40 | D 337 (±1 or 3) Wk 48 | D 421 (±1 or 3) Wk 60 | D 505 (±1 or 3) Wk 72 | D 589 (±1 or 3) Wk 84 | Wk 96 for Portion 3 | EOT + 6 Wks: Wk 102 for Portion 3 |
| Concomitant medication | | | X | | X | | X | X | X | X | X | X |
| Home diary/ compliance[e] | | | X | | X | | X | X | X | X | X | |
| Physical examination[f] | | | X | | | | X | | X | | X | |
| Call IVRS | | | X | | X | | X | X | X | X | X | X |
| Tanner stage and menstruation status | | | X | | | | X | | X | | X | X |
| Treatment | | | | | | | | | | | | |
| IMP administration[g] | | | X | | X | | X | X | X | X | | |
| IMP dispense | | | X | | X | | X | X | X | X | | |
| Vital signs | | | | | | | | | | | | |
| Temperature, heart rate, blood pressure | | | X | | X | | X | X | X | X | X | X |
| Weight | | | X | | X | | X | X | X | X | X | X |
| Height (stadiometer)[h] | | | X | | | | X | | X | | X | |
| Efficacy | | | | | | | | | | | | |
| JIA ACR core set[i] | | | X | | | | X | | X | | X | |
| JADAS-27[j] | | | X | | | | X | | X | | X | |
| Safety assessment | | | | | | | | | | | | |
| AE/SAE recording | | | X | | X | | X | X | X | X | X | X |
| Tuberculosis risk assessment | | | X | | X | | X | X | X | X | X | X |
| PPD tuberculin skin test for patients ≤5 years; QuantiFERON-TB test for patients >5 years | | | | | | | X | | | | | |
| Local | | | X | | X | | X | X | X | X | X | |

TABLE 32-continued

Flow chart for patients enrolled directly under the selected dose regimen in the third portion

| | Extension phase (up to 84 weeks of sarilumab exposure from V12 for third portion [Portion 3]) | | | | | | | | | | Post-treatment follow-up (6 weeks) |
|---|---|---|---|---|---|---|---|---|---|---|---|---|
| | Visit | | | | | | | | | | | |
| | V13[a] | V14[a] | V15 | V16[a] | V16.1[b] | V17[a] | V18 | V19 | V20 | V21 | V27/EOT[c] | V28/EOS[d] |
| | Day | | | | | | | | | | | |
| Week | D 113 (±1 or 3) Wk 16 | D 141 (±1 or 3) Wk 20 | D 169 (±1 or 3) Wk 24 | D 225 (±1 or 3) Wk 32 | D 253 (±1 or 3) Wk 36 | D 281 (±1 or 3) Wk 40 | D 337 (±1 or 3) Wk 48 | D 421 (±1 or 3) Wk 60 | D 505 (±1 or 3) Wk 72 | D 589 (±1 or 3) Wk 84 | Wk 96 for Portion 3 | EOT + 6 Wks: Wk 102 for Portion 3 |
| tolerability | | | | | | | | | | | | |
| Laboratory testing | | | | | | | | | | | | |
| Hematology[k] | | | X | | X | | X | X | X | X | X[k] | |
| Chemistry[l] | | | X | | X | | X | X | X | X | X[l] | |
| Fasting lipids[m] | | | X | | | | X | | | | X[m] | |
| hs-CRP | | | X | | | | X | | X | | X[i] | |
| ESR | | | X | | | | X | | X | | X | |
| ANA/anti-dsDNA antibody[n] | | | X | | | | X | | | | X[n] | |
| Local urine pregnancy test for females who are menstruating[o] | | | X | | X | | X | X | X | X | X | |
| Pharmacokinetics and ADA | | | | | | | | | | | | |
| Serum sarilumab[p] | | | X | | | | X | | X | | X | X |
| Antibodies to sarilumab[p] | | | X | | | | X | | X | | X | X |

Abbreviations: ADA = anti-drug antibody, AE = adverse event, ALP = alkaline phosphatase, ALT = alanine aminotransferase, ANA = antinuclear antibodies, ANC = absolute neutrophil counts, AST = aspartate aminotransferase, BP = blood pressure, DNA = deoxyribonucleic acid, D = day, EOT = End-of-Treatment, EOS = End-of-Study, ESR = erythrocyte sedimentation rate, hs-CRP = high sensitivity C-reactive protein, IMP = investigational medicinal product, IVRS = Interactive Voice Response System, JADAS = Juvenile Arthritis Disease Activity Score, JIA ACR = Juvenile Idiopathic Arthritis American College of Rheumatology, PK = pharmacokinetics, PPD = Purified Protein Derivative, SAE = serious adverse event, TB = Tuberculosis, V = visit, Wk/Wks = week, yrs = years.

[a]Visits 13, 14, 16, and 17 are not applicable for patients in the third portion.

[b]Visit 16.1 is only applicable for patients in the third portion.

[c]Visit 27 (Week 96 for third portion) is the study planned End-of-Treatment (EOT) visit. If patients discontinue the study treatment prematurely, EOT will occur 2 weeks after the last IMP injection.

[d]Visit 28 (Week 102 for third portion) is the study planned End-of-Study (EOS) visit. If patients discontinue study treatment prematurely, these patients will be asked to return for the EOT assessment 2 weeks after the last IMP injection and for the EOS assessment 6 weeks after the EOT visit (EOT + 6 weeks). The EOT and EOS visits will be applicable to all the patients prematurely discontinued in both core treatment phase and extension phase.

[e]Home diary for IMP administration to be completed for IMP administered at home.

[f]Complete physical examinations will be performed at Visit 15 (week 24), Visit 18 (Week 48), Visit 20 (Week 72), and Visit 27 (EOT), including skin, nasal cavities, eyes, ears, respiratory, cardiovascular, gastrointestinal, neurological, lymphatic, and musculoskeletal systems.

[g]Investigational medicinal product (IMP) to be administered once every other week (q2w). Patients should be monitored for at least 30 minutes after IMP administration for any signs or symptoms of a hypersensitivity reaction. The last IMP injection will occur at Week 94; then patients will have EOT assessment at the Visit 27 (Week 96 for third portion). There will be no IMP injection at the Visit 27.

[h]Height will be measured using stadiometer at sites during the study.

[i]Juvenile Idiopathic Arthritis American College of Rheumatology (JIA ACR) coreset includes: global assessment of the severity of disease by the physician, global assessment of overall well-being by the patient or parent, number of joints with active arthritis (defined as swelling within the joint not due to deformity OR limitation of motion and with either pain, tenderness, or both), number of joints with limitation of motion, Childhood Health Assessment Questionnaire (CHAQ), and hs-CRP. If a patient discontinues prematurely before Week 48, hs-CRP must beperformed by the central laboratory at EOT.

[j]Juvenile Arthritis Disease Activity Score scoring

[k]Hematology (blood should be drawn PRIOR TO drug administration): Hemoglobin, hematocrit, red blood cell (RBC) count and morphology (if RBC count is abnormal), white blood cell (WBC) differential (neutrophils, lymphocytes, monocytes, eosinophils, basophils), platelet count, absolute neutrophil count (ANC). If a patient discontinues prematurely before Week 48, the test must be performed by the central laboratory at EOT.

[l]Chemistry (blood should be drawn BEFORE drug administration): ALT, AST, ALP, total bilirubin, conjugated bilirubin, unconjugated bilirubin, and albumin will be tested. Complete chemistry should be done at Visit 27 EOT (Week 96 for third portion). If a patient discontinues prematurely before Week 48, the test must be performed by the central laboratory at EOT.

[m]Lipids (blood should be drawn BEFORE drug administration): Triglycerides (TG), total cholesterol, high density lipoprotein (HDL) cholesterol, low density lipoprotein (LDL) cholesterol. Patients are required to fast at least 8 hours before the test. At EOT, the test will be performed only for patient who discontinues prematurely before Week 48 and must be performed by the central laboratory.

[n]At EOT, the ANA/anti-dsDNA antibody test will be performed only for patient who discontinues prematurely before Week 48 and must be performed by the central laboratory.

[o]For females who have commenced menstruating, urine pregnancy tests should be performed prior to exposure to the IMP at each scheduled visit and at the EOT. The urine pregnancy test could be performed locally.

[p]Blood samples will be collected PRIOR TO IMP administration on the dosing days during the treatment period. If an SAE occurs in a patient, blood samples should be collected for determination of sarilumab concentration and anti-drug antibody (ADA) assessment at or near the onset and completion of the occurrence of the event, if possible.

TABLE 33

| Expected response rate at W 12 on the selected dose regimen[a] | Sample size | 95% CI half-width |
|---|---|---|
| Pooled patients who will be enrolled to the selected dose from the dose-finding and second portions | | |
| 90% | 36 | 9.8% |
| 85% | 36 | 11.7% |
| 80% | 36 | 13.1% |
| 75% | 36 | 14.1% |
| 70% | 36 | 15.0% |
| 65% | 36 | 15.6% |
| 60% | 36 | 16.0% |
| 50% | 36 | 16.3% |
| 40% | 36 | 16.0% |
| Pooled patients who will be enrolled to the selected dose from all 3 portions | | |
| 90% | 60 | 7.6% |
| 85% | 60 | 9.0% |
| 80% | 60 | 10.1% |
| 75% | 60 | 11.0% |
| 70% | 60 | 11.6% |
| 65% | 60 | 12.1% |
| 60% | 60 | 12.4% |
| 50% | 60 | 12.7% |
| 40% | 60 | 12.4% |

Estimates of the precision on the JIA ACR response rate

Abbreviation: CI = confidence interval, W 12 = Week 12, JIA ACR = Juvenile Idiopathic Arthritis American College of Rheumatology.
[a]The expected response rate at W 12 on the selected dose regimen is estimated based on the effect sizes observed on tocilizumab (27).
Note:
The "sample size" is the approximate number of patients who will be enrolled to the selected dose and completed the 12-week core treatment period;
a 15% dropout rate was assumed.

REFERENCES

1. Petty R E, Southwood T R, Manners P, Baum J, Glass D N, Goldenberg J, et al. International League of Associations for Rheumatology classification of juvenile idiopathic arthritis: second revision, Edmonton, 2001. J Rheumatol 2004; 31:390-2.
2. Ravelli A, Martini A. Juvenile idiopathic arthritis. Lancet (London) 2007; 369:767-78.
3. Gabriel S E, Michaud K. Epidemiological studies in incidence, prevalence, mortality, and comorbidity of the rheumatic diseases. Arthritis Res Ther 2009; 11:229-29.
4. Oberle E J, Harris J G, Verbsky J W. Polyarticular juvenile idiopathic arthritis—epidemiology and management approaches. Clin Epidemiol 2014; 6:379-93.
5. Shepherd J, Cooper K, Harris P, Picot J, Rose M. The clinical effectiveness and cost-effectiveness of abatacept, adalimumab, etanercept and tocilizumab for treating juvenile idiopathic arthritis: a systematic review and economic evaluation. Health Technol Assess (Winchester) 2016; 20:1-222.
6. Hissink Muller P C E, Brinkman D M C, Schonenberg D, Koopman-Keemink Y, Brederije I C J, Bekkering W P, et al. A comparison of three treatment strategies in recent onset non-systemic Juvenile Idiopathic Arthritis: initial 3-months results of the BeSt for Kids-study. Pediatr Rheumatol Online J 2017; 15.
7. Lovell D J, Johnson A L, Huang B, Gottlieb B S, Morris P W, Kimura Y, et al. Risk, timing, and predictors of disease flare after discontinuation of anti-tumor necrosis factor therapy in children with polyarticular forms of juvenile idiopathic arthritis with clinically inactive disease. Arthritis Rheumatol (Hoboken) 2018; 70:1508-18.
8. Wallace C A, Giannini E H, Spalding S J, Hashkes P J, O'Neil K M, Zeft A S, et al. Trial of early aggressive therapy in polyarticular juvenile idiopathic arthritis. Arthritis Rheum 2012; 64:2012-21.
9. Guzman J, Oen K, Tucker L B, Huber A M, Shiff N, Boire G, et al. The outcomes of juvenile idiopathic arthritis in children managed with contemporary treatments: results from the ReACCh-Out cohort. Ann Rheum Dis 2015; 74:1854-60.
10. Simonini G, Ferrara G, Pontikaki I, Scoccimarro E, Giani T, Taddio A, et al. Flares after withdrawal of biologic therapies in juvenile idiopathic arthritis: clinical and laboratory correlates of remission duration. Arthritis Care Res 2018; 70:1046-51.
11. Ravelli A, Consolaro A, Horneff G, Laxer R M, Lovell D J, Wulffraat N M, et al. Treating juvenile idiopathic arthritis to target: recommendations of an international task force. Ann Rheum Dis 2018; 77:819-28.
12. Swart J, Giancane G, Horneff G, Magnusson B, Hofer M, Alexeeva E, et al. Pharmacovigilance in juvenile idiopathic arthritis patients treated with biologic or synthetic drugs: combined data of more than 15,000 patients from Pharmachild and national registries. Arthritis Res Ther 2018; 20:285.
13. De Benedetti F, Robbioni P, Massa M, Viola S, Albani S, Martini A. Serum interleukin-6 levels and joint involvement in polyarticular and pauciarticular juvenile chronic arthritis. Clin Exp Rheumatol 1992; 10:493-8.
14. Spirchez M, Samasca G, Iancu M, Bolba C, Miu N. Relation of interleukin-6, TNF-alpha and interleukin-1alpha with disease activity and severity in juvenile idiopathic arthritis patients. Clin Lab 2012; 58:253-60.
15. De Benedetti F. Targeting interleukin-6 in pediatric rheumatic diseases. Curr Opin Rheumatol 2009; 21:533-7.
16. De Benedetti F, Pignatti P, Gerloni V, Massa M, Sartirana P, Caporali R, et al. Differences in synovial fluid cytokine levels between juvenile and adult rheumatoid arthritis. J Rheumatol 1997; 24:1403-9.
17. KEVZARA. U S prescribing information. Available: https://www-accessdata-fda-gov/drugsatfda_docs/label/2017/761037s0001bl.pdf [Accessed Mar. 14, 2018].
18. Brunner H I, Ruperto N, Zuber Z, Keane C, Harari O, Kenwright A, et al. Efficacy and safety of tocilizumab in patients with polyarticular-course juvenile idiopathic arthritis: results from a phase 3, randomised, double-blind withdrawal trial. Ann Rheum Dis 2015; 74:1110-17.
19. ACTEMRA (tocilizumab) product labelling. [Accessed 24 May 2019].
20. Huizinga T W, Fleischmann R M, Jasson M, Radin A R, van Adelsberg J, Fiore S, et al. Sarilumab, a fully human monoclonal antibody against IL-6Ralpha in patients with rheumatoid arthritis and an inadequate response to methotrexate: efficacy and safety results from the randomised SARIL-RA-MOBILITY Part A trial. Ann Rheum Dis 2014; 73:1626-34.
21. Guidance for Industry Drug-Induced Liver Injury: Premarketing Clinical Evaluation. Available: https://www-fda-gov/media/116737/download [Accessed 9 Jul. 2019].

22. Wallace C A, Giannini E H, Huang B, Itert L, Ruperto N. American College of Rheumatology provisional criteria for defining clinical inactive disease in select categories of juvenile idiopathic arthritis. Arthrit Care Res 2011; 63:929-36.
23. Germovsek E, Barker C I S, Sharland M, Standing J F. Pharmacokinetic—pharmacodynamic modeling in pediatric drug development, and the importance of standardized scaling of clearance. Clin Pharmacokinet 2019; 58:39-52.
24. Barker C I S, Standing J F, Kelly L E, Hanly Faught L, Needham A C, Rieder M J, et al. Pharmacokinetic studies in children: recommendations for practice and research. Arch Dis Child 2018; 103:695.
25. Gill K L, Machavaram K K, Rose R H, Chetty M. Potential sources of inter-subject variability in monoclonal antibody pharmacokinetics. Clin Pharmacokinet 2016; 55:789-805.
26. Kojima T, Yabe Y, Kaneko A, Hirano Y, Ishikawa H, Hayashi M, et al. Monitoring C-reactive protein levels to predict favourable clinical outcomes from tocilizumab treatment in patients with rheumatoid arthritis. Modern rheumatology 2013; 23:977-85.
27. Madhok R, Crilly A, Watson J, Capell H A. Serum interleukin 6 levels in rheumatoid arthritis: correlations with clinical and laboratory indices of disease activity. Ann Rheum Dis 1993; 52:232-4.
28. Nishimoto N, Terao K, Mima T, Nakahara H, Takagi N, Kakehi T. Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease. Blood 2008; 112:3959-64.
29. Emery P, Keystone E, Tony H P, Cantagrel A, van Vollenhoven R, Sanchez A, et al. IL-6 receptor inhibition with tocilizumab improves treatment outcomes in patients with rheumatoid arthritis refractory to anti-tumour necrosis factor biologicals: results from a 24-week multicentre randomised placebo-controlled trial. Ann Rheum Dis 2008; 67:1516-23.
30. Fleischmann R, van Adelsberg J, Lin Y, Castelar-Pinheiro G D, Brzezicki J, Hrycaj P, et al. Sarilumab and nonbiologic disease-modifying antirheumatic drugs in patients with active rheumatoid arthritis and inadequate response or intolerance to tumor necrosis factor inhibitors. Arthritis Rheumatol (Hoboken) 2017; 69:277-90.
31. Genovese M C, Fleischmann R, Kivitz A J, Rell-Bakalarska M, Martincova R, Fiore S, et al. Sarilumab plus methotrexate in patients with active rheumatoid arthritis and inadequate response to methotrexate: results of a Phase III study. Arthritis Rheumatol (Hoboken) 2015; 67:1424-37.
32. Burmester G R, Lin Y, Patel R, van Adelsberg J, Mangan E K, Graham N M, et al. Efficacy and safety of sarilumab monotherapy versus adalimumab monotherapy for the treatment of patients with active rheumatoid arthritis (MONARCH): a randomised, double-blind, parallel-group phase III trial. Ann Rheum Dis 2017; 76:840-47.
33. Emery P, Rondon J, Parrino J, Lin Y, Pena-Rossi C, van Hoogstraten H, et al. Safety and tolerability of subcutaneous sarilumab and intravenous tocilizumab in patients with rheumatoid arthritis. Rheumatology (Oxford) 2018; 58:849-58.
34. Pardeo M, Wang J, Ruperto N, Alexeeva E, Chasnyk V, Schneider R, et al. Neutropenia during tocilizumab treatment is not associated with infection risk in systemic or polyarticular-course juvenile idiopathic arthritis. J Rheumatol 2019. Available: https://www-ncbi-nlm-nih-gov/pubmed/30824645 [Accessed 29 Aug. 2019].
35. ACTEMRA (tocilizumab) European Medicines Agency Assessment report. Available: https://www-ema-europa-eu/en/documents/variation-report/ro-actemra-h-c-955-ii-0072-epar-assessment-report-variation en.pdf [Accessed 28 May 2019].
36. Hsieh M M, Everhart J E, Byrd-Holt D D, Tisdale J F, Rodgers G P. Prevalence of neutropenia in the U.S. population: age, sex, smoking status, and ethnic differences. Ann Intern Med 2007; 146:486-92.
37. Moots R J, Sebba A, Rigby W, Ostor A, Porter-Brown B, Donaldson F, et al. Effect of tocilizumab on neutrophils in adult patients with rheumatoid arthritis: pooled analysis of data from phase 3 and 4 clinical trials. Rheumatology (Oxford) 2017; 56:541-49.
38. Genovese M C, van Adelsberg J, Fan C, Graham N M H, van Hoogstraten H, Parrino J, et al. Two years of sarilumab in patients with rheumatoid arthritis and an inadequate response to MTX: safety, efficacy and radiographic outcomes. Rheumatology 2018; 57:1423-31.
39. European Medicines Agency. Ethical considerations for clinical trials on medicinal products conducted with the paediatric population. Recommendations of the ad hoc group for the development of implementing guidelines for Directive 2001/20/E C relating to good clinical practice in the conduct of clinical trials on medicinal products for human use London: European Medicines Agency. 2008.

The invention claimed is:

1. A method for treating polyarticular juvenile idiopathic arthritis (pJIA) in a pediatric subject, the method comprising administering to a pediatric subject having pJIA an antibody that specifically binds to an interleukin-6 receptor (IL-6R), wherein the antibody comprises three heavy chain complementarity determining regions (HCDRs) of a heavy chain variable region comprising the amino acid sequence of SEQ ID NO: 1 and three light chain complementarity determining regions (LCDRs) of a light chain variable region comprising the amino acid sequence of SEQ ID NO: 2, and wherein the antibody is administered to the pediatric subject subcutaneously at a dose of about 200 mg every two weeks.

2. The method of claim 1, wherein the three HCDRs comprise the amino acid sequences of SEQ ID NO: 3, SEQ ID NO: 4, and SEQ ID NO: 5, respectively; and the three LCDRs comprise the amino acid sequences of SEQ ID NO: 6, GAS, and SEQ ID NO: 8, respectively.

3. The method of claim 1, wherein the antibody comprises a heavy chain variable region comprising the amino acid sequence of SEQ ID NO: 1, and a light chain variable region comprising the amino acid sequence of SEQ ID NO: 2.

4. The method of claim 1, wherein the antibody comprises a heavy chain comprising the amino acid sequence of SEQ ID NO: 9, and a light chain comprising the amino acid sequence of SEQ ID NO: 10.

5. The method of claim 1, wherein the antibody is sarilumab.

6. The method of claim 1, wherein the pJIA is selected from: rheumatoid factor-negative polyarticular juvenile idiopathic arthritis; rheumatoid factor-positive polyarticular juvenile idiopathic arthritis; and extended oligoarticular juvenile idiopathic arthritis.

7. The method of claim 1, wherein the pediatric subject is about 2 to about 17 years old.

8. The method of claim 1, wherein the pediatric subject weighs 63 kg or greater.

9. The method of claim 1, wherein the antibody is sarilumab and the pediatric subject weighs 63 kg or greater.

10. The method of claim 8, wherein the antibody is not administered with any other disease-modifying antirheumatic drug (DMARD) during a course of administration with the antibody.

11. The method of claim 8, wherein the antibody is administered in combination with at least one additional DMARD different from the antibody.

12. The method of claim 11, wherein the at least one additional DMARD different from the antibody comprises a synthetic disease-modifying antirheumatic drug (sDMARD) or a biological disease-modifying antirheumatic drug (bDMARD).

13. The method of claim 12, wherein the at least one additional DMARD different from the antibody comprises a sDMARD that comprises methotrexate, sulfasalazine, leflunomide, or hydroxychloroquine.

14. The method of claim 12, wherein the at least one additional DMARD different from the antibody comprises a sDMARD that comprises methotrexate.

15. The method of claim 12, wherein the at least one additional DMARD different from the antibody comprises a bDMARD that comprises adalimumab, golimumab, etanercept, abatacept, infliximab, rituximab, or tocilizumab.

16. The method of claim 1, wherein the antibody is administered using a prefilled syringe.

17. A method of treating polyarticular juvenile idiopathic arthritis (pJIA) in a subject in need thereof comprising administering to a subject having pJIA an anti-interleukin-6 receptor (IL-6R) antibody, wherein the antibody comprises three heavy chain complementarity determining regions (HCDRs) of a heavy chain variable region comprising the amino acid sequence of SEQ ID NO: 1 and three light chain complementarity determining regions (LCDRs) of a light chain variable region comprising the amino acid sequence of SEQ ID NO: 2, and wherein the antibody is administered to the subject subcutaneously at (i) a dose of about 4 mg/kg once every two weeks when the subject has a body weight of greater than or equal to 10 kg and less than 30 kg, or (ii) a dose of about 3 mg/kg once every two weeks when the subject has a body weight of at least 30 kg.

18. The method of claim 17, wherein the subject is a pediatric subject.

19. The method of claim 17, wherein the dose is capped at 200 mg once every 2 weeks when the subject has a body weight of equal to or greater than 63 kg.

20. The method of claim 17, wherein the three HCDRs comprise the amino acid sequences of SEQ ID NO: 3, SEQ ID NO: 4, and SEQ ID NO: 5, respectively; and the three LCDRs comprise the amino acid sequences of SEQ ID NO: 6, GAS, and SEQ ID NO: 8, respectively.

21. The method of claim 17, wherein the antibody comprises a heavy chain variable region comprising the amino acid sequence of SEQ ID NO: 1, and a light chain variable region comprising the amino acid sequence of SEQ ID NO: 2.

22. The method of claim 17, wherein the antibody comprises a heavy chain comprising the amino acid sequence of SEQ ID NO: 9, and a light chain comprising the amino acid sequence of SEQ ID NO: 10.

23. The method of claim 17, wherein the antibody is sarilumab.

24. The method of claim 17, wherein the pJIA is selected from: rheumatoid factor-negative polyarticular juvenile idiopathic arthritis; rheumatoid factor-positive polyarticular juvenile idiopathic arthritis; and extended oligoarticular juvenile idiopathic arthritis.

25. The method of claim 18, wherein the pediatric subject is about 2 to about 17 years old.

26. The method of claim 17, wherein the antibody is not administered with any other disease-modifying antirheumatic drug (DMARD) during a course of administration with the antibody.

27. The method of claim 17, wherein the antibody is administered in combination with at least one additional DMARD different from the antibody.

28. The method of claim 27, wherein the at least one additional DMARD different from the antibody comprises a synthetic disease-modifying antirheumatic drug (sDMARD) or a biological disease-modifying antirheumatic drug (bDMARD).

29. The method of claim 17, wherein the at least one additional DMARD different from the antibody comprises a sDMARD that comprises methotrexate, sulfasalazine, leflunomide, or hydroxychloroquine.

30. The method of claim 27, wherein the at least one additional DMARD different from the antibody comprises a sDMARD that comprises methotrexate.

31. The method of claim 17, wherein the subject has previously had an inadequate response to a prior therapy comprising a synthetic DMARD, or the subject was previously intolerant to a prior therapy comprising a synthetic DMARD.

32. The method of claim 17, wherein the subject is a pediatric subject who (i) has previously had an inadequate response to a prior therapy comprising a synthetic DMARD, or (ii) was previously intolerant to a prior therapy comprising a synthetic DMARD; and wherein the antibody is sarilumab.

* * * * *